(12) United States Patent
Bhattacharjee et al.

(10) Patent No.: US 8,470,985 B2
(45) Date of Patent: Jun. 25, 2013

(54) TRIAZOLE COMPOUNDS AND METHODS OF MAKING AND USING THE SAME

(75) Inventors: Ashoke Bhattacharjee, Cheshire, CT (US); Zoltan F. Kanyo, North Haven, CT (US)

(73) Assignee: Rib-X Pharmaceuticals, Inc., New Haven, CT (US)

(*) Notice: Subject to any disclaimer, the term of this patent is extended or adjusted under 35 U.S.C. 154(b) by 773 days.

(21) Appl. No.: 11/990,833

(22) PCT Filed: Aug. 24, 2006

(86) PCT No.: PCT/US2006/033157
§ 371 (c)(1),
(2), (4) Date: Sep. 16, 2009

(87) PCT Pub. No.: WO2007/025089
PCT Pub. Date: Mar. 1, 2007

(65) Prior Publication Data
US 2010/0016955 A1    Jan. 21, 2010

Related U.S. Application Data

(60) Provisional application No. 60/711,440, filed on Aug. 24, 2005, provisional application No. 60/797,926, filed on May 5, 2006.

(51) Int. Cl.
*C07H 17/08* (2006.01)
(52) U.S. Cl.
USPC ............................................. 536/7.4; 536/7.2
(58) Field of Classification Search
None
See application file for complete search history.

(56) References Cited

U.S. PATENT DOCUMENTS

| 5,792,765 A | 8/1998 | Riedl et al. |
| 7,091,196 B2 * | 8/2006 | Wang et al. ................... 514/183 |
| 2008/0045585 A1 | 2/2008 | Farmer et al. |

FOREIGN PATENT DOCUMENTS

| EP | 0643068 A1 | 3/1995 |
| WO | WO-9916779 A1 | 4/1999 |
| WO | WO-9922722 A2 | 5/1999 |
| WO | WO-9963937 A2 | 12/1999 |
| WO | WO-0040589 A2 | 7/2000 |
| WO | WO-0140222 A1 | 6/2001 |
| WO | WO-0142242 A1 | 6/2001 |
| WO | WO-0158885 A1 | 8/2001 |
| WO | WO-0181350 A1 | 11/2001 |
| WO | WO-02051855 | 7/2002 |
| WO | WO-03011882 A1 | 2/2003 |
| WO | WO-03022824 A1 | 3/2003 |
| WO | WO-03035073 A1 | 5/2003 |
| WO | WO-2004013153 A2 | 2/2004 |
| WO | WO2004/029066 * | 4/2004 |
| WO | WO-2005042554 A1 | 5/2005 |
| WO | WO-2005049632 A1 | 6/2005 |
| WO | WO-2005085266 A2 | 9/2005 |
| WO | WO2005/118610 * | 12/2005 |
| WO | WO-2007025284 A1 | 3/2007 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Hwang et al. "1,3-Dipolar Cycloaddition of Nitrile Oxides to 1-phenylsulfonyl-1,3-butadienes: Synthesis of 3-(4,5-dihydroisoxazol-5-yl)pyrroles." *Tetrahed. Lett.* 43.1(2002):53-56.
Phan et al. "Synthesis and Antibacterial Activity of a Novel Class of 4'-Substituted 16-Membered Ring Macrolides Derived from Tylosin." *J. Med. Chem.* 47.12(2004):2965-2968.
Sano et al. "Chemical Modification of Spiramycins." *J. Antibiotics.* 38.2(1985):186-196.

* cited by examiner

*Primary Examiner* — Traviss C McIntosh, III
(74) *Attorney, Agent, or Firm* — Mintz Levin Cohn Ferris Glovsky and Popeo, P.C.; Ivor R. Elrifi; Jennifer L. Loebach

(57) ABSTRACT

The present invention provides triazole macrocyclic compounds useful as therapeutic agents. More particularly, these compounds are useful as anti-infective, antiproliferative, anti-inflammatory, and prokinetic agents. These compounds are represented by the following formula (I): wherein $R^1$, $R^2$, ect. Are defined in claim 1.

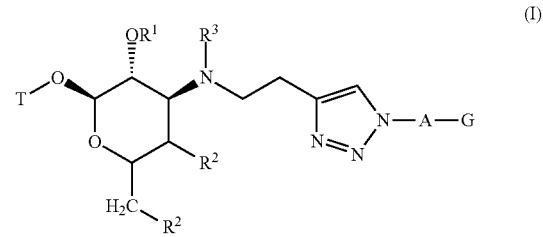

1 Claim, No Drawings

TRIAZOLE COMPOUNDS AND METHODS OF MAKING AND USING THE SAME

RELATED APPLICATIONS

This application is a national stage application, filed under 35 U.S.C. §371, of International Application No. PCT/US2006/033157, filed on Aug. 24, 2006, which claims the benefit of and priority to U.S. Patent Application Ser. No. 60/711,440, filed Aug. 24, 2005 and U.S. Patent Application Ser. No. 60/797,926, filed May 5, 2006, the disclosure of each is incorporated by reference herein.

FIELD OF THE INVENTION

The present invention relates generally to the field of anti-infective, anti-proliferative, anti-inflammatory, and prokinetic agents. More particularly, the invention relates to a family of triazole macrocyclic compounds that are useful as such agents.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. However, such beliefs have been shaken because strains of cells or microorganisms resistant to currently effective therapeutic agents continue to evolve. In fact, virtually every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant enterococci have developed. These resistant bacteria can cause serious and even fatal results for patients infected with such resistant bacteria. Bacteria that are resistant to macrolide antibiotics have emerged. Also, resistant strains of Gram-negative bacteria such as *H. influenzae* and *M. catarrhalis* have been identified. See, e.g., F. D. Lowry, "Antimicrobial Resistance: The Example of *Staphylococcus aureus*," *J. Clin. Invest.*, vol. 111, no. 9, pp. 1265-1273 (2003); and Gold, H. S, and Moellering, R. C., Jr., "Antimicrobial-Drug Resistance," *N. Engl. J. Med.*, vol. 335, pp. 1445-53 (1996).

The problem of resistance is not limited to the area of anti-infective agents. Resistance has also been encountered with anti-proliferative agents used in cancer chemotherapy. Therefore, the need exists for new anti-infective and anti-proliferative agents that are both effective against resistant bacteria and resistant strains of cancer cells.

Despite the problem of increasing antibiotic resistance, no new major classes of antibiotics have been developed for clinical use since the approval in the United States in 2000 of the oxazolidinone ring-containing antibiotic, linezolid, which is sold under the trade name Zyvox®. See, R. C. Moellering, Jr., "Linezolid: The First Oxazolidinone Antimicrobial," *Annals of Internal Medicine*, vol. 138, no. 2, pp. 135-142 (2003). Linezolid was approved for use as an antibacterial agent active against Gram-positive organisms. However, linezolid-resistant strains of organisms are already being reported. See, Tsiodras et al., *Lancet*, vol. 358, p. 207 (2001); Gonzales et al., *Lancet*, vol 357, p. 1179 (2001); Zurenko et al., *Proceedings Of The 39th Annual Interscience Conference On Antibacterial Agents And Chemotherapy* (ICAAC), San Francisco, Calif., USA (Sep. 26-29, 1999).

Another class of antibiotics is the macrolides, so named for their characteristic 14- to 16-membered ring. The macrolides also often have one or more 6-membered sugar-derived rings attached to the main macrolide ring. The first macrolide antibiotic to be developed was erythromycin, which was isolated from a soil sample from the Philippines in 1952. Even though erythromycin has been one of the most widely prescribed antibiotics, its disadvantages are relatively low bioavailability, gastrointestinal side effects, and a limited spectrum of activity. Another macrolide is the compound, azithromycin, which is an azolide derivative of erythromycin incorporating a methyl-substituted nitrogen in the macrolide ring. Azithromycin is sold under the trade name Zithromax®. A more recently introduced macrolide is telithromycin, which is sold under the trade name Ketek®. Telithromycin is a semisynthetic macrolide in which a hydroxyl group of the macrolide ring has been oxidized to a ketone group. See Yong-Ji Wu, Highlights of Semi-synthetic Developments from Erythromycin A, *Current Pharm. Design*, vol. 6, pp. 181-223 (2000), and Yong-Ji Wu and Wei-uo Su, Recent Developments on Ketolides and Macrolides, *Curr. Med. Chem.*, vol. 8, no. 14, pp. 1727-1758 (2001).

In the search for new therapeutic agents, researchers have tried combining or linking various portions of antibiotic molecules to create multifunctional or hybrid compounds. Other researches have tried making macrolide derivatives by adding further substituents to the large macrolide ring or associated sugar rings. However, this approach for making macrolide derivatives has also met with limited success.

Notwithstanding the foregoing, there is an ongoing need for new anti-infective and anti-proliferative agents. Furthermore, because many anti-infective and anti-proliferative agents have utility as anti-inflammatory agents and prokinetic agents, there is also an ongoing need for new compounds useful as anti-inflammatory and prokinetic agents. The present invention provides compounds that meet these needs.

SUMMARY OF THE INVENTION

The invention provides compounds useful as anti-infective agents and/or anti-proliferative agents, for example, anti-biotic agents, anti-microbial agents, anti-bacterial agents, anti-fungal agents, anti-parasitic agents, anti-viral agents, and chemotherapeutic agents. The present invention also provides compounds useful as anti-inflammatory agents, and/or prokinetic (gastrointestinal modulatory) agents. The present invention also provides pharmaceutically acceptable salts, esters, N-oxides, or prodrugs thereof.

The present invention provides compounds having the structure:

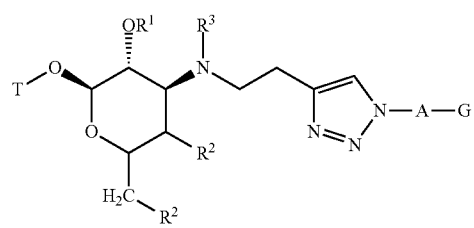

or a stereoisomer, pharmaceutically acceptable salt, ester, N-oxide, or prodrug thereof. In the formula, variables A, G, T, $R^1$, $R^2$, and $R^3$ can be selected from the respective groups of chemical moieties later defined in the detailed description. In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use as an anti-cancer, anti-biotic, anti-microbial, anti-bacterial, anti-fungal, anti-parasitic or anti-viral agent, or to treat a proliferative disease, an inflammatory disease or a gastrointestinal motility disorder, or to suppress disease states or conditions caused or mediated by nonsense or missense mutations. Accordingly, the compounds or the formulations can be administered, for example, via oral, parenteral, or topical routes, to provide an effective amount of the compound to the mammal.

The foregoing and other aspects and embodiments of the invention can be more fully understood by reference to the following detailed description and claims.

DETAILED DESCRIPTION OF THE INVENTION

The present invention provides a family of compounds that can be used as anti-proliferative agents and/or anti-infective agents. The compounds can be used without limitation, for example, as anti-cancer, anti-microbial, anti-bacterial, anti-fungal, anti-parasitic and/or anti-viral agents. Further, the present invention provides a family of compounds that can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation. Further, the compounds can be used to treat or prevent a disease state in a mammal caused or mediated by a nonsense or missense mutation.

The compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

1. DEFINITIONS

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^3$) occurs more than one time in any constituent or formula for a compound, its definition at each occurrence is independent of its definition at every other occurrence. Thus, for example, if a group is shown to be substituted with one or more $R^3$ moieties, then the group can optionally be substituted with one, two, three, four, five, or more $R^3$ moieties, and $R^3$ at each occurrence is selected independently from the definition of $R^3$. Also, combinations of substituents and/or variables are permissible, but only if such combinations result in stable compounds.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein there are nitrogens in the compounds of the present invention, these can be converted to N-oxides by treatment with an oxidizing agent (e.g., MCPBA and/or hydrogen peroxides) to afford other compounds of the present invention. Thus, all shown and claimed nitrogens are considered to cover both the shown nitrogen and its N-oxide (N→O) derivative.

As used herein, the term "anomeric carbon" means the acetal carbon of a glycoside.

As used herein, the term "glycoside" is a cyclic acetal.

As used herein, "allyl" is intended to include both branched and straight-chain saturated aliphatic hydrocarbon groups having the specified number of carbon atoms. $C_{1-6}$ alkyl is intended to include $C_1$, $C_2$, $C_3$, $C_4$, $C_5$, and $C_6$ alkyl groups. $C_{1-8}$ alkyl is intended to include $C_1$, $C_2$, $C_3$, $C_4$, $C_5$, $C_6$, $C_7$, and $C_8$ alkyl groups. Examples of allyl include, but are not limited to, methyl, ethyl, n-propyl, i-propyl, n-butyl, s-butyl, t-butyl, n-pentyl, s-pentyl, n-hexyl, n-leptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. $C_{2-6}$ alkenyl is intended to include $C_2$, $C_3$, $C_4$, $C_5$, and $C_6$ alkenyl groups. $C_{2-8}$ alkenyl is intended to include $C_2$, $C_3$, $C_4$, $C_5$, $C_6$, $C_7$, and $C_8$ alkenyl groups.

As used herein, "alkynyl" is intended to include hydrocarbon chains of either straight or branched configuration and one or more triple carbon-carbon bonds that can occur in any stable point along the chain, such as ethynyl and propynyl. $C_{2-6}$ alkynyl is intended to include $C_2$, $C_3$, $C_4$, $C_5$, and $C_6$ alkynyl groups. $C_{2-8}$ alkynyl is intended to include $C_2$, $C_3$, $C_4$, $C_5$, $C_6$, $C_7$, and C8 alkynyl groups.

Furthermore, "alkyl", "alkenyl", and "alkynyl" are intended to include moieties which are diradicals, i.e., having two points of attachment, an example of which in the present invention is when D is selected from these chemical groups. A nonlimiting example of such an alkyl moiety that is a diradical is —CH$_2$CH$_2$, i.e., a C$_2$ alkyl group that is covalently bonded via each terminal carbon atom to the remainder of the molecule.

As used herein, the terms used to describe various carbon-containing moieties, including, for example, "alkyl," "alkenyl," "alkynyl," "phenyl," and any variations thereof, are intended to include univalent, bivalent, or multivalent species. For example, "C$_{1-6}$ alkyl-R$^3$" is intended to represent a univalent C$_{1-6}$ alkyl group substituted with a R$^3$ group, and "O—C$_{1-6}$ allyl-R$^3$" is intended to represent a bivalent C$_{1-6}$ alkyl group, i.e., an "alkylene" group, substituted with an oxygen atom and a R$^3$ group.

As used herein, "cycloallyl" is intended to include saturated ring groups, such as cyclopropyl, cyclobutyl, or cyclopentyl. C$_{3-8}$ cycloalkyl is intended to include C$_3$, C$_4$, C$_5$, C$_6$, C$_7$, and C$_8$ cycloalkyl groups.

As used herein, "halo" or "halogen" refers to fluoro, chloro, bromo, and iodo. "Counterion" is used to represent a small, negatively charged species such as chloride, bromide, hydroxide, acetate, and sulfate.

As used herein, "haloalkyl" is intended to include both branched and straight-chain saturated aliphatic hydrocarbon groups having the specified number of carbon atoms, substituted with 1 or more halogen (for example —C$_v$F$_w$ where v=1 to 3 and w=1 to (2 v+1)). Examples of haloalkyl include, but are not limited to, trifluoromethyl, trichloromethyl, pentafluoroethyl, and pentachloroethyl.

As used herein, "alkoxy" refers to an alkyl group as defined above with the indicated number of carbon atoms attached through an oxygen bridge. C$_{1-6}$ alkoxy, is intended to include C$_1$, C$_2$, C$_3$, C4, C$_5$, and C$_6$ alkoxy groups. C$_{1-8}$ alkoxy, is intended to include C$_1$, C$_2$, C$_3$, C$_4$, C$_5$, C$_6$, C$_7$, and C$_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "alkylthio" refers to an alkyl group as defined above with the indicated number of carbon atoms attached through an sulfur bridge. C$_{1-6}$ alkylthio, is intended to include C$_1$, C$_2$, C$_3$, C$_4$, C$_5$, and C$_6$ alkylthio groups. C$_{1-8}$ alkylthio, is intended to include C$_1$, C$_2$, C$_3$, C$_4$, C$_5$, C$_6$, C$_7$, and C$_8$ allylthio groups.

As used herein, "carbocycle" or "carbocyclic ring" is intended to mean, unless otherwise specified, any stable 3, 4, 5, 6, 7, 8, 9, 10, 11, or 12-membered monocyclic, bicyclic or tricyclic ring, any of which can be saturated, unsaturated (including partially and fully unsaturated), or aromatic, recognizing that rings with certain numbers of members cannot be bicyclic or tricyclic, e.g., a 3-membered ring can only be a monocyclic ring. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0] bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

As used herein, the term "heterocycle" means, unless otherwise stated, a stable 3, 4, 5, 6, 7, 8, 9, 10, 11, or 12-membered monocyclic, bicyclic or tricyclic ring (recognizing that rings with certain numbers of members cannot be bicyclic or tricyclic, e.g., a 3-membered ring can only be a monocyclic ring), which is saturated, unsaturated (including partially and fully unsaturated), or aromatic, and consists of carbon atoms and one or more ring heteroatoms, e.g., 1 or 1-2 or 1-3 or 1-4 or 1-5 or 1-6 heteroatoms, independently selected from nitrogen, oxygen, and sulfur, and including any bicyclic or tricyclic group in which any of the above-defined heterocyclic rings is fused to a second ring (e.g., a benzene ring). The nitrogen and sulfur heteroatoms can optionally be oxidized (i.e., N→O and S(O)$_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom can be substituted or unsubstituted (i.e., N or NR wherein R is H or another substituent, as defined). The heterocyclic ring can be attached to its pendant group at any heteroatom or carbon atom that results in a stable structure. The heterocyclic rings described herein can be substituted on carbon or on a nitrogen atom if the resulting compound is stable. A nitrogen in the heterocycle can optionally be quaternized. It is preferred that the total number of S and O atoms in the heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring can also be present on the bridge. Spiro and fused rings are also included.

As used herein, the term "aromatic heterocycle" or "heteroaryl" is intended to mean a stable 5, 6, 7, 8, 9, 10, 11, or 12-membered monocyclic or bicyclic aromatic ring (recognizing that rings with certain numbers of members cannot be a bicyclic aromatic, e.g., a 5-membered ring can only be a monocyclic aromatic ring), which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic heterocyclic aromatic rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds, materials, compositions, and/or dosage forms which are, within the scope of sound medical judgment, suitable for administration to a human, e.g., use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" means the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

As used herein, "mammal" refers to human and non-human patients.

As used herein, the term "therapeutically effective amount" refers to a compound, or a combination of compounds, of the present invention present in or on a recipient in an amount sufficient to elicit biological activity, for example, anti-microbial activity, anti-fungal activity, anti-viral activity, anti-parasitic activity, and/or anti-proliferative activity. The combination of compounds is preferably a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-proliferative and/or anti-infective effect, or some other beneficial effect of the combination compared with the individual components.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

2. COMPOUNDS OF THE INVENTION

The invention provides a compound having the structure:

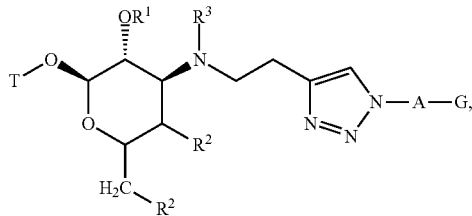

or a pharmaceutically acceptable salt, ester, N-oxide, or prodrug thereof, wherein:

T is a 14- or 15-membered macrolide connected via a macrocyclic ring carbon atom;

$R^1$ and $R^3$ independently are selected from: (a) H; (b) a $C_{1-6}$ alkyl group; (c) a $C_{2-6}$ alkenyl group; (d) a $C_{2-6}$ alkynyl group; (e) —C(O)$R^5$; (f) —C(O)O$R^5$; (g) —C(O)—NR$^4$R$^4$; (h) —C(S)$R^5$; (i) —C(S)O$R^5$; (j) —C(O)S$R^5$; or (k) —C(S)—NR$^4$R$^4$;

$R^1$ is hydrogen or —O$R^{12}$;

A is selected from: (a) a $C_{1-6}$ alkyl group, (b) a $C_{2-6}$ alkenyl group, (c) a $C_{2-6}$ alkynyl group, (d) a $C_{3-12}$ saturated, unsaturated, or aromatic carbocycle, (e) a 3-12 membered saturated, unsaturated, or aromatic heterocycle containing one or more heteroatoms selected from nitrogen, oxygen, and sulfur; wherein 0-2 carbon atoms in any of (a)-(c) of A immediately above optionally is replaced by a moiety selected from O, S(O)$_p$, and NR$^5$, and each of the groups (a)-(e) immediately above optionally is substituted with one or more R$^5$ groups;

G is selected from: (a) —B' and (b) —B'—Z—B", wherein each B' and B" is independently selected from (aa) an aryl group, (bb) a heteroaryl group, (cc) a biaryl group, (dd) a fused bicyclic or tricyclic saturated, unsaturated or aromatic ring system optionally containing one or more heteroatoms selected from nitrogen, oxygen, and sulfur, (ee) a 3-10 membered saturated or unsaturated heterocycle containing one or more heteroatoms selected from nitrogen, oxygen, and sulfur, (ff) a 3-10 membered saturated, or unsaturated carbocycle, wherein each (aa)-(ff) optionally is substituted with one or more $R^{11}$ or $R^{11a}$ groups; and Z is selected from (aa) a single bond, (bb) a $C_{1-6}$ alkyl group, (cc) a $C_{2-6}$ alkenyl group, (dd) a $C_{2-6}$ alkynyl group, (ee) —C(O)—, (ff) —C(O)O—, (gg) —C(O)NR$^4$—, (hh) —C(=NR$^4$)—, (ii) —C(—NR$^4$)O—, (jj) —C(=NR$^4$)NR$^4$—, (kk) —S(O)$_p$—, (ll) —OC(O)—, (mm) —C(S)—, (nn) —C(S)NR$^4$—, (oo) —C(R$^4$)S—, (pp) —C(O)S—, (qq) —O—, (rr) —NR$^4$—, (ss) —NR$^4$C(O)—, (tt) —OC(NR$^4$)—, (uu) —NC(NR$^4$)—, (vv) —C(S)O—, (ww) —SC(O)—, (xx) —OC(S)— or (yy) —S(O)$_p$—;

$R^4$, at each occurrence, independently is selected from (a) H, (b) a $C_{1-6}$ alkyl group, (c) a $C_{2-6}$ alkenyl group, (d) a $C_{2-6}$ alkynyl group, (e) a $C_{6-10}$ saturated, unsaturated, or aromatic carbocycle, (f) a 3-12 membered saturated, unsaturated, or aromatic heterocycle containing one or more heteroatoms selected from nitrogen, oxygen, and sulfur, (g) —C(O)—$C_{1-6}$ alkyl, (h) —C(O)—$C_{2-6}$ alkenyl, (i) —C(O)—$C_{2-6}$ alkynyl, (j) —C(O)—$C_{6-10}$ saturated, unsaturated, or aromatic carbocycle, (k) —C(O)-3-12 membered saturated, unsaturated, or aromatic heterocycle containing one or more heteroatoms selected from nitrogen, oxygen, and sulfur, (l) —C(O)O—$C_{1-6}$ alkyl, (m) —C(O)O—$C_{2-6}$ alkenyl, (n) —C(O)O—$C_{2-6}$ alkynyl, (o) —C(O)O—$C_{6-10}$ saturated, unsaturated, or aromatic carbocycle, p) —C(O)O-3-12 membered saturated, unsaturated, or aromatic heterocycle containing one or more heteroatoms selected from nitrogen, oxygen, and sulfur, and q) —C(O)NR$^6$R$^6$, wherein any of (b)-(p) of R$^4$, as defined above, optionally is substituted with one or more R$^5$ groups, or alternatively, NR$^4$R$^4$ forms a 3-7 membered saturated, unsaturated or aromatic ring including the nitrogen atom to which the R$^4$ groups are bonded, wherein the ring is optionally substituted at a position other than the nitrogen atom to which the R$^4$ groups are bonded, with one or more moieties selected from O, S(O)$_p$, N, and NR$^8$;

$R^5$ is selected from (a) $R^7$, (b) a $C_{1-8}$ alkyl group, (c) a $C_{2-8}$ alkenyl group, (d) a $C_{2-8}$ alkynyl group, (e) a $C_{3-12}$ saturated, unsaturated, or aromatic carbocycle, and (f) a 3-12 membered saturated, unsaturated, or aromatic heterocycle containing one or more heteroatoms selected from nitrogen, oxygen, and sulfur, or two $R^5$ groups, when present on the same carbon atom can be taken together with the carbon atom to which they are attached to form a spiro 3-6 membered carbocyclic ring or heterocyclic ring containing one or more heteroatoms selected form nitrogen, oxygen, and sulfur; wherein any of (b)-(f) of $R^5$ as defined above optionally is substituted with one or more $R^7$ groups;

$R^6$, at each occurrence, independently is selected from (a) H, (b) a $C_{1-6}$ alkyl group, (c) a $C_{2-6}$ alkenyl group, (d) a $C_{2-6}$ alkynyl group, (e) a $C_{3-10}$ saturated, unsaturated, or aromatic carbocycle, and (f) a 3-10 membered saturated, unsaturated, or aromatic heterocycle containing one or more heteroatoms selected from nitrogen, oxygen, and sulfur, wherein any of (b)-(f) of $R^6$ as defined above optionally is substituted with one or more moieties selected from (aa) a carbonyl group, (bb) a formyl group, (cc) F, (dd) Cl, (ee) Br, (ff) I, (gg) CN, (hh) NO$_2$, (ii) —OR$^8$, (jj) —S(O)$_p$R$^8$, (kk) —C(O)R$^8$, (ll) —C(O)OR$^8$, (mm) —OC(O)R$^8$, (nn) —C(O)NR$^8$R$^8$, (oo) —OC(O)NR$^8$R$^8$, (pp) —C(=NR$^8$)R$^8$, (qq) —C(R$^8$)(R$^8$)OR$^8$, (rr) —C(R$^8$)$_2$OC(O)R$^8$, (ss) —C(R$^8$)(OR)(CH$_2$)$_r$NR$^8$R$^8$, (tt) —NR$^8$R$^8$, (uu) —NR$^8$OR$^8$, (vv) —NR$^8$C(O)R$^8$, (ww) —NR$^8$C(O)OR$^8$, (xx) —NR$^8$C(O)NR$^8$R$^8$, (yy) —NR$^8$S(O)$_r$R$^8$, (zz) —C(OR$^8$)(OR$^8$)R$^8$, (ab) —C(R$^8$)$_2$NR$^8$R$^8$, (ac) =NR$^8$, (ad) —C(S)NR$^8$R$^8$, (ae) —NR$^8$C(S)R$^8$, (af) —OC(S)NR$^8$R$^8$, (ag) —NR$^8$C(S)OR$^8$, (ah) —NR$^8$C(S)NR$^8$R$^8$, (ai) —SC(O)R$^8$, (aj) a $C_{1-8}$ alkyl group, (ak) a $C_{2-8}$ alkenyl group, (al) a $C_{2-8}$ alkynyl group, (am) a $C_{1-8}$ alkoxy group, (an) a $C_{1-8}$ allylthio group, (ao) a $C_{1-8}$ acyl group, (ap) —CF$_3$, (aq) —SCF$_3$, (ar) a $C_{3-10}$ saturated, unsaturated, or aromatic carbocycle, and (as) a 3-10 membered saturated, unsaturated, or aromatic heterocycle containing one or more heteroatoms selected from nitrogen, oxygen, and sulfur, or alternatively, NR$^6$R$^6$ forms a 3-10 membered saturated, unsaturated or aromatic ring including the nitrogen atom to which the R$^6$ groups are attached wherein the ring is optionally substituted at a position other than the nitrogen atom to which the R$^6$ groups are bonded, with one or more moieties selected from O, S(O)$_p$, N, and NR$^8$; or alternatively, CR$^6$R$^6$ forms a carbonyl group;

$R^7$, at each occurrence, is selected from (a) H, (b) =O, (c) F, (d) Cl, (e) Br, (f) I, (g) —CF$_3$, (h) —CN, (i) —N$_3$ (j) —NO$_2$, (k) —NR$^6$(CR$^6$R$^6$)$_r$R$^9$, (l) —OR$^9$, (m) —S(O)$_p$C(CR$^6$R$^6$)$_r$R$^9$, (n) —C(O)(CR$^6$R$^6$)$_r$R$^9$, (o) —OC(O)(CR$^6$R$^6$)$_r$R$^9$, (p) —SC(O)(CR$^6$R$^6$)$_r$R$^9$, (q) —C(O)O(CR$^6$R$^6$)$_r$R$^9$, (r) —NR$^6$C(O)(CR$^6$R$^6$)$_r$R$^9$, (s) —C(O)NR$^6$(CR$^6$R$^6$)$_r$R$^9$, (t) —C(=NR$^6$)(CR$^6$R$^6$)$_r$R$^9$, (u) —C(=NNR$^6$R$^6$)(CR$^6$R$^6$)$_r$R$^9$, (v) —C(=NNR$^6$C(O)R$^9$)(CR$^6$R$^6$)$_r$R$^9$, (w) —C(=NOR$^9$)(CR$^6$R$^6$)$_r$R$^9$, (x) —NR$^6$C(O)O(CR$^6$R$^6$)$_r$R$^9$, (y) —OC(O)NR$^6$(CR$^6$R$^6$)$_r$R$^9$, (z) —NR$^6$C(O)NR$^6$(CR$^6$R$^6$)$_r$R$^9$, (aa) —NR$^6$S(O)$_p$(CR$^6$R$^6$)$_r$R$^9$, (bb) —S(O)$_p$NR$^6$(CR$^6$R$^6$)$_r$R$^9$, (cc) —NR$^6$S(O)$_p$NR$^6$(CR$^6$R$^6$)$_r$R$^9$, (dd) —NR$^6$R$^6$, (ee) —NR$^6$(CR$^6$R$^6$), (ff) —OH, (gg) —NR$^6$R$^6$, (hh) —OCH$_3$, (ii) —S(O)$_p$R$^6$, (jj) —NC(O)

R⁶, (kk) a C₁₋₆ alkyl group, (ll) a C₂₋₆ alkenyl group, (mm) a C₂₋₆ alkynyl group, (nn) —C₃₋₁₀ saturated, unsaturated, or aromatic carbocycle, and (oo) 3-10 membered saturated, unsaturated, or aromatic heterocycle containing one or more heteroatoms selected from nitrogen, oxygen, and sulfur, wherein any of (kk)-(oo) of R⁷ as defined above optionally is substituted with one or more R⁹ groups; or alternatively, two R⁷ groups can form —O(CH₂)ᵤO—;

R⁸ is selected from (a) R⁵, (b) H, (c) a C₁₋₆ alkyl group, (d) a C₂₋₆ alkenyl group, (e) a C₂₋₆ alkynyl group, (f) a C₃₋₁₀ saturated, unsaturated, or aromatic carbocycle, (g) a 3-10 membered saturated, unsaturated, or aromatic heterocycle containing one or more heteroatoms selected from nitrogen, oxygen, and sulfur, (h) —C(O)—C₁₋₆ alkyl, (i) —C(O)—C₁₋₆ alkenyl, (j) —C(O)—C₁₋₆ alkynyl, (k) —C(O)C₃₋₁₀ saturated, unsaturated, or aromatic carbocycle, and (l) —C(O)-3-10 membered saturated, unsaturated, or aromatic heterocycle containing one or more heteroatoms selected from nitrogen, oxygen, and sulfur, wherein any of (c)-(k) of R⁸ as defined above optionally is substituted with one or more moieties selected from: (aa) H, (bb) F, (cc) Cl, (dd) Br, (ee) I, (ff) CN, (gg) NO₂, (hh) OH, (ii) NH₂, (jj) NH(C₁₋₆ alkyl), (kk) N(C₁₋₆ alkyl)₂, (ll) a C₁₋₆ alkoxy group, (mm) an aryl group, (nn) a substituted aryl group, (oo) a heteroaryl group, (pp) a substituted heteroaryl group, and qq) a C₁₋₆ alkyl group optionally substituted with one or more moieties selected from an aryl group, a substituted aryl group, a heteroaryl group, a substituted heteroaryl group, F, Cl, Br, I, CN, NO₂, CF₃, SCF₃, and OH;

R⁹, at each occurrence, independently is selected from (a) R¹⁰, (b) a C₁₋₆ alkyl group, (c) a C₂₋₆ alkenyl group, (d) a C₂₋₆ alkynyl group, e) a C₃₋₁₀ saturated, unsaturated, or aromatic carbocycle, and f) a 3-10 membered saturated, unsaturated, or aromatic heterocycle containing one or more heteroatoms selected from nitrogen, oxygen, and sulfur, wherein any of (b)-(f) of R⁹ as defined above optionally is substituted with one or more R¹⁰ groups;

R¹⁰, at each occurrence, independently is selected from (a) H, (b) =O, (c) F, (d) Cl, (e) Br, (f) I, (g) —CF₃, (h) —CN, (i) —NO₂, (j) —NR⁶R⁶, (k) —OR⁶, (l) —S(O)$_p$R⁶, (m) —C(O)R⁶, (n) —C(O)OR⁶, (o) —OC(O)R⁶, (p) NR⁶C(O)R⁶, (q) —C(O)NR⁶R⁶, (r) —C(=NR⁶)R⁶, (s) —NR⁶C(O)NR⁶R⁶, (t) —NR⁶S(O)$_p$R⁶, (u) —S(O)$_p$NR⁶R⁶, (v) —NR⁶S(O)$_p$NR⁶R⁶, (w) a C₁₋₆ alkyl group, (x) a C₂₋₆ alkenyl group, (y) a C₂₋₆ alkynyl group, (z) a C₃₋₁₀ saturated, unsaturated, or aromatic carbocycle, and (aa) a 3-10 membered saturated, unsaturated, or aromatic heterocycle containing one or more heteroatoms selected from nitrogen, oxygen, and sulfur, wherein any of (w)-(aa) of R¹⁰ as defined above optionally is substituted with one or more moieties selected from R⁶, F, Cl, Br, I, CN, NO₂, —OR⁶, —NH₂, —NH(C₁₋₆ alkyl), —N(C₁₋₆ alkyl)₂, a C₁₋₆ alkoxy group, a C₁₋₆ alkylthio group, and a C₁₋₆ acyl group;

R¹¹ and R¹¹ᵃ each occurrence, independently is selected from (a) a carbonyl group, (b) a formyl group, (c) F, (d) Cl, (e) Br, (f) I, (g) CN, (h) NO₂, (i) OR⁸, (j) —S(O)$_p$R⁸, (k) —C(O)R⁸, (l) —C(O)OR⁸, (m) —OC(O)R⁸, (n) —C(O)NR⁸R⁸, (o) —OC(O)NR⁸R⁸, (p) —C(=NR⁸)R⁸, (q) (R⁸)(R⁸)OR⁸, (r) C(R⁸)₂OC(O)R⁸, (s) —C(R⁸)(OR⁸)(CH₂)ᵣNR⁸R⁸, (t) —NR⁸R⁸, (u) —NR⁸OR⁸, (v) —NR⁸C(O)R⁸, (w) —NR⁸C(O)OR⁸, (x) —NR⁸C(O)NR⁸R⁸, (y) —NR⁸S(O)R⁸, (z) —C(OR⁸)(OR⁸)R⁸, (aa) —C(R⁸)₂NR⁸R⁸, (bb) =NR⁸, (cc) —C(S)NR⁸R⁸, (dd) —NR⁸C(S)R⁸, (ee) —OC(S)NR⁸R⁸, (ff) —NR⁸C(S)OR⁸, (gg) —NR⁸C(S)NR⁸R⁸, (hh) —SC(O)R⁸, (ii) a C₁₋₈ alkyl group, (jj) a C₂₋₈ alkenyl group, (kk) a C₂₋₈ alkynyl group, (ll) a C₁₋₈ alkoxy group, (mm) a C₁₋₈ alkylthio group, (nn) a C₁₋₈ acyl group, (oo) a C₃₋₁₀ saturated, unsaturated, or aromatic carbocycle, and (pp) a 3-10 membered saturated, unsaturated, or aromatic heterocycle containing one or more heteroatoms selected from nitrogen, oxygen, and sulfur, wherein (ii)-(kk) optionally are substituted with one or more R⁵ groups;

R¹² is selected from (a) H, (b) a C₁₋₆ alkyl group, (c) a C₂₋₆ alkenyl group, (d) a C₂₋₆ alkynyl group, (e) —C(O)R⁵, (f) —C(O)OR⁵, (g) —C(O)—NR⁴R⁴, (h) —C(S)R⁵, (i) —C(S)OR⁵, (j) —C(O)SR⁵, (k) —C(S)—NR⁴R⁴, (l) a C₃₋₁₀ saturated, unsaturated, or aromatic carbocycle, or (m) a 3-10 membered saturated, unsaturated, or aromatic heterocycle containing one or more heteroatoms selected from nitrogen, oxygen, and sulfur, (n) a —(C₁₋₆ alkyl) —C₃₋₁₀ saturated, unsaturated, or aromatic carbocycle, or (o) a —(C₁₋₆ alkyl)-3-10 membered saturated, unsaturated, or aromatic heterocycle containing one or more heteroatoms selected from nitrogen, oxygen, and sulfur, wherein (a)-(d) and (l)-(o) of R¹² as defined above optionally are substituted with one or more R⁵ groups;

p at each occurrence is 0, 1, or 2;
r at each occurrence is 0, 1, or 2;
t at each occurrence is 0, 1, or 2;
and u at each occurrence is 1, 2, 3, or 4.

In the present invention, the macrolide, "T" is defined to include various 14- and 15-membered ring systems, which can contain one or more heteroatoms. Also, as defined herein, the macrolide, "T" is connnected via a macrocyclic ring carbon atom", which means that the connection or bond is made to a carbon atom on the 14- or 15-membered ring of the macrolide moiety. The macrolide can include further substituents, including ring substituents. For example, the substituent designated as R¹⁰³ (as defined below) can in certain embodiments be a sugar moiety, e.g. a cladinose sugar, or the substituents such as R¹⁰⁴ and R¹⁰⁵ (as defined below) are taken together in certain embodiments to form a bridged bicyclic ring system with the macrolide ring, or the substituents R¹⁰⁵ and R¹⁰⁶ (as defined below), are taken together in certain embodiments to form a fused bicyclic ring system with the macrolide ring, or the substituents or components M, R¹⁰⁵, and R¹⁰⁶ are taken together to form a fused tricyclic ring system with the macrolide ring, etc. It is also recognized in the present invention that "T" is depicted as being connected to a 6-membered ring, for example in certain embodiments a desosamine sugar ring.

The invention also provides a compound according to claim 1, having the structure:

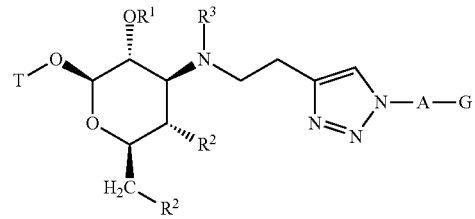

or a pharmaceutically acceptable salt, ester, N-oxide, or prodrug thereof wherein A, G, T, R¹, R² and R³ are as defined above.

In the compounds described above, A is, for example, is a C₁₋₆ alkyl group, wherein 0-2 carbon atoms in any of the C₁₋₆ alkyl group optionally is replaced by a moiety selected from O, S(O)$_p$, and NR⁴, and the C₁₋₆ alkyl group optionally is substituted with one or more R⁵ groups. In compounds where A is, for example, a C₁₋₆ allyl group, A-G is selected from the group consisting of: (a) —(CH$_2$)$_2$-G, (b) —(CH$_2$)$_3$-G, (c) —(CH$_2$)$_4$-G, (d) —(CH$_2$)$_3$O-G, (e) —(CH$_2$)$_3$—NH-G, (f) —CH(CH$_2$F)CH$_2$NHC(O)-G, (g) —CH(CH$_2$F)CH$_2$NHS(O)$_2$-G, (h) —(CH$_2$)$_2$NHS(O)$_2$-G, (i) —(CH$_2$)$_2$NHCH$_2$-G, (j) —(CH$_2$)$_3$S-G, (k) —(CH$_2$)$_3$S(O)$_2$-G, (l) —(CH$_2$)$_2$N(CH$_3$)CH$_2$-G, (m) —(CH$_2$)$_2$NHCH$_2$-G, (n) —CH$_2$CH(OH)CH$_2$O-G, (o) —CH$_2$CHFCH$_2$O-G, and (p) —CH$_2$CH(CH$_3$)CH$_2$O-G. In compounds where A, for example, is a C$_{1-6}$ alkyl group, -A-G is also selected from the group consisting of (a) —(CH$_2$)$_4$-G, (b) —(CH$_2$)$_3$O-G, (c) —(CH$_2$)$_3$—NH-G, (d) —CH(CH$_2$F)CH$_2$NHC(O)-G, (e) —CH(CH$_2$F)CH$_2$NHS(O)$_2$-G, (f) —(CH$_2$)$_2$NHS(O)$_2$-G, (g) —(CH$_2$)$_2$NHCH$_2$-G, (h) —(CH$_2$)$_3$S-G, (i) —(CH$_2$)$_3$S(O)$_2$-G, (j) —(CH$_2$)$_2$N(CH$_3$)CH$_2$-G, (k) —(CH$_2$)$_2$NHCH$_2$-G, (l) —CH$_2$CH(OH)CH$_2$O-G, (m) —CH$_2$CHFCH$_2$O-G, and (n) —CH$_2$CH(CH$_3$)CH$_2$O-G.

In the compounds described above, -A-G is also selected from the group consisting of:

(a) —CH$_2$-G, (b) —(CH$_2$)$_2$-G, (c) —(CH$_2$)$_3$-G, (d) —(CH$_2$)$_4$-G, (e) —CH$_2$O(CH$_2$)$_2$-G, (f) —(CH$_2$)$_2$OCH$_2$-G, (g) —(CH$_2$)$_3$O-G, (h) —CH$_2$NR$^5$(CH$_2$)$_2$-G, (i) —(CH$_2$)$_2$NR$^5$CH$_2$-G, (o) —(CH$_2$)$_3$—NR$^5$-G, (m) —SO—(CH$_2$)$_3$-G, (n) —SO$_2$—(CH$_2$)$_3$-G, (o)—CH$_2$S(O)p(CH$_2$)$_2$-G, (o) —(CH$_2$)$_2$S(O)pCH$_2$-G, (p) —(CH$_2$)$_3$S(O)p-G, (q) —CO(CH$_2$)$_3$-G, (r) —CH$_2$CO(CH$_2$)$_2$-G, (s) —(CH$_2$)$_2$COCH$_2$-G, (t) —(CH$_2$)$_3$CO-G, (u) —CH$_2$CH(OR$^9$)(CH$_2$)$_2$-G, (v) —(CH$_2$)$_2$CH(OR$^9$)CH$_2$-G, (w) —(CH$_2$)$_3$CH(OR$^9$)-G, (x) —CHOR$^5$(CH$_2$)$_3$-G, (y) —CH$_2$CHOR$^9$(CH$_2$)$_2$-G, (z) —(CH$_2$)$_2$CHOR$^9$CH$_2$-G, (aa) —(CH$_2$)$_3$CHOR$^9$-G, (bb) —CONR$^5$(CH$_2$)$_2$-G, (cc) —CH$_2$CONR$^5$CH$_2$-G, (dd) —(CH$_2$)$_2$CONR$^5$-G, (ee) —CH$_2$NR$^5$COCH$_2$-G, (ff) —(CH$_2$)$_2$NR$^5$CO-G, (gg) —S(O)NR$^5$(CH$_2$)$_2$-G, (hh) —S(O)$_2$NR$^5$(CH$_2$)$_2$-G, (ii) —CH$_2$S(O)pNR$^5$CH$_2$-G, (jj) —(CH$_2$)$_2$S(O)pNR$^5$-G, (kk) —NR$^5$S(O)p(CH$_2$)$_2$-G, (ll) —CH$_2$NR$^5$S(O)pCH$_2$-G, (mm) —(CH$_2$)$_2$NR$^5$S(O)p-G, (nn) —CH$_2$CH(CH$_3$)CH$_2$O-G, (oo) —CH$_2$CH(OR$^9$)CH$_2$O-G,

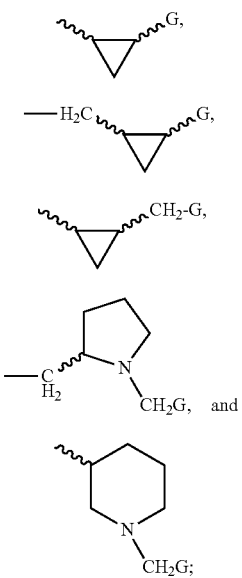

wherein p is 0, 1, or 2, and R$^5$ and R$^9$ are independently C$_{1-6}$ alkyl, optionally substituted with fluorine, and wherein in any of the foregoing (a) through (tt) one or more hydrogens on a carbon atom is optionally replaced with fluorine.

In the compounds described above, -A-G is also selected from the group consisting of:

(a) —(CH$_2$)$_4$-G, (b) —(CH$_2$)$_2$OCH$_2$-G, (c) —(CH$_2$)$_3$O-G, (d) —(CH$_2$)$_2$NR$^5$CH$_2$-G, (e) —(CH$_2$)$_3$—NR$^5$-G, (f) —(CH$_2$)$_3$S(O)p-G, (g) —(CH$_2$)$_3$CO-G, (h) —CH$_2$CH(OR$^5$)CH$_2$O-G, (i) —CH$_2$CH(CH$_3$)CH$_2$O-G, (j) —(CH$_2$)$_2$NR$^5$CO-G, (k) —(CH$_2$)$_2$N$^5$S(O)p-G,

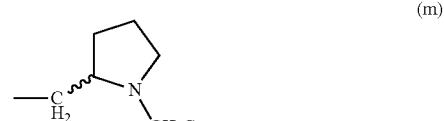

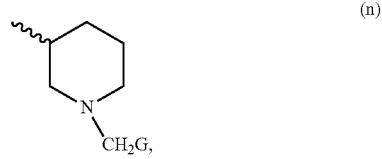

wherein p is 0, 1, or 2, and R$^5$, and wherein in any of the foregoing (a) through (n) one or more hydrogens on a carbon atom is optionally replaced with fluorine.

In the compounds described above, -A-G is also selected from the group consisting of: (a) —(CH$_2$)$_4$-G, and (b) —(CH$_2$)$_3$O-G.

In the compounds described above, R$^1$ is, for example, H. In the compounds described above, R$^2$ is, e.g., H. In the compounds described above, R$^3$ is, e.g., C$_{1-6}$ allyl. In the compounds described above, R$^3$ is, e.g., methyl. In the In the compounds described above, G is, e.g., B'. In the compounds described above, B' is selected from, for example: (a) an aryl group, (b) a heteroaryl group, (c) a biaryl group, and (d) a fused bicyclic or tricyclic unsaturated or aromatic ring system optionally containing one or more carbonyl groups and one or more heteroatoms selected from nitrogen, oxygen, and sulfur, wherein each (a)-(d) of B' as defined herein optionally is substituted with one or more R$^{11}$ groups.

In the compounds described above, G is, e.g., —B'—Z—B". In these compounds where G is —B'—Z—B", B' and B" are, for example, independently selected from: (a) an aryl group, (b) a heteroaryl group, (c) a biaryl group, and (d) a fused bicyclic or tricyclic unsaturated or aromatic ring system optionally containing one or more carbonyl groups and one or more heteroatoms selected from nitrogen, oxygen, and sulfur, wherein each (a)-(d) of B' and B" as defined herein optionally is substituted with one or more R$^{11}$ groups, and Z is selected from (aa) a single bond, (bb) —O—, (cc) —NR$^4$—, (dd) —C(O)—, (ee) —C(S)—, (ff) —S(O)$_p$—, and (gg) a C$_{1-6}$ alkyl.

The invention also provides a compound according having the structure:

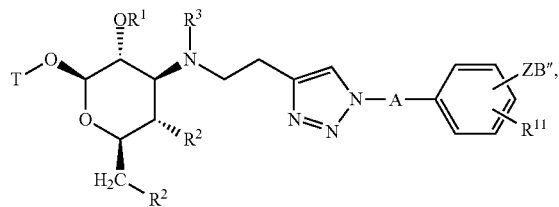

or a pharmaceutically acceptable slat, ester, N-oxide, or prodrug thereof wherein T is a 14- or 15-membered macrolide connected via a macrocyclic ring carbon atom;

$R^1$ and $R^3$ independently are selected from: (a) H; (b) a $C_{1-6}$ alkyl group; (c) a $C_{2-6}$ alkenyl group; (d) a $C_{2-6}$ alkynyl group; (e) —C(O)$R^5$; (f) C(O)O$R^5$; (g) —C(O)—NR$^4$R$^4$; (h) —C(S)$R^5$; (i) —C(S)O$R^5$; (j) —C(O)S$R^5$; or (k) —C(S)—NR$^4$R$^4$;

$R^2$ is hydrogen or —OR$^{12}$, where $R^{12}$ is as defined above;

A is selected from: (a) a $C_{1-6}$ alkyl group, (b) a $C_{2-6}$ alkenyl group; (c) a $C_{2-6}$ alkynyl group; wherein 0-2 carbon atoms in any of (a)-(c) of A, as defined above, optionally is replaced by a moiety selected from O, S(O)$_p$, and NR$^4$, and each of the groups (a)-(c) of A, as defined above, optionally is substituted with one or more $R^W$ groups as defined above;

B" is selected from (aa) an aryl group, (bb) a heteroaryl group, (cc) a biaryl group, (dd) a fused bicyclic or tricyclic saturated, unsaturated or aromatic ring system optionally containing one or more heteroatoms selected from nitrogen, oxygen, and sulfur, (ee) a 3-10 membered saturated or unsaturated heterocycle containing one or more heteroatoms selected from nitrogen, oxygen, and sulfur, (ff) a 3-10 membered saturated, or unsaturated carbocycle, wherein each (aa)-(ff) optionally is substituted with one or more $R^{11}$ or $R^{11a}$ groups; and Z is selected from (aa) a single bond, (bb) a $C_{1-6}$ alkyl group, (cc) a $C_{2-6}$ alkenyl group, (dd) a $C_{2-6}$ alkynyl group, (ee) —C(O)—, (ff) —C(O)O—, (gg) —C(O)NR$^4$—, (hh) —C(=NR$^4$)—, (ii) —C(=NR$^4$)O—, (jj) —C(=NR$^4$)NR$^4$—, (kk) —S(O)O—, (ll) —OC(O)—, (mm) —C(S)—, (nn) —C(S)NR$^4$—, (oo) —C(NR$^4$)S—, (pp) —C(O)S—, (qq) —O—, (rr) —NR$^4$—, (ss) —NR$^4$C(O)—, (tt) —OC(NR$^4$)—, (uu) —NC(NR$^4$)—, (vv) —C(S)O—, (ww) —SC(O)—, (xx) —OC(S)— or (yy) —S(O)$_p$—;

$R^{11}$ and $R^{11a}$ at each occurrence, independently is selected from (a) a carbonyl group, (b) a formyl group, (c) F, (d) Cl, (e) Br, (f) I, (g) CN, (h) NO$_2$, (i) OR$^8$ (as defined above) (j) —S(O)$_p$R$^8$, (k) —C(O)R$^8$, (l) —C(O)OR$^8$, (m) —OC(O)R$^8$, (n) —C(O)NR$^8$R$^8$, (o) —OC(O)NR$^8$R$^8$, (p) —C(=NR$^8$)R$^8$, (q) —C(R$^8$)(R$^8$)OR$^8$, (r) —C(R$^8$)$_2$OC(O)R$^8$, (s) —C(R$^8$)(OR$^8$)(CH$_2$)$_n$NR$^8$R$^8$, (t) —NR$^8$R$^8$, (u) —NR$^8$OR$^8$, (v) —NR$^8$C(O)R$^8$, (w) —NR$^8$C(O)OR$^8$, (x) —NR$^8$C(O)NR$^8$R$^8$, (y) —NR$^8$S(O)$_p$R$^8$, (z) —C(OR$^8$)(OR$^8$)R$^8$, (aa) —C(R$^8$)$_2$NR$^8$R$^8$, (bb) =NR$^8$, (cc) —C(S)NR$^8$R$^8$, (dd) —NR$^8$C(S)R$^8$, (ee) —OC(S)NR$^8$R$^8$, (ff) —NR$^8$C(S)OR$^8$, (gg) —NR$^8$C(S)NR$^8$R$^8$, (hh) —SC(O)R$^8$, (ii) a $C_{1-8}$ alkyl group, (jj) a $C_{2-8}$ alkenyl group, (kk) a $C_{2-8}$ alkynyl group, (ll) a $C_{1-8}$ alkoxy group, (mm) a $C_{1-8}$ alkylthio group, (nn) a $C_{1-8}$ acyl group, (oo) a $C_{3-10}$ saturated, unsaturated, or aromatic carbocycle, and (pp) a 3-10 membered saturated, unsaturated, or aromatic heterocycle containing one or more heteroatoms selected from nitrogen, oxygen, and sulfur, wherein (ii)-(kk) optionally are substituted with one or more $R^5$ groups, as defined above.

In compounds having this structure, A is, for example, a $C_{1-6}$ alkyl group, wherein 0-2 carbon atoms in any of the $C_{1-6}$ alkyl group optionally is replaced by a moiety selected from O, S(O)$_p$, and NR$^4$, and the $C_{1-6}$ alkyl group optionally is substituted with one or more $R^5$ groups as defined above.

In the compounds described above, -A is, for example, (a) —CH$_2$—, (b) —(CH$_2$)$_2$—, (c) —(CH$_2$)$_3$—, (d) —(CH$_2$)$_4$—, (e) —CH$_2$—O—(CH$_2$)$_2$—, (f) —(CH$_2$)$_2$OCH$_2$—, (g) —(CH$_2$)$_3$O—, (h) —CH$_2$NR$^5$(CH$_2$)$_2$—, (i) —(CH$_2$)$_2$NR$^5$CH$_2$—, (j) —(CH$_2$)$_3$—NR$^5$—, (m) —SO—(CH$_2$)$_3$—, (n) —SO$_2$—(CH$_2$)$_3$—, (o)—CH$_2$S(O)p(CH$_2$)$_2$—, (o)—(CH$_2$)$_2$S(O)pCH$_2$—, (p) —(CH$_2$)$_3$S(O)p-, (q) —CO(CH$_2$)$_3$—, (r) —CH$_2$CO(CH$_2$)$_2$—, (s) —(CH$_2$)$_2$COCH$_2$—, (t) —(CH$_2$)$_3$CO—, (u) —CH$_2$CH(OR$^9$)(CH$_2$)$_2$—, (v) —(CH$_2$)$_2$CH(OR$^9$)CH$_2$—, (w) —(CH$_2$)$_3$CH(OR$^9$)—, (x) —CHOR$^9$(CH$_2$)$_3$—, (y) —CH$_2$CHOR$^9$(CH$_2$)$_2$—, (z) —(CH$_2$)$_2$CHOR$^9$CH$_2$—, (aa) —(CH$_2$)$_3$CHOR$^9$—, (bb) —CONR$^5$(CH$_2$)$_2$—, (cc) —CH$_2$CONR$^5$CH$_2$—, (dd) —(CH$_2$)$_2$CONR$^5$—, (ee) —CH$_2$NR$^5$COCH$_2$—, (ff) —(CH$_2$)$_2$NR$^5$CO—, (gg) —S(O)NR$^5$(CH$_2$)$_2$—, (hh) —S(O)$_2$NR$^5$(CH$_2$)$_2$—, (ii) —CH$_2$S(O)pNR$^5$CH$_2$—, (jj) —(CH$_2$)$_2$S(O)pNR$^5$—, (kk) —NR$^5$S(O)p(CH$_2$)$_2$—, (ll) —CH$_2$NR$^5$S(O)pCH$_2$—, (mm) —(CH$_2$)$_2$NR$^5$S(O)p-, (nn) —CH$_2$CH(CH$_3$)CH$_2$O—, (oo) —CH$_2$CH(OR$^9$)CH$_2$O—,

(pp)

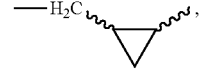
(qq)

(rr)

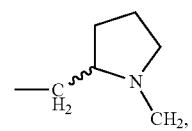
(ss)

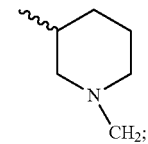
(tt)

(uu) —(CH$_2$)$_3$—NH—, (vv) —CH(CH$_2$F)CH$_2$NHC(O)—, (ww) —CH(CH$_2$F)CH$_2$NHS(O)$_2$—, (xx) —(CH$_2$)$_2$NHS(O)$_2$—, (yy) —(CH$_2$)$_2$NHCH$_2$—, (zz) —(CH$_2$)$_3$S—, (aaa) —(CH$_2$)$_3$S(O)$_2$—, (bbb) —(CH$_2$)$_2$N(CH$_3$)CH$_2$—, (ccc) —(CH$_2$)$_2$NHCH$_2$—, (ddd) —CH$_2$CH(OH)CH$_2$O—, (eee) —CH$_2$CHFCH$_2$O—, and (fff) —CH$_2$CH(CH$_3$)CH$_2$O—, wherein p is 0, 1, or 2, and $R^5$ and $R^9$ are independently $C_{1-6}$ alkyl, optionally substituted with fluorine, and wherein ii any of the foregoing (a) through (fff) one or more hydrogens on a carbon atom is optionally replaced with fluorine.

The invention also provides a compound having the structure:

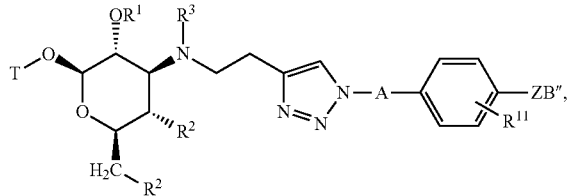

or a pharmaceutically acceptable slat, ester, N-oxide, or prodrug thereof wherein A, B", T, Z, $R^1$, $R^2$, $R^3$, and $R^{11}$ are as described above.

In compounds having this structure, A is, for example, a $C_{1-6}$ alkyl group, wherein 0-2 carbon atoms in any of the $C_{1-6}$ alkyl group optionally is replaced by a moiety selected from O, $S(O)_p$, and)$NR^4$, and the $C_{1-6}$ alkyl group optionally is substituted with one or more $R^5$ groups as defined above.

In the compounds described above, -A is, for example, (a) —$CH_2$—, (b) —$(CH_2)_2$—, (c) —$(CH_2)_3$—, (d) —$(CH_2)_4$—, (e) —$CH_2O(CH_2)_2$—, (f) —$(CH_2)_2OCH_2$—, (g) —$(CH_2)_3O$—, (h) —$CH_2NR^5(CH_2)_2$—, (i) —$(CH_2)_2NR^5CH_2$—, (j) —$(CH_2)_3$—$NR^5$—, (m) —$SO$—$(CH_2)_3$—, (n) —$SO_2$—$(CH_2)_3$—, (o) —$CH_2S(O)p(CH_2)_2$—, (o) —$(CH_2)_2S(O)pCH_2$—, (p) —$(CH_2)_3S(O)p$-, (q) —$CO(CH_2)_3$—, (r) —$CH_2CO(CH_2)_2$—, (s) —$(CH_2)_2COCH_2$—, (t) —$(CH_2)_3CO$—, (u) —$CH_2CH(OR^9)(CH_2)_2$—, (v) —$(CH_2)_2CH(OR^9)CH_2$—, (w) —$(CH_2)_3CH(OR^9)$—, (x) —$CHOR^5(CH_2)_3$—, (y) —$CH_2CHOR^9(CH_2)_2$—, (z) —$(CH_2)_2CHOR^9CH_2$—, (aa) —$(CH_2)_3CHOR^9$—, (bb) —$CONR^5(CH_2)_2$—, (cc) —$CH_2CONR^5CH_2$—, (dd) —$(CH_2)_2CONR^5$—, (ee) —$CH_2NR^5COCH_2$—, (ff) —$(CH_2)_2NR^5CO$—, (gg) —$S(O)NR^5(CH_2)_2$—, (hh) —$S(O)_2NR^5(CH_2)_2$—, (ii) —$CH_2S(O)pNR^5CH_2$—, (jj) —$(CH_2)_2S(O)pNR^5$—, (kk) —$NR^5S(O)p(CH_2)_2$—, (ll) —$CH_2NR^5S(O)pCH_2$—, (mm) —$(CH_2)_2NR^5S(O)p$-, (nn) —$CH_2CH(CH_3)CH_2O$—, (oo) —$CH_2CH(OR^9)CH_2O$—, (pp)

(qq)

(rr)

(ss)

(tt)

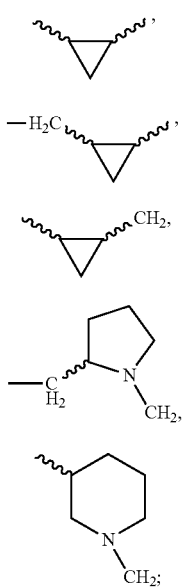

(uu) —$(CH_2)_3$—$NH$—, (vv) —$CH(CH_2F)CH_2NHC(O)$—, (ww) —$CH(CH_2F)CH_2NHS(O)_2$—, (xx) —$(CH_2)_2NHS(O)_2$—, (yy) —$(CH_2)_2NHCH_2$—, (zz) —$(CH_2)_3S$—, (aaa) —$(CH_2)_3S(O)_2$—, (bbb) —$(CH_2)_2N(CH_3)CH_2$—, (ccc) —$(CH_2)_2NHCH_2$—, (ddd) —$CH_2CH(OH)CH_2O$—, (eee) —$CH_2CHFCH_2O$—, and (fff) —$CH_2CH(CH_3)CH_2O$—, wherein p is 0, 1, or 2, and $R^5$ and $R^9$ are independently $C_{1-6}$ alkyl, optionally substituted with fluorine, and wherein in any of the foregoing (a) through (fff) one or more hydrogens on a carbon atom is optionally replaced with fluorine.

For example, in this compound, -A is, e.g., selected from: (a) —$(CH_2)_2$—, (b) —$(CH_2)_3$—, (c) —$(CH_2)_4$—, (d) —$(CH_2)_3O$—, (e) —$(CH_2)_3$—$NH$—, (f) —$CH(CH_2F)CH_2NHC(O)$—, (g) —$CH(CH_2F)CH_2NHS(O)_2$—, (h) —$(CH_2)_2NHS(O)_2$—, (i) —$(CH_2)_2NHCH_2$—, (j) —$(CH_2)_3S$—, (k) —$(CH_2)_3S(O)_2$—, (l) —$(CH_2)_2N(CH_3)CH_2$—, (m) —$(CH_2)_2NHCH_2$—, (n) —$CH_2CH(OH)CH_2O$—, (o) —$CH_2CHFCH_2O$—, (p) —$CH_2CH(CH_3)CH_2O$—, (q) —$O$—$(CH_2)_3$—, (r) —$CH_2$—$O$—$(CH_2)_2$—, (s) —$(CH_2)_2$—$O$—$CH_2$—, (t) —$NH$—$(CH_2)_3$—, (u) —$CH_2$—$NH$—$(CH_2)_2$—, and (v) —$(CH_2)_2$—$NH$—$CH_2$—. For example, -A is selected from: (a) —$(CH_2)_4$—, (b), —$(CH_2)_3O$—, (c) —$(CH_2)_3$—$NH$—, (d) —$CH(CH_2F)CH_2NHC(O)$—, (e) —$CH(CH_2F)CH_2NHS(O)_2$—, (f) —$(CH_2)_2NHS(O)_2$—, (g) —$(CH_2)_2NHCH_2$—, (h) —$(CH_2)_3S$—, (i) —$(CH_2)_3S(O)_2$—, (j) —$(CH_2)_2N(CH_3)CH_2$—, (k) —$(CH_2)_2NHCH_2$—, (l) —$CH_2CH(OH)CH_2$—, (m) —$CH_2CHFCH_2$—, (n) —$CH_2CH(CH_3)CH_2O$— and (O)—$(CH_2)_2$—$O$—$CH_2$—.

The invention also provides a compound having the structure:

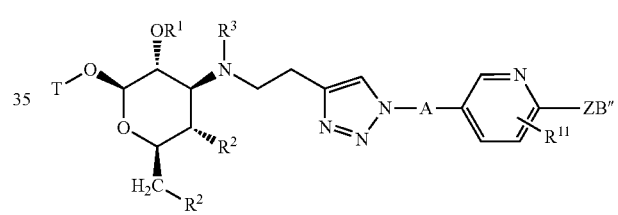

or a pharmaceutically acceptable slat, ester, N-oxide, or prodrug thereof wherein A, B", T, Z, $R^1$, $R^2$, $R^3$, and $R^{11}$ are as described above.

In compounds having this structure, A is, for example, a $C_{1-6}$ allyl group, wherein 0-2 carbon atoms in any of the $C_{1-6}$ alkyl group optionally is replaced by a moiety selected from O, $S(O)_p$, and $NR^4$, and the $C_{1-6}$ alkyl group optionally is substituted with one or more $R^5$ groups as defined above.

In this compound, -A is, e.g., selected from: (a) —$(CH_2)_2$—, (b) —$(CH_2)_3$—, (c) —$(CH_2)_4$—, (d) —$(CH_2)_3O$—, (e) —$(CH_2)_3$—$NH$—, (f) —$CH(CH_2F)CH_2NHC(O)$—, (g) —$CH(CH_2F)CH_2NHS(O)_2$—, (h) —$(CH_2)_2NHS(O)_2$—, (i) —$(CH_2)_2NHCH_2$—, (j) —$(CH_2)_3S$—, (k) —$(CH_2)_3S(O)_2$—, (l) —$(CH_2)_2N(CH_3)CH_2$—, (m) —$(CH_2)_2NHCH_2$—, (n) —$CH_2CH(OH)CH_2O$—, (o) —$CH_2CHFCH_2O$—, (p) —$CH_2CH(CH_3)CH_2O$—, (q) —$O$—$(CH_2)_3$—, (r) —$CH_2$—$O$—$(CH_2)_2$—, (s) —$(CH_2)_2$—$O$—$CH_2$—, (t) —$NH$—$(CH_2)_3$—, (u) —$CH_2$—$NH$—$(CH_2)_2$—, and (v) —$(CH_2)_2$—$NH$—$CH_2$—. For example, -A is selected from: (a) —$(CH_2)_4$—, (b) —$(CH_2)_3O$—, (c) —$(CH_2)_3$—$NH$—, (d) —$CH(CH_2F)CH_2NHC(O)$—, (e) —$CH(CH_2F)CH_2NHS(O)_2$—, (f) —$(CH_2)_2NHS(O)_2$—, (g) —$(CH_2)_2NHCH_2$—, (h) —$(CH_2)_3S$—, (i) —$(CH_2)_3S(O)_2$—, (j) —$(CH_2)_2N(CH_3)CH_2$—, (k) —$(CH_2)_2NHCH_2$—, (l) —$CH_2CH(OH)CH_2O$—, (m) —$CH_2CHFCH_2O$—, (n) —$CH_2CH(CH_3)CH_2O$— and (o) —$(CH_2)_2$—$O$—$CH_2$—.

The invention also provides a compound having the structure:

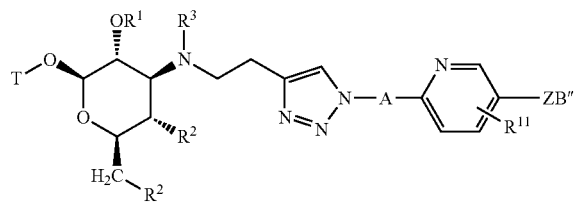

or a pharmaceutically acceptable slat, ester, N-oxide, or prodrug thereof wherein A, B", T, Z, $R^1$, $R^2$, $R^3$, and $R^{11}$ are as described above.

In compounds having this structure, A is, for example, a $C_{1-6}$ alkyl group, wherein 0-2 carbon atoms in any of the $C_{1-6}$ alkyl group optionally is replaced by a moiety selected from O, $S(O)_p$, and $NR^4$, and the $C_{1-6}$ allyl group optionally is substituted with one or more $R^5$ groups as defined above.

In such compounds, -A is, e.g., selected from: (a) —$(CH_2)_2$—, (b) —$(CH_2)_3$—, (c) —$(CH_2)_4$—, (d) —$(CH_2)_3O$—, (e) —$(CH_2)_3$—NH—, (f) —$CH(CH_2F)CH_2NHC(O)$—, (g) —$CH(CH_2F)CH_2NHS(O)_2$—, (h) —$(CH_2)_2NHS(O)_2$—, (i) —$(CH_2)_2NHCH_2$—, (j) —$(CH_2)_3S$—, (k) —$(CH_2)_3S(O)_2$—, (l) —$(CH_2)_2N(CH_3)CH_2$—, (m) —$(CH_2)_2NHCH_2$—, (n) —$CH_2CH(OH)CH_2O$—, (o) —$CH_2CHFCH_2O$—, (p) —$CH_2CH(CH_3)CH_2O$—, (q) —O—$(CH_2)_3$—, (r) —$CH_2$—O—$(CH_2)_2$—, (s) —$(CH_2)_2$—O—$CH_2$—, (t) —NH—$(CH_2)_3$—, (u) —$CH_2$—NH—$(CH_2)_2$—, and (v) —$(CH_2)_2$—NH—$CH_2$—. For example, -A is selected from: (a) —$(CH_2)_4$—, (b) —$(CH_2)_3O$—, (c) —$(CH_2)_3$—NH—, (d) —$CH(CH_2F)CH_2NHC(O)$—, (e) —$CH(CH_2F)CH_2NHS(O)_2$—, (f) —$(CH_2)_2NHS(O)_2$—, (g) —$(CH_2)_2NHCH_2$—, (h) —$(CH_2)_3S$—, (i) —$(CH_2)_3S(O)_2$—, (j) —$(CH_2)_2N(CH_3)CH_2$—, (k) —$(CH_2)_2NHCH_2$—, (l) —$CH_2CH(OH)CH_2O$—, (m) —$CH_2CHFCH_2O$—, (n) —$CH_2CH(CH_3)CH_2O$— and (o) —$(CH_2)_2$—O—$CH_2$—.

The invention also provides a compound having the structure:

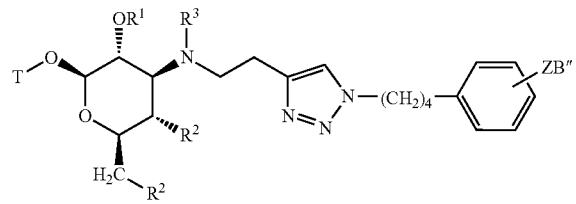

or a pharmaceutically acceptable slat, ester, N-oxide, or prodrug thereof wherein B", T, Z, $R^1$, $R^2$, and $R^3$ are as described in claim 1.

T is a 14- or 15-membered macrolide connected via a macrocyclic ring carbon atom;

$R^1$ and $R^3$ independently are selected from: (a) H; (b) a $C_{1-6}$ alkyl group; (c) a $C_{2-6}$ alkenyl group; (d) a $C_{2-6}$ alkynyl group; (e) —$C(O)R^5$; (f) —$C(O)OR^5$; (g) —$C(O)$—$NR^4R^4$; (h) —$C(S)R^5$; (i) —$C(S)OR^5$; (j) —$C(O)SR^5$; or (k) —$C(S)$—$NR^4R^4$;

$R^2$ is hydrogen or —$OR^{12}$ as defined above;

B" is selected from (aa) an aryl group, (bb) a heteroaryl group, (cc) a biaryl group, (dd) a fused bicyclic or tricyclic saturated, unsaturated or aromatic ring system optionally containing one or more heteroatoms selected from nitrogen, oxygen, and sulfur, (ee) a 3-10 membered saturated or unsaturated heterocycle containing one or more heteroatoms selected from nitrogen, oxygen, and sulfur, (ff) a 3-10 membered saturated, or unsaturated carbocycle, wherein each (aa)-(ff) optionally is substituted with one or more $R^{11}$ or $R^{11a}$ groups; and Z is selected from (aa) a single bond, (bb) a $C_{1-6}$ alkyl group, (cc) a $C_{2-6}$ alkenyl group, (dd) a $C_{2-6}$ alkynyl group, (ee) —C(O)—, (ff) —C(O)O—, (gg) —C(O)$NR^4$—, (hh) —C(—$NR^4$)—, (ii) —C(=$NR^4$)O—, (jj) —C(—$NR^4$)$NR^4$—, (kk) —$S(O)_p$—, (ll) —OC(O)—, (mm) —C(S)—, (nn) —C(S)$NR^4$—, (oo) —C($NR^4$)S—, (pp) —C(O)S—, (qq) —O—, (rr) —$NR^4$—, (ss) —$NR^4$C(O)—, (tt) —OC($N^4$)—, (uu) —NC($NR^4$)—, (vv) —C(S)O—, (ww) —SC(O)—, (xx) —OC(S)— or (yy) —$S(O)_p$—.

The invention also provides a compound having the structure:

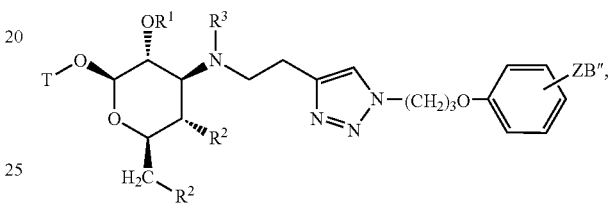

or a pharmaceutically acceptable slat, ester, N-oxide, or prodrug thereof wherein B", T, Z, $R^1$, $R^2$, and $R^3$ are as described above.

The invention also provides a compound having the structure:

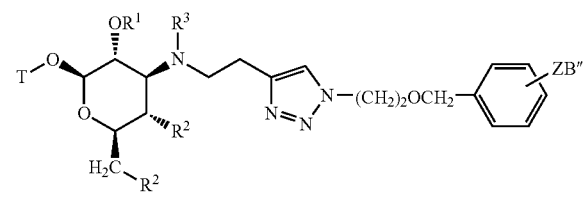

or a pharmaceutically acceptable slat, ester, N-oxide, or prodrug thereof wherein B", T, Z, $R^1$, $R^2$, and $R^3$ are as described above.

In certain of the compounds described above, —ZB" is, e.g., selected from:

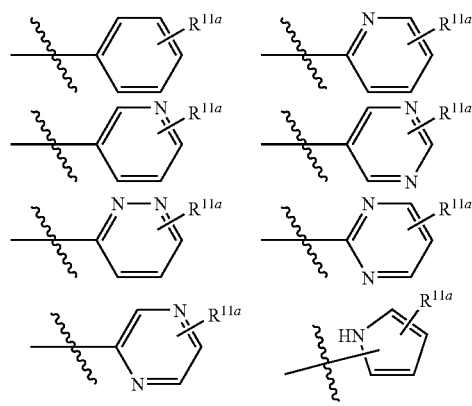

-continued

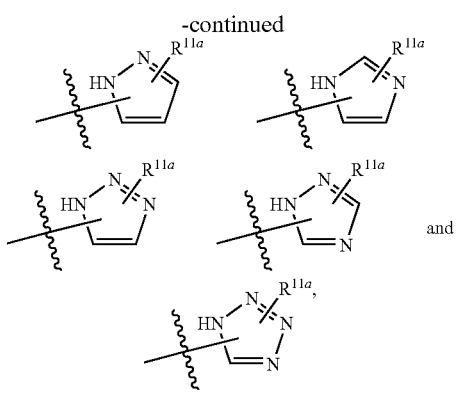

wherein $R^{11a}$ is selected from (a) a carbonyl group, (b) a formyl group, (c) F, (d) Cl, (e) Br, (f) I, (g) CN, (h) $NO_2$, (i) $OR^8$, (j) $—S(O)_pR^8$, (k) $—C(O)R^8$, (l) $—C(O)OR^8$, (m) $—OC(O)R^8$, (n) $—C(O)NR^8R^8$, (o) $—OC(O)NR^8R^8$, (p) $—C(=NR^8)R^8$, (q) $—C(R^8)(R^8)OR^8$, (r) $—C(R^8)_2OC(O)R^8$, (s) $—C(R^8)(OR^8)(CH_2)_nNR^8R^8$, (t) $—NR^8R^8$, (u) $—NR^8OR^8$, (v) $—NR^8C(O)R^8$, (w) $—NR^8C(O)OR^8$, (x) $—NR^8C(O)NR^8R^8$, (y) $—NR^8S(O)_pR^8$, (z) $—C(OR^8)(OR^8)R^8$, (aa) $—C(R^8)_2NR^8R^8$, (bb) $=NR^8$, (cc) $C(S)NR^8R^8$, (dd) $—NR^8C(S)R^8$, (ee) $—OC(S)NR^8R^8$, (ff) $—NR^8C(S)OR^8$, (gg) $—NR^8C(S)NR^8R^8$, (hh) $—SC(O)R^8$, (ii) a $C_{1-8}$ alkyl group, (jj) a $C_{2-8}$ alkenyl group, (kk) a $C_{2-8}$ alkynyl group, (ll) a $C_{1-8}$ alkoxy group, (mm) a $C_{1-8}$ alkylthio group, (nn) a $C_{1-8}$ acyl group, (oo) a $C_{3-10}$ saturated, unsaturated, or aromatic carbocycle, and (pp) a 3-10 membered saturated, unsaturated, or aromatic heterocycle containing one or more heteroatoms selected from nitrogen, oxygen, and sulfur, wherein (ii)-(kk) optionally are substituted with one or more $R^5$ groups.

In the compounds described above, T is, for example,

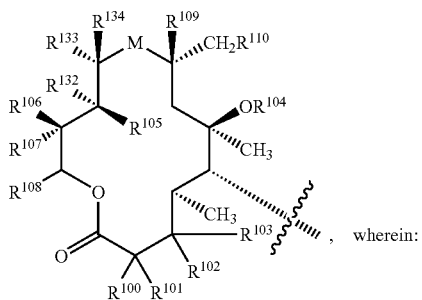

M is selected from: (a) $—C((O)—$, (b) $—CH(—OR^{114})—$, (c) $—NR^{114}—CH_2—$, (d) $—CH_2—NR^{114}—$, (e) $—CH(NR^{114}R^{114})—$, (f) $—C(=NNR^{114}R^{114})—$, (g) $—NR^{114}—C(O)—$, (h) $—C(O)NR^{114}—$, (i) $—C(—NR^{114})—$, (j) $—CR^{115}R^{115}—$, and (k) $—C(=NOR^{127})—$;

$R^{100}$ is selected from (a) H, (b) F, (c) Cl, (d) Br, (e) $—SR^{114}$, and (f) C-6 alkyl, wherein (f) optionally is substituted with one or more $R^{115}$ groups;

$R^{101}$ is selected from: (a) H, (b) Cl, (c) F, (d) Br, (e) I, (f) $—NR^{114}R^{114}$, (g) $—NR^{114}C(O)R^{114}$, (h) $—OR^{114}$, (i) $—OC(O)R^{114}$, (j) $—OC(O)OR^{114}$, (k) $—OC(O)NR^{114}R^{114}$, (l) $—O—C_{1-6}$ alkyl, (m) $—OC(O)—C_{1-6}$ alkyl, (n) $—OC(O)O—C_{1-6}$ alkyl, (o) $—OC(O)NR^{114}—C_{1-6}$ alkyl, (p) $C_{1-6}$ alkyl, (q) $C_{1-6}$ alkenyl, and (r) $C_{1-6}$ alkynyl,
wherein any of (l)-(r) optionally is substituted with one or more $R^{115}$ groups;

$R^{102}$ is H, (b) F, (c) Cl, (d) Br, (e) $—SR^{114}$, (f) $C_{1-6}$ alkyl, wherein (f) optionally is substituted with one or more $R^{115}$ groups;

$R^{103}$ is selected from: (a) H, (b) $—OR^{114}$, (c) $—O—C_{1-6}$ alkyl-$R^{115}$, (d) $—OC((O)R^{114}$,
(e) $—OC(O)—C_{1-6}$ alkyl-$R^{115}$, (f) $—OC(O)OR^{114}$, (g) $—OC(O)O—C_{1-6}$ alkyl-$R^{115}$,
(h) $—OC(O)NR^{114}R^{114}$, (i) $—OC(O)NR^{114}—C_{1-6}$ alkyl-$R^{115}$, and (j)

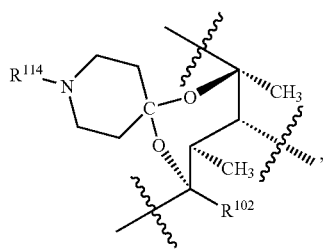

alternatively, $R^{102}$ and $R^{103}$ taken together with the carbon to which they are attached form (a) a carbonyl group or (b) a 3-7 membered saturated, unsaturated or aromatic carbocyclic or heterocyclic ring which can optionally be substituted with one or more $R^{114}$ groups;

alternatively, $R^{101}$ and $R^{103}$ taken together are a single bond between the respective carbons to which these two groups are attached thereby creating a double bond between the carbons to which $R^{100}$ and $R^{102}$ are attached;

alternatively, $R^{101}$ and $R^{103}$ taken together with the carbons to which they are attached form a 3-membered saturated, unsaturated or aromatic carbocyclic or heterocyclic ring which can optionally be substituted with one or more $R^{114}$ groups;

$R^{104}$ is selected from: (a) H, (b) $R^{114}$, (c) $—C(O)R^{114}$ (d) $—C(O)OR^{114}$ (e) $—C(O)NR^{114}R^{114}$, (f) $—C_{1-6}$ allyl-K—$R^{114}$, (g) $—C_{2-6}$ alkenyl-K—$R^{114}$, and (h) $—C_{2-6}$ alkynyl-K—$R^{114}$;

K is selected from: (a) $—C(O)—$, (b) $—C(O)O—$, (c) $—C(O)NR^{114}—$, (d) $—C(=NR^{114})—$, (e) $—C(—NR^{114})O—$, (f) $C(=NR^{114})NR^{114}—$, (g) $—OC(O)—$, (h) $—OC(O)O—$, (i) $—OC(O)NR^{114}—$,
(j) $—NR^{114}C(O)—$, (k) $—NR^{114}C(O)O—$, (l) $—NR^{114}C(O)NR^{114}—$, (m) $—NR^{114}C(=NR^{114})NR^{114}—$, and (O)—S$(O)_p—$;

alternatively $R^{103}$ and $R^{104}$, taken together with the atoms to which are bonded, form:

-continued

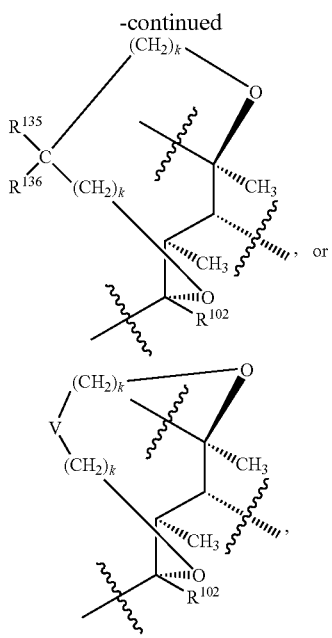

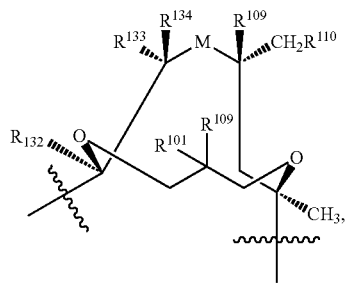

wherein
i) $R^{101}$ is as defined above;
ii) alternately, $R^{101}$ and $R^{109}$ can be taken together with the carbon to which they are attached to form a carbonyl group;
iii) alternately, $R^{101}$ and $R^{109}$ can be taken together to form the group $-O(CR^{116}R^{116})_uO-$;
alternatively, $R^{104}$ and $R^{105}$, taken together with the atoms to which they are bonded, form:

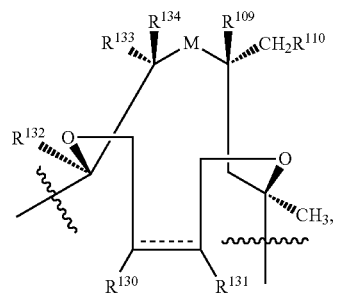

wherein in the preceding structure the dotted line indicates an optional double bond,
i) $R^{130}$ is $-OH$, or $R^{114}$,
ii) $R^{131}$ is $-OH$, or $R^{114}$,
iii) alternately, $R^{130}$ and $R^{131}$ together with the carbons to which they are attached form a 3-7 membered saturated, unsaturated or aromatic carbocyclic or heterocyclic ring which can optionally be substituted with one or more $R^{114}$ groups;
iv) alternatively, $R^{130}$ and the carbon to which it is attached or $R^{131}$ and the carbon to which it is attached are each independently $-C(=O)-$
alternatively, $R^{105}$, $R^{132}$ and M, taken together with the atoms to which they are attached, form:

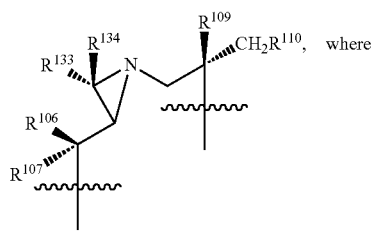

wherein $R^{135}$ and $R^{136}$ are selected from (a) hydrogen, (b) $C_{1-6}$ alkyl, (c) $C_{2-6}$ alkenyl, (d) $C_{2-6}$ alkynyl, (d) $C_{3-14}$ saturated, unsaturated or aromatic carbocycle, (e) 3-14 membered saturated, unsaturated or aromatic heterocycle containing one or more oxygen, nitrogen, or sulfur atoms, (f) F, (g) Br, (h) I, (i) OH, (j) $-N_3$, wherein (b) through (e) are optionally substituted with one or more $R^{117}$; or alternatively, $R^{135}$ and $R^{136}$ are taken together to form $=O$, $=S$ and $=NR^{114}$, $=NOR^{114}$, $=NR^{114}$, and $=N-NR^{114}$, $R^{114}$,
wherein V is selected from (a) $-(C_4\text{-alkyl})-$, (b) $-(C_4\text{-alkenyl})-$, (c) O, (d) S, and (e) $NR^{114}$, wherein (a) and (b) are optionally further substituted with one or more $R^{117}$;
$R^{105}$ is selected from: (a) $R^{114}$, (b) $-OR^{114}$, (c) $-NR^{114}R^{114}$, (d) $-O-C_{1-6}$ alkyl-$R^{115}$, (e) $-C(O)-R^{114}$, (f) $-C(O)-C_{1-6}$ alkyl-$R^{115}$, (g) $-OC(O)-R^{114}$, (h) $-OC(O)-C_{1-6}$ alkyl-$R^{115}$,
(i) $-OC(O)O-R^{114}$, (j) $-OC(O)O-C_{1-6}$ alkyl-$R^{115}$, (k) $-OC(O)NR^{114}R^{114}$, (l) $-OC(O)NR^{114}-C_{1-6}$ alkyl-$R^{115}$, (m) $-C(O)-C_{2-6}$ alkenyl-$R^{115}$, and (n) $-C(O)-C_{2-6}$ alkynyl-$R^{115}$;
alternatively, $R^{104}$ and $R^{105}$, taken together with the atoms to which they are bonded, form

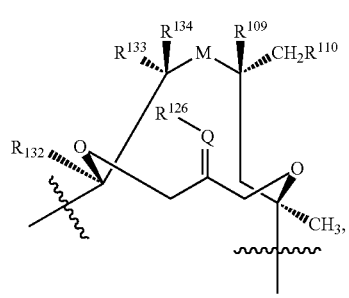

wherein Q is CH or N, and $R^{126}$ is $-OR^{114}$, $-NR^{114}$ or $R^{114}$;
alternatively, $R^{104}$ and $R^{105}$, taken together with the atoms to which they are bonded, form:

$R^{106}$ is selected from:
(a) $-OR^{114}$, (b) $-C_{1-6}$ alkoxy-$R^{115}$, (c) $-C(O)R^{114}$, (d) $-OC(O)R^{114}$, (e) $-OC(O)OR^{114}$, (f) $-OC(O)NR^{114}R^{114}$, and (g) $-NR^{114}R^{114}$.

alternatively, $R^{105}$ and $R^{106}$ taken together with the atoms to which they are attached form a 5-membered ring by attachment to each other through a chemical moiety selected from:
(a) —OC($R^{115}$)$_2$O—, (b) —OC(O)O—, (c) —OC(O)N$R^{114}$—, (d) —N$R^{114}$C(O)O—, (e) —OC(O)NO$R^{114}$—, (f) —NO$R^{114}$—C(O)O—, (g) —OC(O)NN$R^{114}$R$^{114}$—, (h) —NN$R^{114}$R$^{114}$—C(O)O—, (i) —OC(O)C($R^{115}$)$_2$—, (j) —C($R^{115}$)$_2$C(O)O—, (k) —OC(S)O—, (l) —OC((S)N$R^{114}$, (m) —N$R^{114}$C(S)O—, (n) —OC(S)NO$R^{114}$—, (o) —NO$R^{114}$—C(S)O—, (p)—OC(S)NN$R^{114}$R$^{114}$—, (q)—NN$R^{114}$R$^{114}$—C(S)O—, (r) —OC(S)C($R^{115}$)$_2$—, and (s) —C($R^{115}$)$_2$C(S)O—;

alternatively, $R^{105}$, $R^{106}$, and $R^{133}$ taken together with the atoms to which they are attached form:

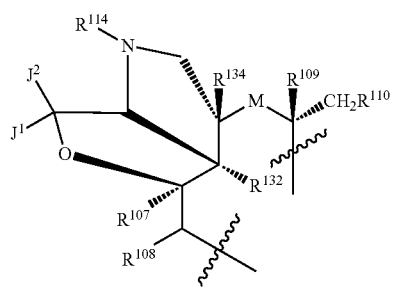

alternatively, M, $R^{105}$, and $R^{106}$ taken together with the atoms to which they are attached form:

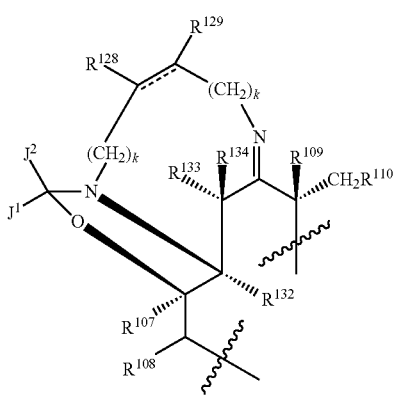

wherein in the preceding structure the dotted line indicates an optional double bond,

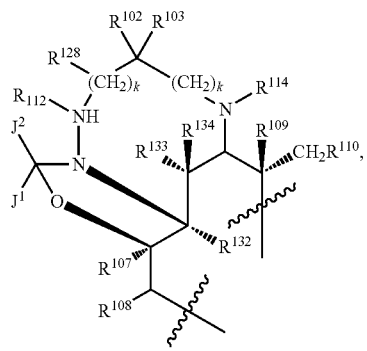

-continued

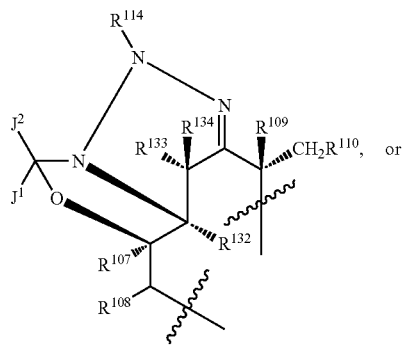

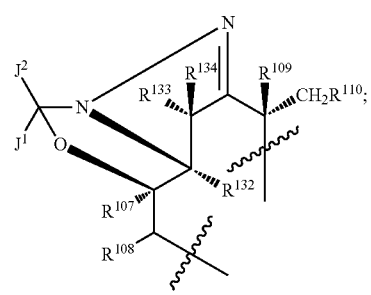

wherein $J^1$ and $J^2$ are selected from hydrogen, Cl, F, Br, I, OH, —C$_{1-6}$ alkyl, and —O(C$_{1-6}$alkyl) or are taken together to form =O, =S, =N$R^{114}$, =NO$R^{114}$, —N$R^{114}$, or =N—N$R^{114}$, $R^{114}$;

alternatively, M and $R^{104}$ taken together with the atoms to which they are attached form:

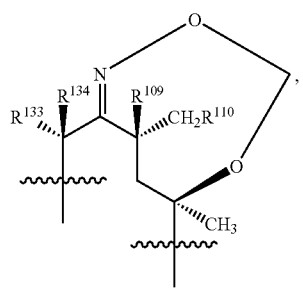

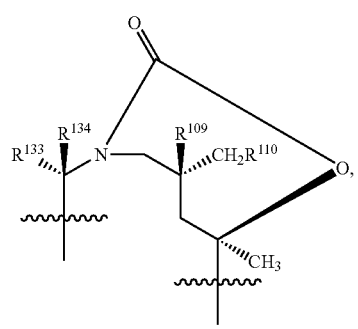

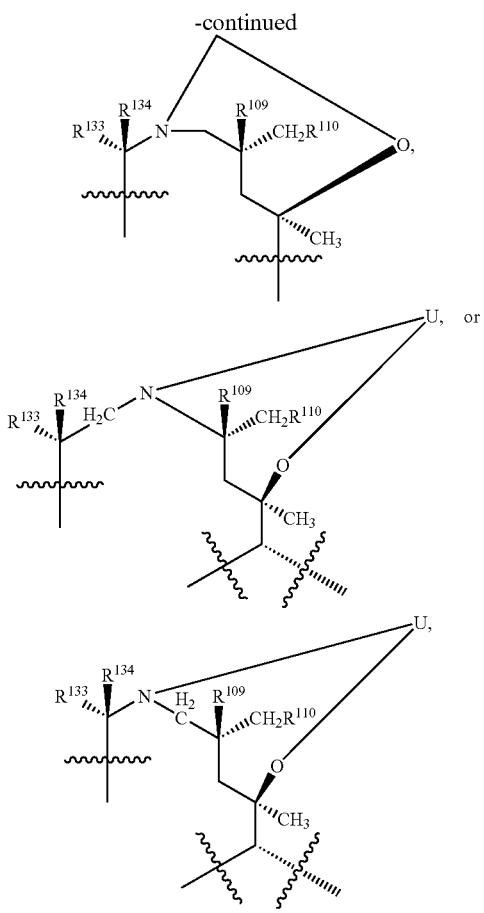

wherein U is selected from (a) —(C$_4$-alkyl)- and (b) —(C$_4$-alkenyl)-, wherein (a) and (b) are optionally further substituted with one or more R$^{117}$;

alternatively, M and R$^{105}$ are taken together with the atoms to which they are attached to form:

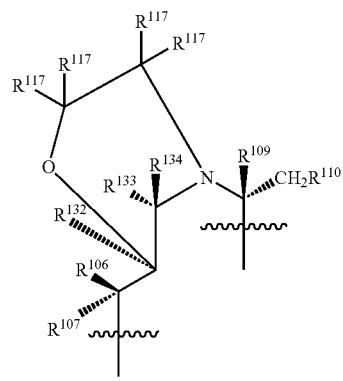

R$^{107}$ is selected from
(a) H, (b) —C$_{1-4}$ alkyl, (c) —C$_{2-4}$ alkenyl, which can be further substituted with C$_{1-12}$ alkyl or one or more halogens, (d) —C$_{2-4}$ alkynyl, which can be further substituted with C$_{1-2}$ alkyl or one or more halogens, (e) aryl or heteroaryl, which can be further substituted with C$_{1-12}$ alkyl or one or more halogens, (f) —C(O)H, (g) —COOH, (h) —CN, (i) —COOR$^{114}$, (j) —C(O)NR$^{114}$R$^{114}$, (k) —C(O)R$^{114}$, and (l) —C(O)SR$^{114}$, wherein (b) is further substituted with one or more substituents selected from (aa) —OR$^{114}$, (bb) halogen, (cc) —SR$^{114}$, (dd) C$_{1-12}$ alkyl, which can be further substituted with halogen, hydroxyl, C$_{1-6}$ alkoxy, or amino, (ee) —OR$^{114}$, (ff) —SR$^{114}$, (gg) —NR$^{114}$R$^{114}$, R$^{114}$—CN, (ii) —NO$_2$, (jj) —NC(O)R$^{114}$, (kk), (ll) —N$_3$, (mm) =N—O—R$^{114}$, (nn) =NR$^{114}$, (oo) =N—NR$^{114}$R$^{114}$, (pp) =N—NH—C(O)R$^{114}$, and (qq) N—NH—C(O)NR$^{114}$R$^{114}$;

alternatively R$^{106}$ and R$^{107}$ are taken together with the atom to which they are attached to form an epoxide, a carbonyl, an olefin, or a substituted olefin, or a C$_3$-C$_7$ carbocyclic, carbonate, or carbamate, wherein the nitrogen of said carbamate can be further substituted with a C$_1$-C$_6$ alkyl;

R$^{108}$ is selected from:
(a) C$_{1-6}$ alkyl, (b) C$_{2-6}$ alkenyl, and (c) C$_{2-6}$ alkynyl, wherein any of (a)-(c) optionally is substituted with one or more R$^{114}$ groups;

R$^{111}$ is selected from H and —C(O)R$^{114}$;

R$^{112}$ is selected from H, OH, and OR$^{114}$;

R$^{113}$ is selected from:
(a) H, (b) R$^{114}$, (c) —C$_{1-6}$ alkyl-K—R$^{114}$, (d) —C$_{2-6}$ alkenyl-K—R$^{114}$, and (e) —C$_{2-6}$ alkynyl-K—R$^{114}$, wherein any of (c)-(e) optionally is substituted with one or more R$^{115}$ groups;

R$^{114}$, at each occurrence, independently is selected from:
(a) H, (b) C$_{1-6}$ alkyl, (c) C$_{2-6}$ alkenyl, (d) C$_{2-6}$ alkynyl, (e) C$_{6-10}$ saturated, unsaturated, or aromatic carbocycle, (f) 3-12 membered saturated, unsaturated, or aromatic heterocycle containing one or more heteroatoms selected from nitrogen, oxygen, and sulfur, (g) —C(O)—C$_{1-6}$ alkyl, (h) —C(O)—C$_{2-6}$ alkenyl, (i) —C(O)—C$_{2-6}$ alkynyl, (j) —C(O)—C$_{6-10}$ saturated, unsaturated, or aromatic carbocycle, (k) —C(O)-3-12 membered saturated, unsaturated, or aromatic heterocycle containing one or more heteroatoms selected from nitrogen, oxygen, and sulfur, (l) —C(O)O—C$_{1-6}$ alkyl, (m) —C(O)O—C$_{2-6}$ alkenyl, (n) —C(O)O—C$_{2-6}$ alkynyl, (o) —C(O)O—C$_{6-10}$ saturated, unsaturated, or aromatic carbocycle, (p) —C(O)O-3-12 membered saturated, unsaturated, or aromatic heterocycle containing one or more heteroatoms selected from nitrogen, oxygen, and sulfur, (q) —C(O)NR$^{116}$R$^{116}$, (r) —NR$^{116}$CO—C2-6 alkyl, (s) —NR$^{116}$CO—C$_{6-10}$ saturated, unsaturated, or aromatic carbocycle, and (t) —NR$^{116}$C(O)-3-12 membered saturated, unsaturated, or aromatic heterocycle containing one or more heteroatoms selected from nitrogen, oxygen, and sulfur, wherein any of (b)-(t) optionally is substituted with one or more R$^{115}$ groups, wherein one or more non-terminal carbon moieties of any of (b)-(d) optionally is replaced with oxygen, S(O)$_p$, or —NR$^{116}$, alternatively, NR$^{114}$R$^{114}$ forms a 3-7 membered saturated, unsaturated or aromatic ring including the nitrogen atom to which the R$^{114}$ groups are bonded and optionally one or more moieties selected from O, S(O)$_p$, N, and NR$^{118}$;

R$^{115}$ is selected from:
(a) R$^{117}$, (b) C$_{1-8}$ alkyl, (c) C$_{2-8}$ alkenyl, (d) C$_{2-8}$ alkynyl, (e) C$_{3-12}$ saturated, unsaturated, or aromatic carbocycle, (f) 3-12 membered saturated, unsaturated, or aromatic heterocycle containing one or more heteroatoms selected from nitrogen, oxygen, and sulfur,
wherein any of (b)-(f) optionally is substituted with one or more R$^{117}$ groups;

R$^{116}$, at each occurrence, independently is selected from:
(a) H, (b) C$_{1-6}$ alkyl, (c) C$_{2-6}$ alkenyl, (d) C$_{2-6}$ alkynyl, (e) C$_{3-10}$ saturated, unsaturated, or aromatic carbocycle, and (f) 3-10 membered saturated, unsaturated, or aromatic heterocycle containing one or more heteroatoms selected from nitrogen, oxygen, and sulfur,
  wherein one or more non-terminal carbon moieties of any of (b)-(d) optionally is replaced with oxygen, $S(O)_p$, or $-NR^{114}$ wherein any of (b)-(f) optionally is substituted with one or more moieties selected from: (aa) carbonyl, (bb) formyl, (cc) F, (dd) Cl, (ee) Br, (ff) I, (gg) CN, (hh) $N_3$, (ii) $NO_2$, (jj) $OR^{118}$, (kk) $-S(O)_pR^{118}$, (ll) $-C(O)R^{118}$, (mm) $-C(O)OR^{118}$, (nn) $-OC(O)R^{118}$, (oo) $-C(O)NR^{118}R^{118}$, (pp) $-OC(O)NR^{118}R^{118}$, (qq) $-C(=NR^{118})R^{118}$, (rr) $-C(R^{118})(R^{118})OR^{118}$, (ss) $-C(R^{118})_2OC(O)R^{118}$, (f) $-C(R^{118})(OR^{118})(CH_2)_rNR^{118}R^{118}$, (uu) $-NR^{118}R^{118}$, (vv) $-NR^{118}OR^{118}$, (ww) $-NR^{118}C(O)R^{118}$, (xx) $-NR^{118}C(O)OR^{118}$, (yy) $-NR^{118}C(O)NR^{118}R^{118}$, (zz) $-NR^{118}S(O)_rR^{118}$, (ab) $-C(OR^{118})(OR^{118})R^{118}$, (ac) $-C(R^{118})_2NR^{118}R^{118}$, (ad) $-NR^{118}$, (ae) $-C(S)NR^{118}R^{118}$, (af) $-NR^{118}C(S)R^{118}$, (ag) $-OC(S)NR^{118}R^{118}$, (ah) $-NR^{118}C(S)OR^{118}$, (ai) $-NR^{118}C(S)NR^{118}R^{118}$, (aj) $-SC(O)R^{118}$, (ak) $C_{1-8}$ alkyl, (al) $C_{2-8}$ alkenyl, (am) $C_{2-8}$ alkynyl, (an) $C_{1-8}$ alkoxy, (ao) $C_{1-8}$ alkylthio, (ap) $C_{1-8}$ acyl, (aq) saturated, unsaturated, or aromatic $C_{3-10}$ carbocycle, and (ar) saturated, unsaturated, or aromatic 3-10 membered heterocycle containing one or more heteroatoms selected from nitrogen, oxygen, and sulfur,
alternatively, $NR^{116}R^{116}$ forms a 3-10 membered saturated, unsaturated or aromatic ring including the nitrogen atom to which the $R^{116}$ groups are attached and optionally one or more moieties selected from O, $S(O)_p$, N, and $NR^{118}$;
alternatively, $CR^{116}R^{116}$ forms a carbonyl group;
$R^{117}$, at each occurrence, is selected from:
  (a) H, (b) =O, (c) F, (d) Cl, (e) Br, (f) I, (g) $(CR^{116}R^{116})_rCF_3$, (h) $(CR^{116}R^{116})_rCN$, (i) $(CR^{116}R^{116})_rNO_2$, (j) $(CR^{116}R^{116})_rNR^{116}(CR^{116}R^{116})_rR^{119}$, (k) $(CR^{116}R^{116})_rR^{119}$, (l) $(CR^{116}R^{116})_rS(O)_p(CR^{116}R^{116})_rR^{119}$, (m) $(CR^{116}R^{116})_rC(O)(CR^{116}R^{116})_rR^{119}$, (n) $(CR^{116}R^{116})_rOC(O)(CR^{116}R^{116})_rR^{119}$, (o) $(CR^{116}R^{116})_rSC(O)(CR^{116}R^{116})_rR^{119}$, (p) $(CR^{116}R^{116})_rC(O)O(CR^{116}R^{116})_rR^{119}$, (q) $(CR^{116}R^{116})_rR^{116}C(O)(CR^{116}R^{116})_rR^{119}$, (r) $(CR^{116}R^{116})_rC(O)NR^{116}(CR^{116}R^{116})_rR^{119}$, (s) $(CR^{116}R^{116})_rC(=NR^{116})(CR^{116}R^{116})_rR^{119}$, (t) $(CR^{116}R^{116})_rC(=NNR^{116}R^{116})(CR^{116}R^{116})_rR^{119}$, (u) $(CR^{116}R^{116})_rC(=NNR^{116}C(O)R^{116})(CR^{116}R^{116})_rR^{119}$, (v) $(CR^{116}R^{116})_rC(=NOR^{119})(CR^{116}R^{116})_rR^{119}$, (w) $(CR^{116}R^{116})_rNR^{116}C(O)O(CR^{116}R^{116})_rR^{119}$, (x) $(CR^{116}R^{116})_rOC(O)NR^{116}(CR^{116}R^{116})_rR^{119}$, (y) $(CR^{116}R^{116})_rNR^{116}C(O)NR^{116}(CR^{116}R^{116})_rR^{119}$, (z) $(CR^{116}R^{116})_rNR^{116}S(O)_p(CR^{116}R^{116})_rR^{119}$, (aa) $(CR^{116}R^{116})_rS(O)_pNR^{116}(CR^{116}R^{116})_rR^{119}$, (bb) $(CR^{116}R^{116})_rNR^{116}S(O)_pNR^{116}(CR^{116}R^{116})_rR^{119}$, (cc) $(CR^{116}R^{116})_rNR^{116}R^{116}$, (dd) $C_{1-6}$ alkyl, (ee) $C_{2-6}$ alkenyl, (ff) $C_{2-6}$ alkynyl, (gg) $(CR^{116}R^{116})_rC_{3-10}$ saturated, unsaturated, or aromatic carbocycle, and (hh) $(CR^{116}R^{116})_r$-3-10 membered saturated, unsaturated, or aromatic heterocycle containing one or more heteroatoms selected from nitrogen, oxygen, and sulfur,
  wherein any of (dd)-(hh) optionally is substituted with one or more $R^{119}$ groups;
alternatively, two $R^{117}$ groups can form $-O(CH_2)_uO-$;
$R^{118}$ is selected from:
  (a) H, (b) $C_{1-6}$ alkyl, (c) $C_{2-6}$ alkenyl, (d) $C_{2-6}$ alkynyl, (e) $C_{3-10}$ saturated, unsaturated, or aromatic carbocycle, (f) 3-10 membered saturated, unsaturated, or aromatic heterocycle containing one or more heteroatoms selected from nitrogen, oxygen, and sulfur, (g) $-C(O)-C_{1-6}$ allyl, (h) $-C(O)-C_{1-6}$ alkenyl, (g) $-C(O)-C_{1-6}$ alkynyl, (i) $-C(O)-C_{3-10}$ saturated, unsaturated, or aromatic carbocycle, and (j) $-C(O)$-3-10 membered saturated, unsaturated, or aromatic heterocycle containing one or more heteroatoms selected from nitrogen, oxygen, and sulfur,
  wherein any of (b)-(j) optionally is substituted with one or more moieties selected from: (aa) H, (bb) F, (cc) Cl, (dd) Br, (ee) I, (ff) CN, (gg) $NO_2$, (hh) OH, (ii) $NH_2$, (jj) $NH(C_{1-6}$ alky(l), (kk) $N(C_{1-6}$ alky(l)$_2$, (ll) $C_{1-6}$ alkoxy, (mm) aryl, (nn) substituted aryl, (oo) heteroaryl, (pp) substituted heteroaryl, and (qq) $C_{1-6}$ alkyl, optionally substituted with one or more moieties selected from aryl, substituted aryl, heteroaryl, substituted heteroaryl, F, Cl, Br, I, CN, $NO_2$, and OH;
$R^{119}$, at each occurrence, independently is selected from:
  (a) $R^{120}$, (b) $C_{1-6}$ alkyl, (c) $C_{2-6}$ alkenyl, (d) $C_{2-6}$ alkynyl, (e) $C_{3-10}$ saturated, unsaturated, or aromatic carbocycle, and (f) 3-10 membered saturated, unsaturated, or aromatic heterocycle containing one or more heteroatoms selected from nitrogen, oxygen, and sulfur,
  wherein any of (b)-(f) optionally is substituted with one or more $R^{119}$ groups;
$R^{120}$, at each occurrence, independently is selected from:
  (a) H, (b) =O, (c) F, (d) Cl, (e) Br, (f) I, (g) $(CR^{116}R^{116})_rCF_3$, (h) $(CR^{116}R^{116})_rCN$, (i) $(CR^{116}R^{116})_rNO_2$, (j) $(CR^{116}R^{116})_rNR^{116}R^{116}$, (k) $(CR^{116}R^{116})_rOR^{114}$, (l) $(CR^{116}R^{116})_rS(O)_pR^{116}$, (m) $(CR^{116}R^{116})_rC(O)R^{116}$, (n) $(CR^{116}R^{116})_rC(O)OR^{116}$, (o) $(CR^{116}R^{116})_rOC(O)R^{116}$, (p) $(CR^{116}R^{116})_rNR^{116}C(O)R^{116}$, (q) $(CR^{116}R^{116})_rC(O)NR^{116}R^{116}$, (r) $(CR^{116}R^{116})_rC(=NR^{116})R^{116}$, (s) $(CR^{116}R^{116})_rNR^{116}C(O)NR^{116}R^{116}$, (t) $(CR^{116}R^{116})_rR^{116}S(O)_pR^{116}$, (u) $(CR^{116}R^{116})_rS(O)_pNR^{116}R^{116}$, (v) $(CR^{116}R^{116})_rNR^{116}S(O)_pNR^{116}R^{116}$, (w) $C_{1-6}$ alkyl, (x) $C_{2-6}$ alkenyl, (y) $C_{2-6}$ alkynyl, (z) $(CR^{116}R^{116})_r-C_{3-10}$ saturated, unsaturated, or aromatic carbocycle, and (aa) $(CR^{116}R^{116})_r$-3-10 membered saturated, unsaturated, or aromatic heterocycle containing one or more heteroatoms selected from nitrogen, oxygen, and sulfur,
  wherein any of (w)-(aa) optionally is substituted with one or more moieties selected from $R^{116}$, F, Cl, Br, I, CN, $NO_2$, $-OR^{116}$, $-NH_2$, $-NH(C_{1-6}$ alkyl), $-N(C_{1-6}$ alkyl)$_2$, $C_{1-6}$ alkoxy, $C_{1-6}$ alkylthio, and $C_{1-6}$ acyl;
$R^{121}$, at each occurrence, independently is selected from:
  (a) H, (b) $-OR^{118}$, (c) $-O-C_{1-6}$ alkyl-OC(O)$R^{118}$, (d) $-O-C_{1-6}$ alkyl-OC(O)$OR^{118}$, (e) $-O-C_{1-6}$ alkyl-OC(O)NR$^{118}$R$^{118}$, (f) $-O-C_{1-6}$ alkyl-C(O)NR$^{118}$R$^{118}$, (g) $-O-C_{1-6}$ alkyl-NR$^{118}$C(O)R$^{118}$, (h) $-O-C_{1-6}$ alkyl-NR$^{118}$C(O)OR$^{118}$, (i) $-OC_{1-6}$ alkyl-NR$^{118}$C(O)NR$^{118}$R$^{118}$, (j) $-O-C_{1-6}$ alkyl-NR$^{118}$C(=N(H)NR$^{118}$R$^{118}$, (k) $-O-C_{1-6}$ alkyl-S(O)$_p$R$^{118}$, (l) $-O-C_{2-6}$ alkenyl-OC(O)R$^{118}$, (m) $-O-C_{2-6}$ alkenyl-OC(O)OR$^{118}$, (n) $-O-C_{2-6}$ alkenyl-OC(O)NR$^{118}$R$^{118}$, (o) $-O-C_{2-6}$ alkenyl-C(O)NR$^{118}$R$^{118}$, (p) $-O-C_{2-6}$ alkenyl-NR$^{118}$C(O)R$^{118}$, (q) $-O-C_{2-6}$ alkenyl-NR$^{118}$C(O)OR$^{118}$, (r) $-O-C_{2-6}$ alkenyl-NR$^{118}$C(O)NR$^{118}$R$^{118}$, (s) $-O-C_{2-6}$ alkenyl-NR$^{118}$C(=N(H)NR$^{118}$R$^{118}$, (t) $-O-C_{2-6}$ alkenyl-S(O)$_p$R$^{118}$, (u) $-O-C_{2-6}$ alkynyl-OC(O)R$^{118}$, (v) $-O-C_{2-6}$ alkynyl-OC(O)OR$^{118}$, (w) $-O-C_{2-6}$ alkynyl-OC(O)NR$^{118}$R$^{118}$, (x) $-O-C_{2-6}$ alkynyl-C(O)NR$^{118}$R$^{118}$, (y) $-O-C_{2-6}$ alkynyl-NR$^{118}$C(O)R$^{118}$, (z) $-O-C_{2-6}$ alkynyl-NR$^{118}$C(O)OR$^{118}$, (aa) —O—C$_{2-6}$ alkynyl-NR$^{118}$C(O)NR$^{118}$R$^{118}$, (bb) —O—C$_{2-6}$ alkynyl-NR$^{118}$C(=N(H)NR$^{118}$R$^{118}$, (cc) —O—C$_{2-6}$ alkynyl-S(O)$_p$R$^{118}$; and (dd) —NR$^{118}$R$^{118}$;

alternatively, two R$^{12}$ groups taken together form =O, =NOR$^{118}$, or =NNR$^{118}$R$^{118}$; R$^{122}$ is R$^{115}$ R$^{123}$ is selected from:
(a) R$^{116}$, (b) F, (c) Cl, (d) Br, (e) I, (f) CN, (g) NO$_2$, and (h) —OR$^{114}$; alternatively, R$^{122}$ and R$^{123}$ taken together are —O(CH$_2$)$_u$O—;

R$^{124}$, at each occurrence, independently is selected from:
(a) H, (b) F, (c) Cl, (d) Br, (e) I, (f) CN, (g) —OR$^{114}$, (—NO$_2$, (i) —NR$^{114}$R$^{114}$, (j) C$_{1-6}$ alkyl, (k) C$_{1-6}$ acyl, and (l) C$_{1-6}$ alkoxy;

R$^{125}$ is selected from:
(a) C$_{1-6}$ alkyl, (b) C$_{2-6}$ alkenyl, (c) C$_{2-6}$ alkynyl, (d) C$_{1-6}$ acyl, (e) C$_{1-6}$ alkoxy, (f) C$_{1-6}$ alkylthio, (g) saturated, unsaturated, or aromatic C$_{5-10}$ carbocycle, (h) saturated, unsaturated, or aromatic 5-10 membered heterocycle containing one or more heteroatoms selected from nitrogen, oxygen, and sulfur, (i) —O—C$_{1-6}$ alkyl-saturated, unsaturated, or aromatic 5-10 membered heterocycle containing one or more heteroatoms selected from nitrogen, oxygen, and sulfur, (j) —NR$^{114}$—C$_{1-6}$ alkyl-saturated, unsaturated, or aromatic 5-10 membered heterocycle containing one or more heteroatoms selected from nitrogen, oxygen, and sulfur, (k) saturated, unsaturated, or aromatic 10-membered bicyclic ring system optionally containing one or more heteroatoms selected from nitrogen, oxygen, and sulfur, (l) saturated, unsaturated, or aromatic 13-membered tricyclic ring system optionally containing one or more heteroatoms selected from nitrogen, oxygen, and sulfur, (m) —OR$^{114}$, (n) —NR$^{114}$R$^{114}$, (o)—S(O)$_p$R$^{114}$, and (p) —R$^{124}$, wherein any of (a)-(l) optionally is substituted with one or more R$^{115}$ groups;

alternatively, R$^{125}$ and one R$^{124}$ group, taken together with the atoms to which they are bonded, form a 5-7 membered saturated or unsaturated carbocycle, optionally substituted with one or more R$^{115}$ groups; or a 5-7 membered saturated or unsaturated heterocycle containing one or more atoms selected from nitrogen, oxygen, and sulfur, and optionally substituted with one or more R$^{115}$ groups;

R$^{126}$ at each occurrence, independently is selected from:
(a) hydrogen, (b) an electron-withdrawing group, (c) aryl, (d) substituted aryl, (e) heteroaryl, (f) substituted heteroaryl, and (g) C$_{1-6}$ alkyl, optionally substituted with one or more R$^{115}$ groups;

alternatively, any R$^{126}$ and any R$^{123}$, taken together with the atoms to which they are bonded, form a 5-7 membered saturated or unsaturated carbocycle, optionally substituted with one or more R$^{115}$ groups; or a 5-7 membered saturated or unsaturated heterocycle containing one or more atoms selected from nitrogen, oxygen, and sulfur, and optionally substituted with one or more R$^{115}$ groups;

R$^{109}$ is H or F;

R$^{127}$ is R$^{114}$, a monosaccharide or disaccharide (including amino sugars and halo sugar(s), —(CH$_2$)$_n$—(O—CH$_2$CH$_2$—)$_m$—O(CH$_2$)$_p$CH$_3$ or —(CH$_2$)$_n$—(O—CH$_2$CH$_2$—)$_m$—OH, R$^{128}$ is R$^{114}$, R$^{129}$ is R$^{114}$, and
R$^{110}$ is R$^{114}$.

Alternatively, R$^{109}$ and R$^{110}$ taken together with the carbons to which they are attached form:

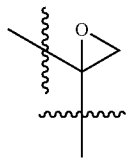 [SMILES: *C1(*)CO1]

Alternately, R$^{128}$ and R$^{129}$ together with the carbons to which they are attached form a 3-6 membered saturated, unsaturated or aromatic carbocyclic or heterocyclic ring which can optionally be substituted with one or more R$^{114}$ groups;

R$^{132}$, R$^{133}$, and R$^{134}$ are each independently selected from (a) H, (b) F, (c) Cl, (d) Br, (e) —OR$^{114}$, (f) —SR$^{114}$, (g) —NR$^{114}$R$^{114}$, and (h) C$_{1-6}$ alkyl, wherein (h) optionally is substituted with one or more R$^{115}$ groups;

alternatively, R$^{132}$ and R$^{133}$ are taken together to form a carbon-carbon double;

alternatively, R$^{133}$ and R$^{134}$ are taken together to form =O, =S, =NOR$^{114}$, =NR$^{114}$, and =N—NR$^{114}$, R$^{114}$;

alternatively, R$^{105}$ and R$^{134}$ are taken together with the carbons to which they are attached to form a 3-membered ring, said ring optionally containing an oxygen or nitrogen atom, and said ring being optionally substituted with one or more R$^{114}$ groups;

alternatively when M is a carbon moiety, R$^{134}$ and M are taken together to form a carbon-carbon double bond;

k, at each occurrence is 0, 1, or 2;
m, at each occurrence is 0, 1, 2, 3, 4, or 5;
n, at each occurrence is 1, 2, or 3.

In the compounds described above, T is, for example, a macrolide selected from:

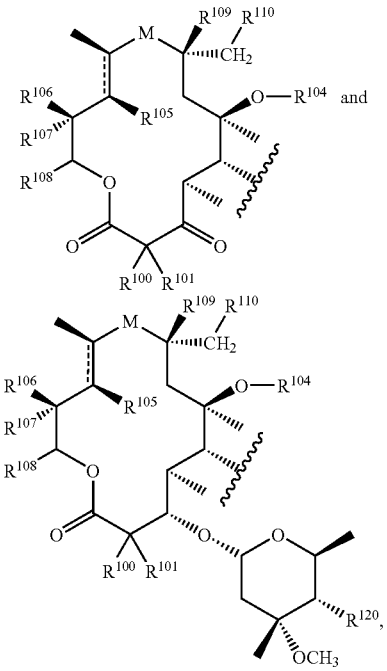

or an N-oxide pharmaceutically acceptable salt, ester, or prodrug thereof, wherein M, R$^{100}$, R$^{101}$, R$^{104}$, R$^{105}$, R$^{106}$, R$^{107}$, R$^{108}$, R$^{109}$, R$^{110}$, and R$^{120}$ are as described above.

In the compounds described above, T is, for example, a macrolide selected from:

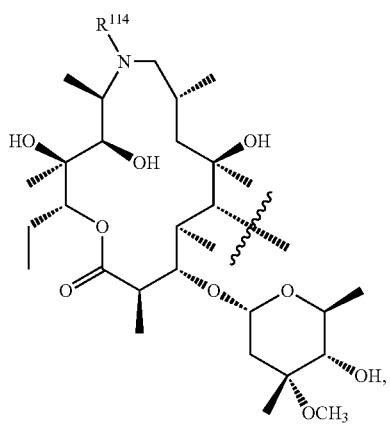
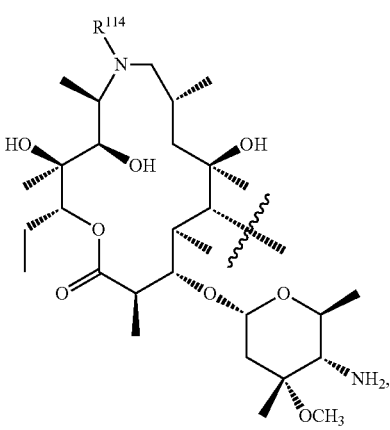
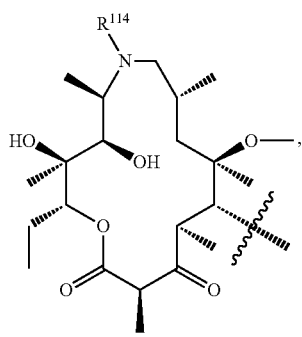
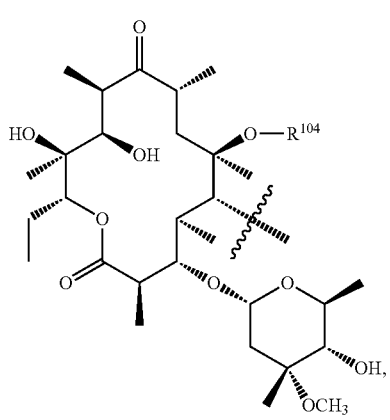
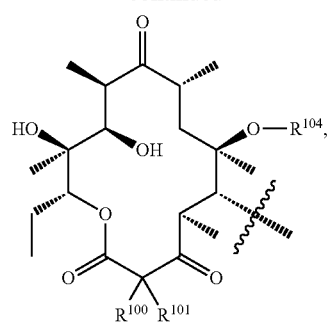
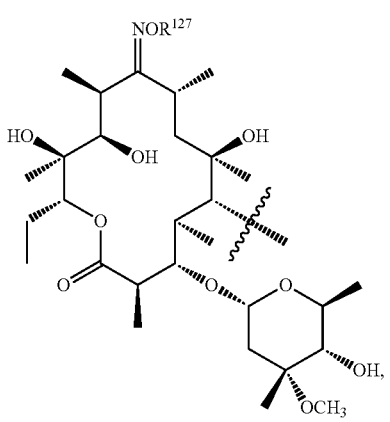
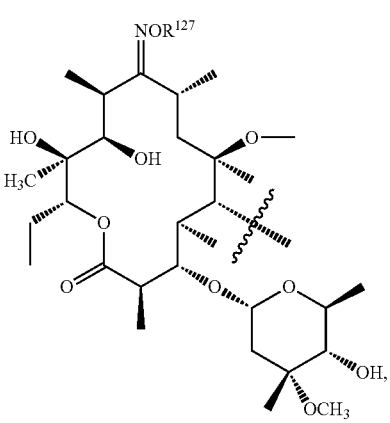
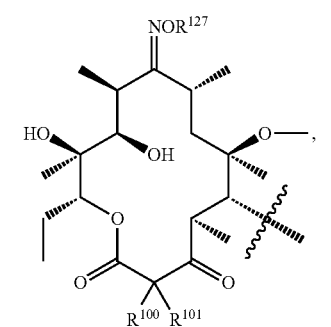

-continued
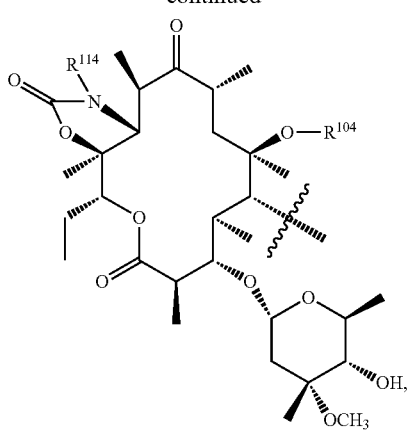
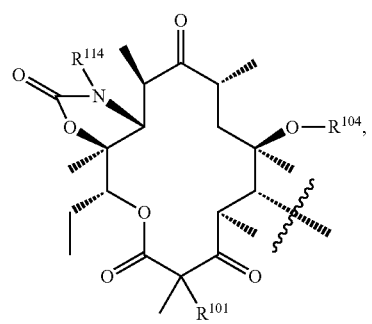
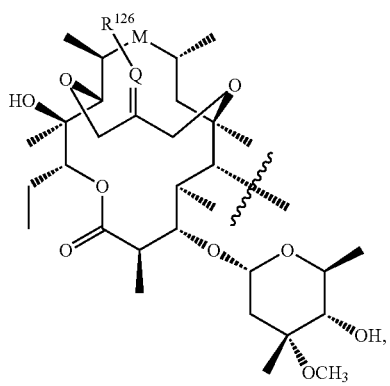
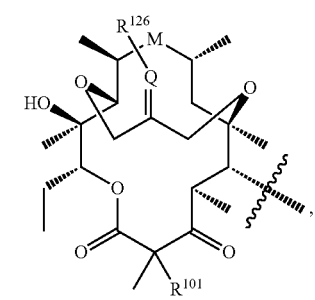
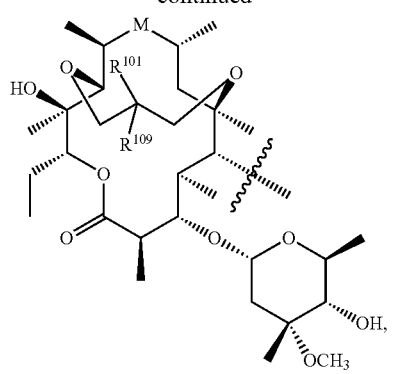
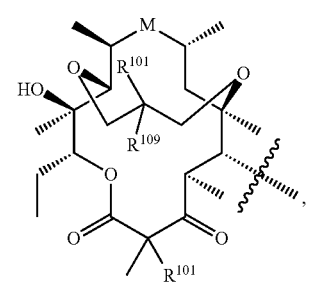
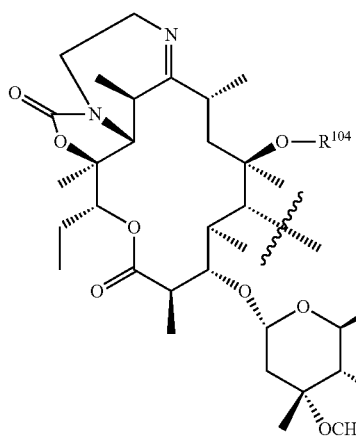
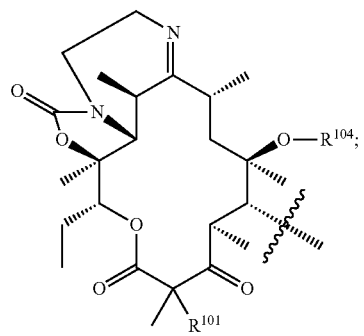
or an N-oxide pharmaceutically acceptable salt, ester, or prodrug thereof, wherein M, $R^{100}$, $R^{101}$, $R^{102}$, $R^{104}$, $R^{109}$, $R^{114}$, $R^{126}$ and $R^{127}$ are as described above.

In the compounds described above, T is, for example, a macrolide selected from:
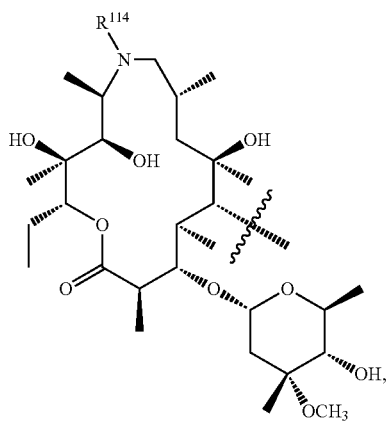
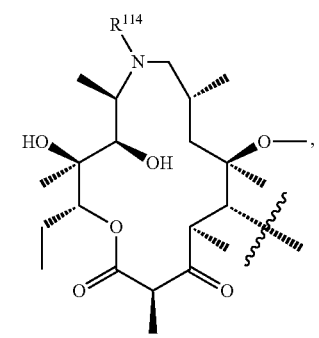
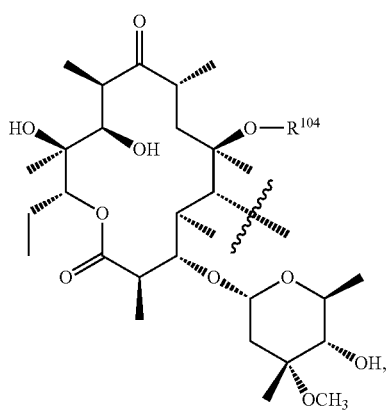
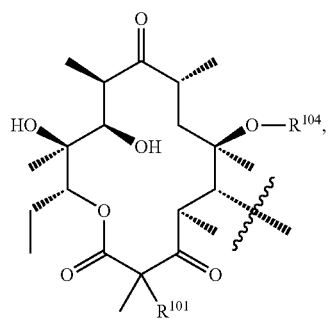
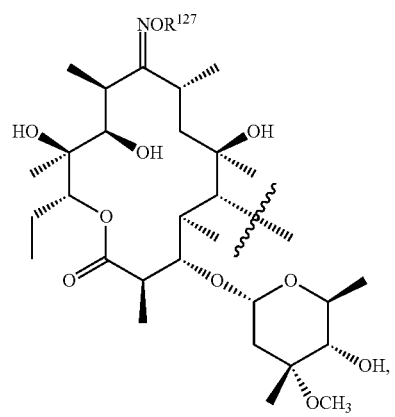
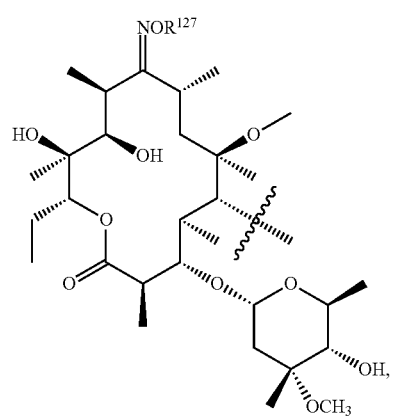
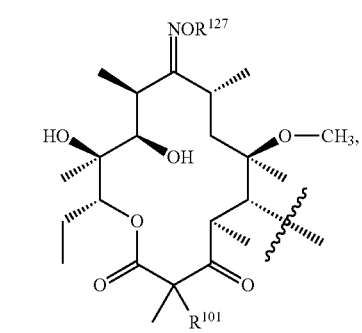
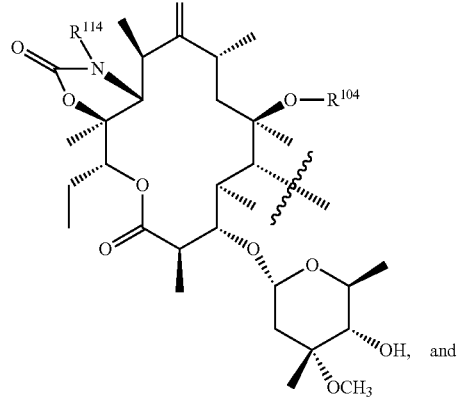

-continued
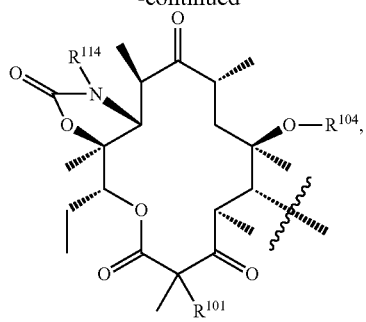
or an N-oxide pharmaceutically acceptable salt, ester, or prodrug thereof, wherein M, $R^1$, $R^2$, $R^{104}$, $R^{114}$, $R^{109}$ and $R^{127}$ are as described above.
In the compounds described above, T is, for example, a macrolide selected from T1 through T33:
T1
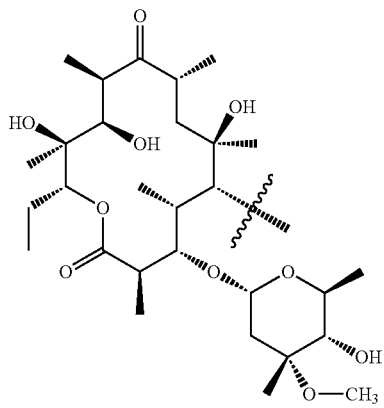
T2
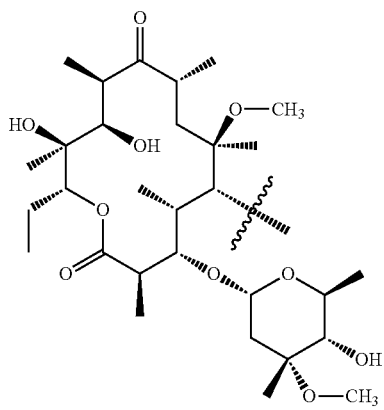
T3
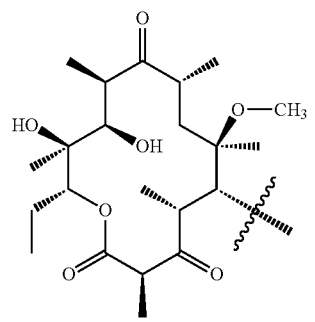
-continued
T4
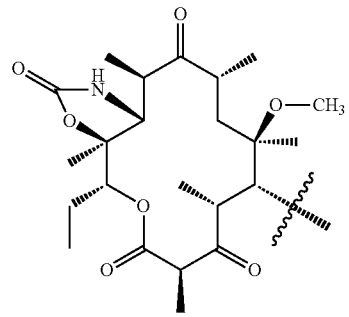
T5
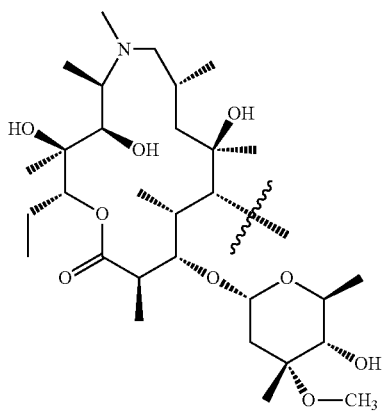
T6
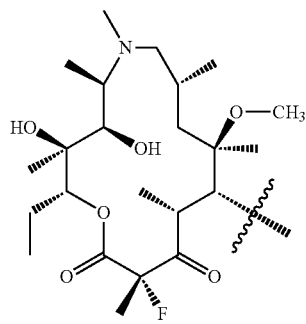
T7
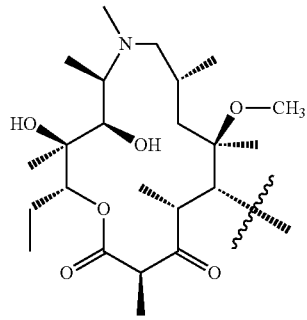

41
-continued
T8
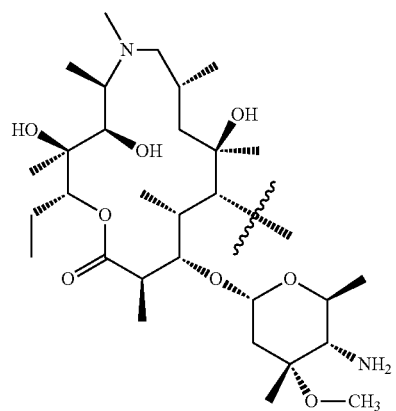
T9
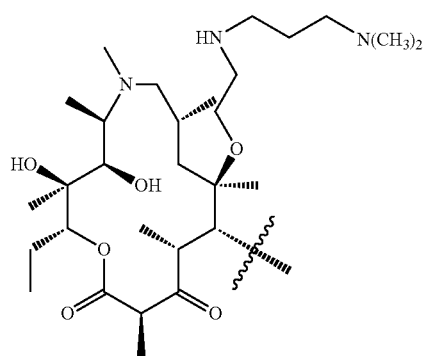
T10
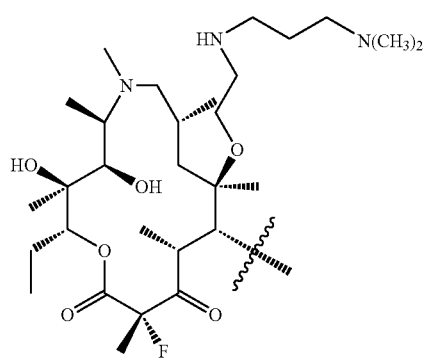
T11
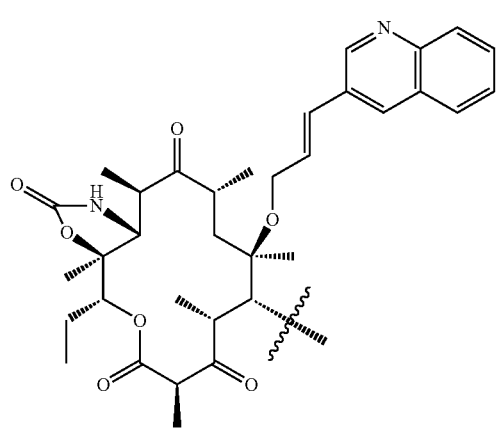
42
-continued
T12
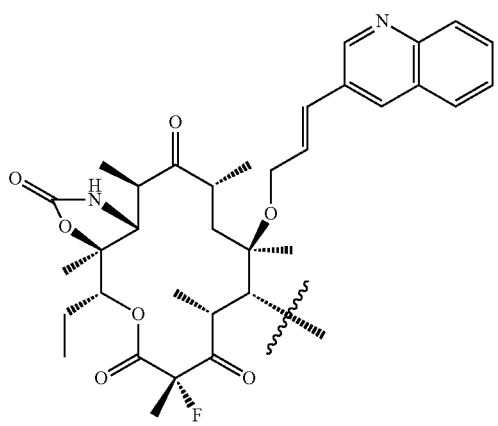
T13
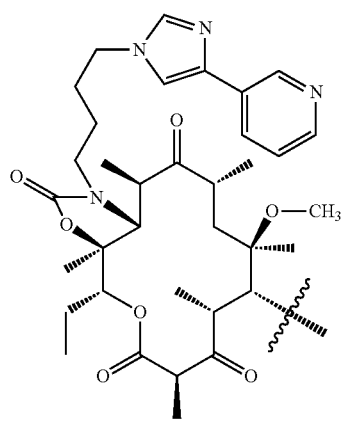
T14
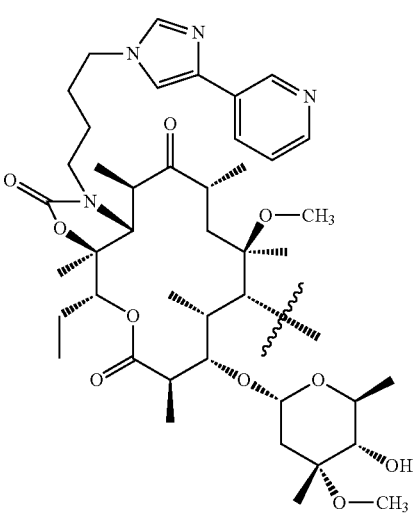

T15
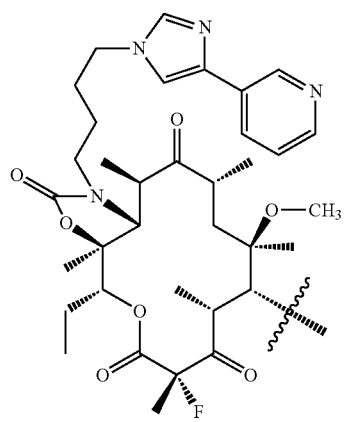
T16
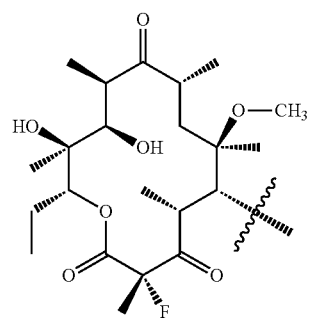
T17
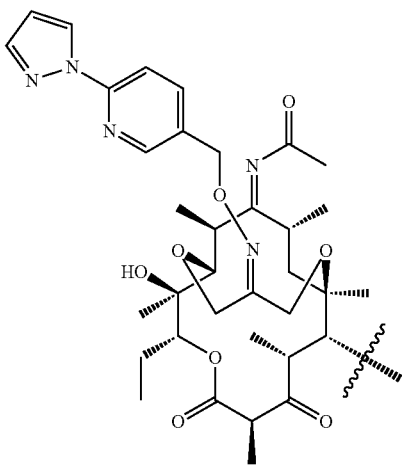
T18
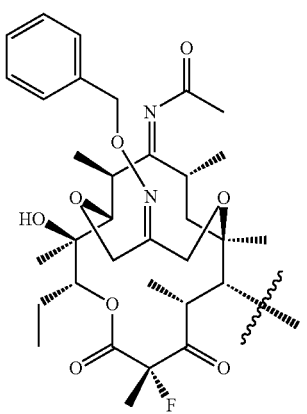
T19
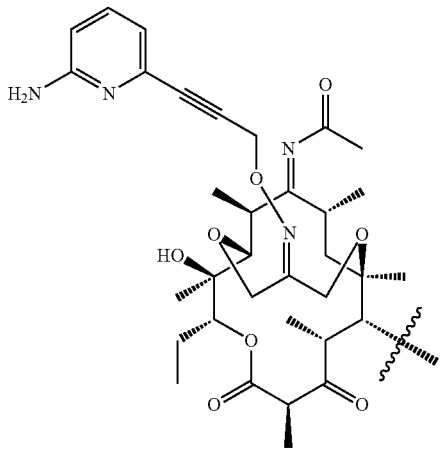
T20
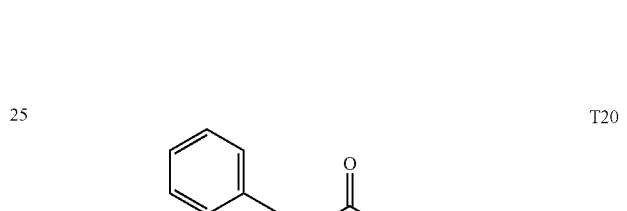
T21
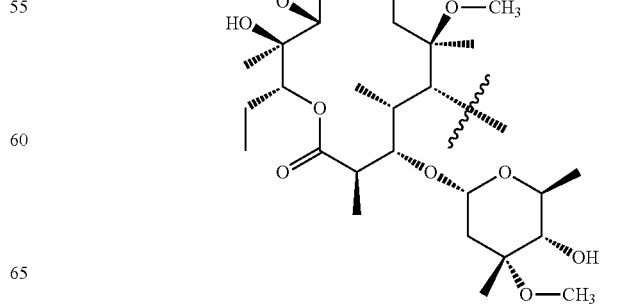

T22
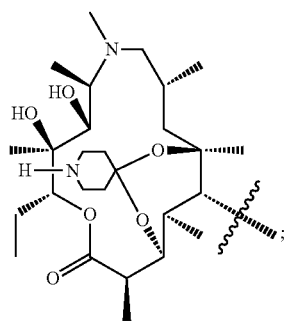
T23
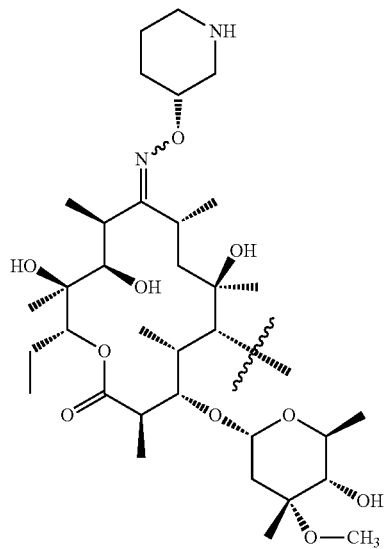
T24
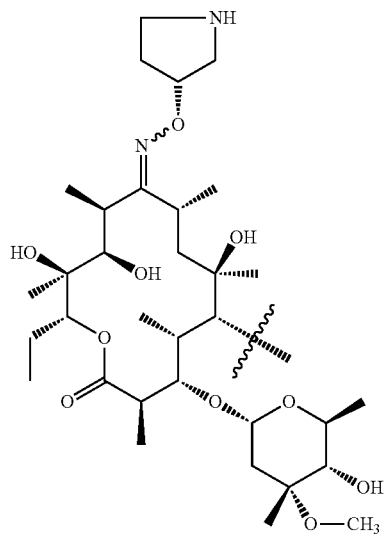
T25
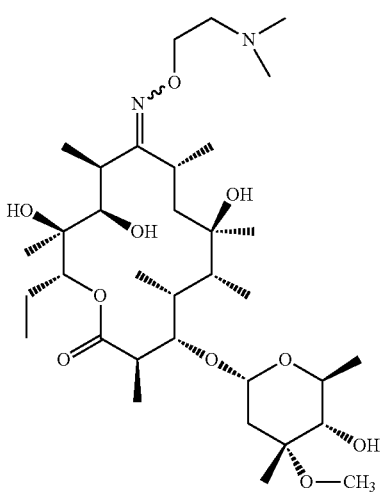
T26
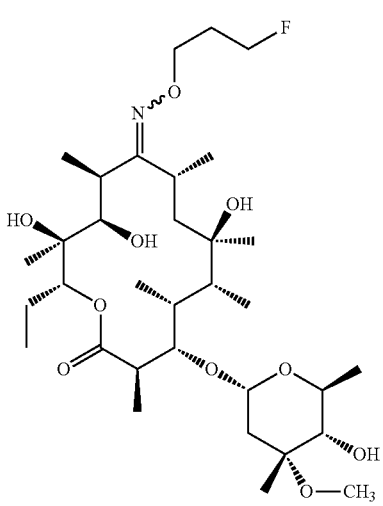
T27
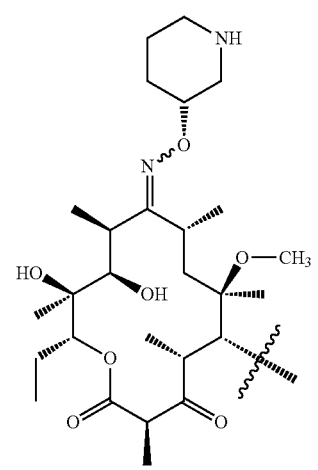

47
-continued
T28
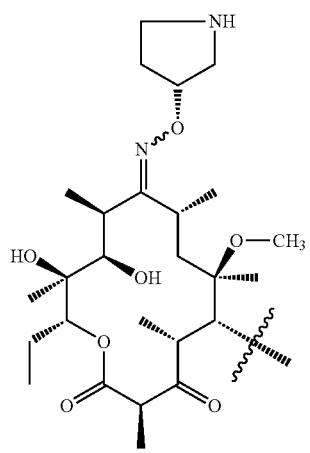
T29
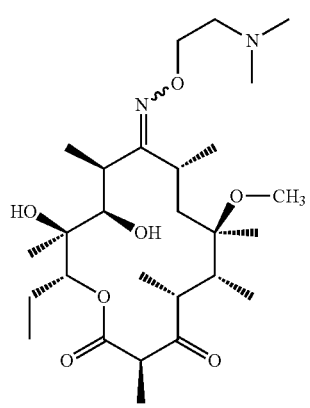
T30
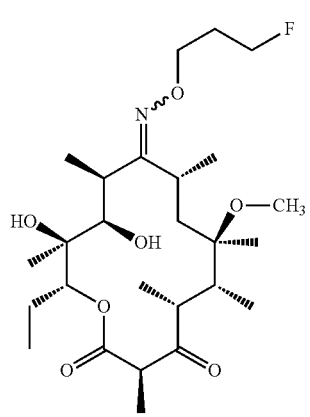
48
-continued
T31
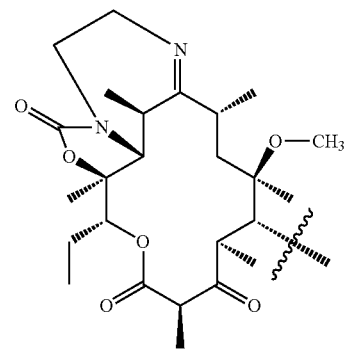
T32
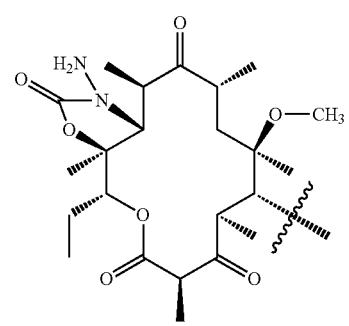
T33
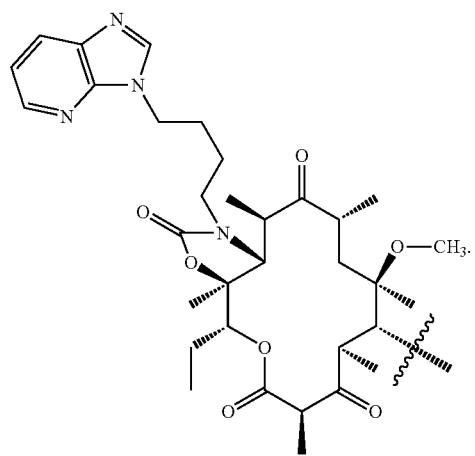

As is seen from the foregoing, the macrolide component of the compounds of the present invention can comprise a wide range of structures. Examples of such macrolide components and their syntheses are provided in the following documents, all of which are incorporated by reference in their entirety: PCT application No. WO 2005/118610, published Dec. 15, 2005, to Rib-X Pharmaceuticals, Inc.; PCT application No. WO 2005/085266, published Sep. 15, 2005, to Rib-X Pharmaceuticals, Inc.; PCT application No. WO 2005/049632, published Jun. 2, 2005, to Rib-X Pharmaceuticals, Inc.; PCT application No. WO 2005/042554, published May 12, 2005, to Rib-X Pharmaceuticals, Inc.; PCT application No. WO 2004/078770, published Sep. 16, 2004, to Rib-X Pharmaceuticals, Inc.; PCT application No. WO 2004/029066, published Apr. 8, 2004, to Rib-X Pharmaceuticals, Inc.; U.S. Pat. No. 6,992,069, to Gu et al., issued Jan. 31, 2006; U.S. Pat. No. 6,953,782, to Phan et al., issued Oct. 11, 2005; U.S. Pat. No. 6,939,861, to Ashley et al., issued Sep. 6, 2005; U.S. Pat. No. 6,927,057, to Khosla et al., issued Aug. 9, 2005; U.S. Pat. No. 6,794,366, to Chu et al., issued Sep. 21, 2004; U.S. Pat. No. 6,762,168, to Chu, issued Jul. 13, 2004; U.S. Pat. No. 6,756,359, to Chu et al, issued Jun. 29, 2994; U.S. Pat. No. 6,750,205, to Ashley et al, issued Jun. 15, 2004; U.S. Pat. No. 6,740,642, to Angehrn et al., issued May 25, 2004; U.S. Pat. No. 6,727,352, to Cheng et al., issued Apr. 27, 2004; U.S. Patent Application Publication No. US 2006/0154881, to Or et al., published Jul. 13, 2006; U.S. Patent Application Publication No. US 2006/0142215, to Tang et al., published Jun. 29, 2006; U.S. Patent Application Publication No. US 2006/0142214, to Or et al, published Jun. 29, 2006; U.S. Patent Application Publication No. US 2006/0122128, to Or et al., published Jun. 8, 2006; U.S Patent Application Publication No. US 2006/0069048, to Or et al. published Mar. 30, 2006; U.S. Patent Application Publication No. US 2005/0272672, to Li et al., published Dec. 8, 2005; U.S. Patent Application Publication No US 2005/0009764, to Burger et al, published Jan. 13, 2005; PCT application No. WO 2006/067589, to Pfizer Products Inc., published Jun. 29, 2006; PCT application No. WO 2004/096823, to Chiron Corporation, published Nov. 11, 2004; PCT application No. WO 2004/096822, to Chiron Corporation, published Nov. 11, 2004; PCT application No. WO 2004/080391, to Optimer Pharmaceuticals, Inc., published Sep. 23, 2004; PCT application No. WO 2004/078771, to Taisho Pharmaceutical Co., Ltd., published Sep. 16, 2004; PCT application no. WO 03/061671, to Kosan Biosciences, Inc. published Jul. 31, 2003; and European Patent Document EP 1 256 587 B1, to the Kitasato Institute, granted Mar. 29, 2006.

The invention also provides a compound having the structure corresponding to any one of the structures listed in Table 1, or a pharmaceutically acceptable salt, ester, N-oxide, or prodrug thereof.

The invention also provides a pharmaceutical composition that contains one or more of the compounds described above and a pharmaceutically acceptable carrier.

The invention also provides a method for treating or preventing a disease state in a mammal by administering to a mammal in need thereof an effective amount of one or more of the compounds described above.

The invention also provides a method of treating a microbial infection in a mammal by administering to the mammal an effective amount of one or more of the compounds described above.

The invention also provides a method of treating a fungal infection in a mammal by administering to the mammal an effective amount of one or more of the compounds described above.

The invention also provides a method of treating a parasitic disease in a mammal by administering to the mammal an effective amount of one or more of the compounds described above.

The invention also provides a method of treating a proliferative disease in a mammal by administering to the mammal an effective amount of one or more of the compounds described above.

The invention also provides a method of treating a viral infection in a mammal by administering to the mammal an effective amount of one or more of the compounds described above.

The invention also provides a method of treating an inflammatory disease in a mammal by administering to the mammal an effective amount of one or more of the compounds described above.

The invention also provides a method of treating a gastrointestinal motility disorder in a mammal by administering to the mammal an effective amount of one or more of the compounds described above.

The invention also provides a method of treating or preventing a disease state in a mammal caused or mediated by a nonsense or missense mutation by administering to the mammal an effective amount of one or more of the compounds described above to suppress expression of the nonsense or missense mutation.

In the methods described herein, the compound or compounds are administered orally, parentally, or topically.

The invention also provides a method of synthesizing the compounds described above.

The invention also provides a medical device containing one or more of the compounds described above. For example, the device is a stent.

3. SYNTHESIS OF THE COMPOUNDS OF THE INVENTION

The invention provides methods for making the compounds of the invention. The following schemes depict exemplary chemistries available for synthesizing the compounds of the invention.

Scheme 1 illustrates the synthesis of triazole compounds of type 5 and 6. Erythromycin can be N-demethylated as described in the art (U.S. Pat. No. 3,725,385; Flynn et al. (1954) J. AM. CHEM. SOC. 76: 3121; Ku et al. (1997) BIOORG. MED. CHEM. LETT. 7: 1203; Stenmark et al. (2000) J. ORG. CHEM. 65: 3875) to afford secondary amine 1. Alkylation of 1 with electrophiles of type 2 yields alkynes of type 3 containing an alkyl chain of appropriate length, generally between one and about four carbon atoms between the nitrogen atom and the alkyne group. Cycloaddition of azides of type 4 with alkynes 3 generates two regioisomeric triazole products. The reaction can be thermally catalyzed, or a number of catalysts could be added to facilitate the reaction (such as, but not limited to, copper (I) iodide: see Tornoe, C. W. et al. (2002) J. ORG. CHEM. 67: 3057). The major isomer (for steric reasons) is the "anti" isomer 5, a 1,4 disubstituted triazole. The minor component is the "syn" isomer 6, a 1,5 disubstituted triazole.

Scheme 1

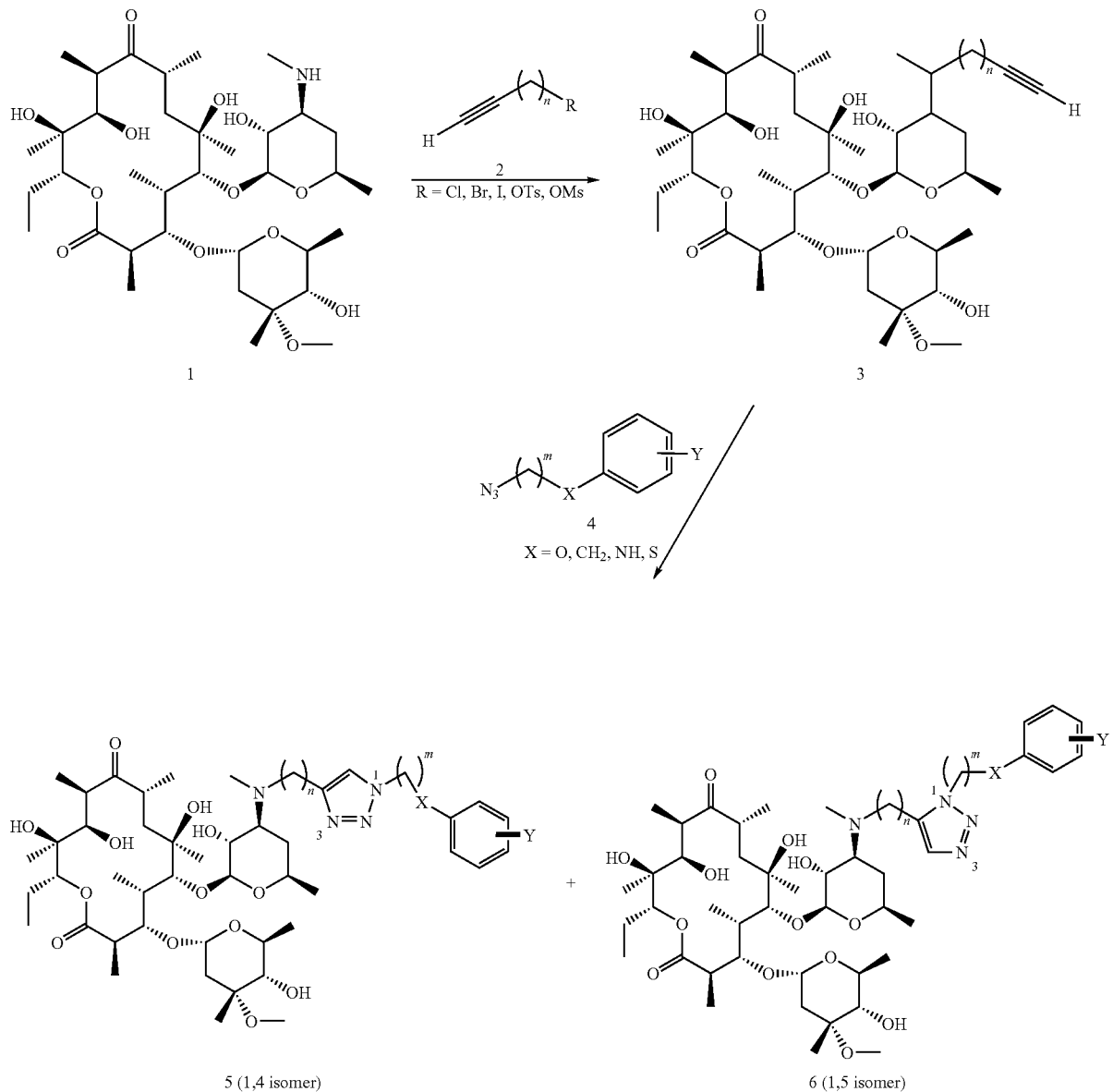

It is to be understood that other macrolide compounds such as, but not limited to, azithromycin and clarithromycin, could be N-demethylated and serve as starting materials for the chemistry exemplified in Scheme 1. Target compounds derived from such alternate macrolide precursors are to be considered within the scope of the present invention.

An alternate approach to compounds similar to compounds 5 and 6 is illustrated by Scheme 2. Acetylenic alcohols of type 14 can be treated with azides 4 to yield intermediate alcohol 15 (along with a minor amount of the regioisomeric triazole). Tosylation of 15 will provide tosylates 16 which can serve as alkylating agents for macrolide amines of type 1 to afford targets 5 (and its isomer 6). (It will be appreciated that order sulfonate derivatives or halides could be formed from intermediate alcohol 15, and these would be useful as electrophiles for the allylation of macrolide amines such as 1 to afford compounds of the invention.)

Scheme 2

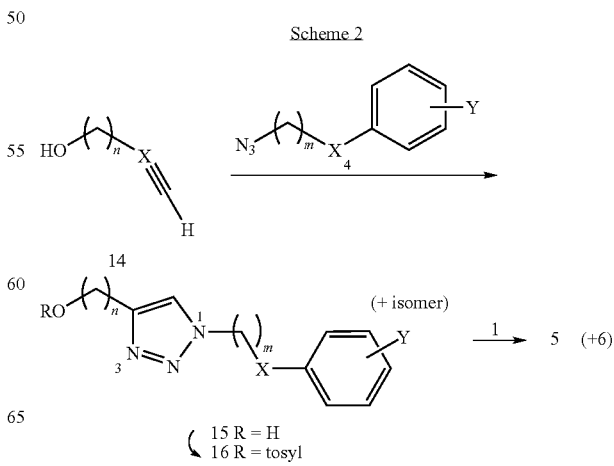

Other starting materials for the synthesis of compounds of the present invention are readily synthesizable. For example, des-methyl macrolide amines 22 and 23 can be prepared from azithromycin and clarithromycin respectively, using the same procedure for the synthesis of 1 from erythromycin. Ketolide derivatives (C-3 keto compounds synthesized from macrolides) of the present invention can be prepared by chemistry such as that shown in Scheme 5. Clarithromycin-derived amine 23 is alkylated with tosylate 24 to afford alkyne 25. The cladinose sugar at C-3 is hydrolyzed to afford the C-3 hydroxy intermediate 26, which is then selectively acetylated on the hydroxyl of the aminosaccharide group to yield 27. Oxidation of 27 yields C-3 keto derivative 28 which is then deacylated to provide alkyne 29. Alkyne 29 can be exposed to the chemistry of Schemes 1 and 3 above to deliver triazole and isoxazole compounds of the present invention that have C-3 keto clarithromycin-derived structures. It will be understood that alkylation of 23 with electrophiles of type 7, and then exposure of the product nitriles to the chemistry shown in Schemes 5 and 2, will yield tetrazoles that have C-3 keto clarithromycin-derived structures. Additionally, C-3 keto azithromycin and erythromycin intermediates could be prepared from 1 and 22 using the chemistry of Scheme 3, and subsequently serve as starting materials for compounds of the present invention.

Scheme 3

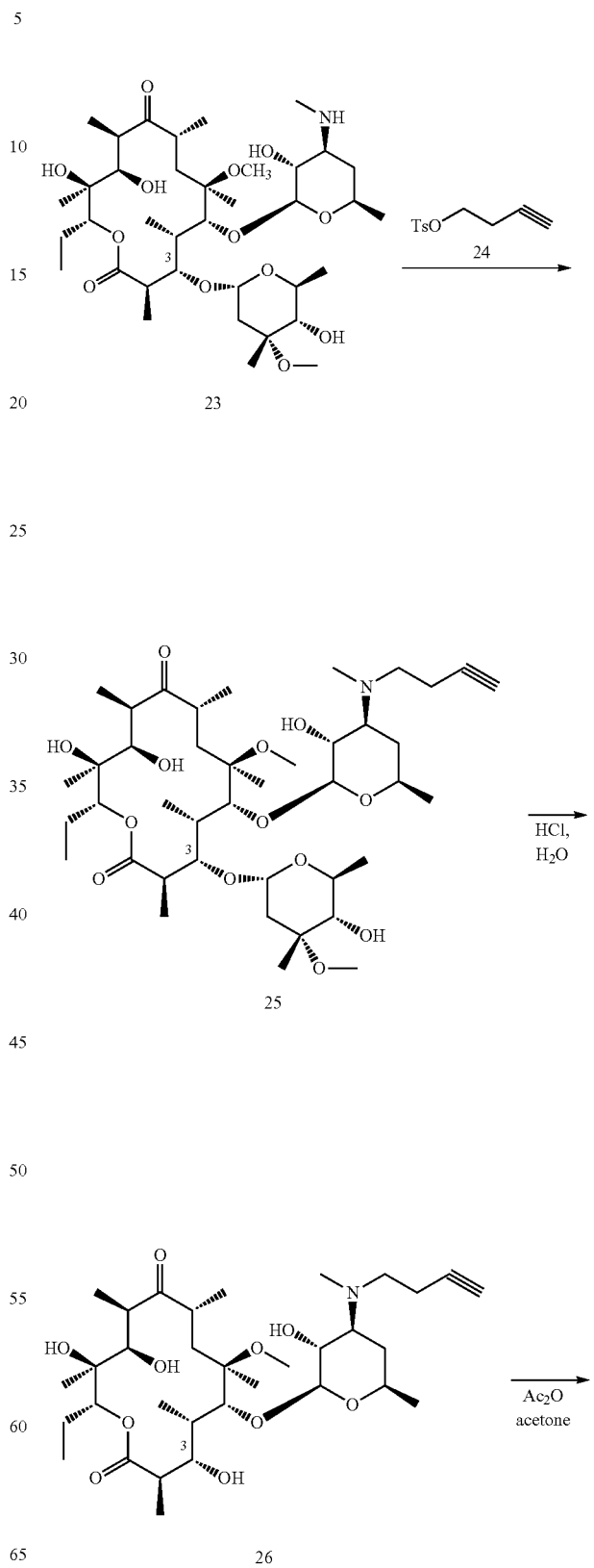

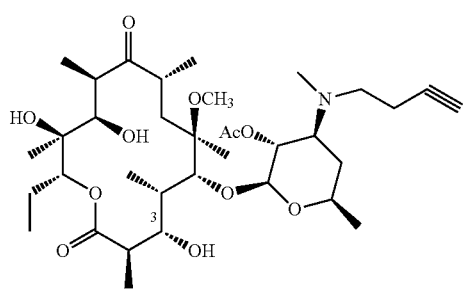

27

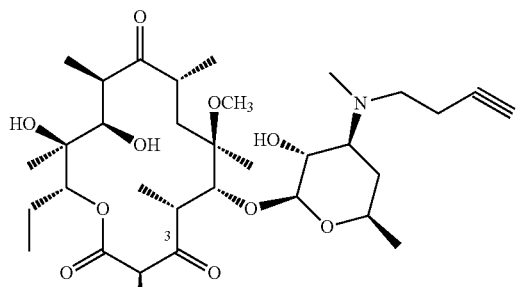

29

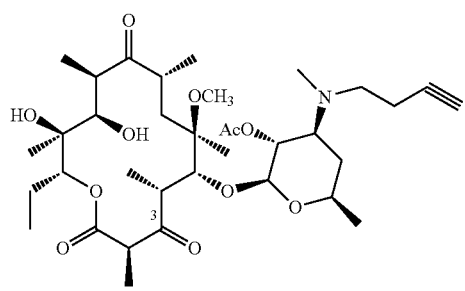

28

Intermediate azides of type 4 used to make compounds of the present invention can be synthesized using the methods exemplified in Schemes 4 and 5. Phenols, anilines, and thiophenols of type 30 can undergo Mitsunobu etherification processes with α,ω-halo alcohols (such as, but not limited to, 2-bromoethanol) to generate halides of type 31. Displacement of the halogen with sodium azide yields azides 4a. Alternatively, direct alkylation of intermediates 30 with α,ω-halo alcohols yields alcohols of type 32, which can be converted to halides 31 or converted to a sulfonate derivative such as 33, for subsequent azide displacement to afford azides 4a. Arylpropanols of type 34, and pyridylpropanols of type 35, can be converted to azides 4b and 4c via sulfonates such as 36 and 37. It will be appreciated that pyridyl derivatives with alternate substitution patterns (ortho and para), and alternate chain-lengths between the aryl moiety and the azide group can also be made using chemistry known in the art. It is intended that all such isomers and homologues are within the scope of the present invention.

Scheme 4

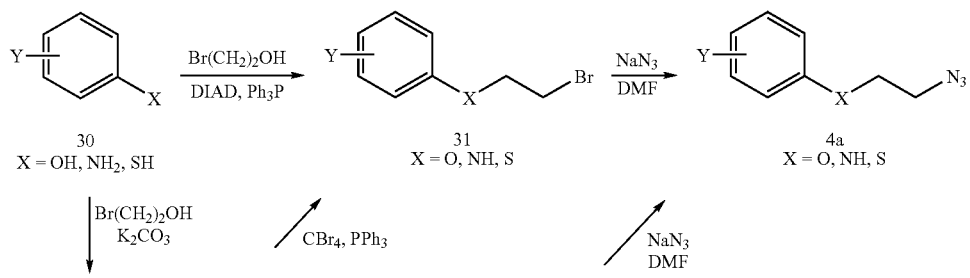

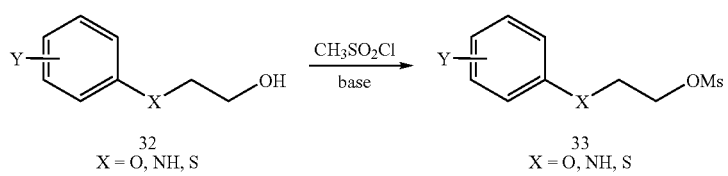

Scheme 5

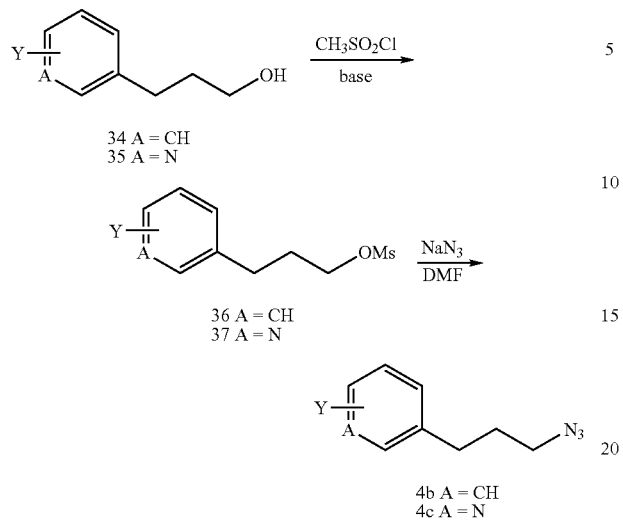

Nitrile oxides of type 11 used to make compounds of the present invention can be synthesized using the method exemplified in Scheme 6. Substituted arylalkanols of type 32 (or pyridylalkanols) of various chain length between the aryl moiety and the alcohol group can be oxidized to aldehydes 38. Conversion of the aldehyde to oximes 39 can be followed by conversion to intermediate nitrile oxides 11 using chloramine T (or other reagents used in combination with organic amine bases such as N-bromosuccinimide, N-chlorosuccinimide, t-butyl hypochlorite, lead tetraacetate etc.). The reaction to form the nitrile oxide can be run in the presence of an appropriate alkyne to trap the unstable intermediates 11 directly, affording a mixture of anti and syn isoxazole products.

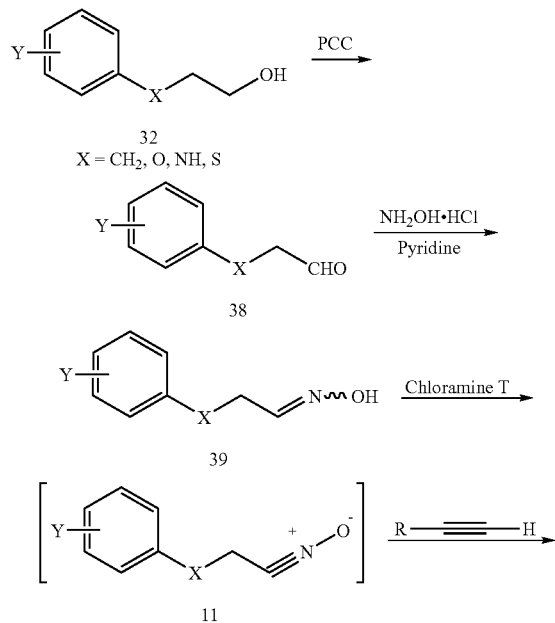

4. CHARACTERIZATION OF COMPOUNDS OF THE INVENTION

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. *High-throughput assays can use one or more different assay techniques including, but not limited to, those described below.*

(1) Surface Binding Studies. A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays can be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9)).

5. FORMULATION AND ADMINISTRATION

The compounds of the invention can be useful in the prevention or treatment of a variety of human or other animal, including mammalian and non mammalian, disorders, including for example, bacterial infection, fungal infections, viral infections, parasitic diseases, and cancer. It is contemplated that, once identified, the active molecules of the invention can be incorporated into any suitable carrier prior to use. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's *Pharmaceutical Sciences*, (Gennaro, A., ed.), Mack Pub., (1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or moulding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Moulded tablets can be made by moulding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, and/or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in therapeutically effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

The compounds of the present invention can be administered directly to a tissue locus by applying the compound to a medical device that is placed in contact with the tissue. An example of a medical device is a stent, which contains or is coated with one or more of the compounds of the present invention.

For example, an active compound can be applied to a stent at the site of vascular injury. Stents can be prepared by any of the methods well known in the pharmaceutical art. See, e.g., Fattori, R. and Piva, T., "Drug Eluting Stents in Vascular Intervention," Lancet, 2003, 361, 247-249; Morice, M. C., "A New Era in the Treatment of Coronary Disease?"European Heart Journal, 2003, 24, 209-211; and Toutouzas, K. et al., "Sirolimus-Eluting Stents: A Review of Experimental and Clinical Findings," Z. Kardiol., 2002, 91(3), 49-57. The stent can be fabricated from stainless steel or another bio-compatible metal, or it can be made of a bio-compatible polymer. The active compound can be linked to the stent surface, embedded and released from polymer materials coated on the stent, or surrounded by and released through a carrier which coats or spans the stent. The stent can be used to administer single or multiple active compounds to tissues adjacent to the stent.

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the compounds or pharmaceutical compositions thereof will be administered orally, parenterally and/or topically at a dosage to obtain and maintain a concentration, that is, an amount, or blood-level or tissue level of active component in the animal undergoing treatment which will be anti-microbially effective. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum and the daily dosage can be progressively increased during the course of treatment depending on the particular situation. If desired, the daily dose can also be divided into multiple doses for administration, for example, two to four times per day.

Various disease states or conditions in humans and other mammals are found to be caused by or mediated by nonsense or missense mutations. These mutations cause or mediate the disease state or condition by adversely affecting, for example, protein synthesis, folding, trafficking and/or function. Examples of disease states or conditions in which an appreciable percentage of the disease or condition is believed to result from nonsense or missense mutations include hemophilia (factor VIII gene), neurofibromatosis (NF1 and NF2 genes), retinitis pigmentosa (human USH2A gene), bullous skin diseases like Epidermolysis bullosa pruriginosa (COL7A1 gene), cystic fibrosis (cystic fibrosis transmembrane regulator gene), breast and ovarian cancer (BRCA1 and BRCA2 genes), Duchenne muscular dystrophy (dystrophin gene), colon cancer (mismatch repair genes, predominantly in MLH1 and MSH2), and lysosomal storage disorders such as Neimann-Pick disease (acid sphingomyelinase gene). See Sanders C R, Myers J K. Disease-related misassembly of membrane proteins. Annu Rev Biophys Biomol Struct. 2004; 33:25-51; National Center for Biotechnology Information (U.S.) *Genes and disease* Bethesda, Md.: NCBI, NLM ID: 101138560; and Raskó, István; Downes, C S *Genes in medicine: molecular biology and human genetic disorders* 1st ed. London; New York: Chapman & Hall, 1995. NLM ID: 9502404. The compounds of the present invention can be used to treat or prevent a disease state in a mammal caused or mediated by such nonsense or missense mutations by administering to a mammal in need thereof an effective amount of the present invention to suppress the nonsense or missense mutation involved in the disease state.

6. EXAMPLES

Nuclear magnetic resonance (NMR) spectra were obtained on a Biuker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

Some of the abbreviations used in the following experimental details of the synthesis of the examples are defined below:

hr=hour(s); min=minute(s); mol=mole(s); mmol=millimole(s); M=molar; µM=micromolar; g=gram(s); µg=microgram(s); rt=room temperature; L=liter(s); mL=milliliter(s); $Et_2O$=diethyl ether; THF=tetrahydrofuran; DMSO=dimethyl sulfoxide; EtOAc=ethyl acetate; $Et_3N$=triethylamine; i-$Pr_2NEt$=diisopropylethylamine; $CH_2Cl_2$=methylene chloride; $CHCl_3$=chloroform; $CDCl_3$=deuterated chloroform; $CCl_4$=carbon tetrachloride; MeOH=methanol; $CD_3OD$=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCl=t-butyldiphenylchlorosilane; Hunig's Base=N,N-diisopropylethylamine; DMAP=4-dimethylaminopyridine; CuI=copper (I) iodide; MsCl=methanesulfonyl chloride; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; Pd(dppf)$Cl_2$=dichloro[1,1'-bis(diphenylphosphino)ferrocene]palladium (II).

Exemplary compounds synthesized in accordance with the invention are listed in Table 1. A bolded or dashed bond is shown to indicate a particular stereochemistry at a chiral center, whereas a wavy bond indicates that the substitutent can be in either orientation or that the compound is a mixture thereof. It should also be known that in the interest of space, the chemical structures for some compounds have been condensed, for example the methyl and ethyl group substituents are designated with just a carbon backbone representation, and the unsaturated bonds in the triazole rings might not always be visible.

The compounds of the present invention can be prepared, formulated, and delivered as pharmaceutically acceptable salts, esters, and prodrugs. For convenience, the compounds are generally shown without indicating a particular salt, ester, or prodrug form.

TABLE 1
| Compound | Structure |
|---|---|
| 101 | 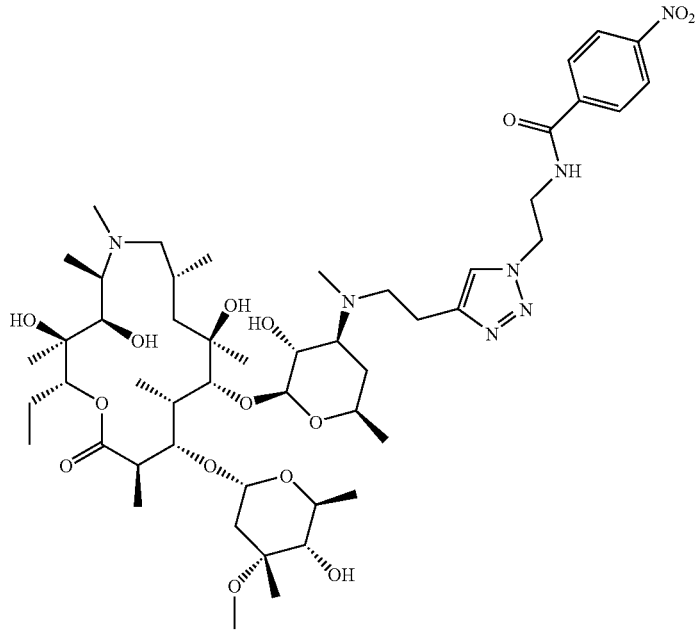 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNC(=O)c4ccc([N+](=O)[O-])cc4)nn3)[C@H]2O)[C@](C)(O)C[C@@H](C)CN(C)[C@H](C)[C@@H](O)[C@]1(C)O] |
| 102 | 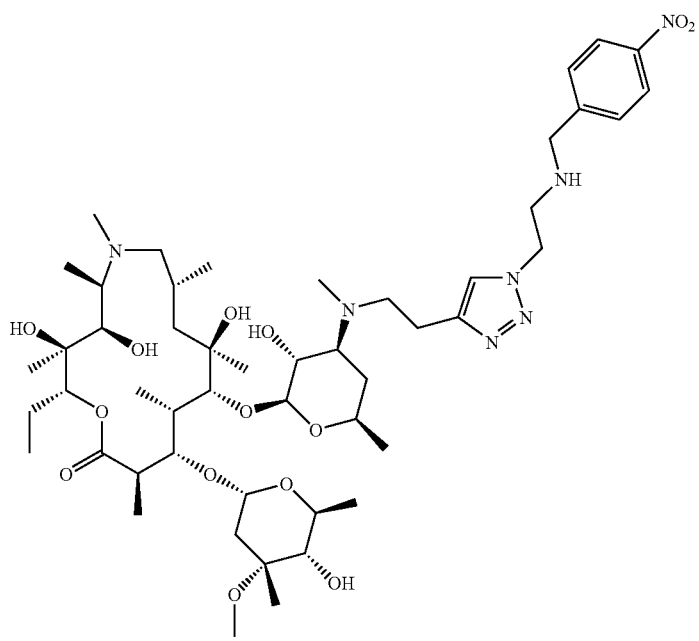 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNCc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 103 | 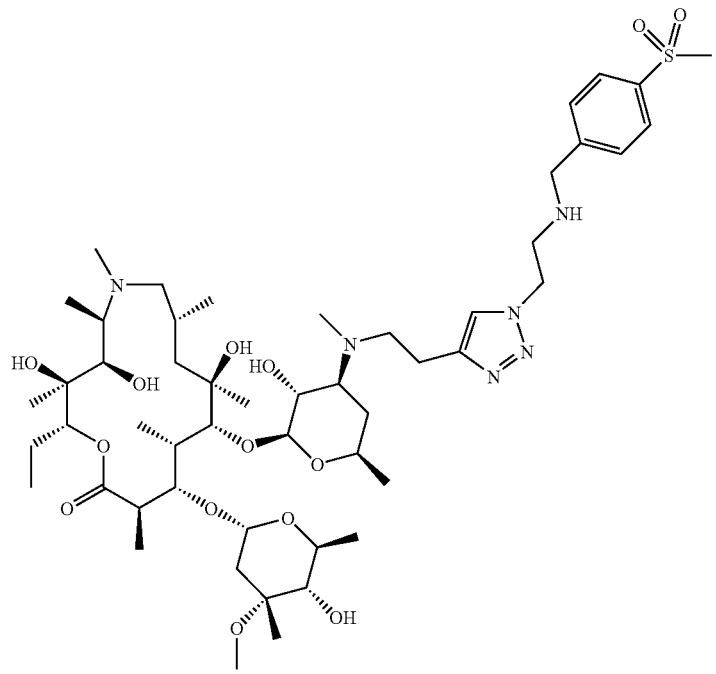 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNCc4ccc(S(C)(=O)=O)cc4)nn3)[C@H]2O)[C@](C)(O)C[C@@H](C)CN(C)[C@H](C)[C@@H](O)[C@]1(C)O] |
| 104 | 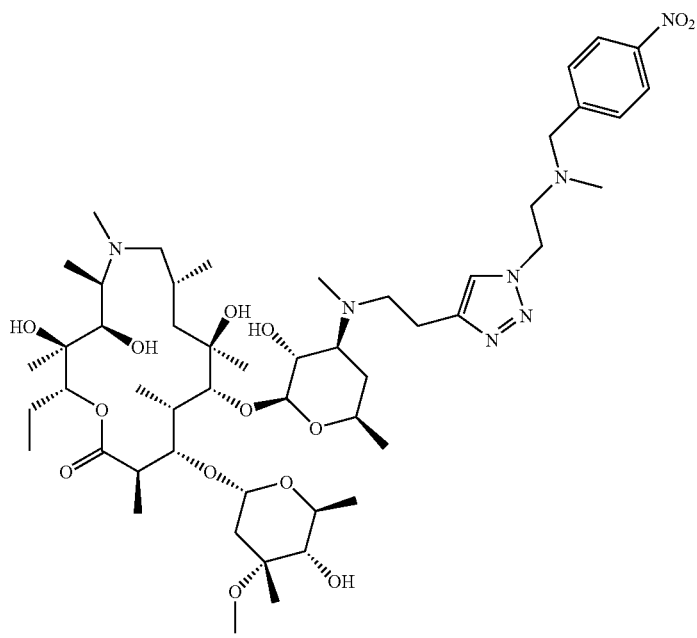 |

TABLE 1-continued
| Compound | Structure |
|---|---|
| 105 | 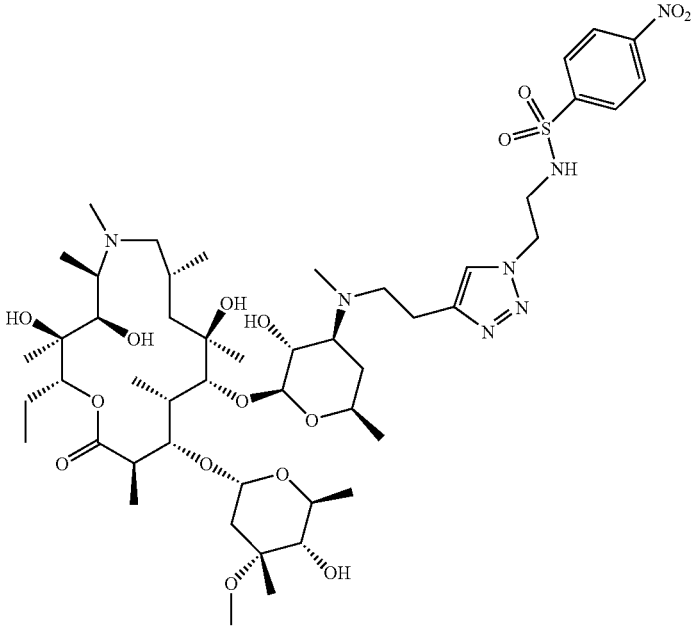 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNS(=O)(=O)c4ccc([N+](=O)[O-])cc4)nn3)[C@H]2O)[C@](C)(O)C[C@@H](C)CN(C)[C@H](C)[C@@H](O)[C@]1(C)O] |
| 106 | 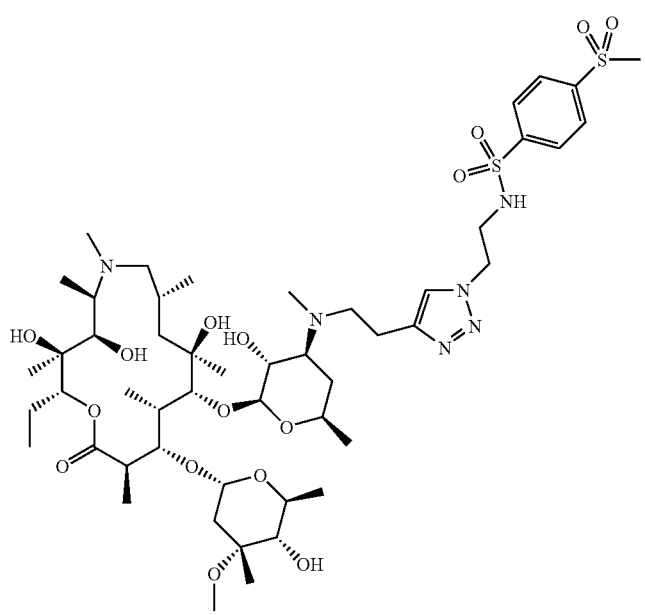 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNS(=O)(=O)c4ccc(S(C)(=O)=O)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 107 | 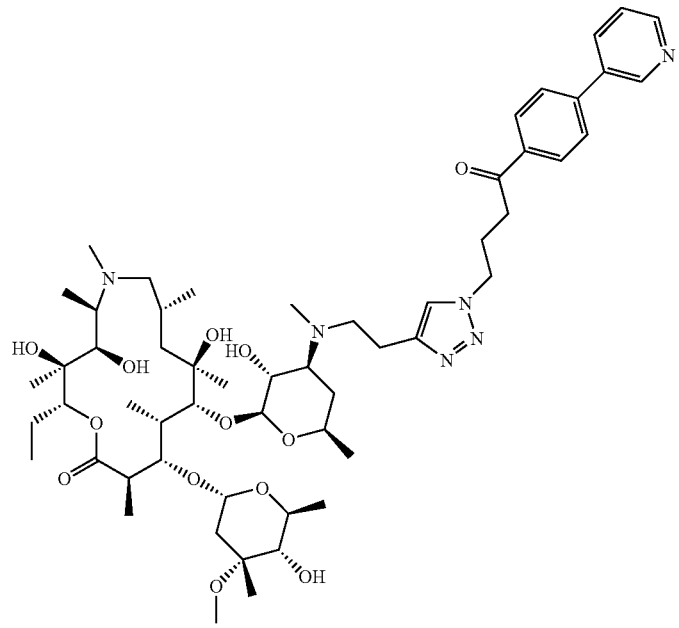 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCC(=O)c4ccc(-c5cccnc5)cc4)nn3)[C@H]2O)[C@](C)(O)C[C@@H](C)CN(C)[C@H](C)[C@@H](O)[C@]1(C)O] |
| 108 | 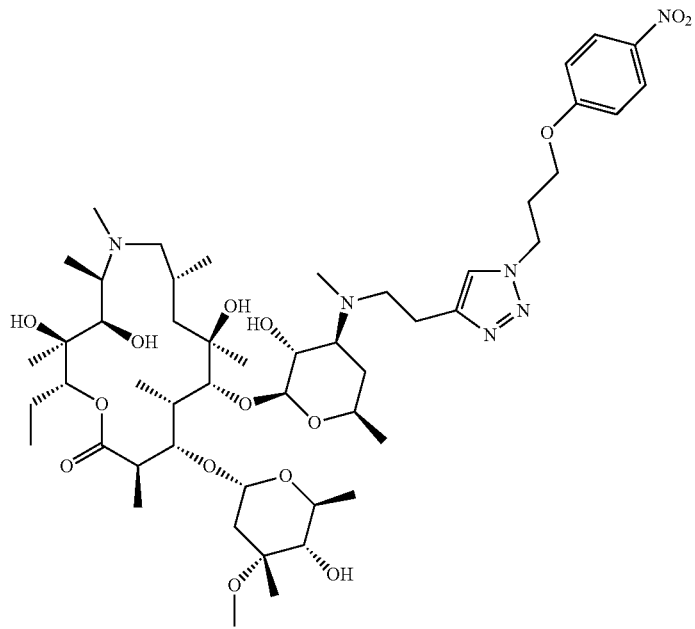 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 109 | 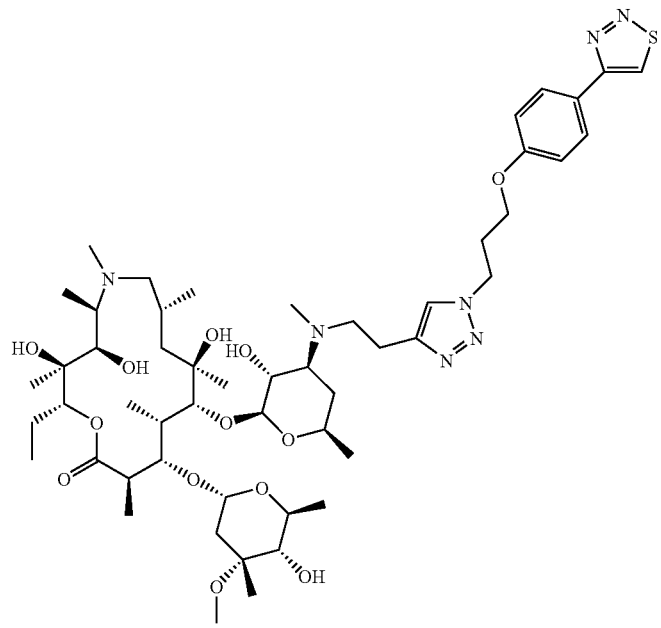 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5csnn5)cc4)nn3)[C@H]2O)[C@](C)(O)C[C@@H](C)CN(C)[C@H](C)[C@@H](O)[C@]1(C)O] |
| 110 | 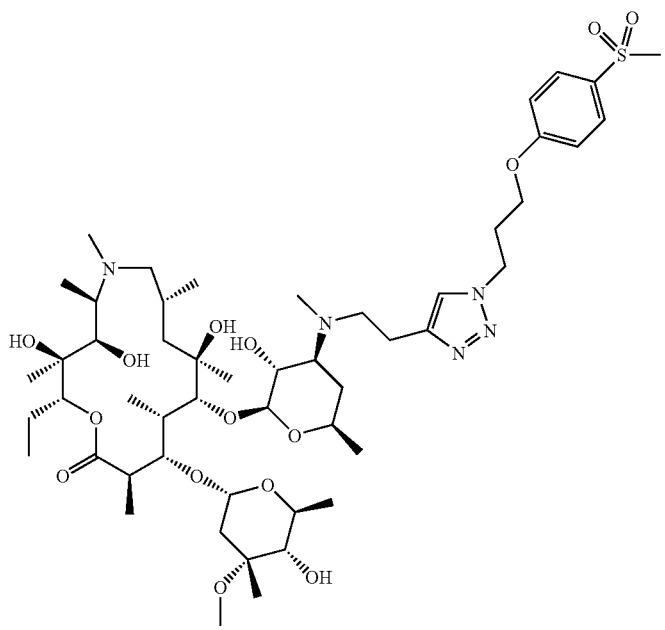 |

TABLE 1-continued
| Compound | Structure |
|---|---|
| 111 | 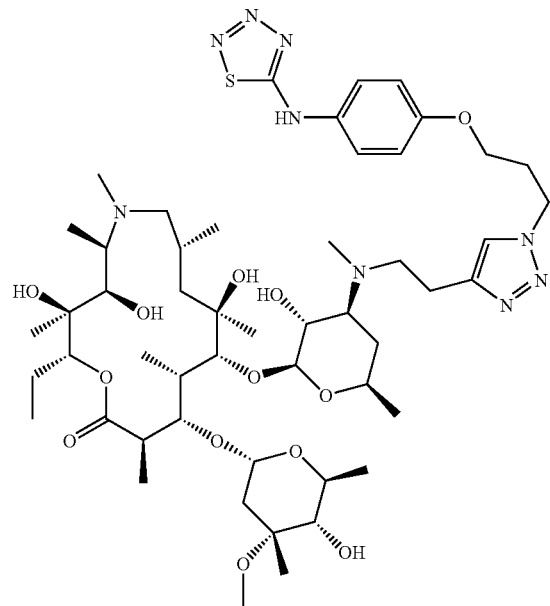 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(Nc5nnns5)cc4)nn3)[C@H]2O)[C@](C)(O)C[C@@H](C)CN(C)[C@H](C)[C@@H](O)[C@]1(C)O] |
| 112 | 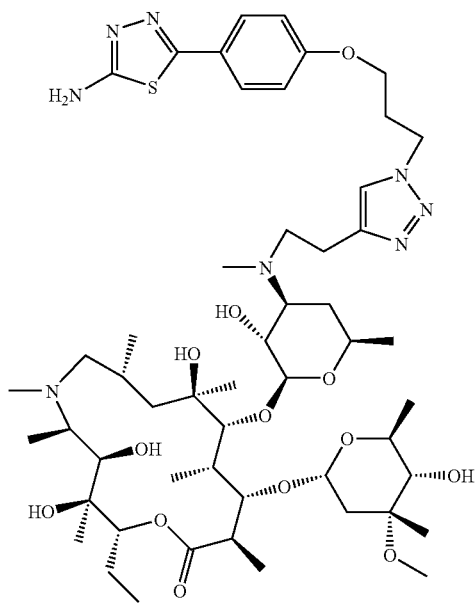 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5nnc(N)s5)cc4)nn3)[C@H]2O)[C@](C)(O)C[C@@H](C)CN(C)[C@H](C)[C@@H](O)[C@]1(C)O] |

TABLE 1-continued

| Compound | Structure |
|---|---|
| 113 | 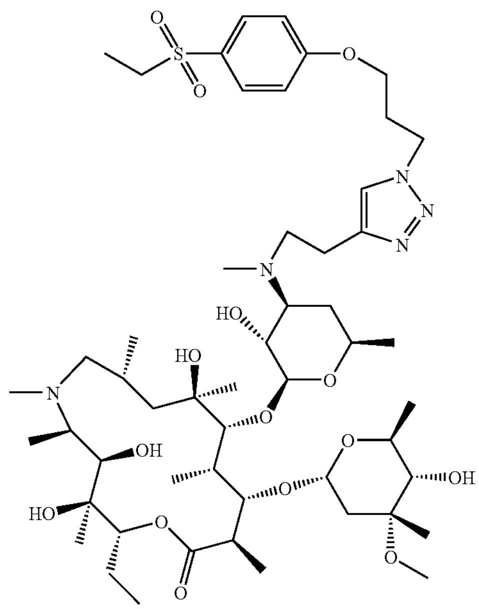 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)CC)cc4)nn3)[C@H]2O)[C@](C)(O)C[C@@H](C)CN(C)[C@H](C)[C@@H](O)[C@]1(C)O] |
| 114 | 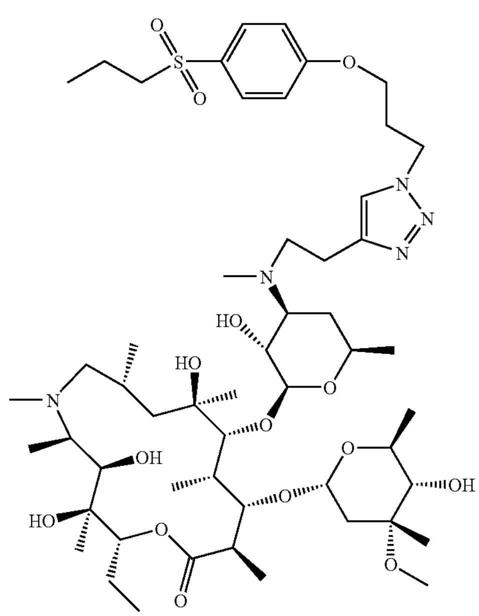 |

TABLE 1-continued

| Compound | Structure |
| --- | --- |
| 115 | 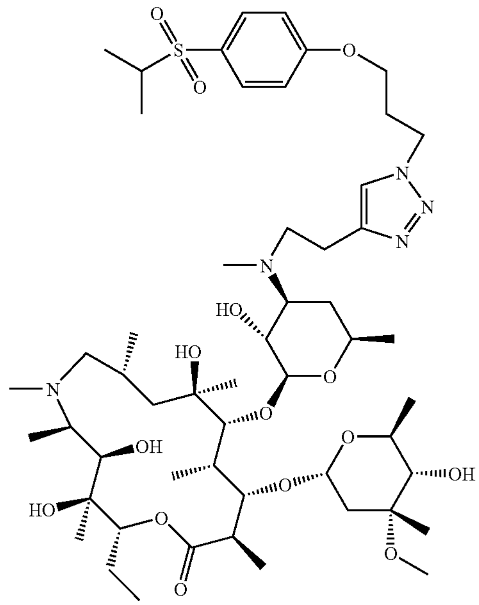 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)C(C)C)cc4)nn3)[C@H]2O)[C@](C)(O)C[C@@H](C)CN(C)[C@H](C)[C@@H](O)[C@]1(C)O] |
| 116 | 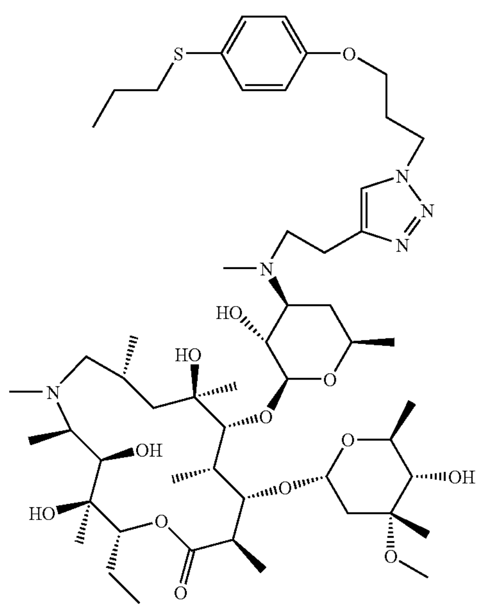 [SMILES: CCCSc1ccc(OCCCn2cc(CCN(C)[C@H]3C[C@@H](C)O[C@@H](O[C@@H]4[C@@H](C)[C@H](O[C@H]5C[C@@](C)(OC)[C@@H](O)[C@H](C)O5)[C@@H](C)C(=O)O[C@H](CC)[C@@](C)(O)[C@H](O)[C@@H](C)N(C)C[C@H](C)C[C@@]4(C)O)[C@@H]3O)nn2)cc1] |

TABLE 1-continued
| Compound | Structure |
|---|---|
| 117 | 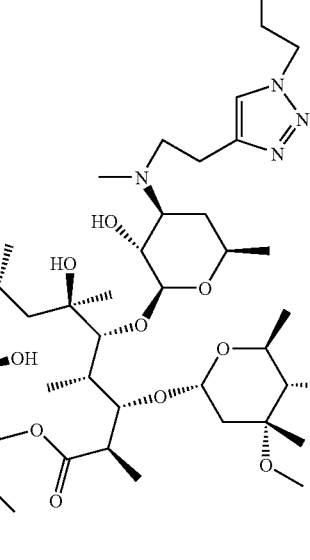 |
| 118 | 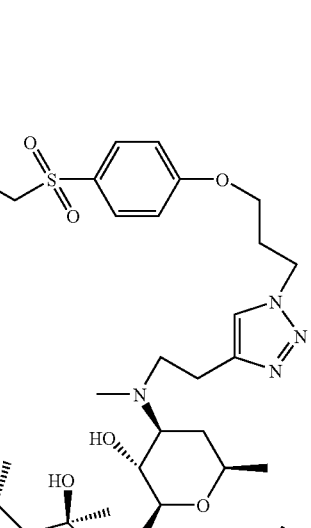 |

TABLE 1-continued

| Compound | Structure |
|---|---|
| 119 | 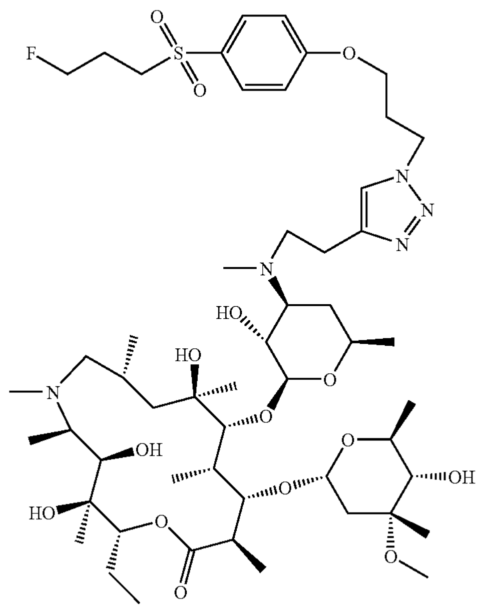 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)CCCF)cc4)nn3)[C@H]2O)[C@](C)(O)C[C@@H](C)CN(C)[C@H](C)[C@@H](O)[C@]1(C)O] |
| 120 | 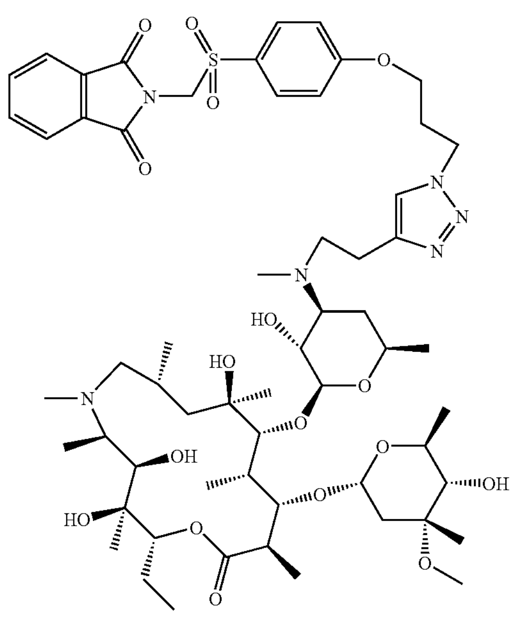 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)CN5C(=O)c6ccccc6C5=O)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 121 | 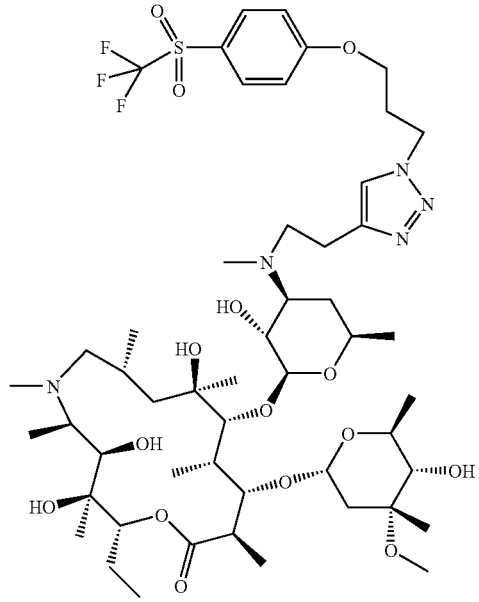 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)C(F)(F)F)cc4)nn3)[C@H]2O)[C@](C)(O)C[C@@H](C)CN(C)[C@H](C)[C@@H](O)[C@]1(C)O] |
| 122 | 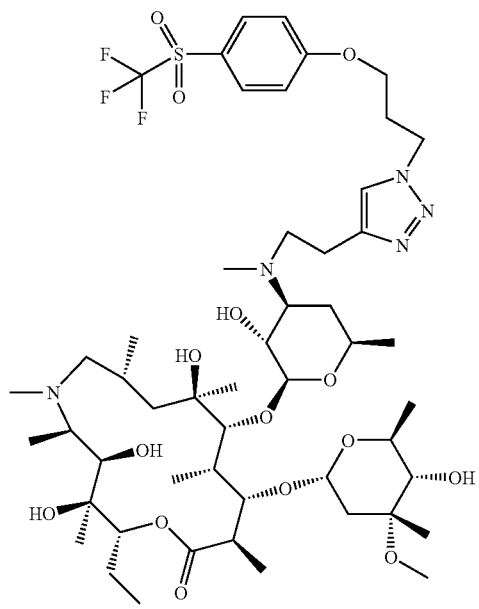 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)C(F)(F)F)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 123 | 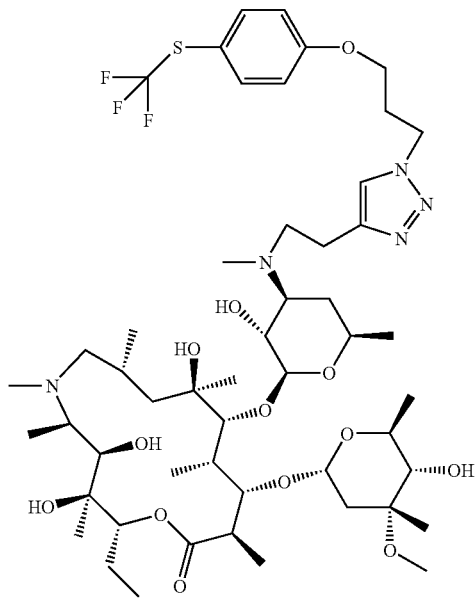 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(SC(F)(F)F)cc4)nn3)[C@H]2O)[C@](C)(O)C[C@@H](C)CN(C)[C@H](C)[C@@H](O)[C@]1(C)O] |
| 124 | 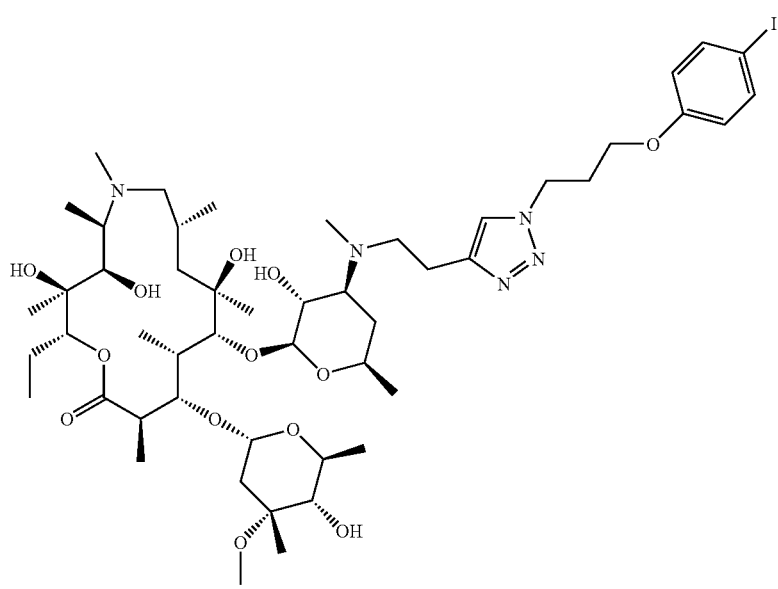 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(I)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 125 | 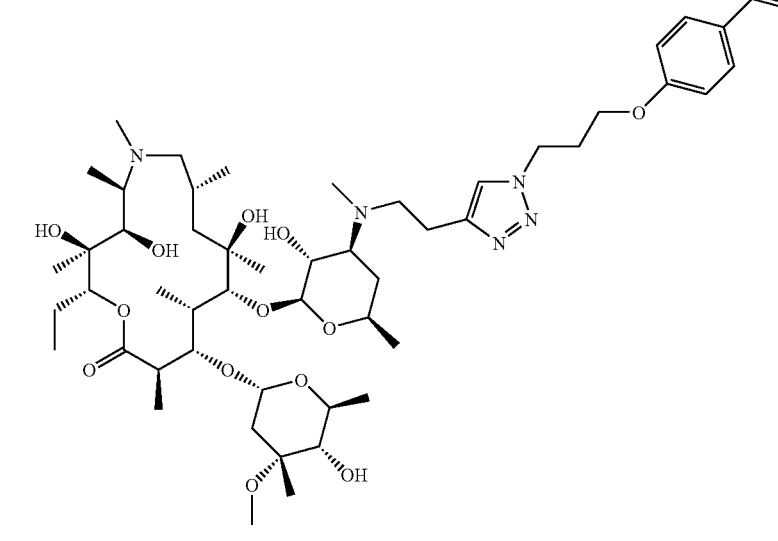 |
| 126 | 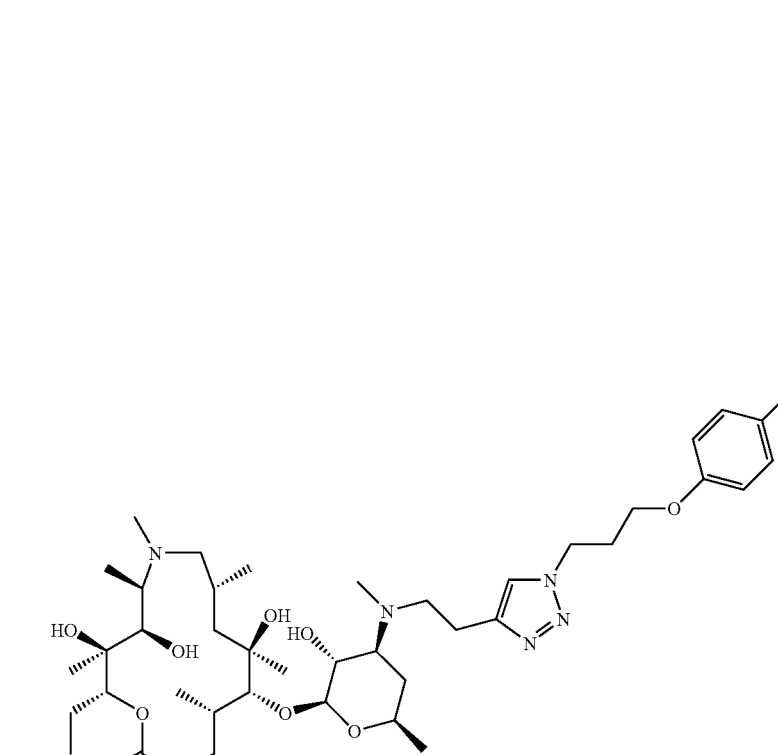 |

TABLE 1-continued
| Compound | Structure |
|---|---|
| 127 | 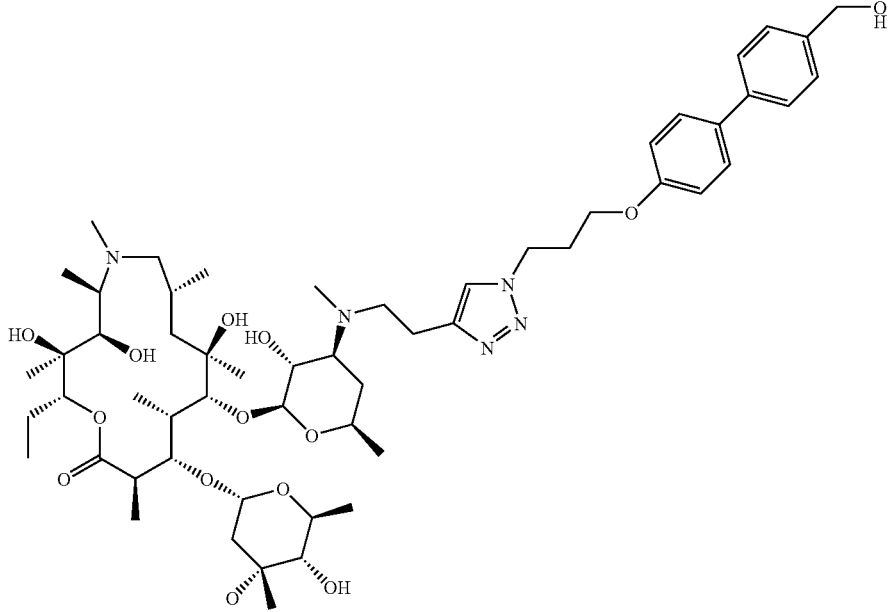 [SMILES: CC[C@H]1OC(=O)[C@H](C)[C@@H](O[C@H]2C[C@@](C)(O)[C@@H](O)[C@H](C)O2)[C@H](C)[C@@H](O[C@@H]2O[C@H](C)C[C@H](N(C)CCc3cn(CCCOc4ccc(-c5ccc(CO)cc5)cc4)nn3)[C@H]2O)[C@](C)(O)C[C@@H](C)CN(C)[C@H](C)[C@@H](O)[C@]1(C)O] |
| 128 | 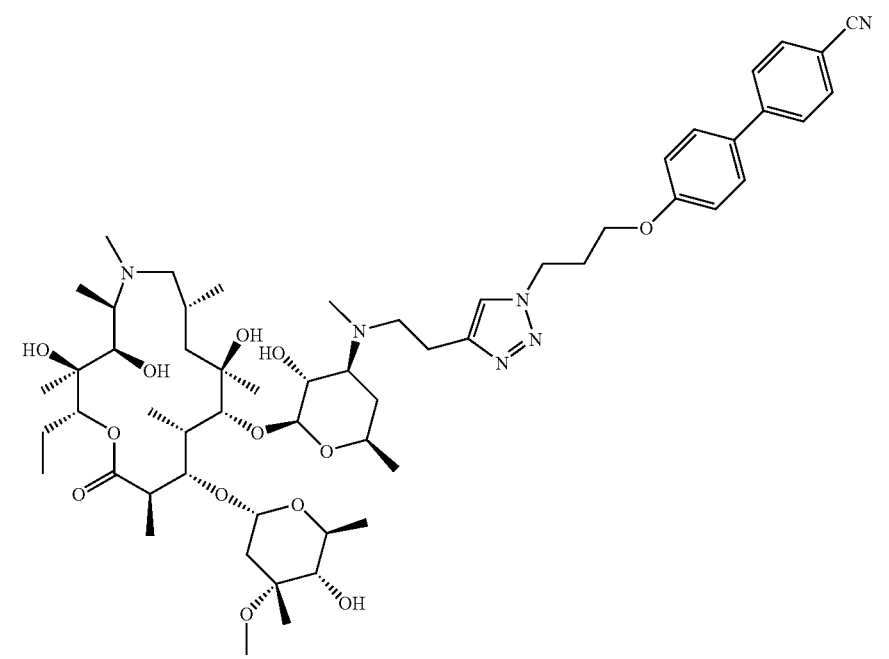 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5ccc(C#N)cc5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 129 | 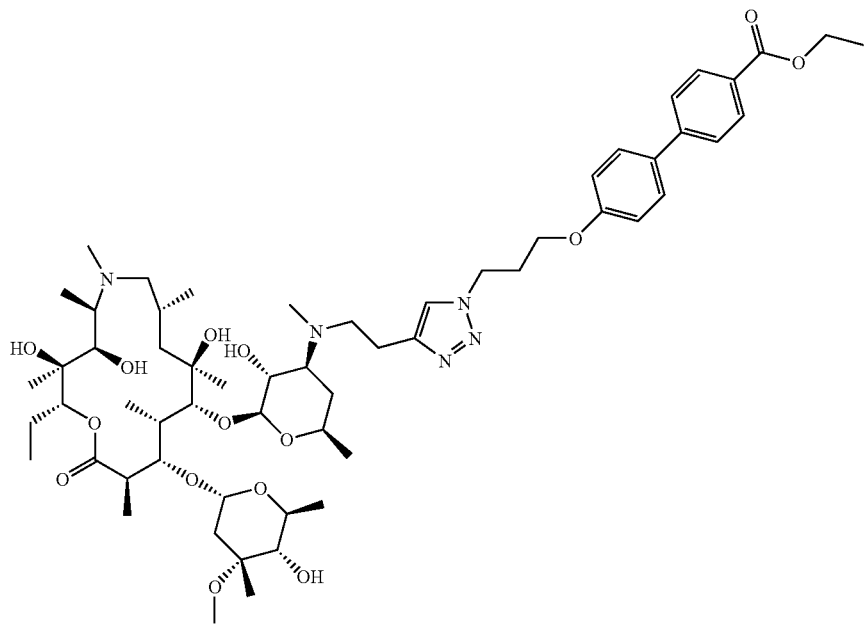 [SMILES: CCOC(=O)c1ccc(-c2ccc(OCCCn3cc(CCN(C)[C@H]4C[C@@H](C)O[C@@H](O[C@@H]5[C@@H](C)[C@H](O[C@H]6C[C@@](C)(OC)[C@@H](O)[C@H](C)O6)[C@@H](C)C(=O)O[C@H](CC)[C@@](C)(O)[C@H](O)[C@@H](C)N(C)C[C@H](C)C[C@@]5(C)O)[C@@H]4O)nn3)cc2)cc1] |
| 130 | 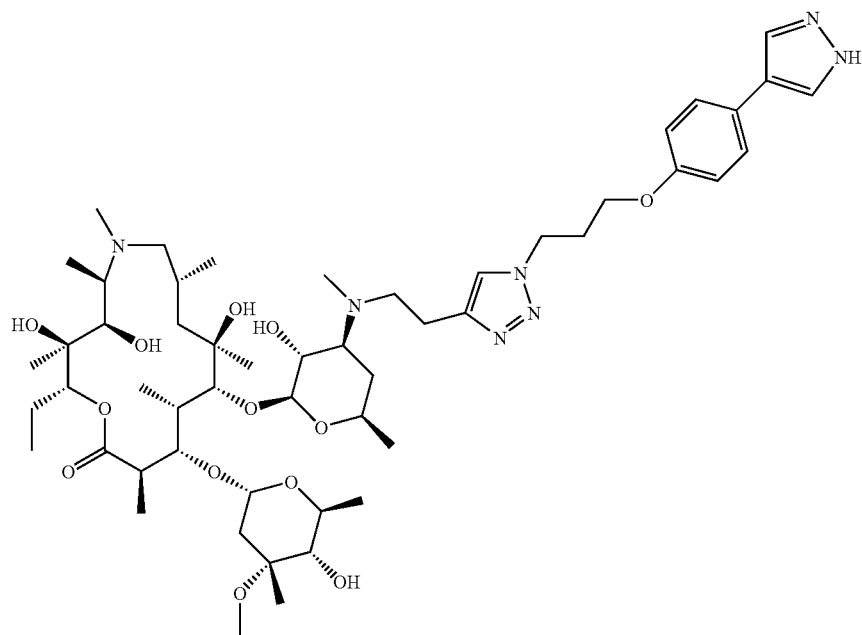 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5cn[nH]c5)cc4)nn3)[C@H]2O)[C@](C)(O)C[C@@H](C)CN(C)[C@H](C)[C@@H](O)[C@]1(C)O] |

TABLE 1-continued

| Compound | Structure |
|---|---|
| 131 | 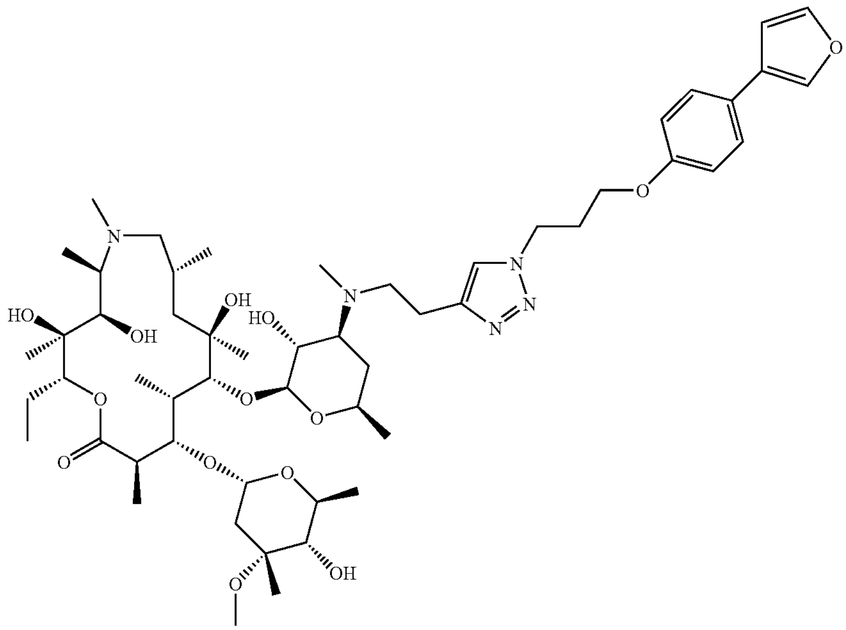 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5ccoc5)cc4)nn3)[C@H]2O)[C@](C)(O)C[C@@H](C)CN(C)[C@H](C)[C@@H](O)[C@]1(C)O] |
| 132 | 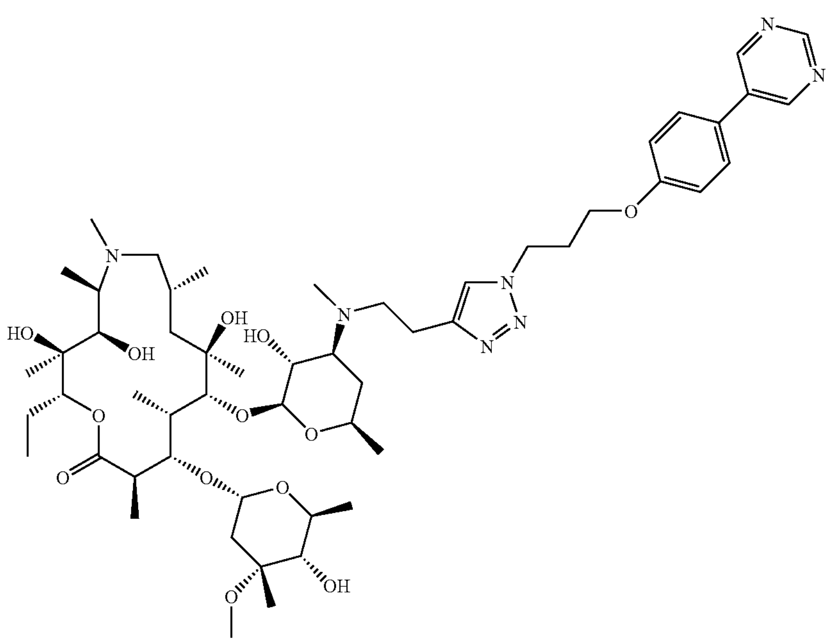 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5cncnc5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 133 | 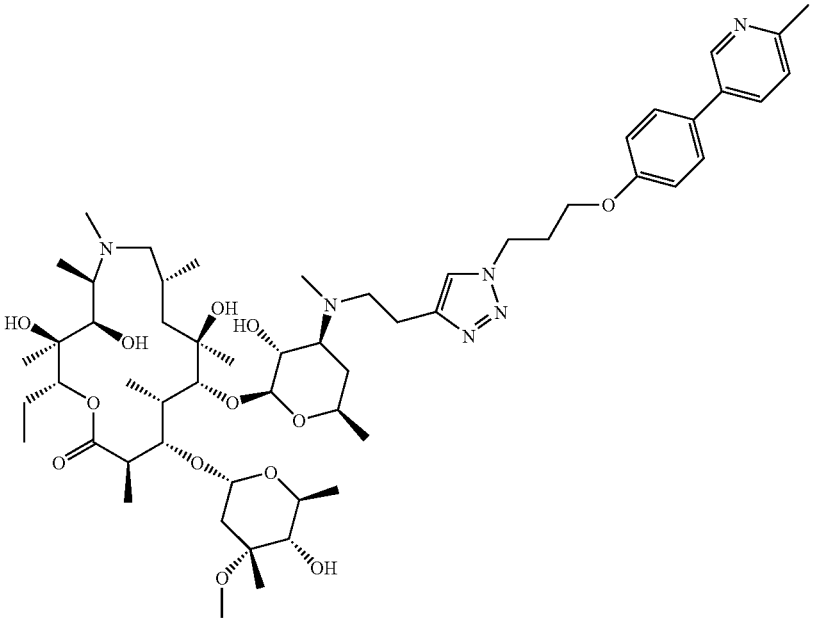 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5ccc(C)nc5)cc4)nn3)[C@H]2O)[C@](C)(O)C[C@@H](C)CN(C)[C@H](C)[C@@H](O)[C@]1(C)O] |
| 134 | 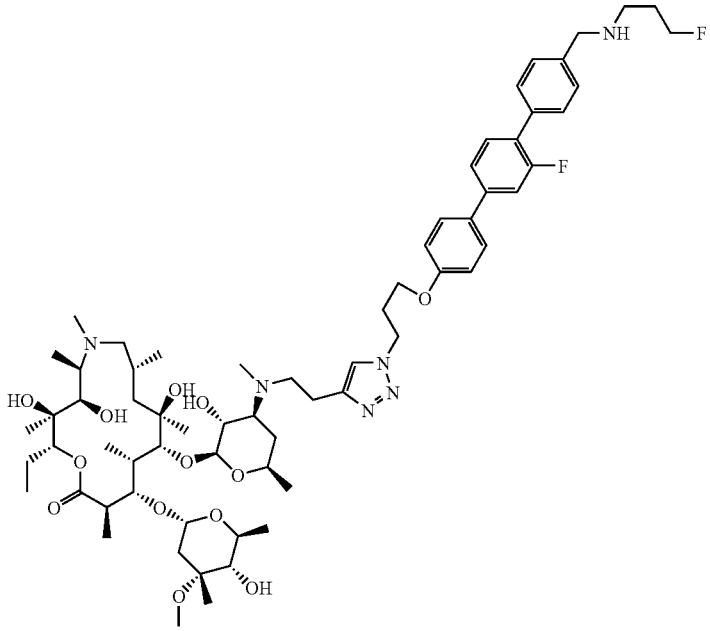 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5ccc(-c6ccc(CNCCCF)cc6)c(F)c5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 135 | 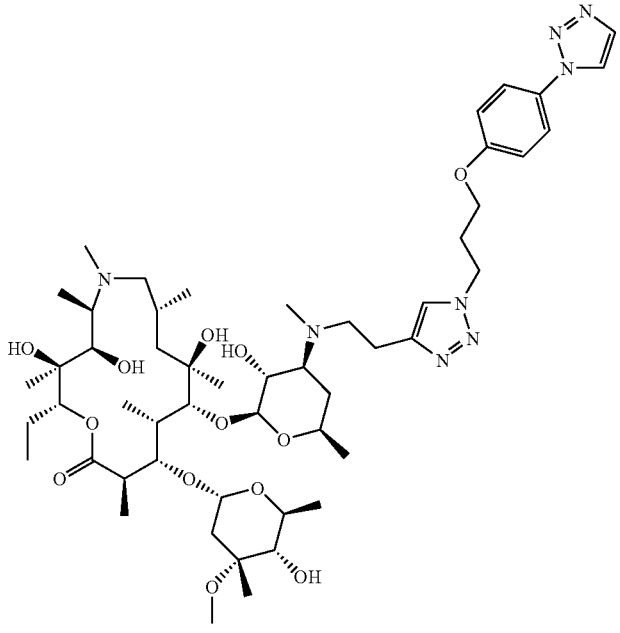 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-n5ccnn5)cc4)nn3)[C@H]2O)[C@](C)(O)C[C@@H](C)CN(C)[C@H](C)[C@@H](O)[C@]1(C)O] |
| 136 | 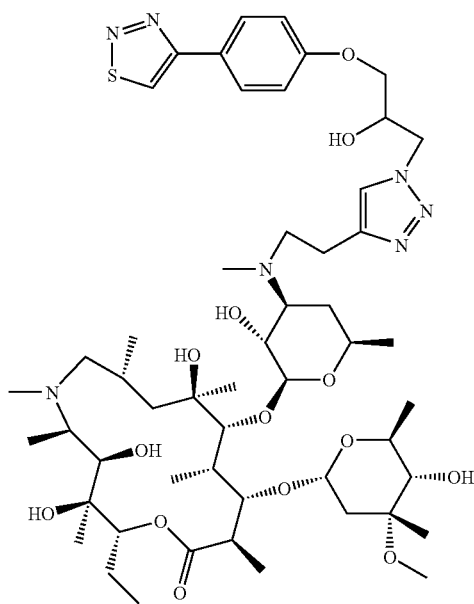 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CC(O)COc4ccc(-c5csnn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 137 | 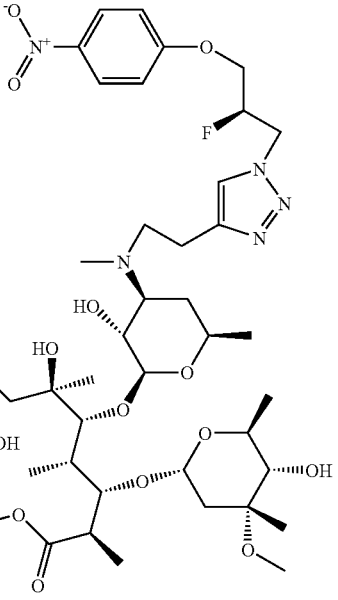 |
| 138 | 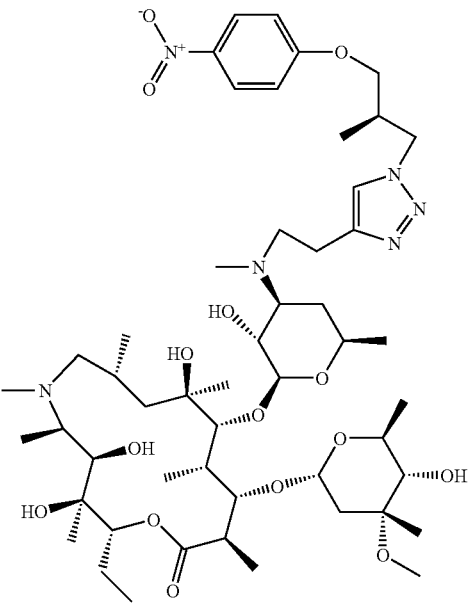 |

TABLE 1-continued

| Compound | Structure |
|---|---|
| 139 | 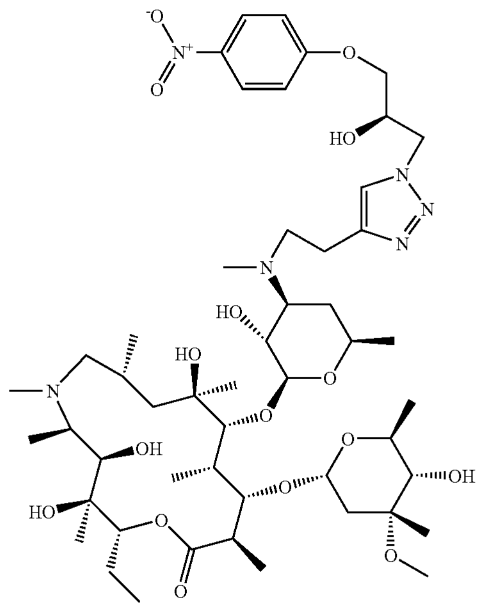 |
| 140 | 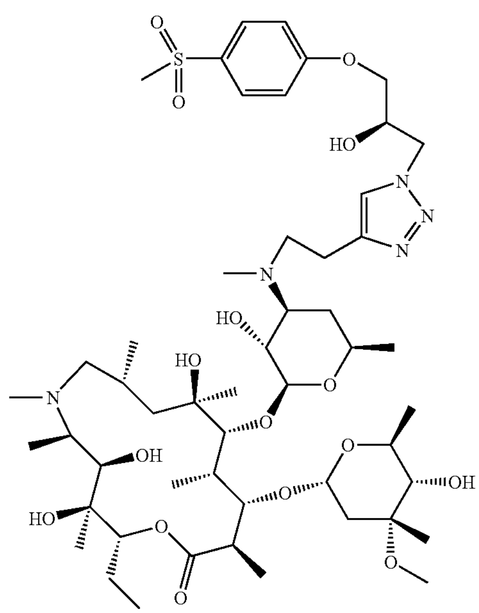 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H](O)COc4ccc(S(C)(=O)=O)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 141 | 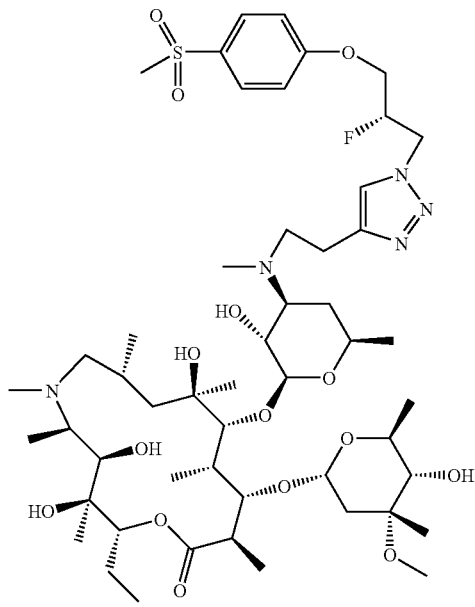 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@H](F)COc4ccc(S(C)(=O)=O)cc4)nn3)[C@H]2O)[C@](C)(O)C[C@@H](C)CN(C)[C@H](C)[C@@H](O)[C@]1(C)O] |
| 142 | 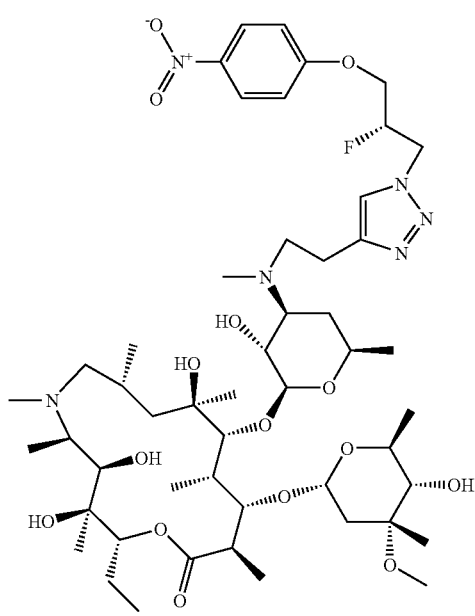 |

TABLE 1-continued
| Compound | Structure |
|---|---|
| 143 | 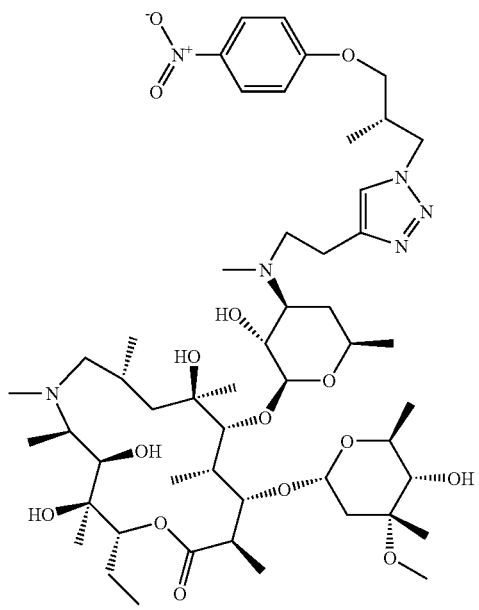 |
| 144 | 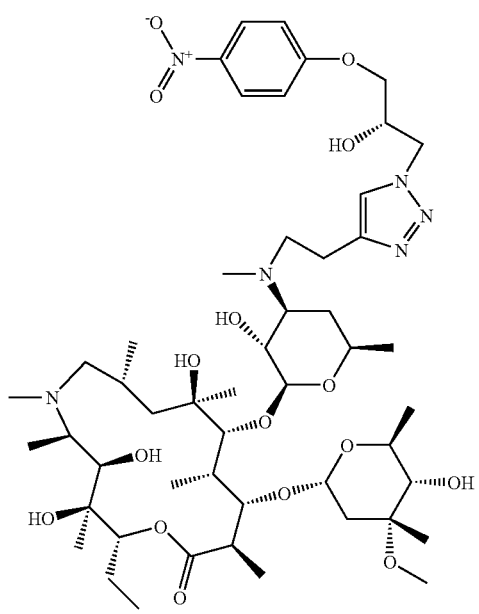 |

TABLE 1-continued
| Compound | Structure |
|---|---|
| 145 | 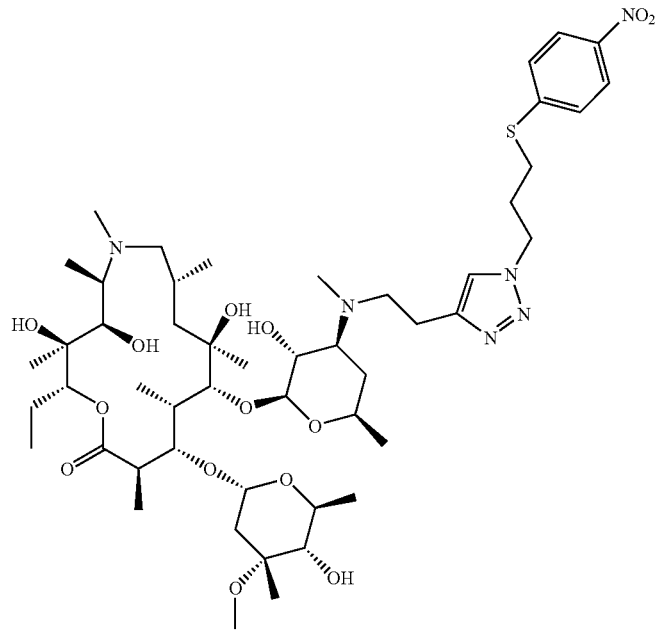 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCSc4ccc([N+](=O)[O-])cc4)nn3)[C@H]2O)[C@](C)(O)C[C@@H](C)CN(C)[C@H](C)[C@@H](O)[C@]1(C)O] |
| 146 | 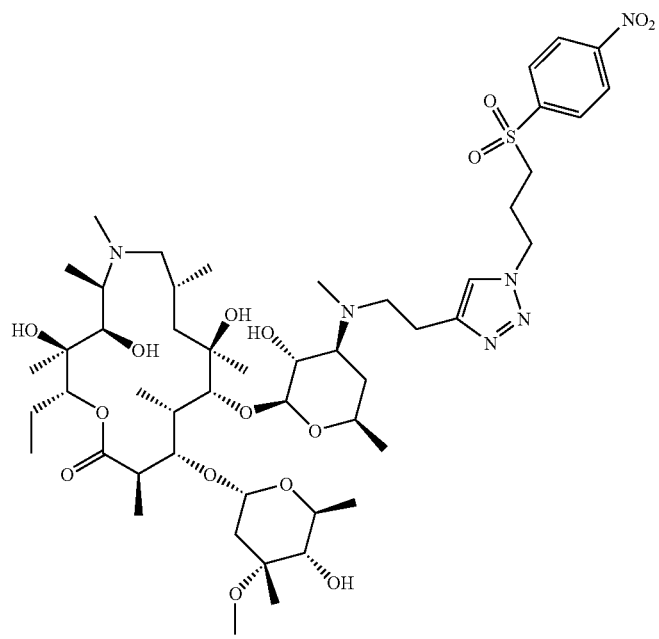 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCS(=O)(=O)c4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 147 | 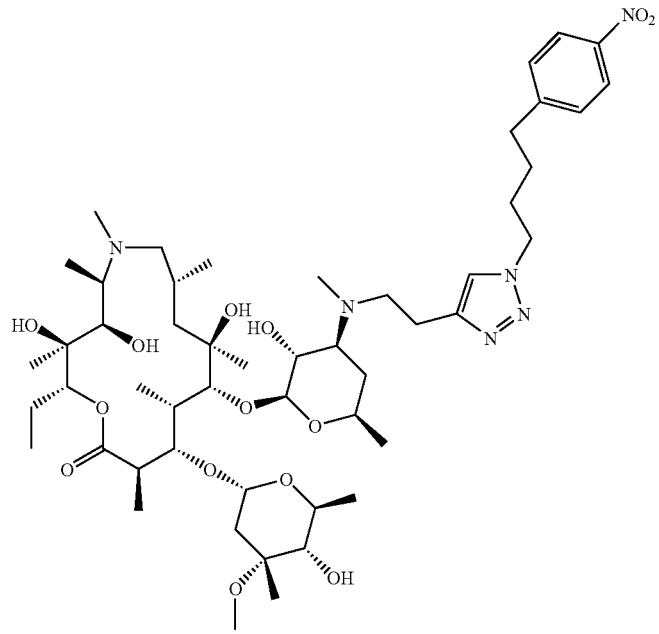 |
| 148 | 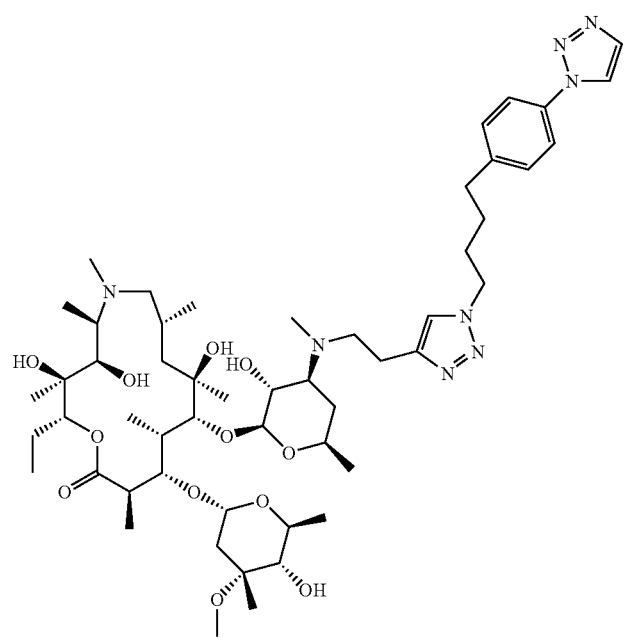 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5ccnn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 149 | 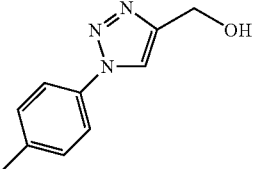 |
| 150 | 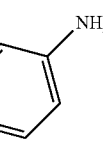 |

| Compound | Structure |
|---|---|
| 151 | 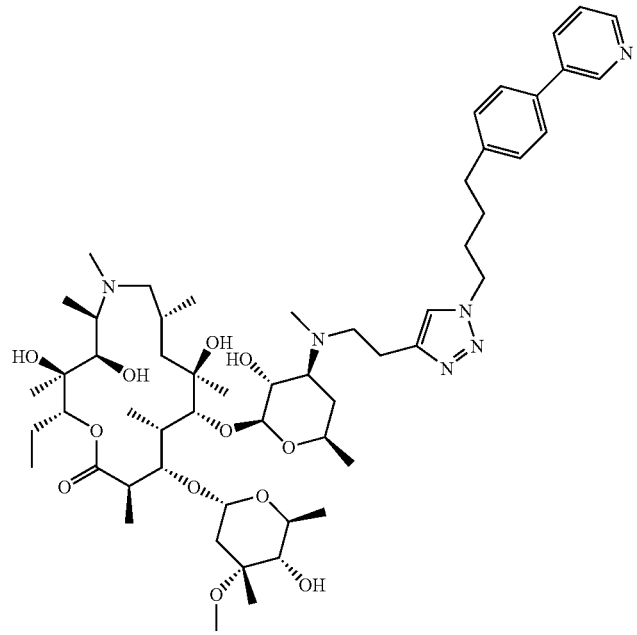 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-c5cccnc5)cc4)nn3)[C@H]2O)[C@](C)(O)C[C@@H](C)CN(C)[C@H](C)[C@@H](O)[C@]1(C)O] |
| 152 | 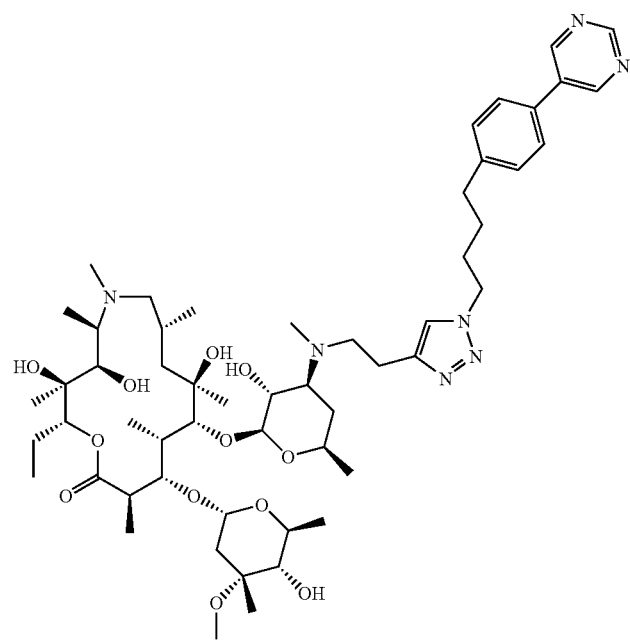 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-c5cncnc5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 153 | 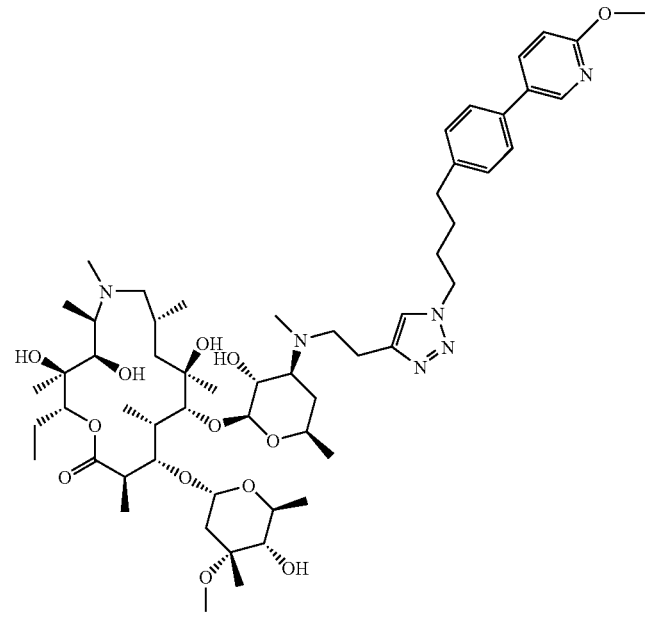 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-c5ccc(OC)nc5)cc4)nn3)[C@H]2O)[C@](C)(O)C[C@@H](C)CN(C)[C@H](C)[C@@H](O)[C@]1(C)O] |
| 154 | 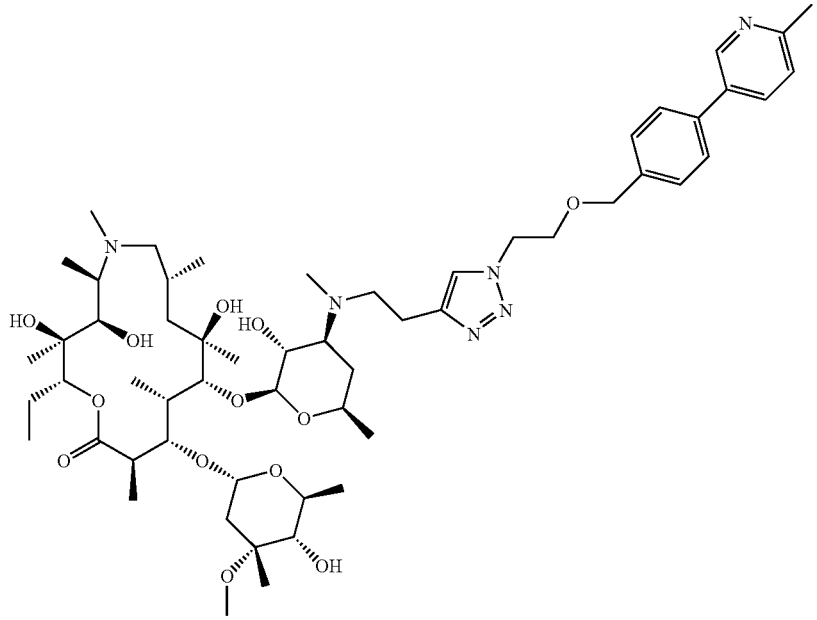 |

TABLE 1-continued
| Compound | Structure |
|---|---|
| 155 | 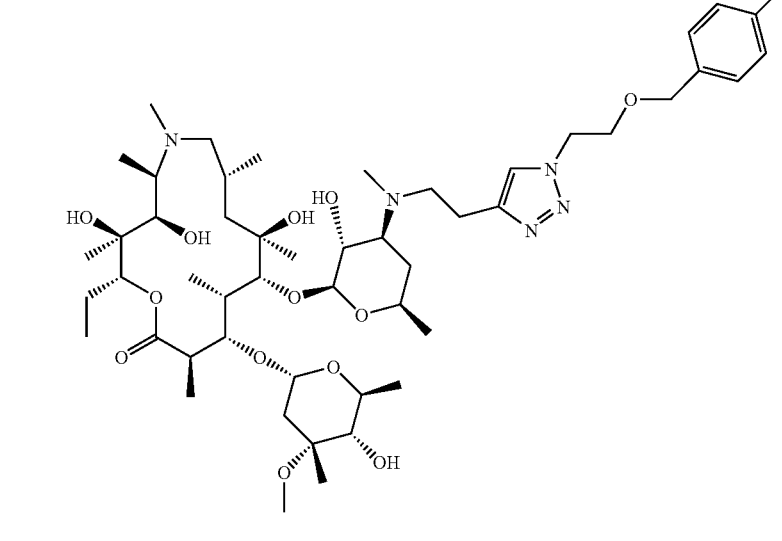 |
| 156 | 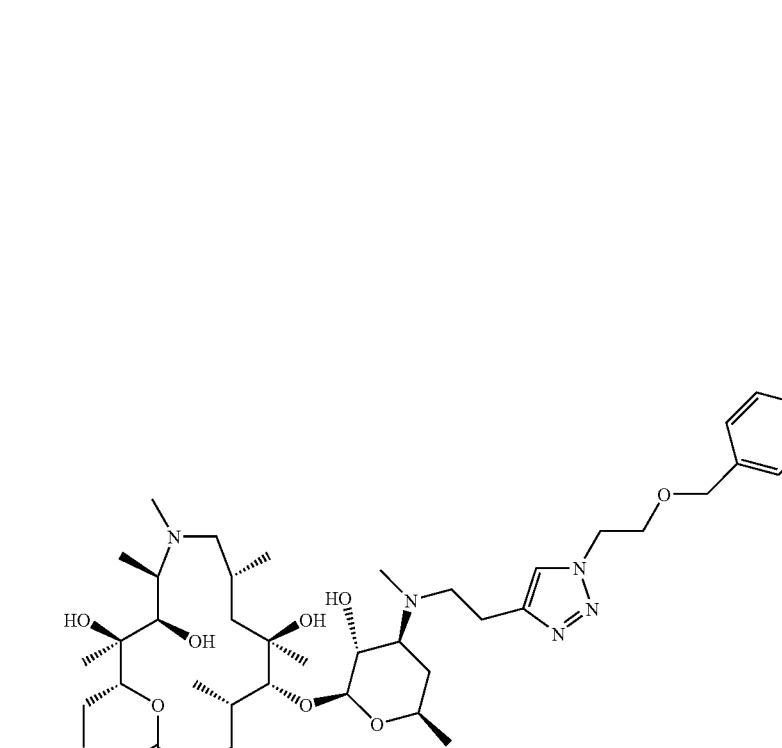 |

TABLE 1-continued

| Compound | Structure |
| --- | --- |
| 157 | 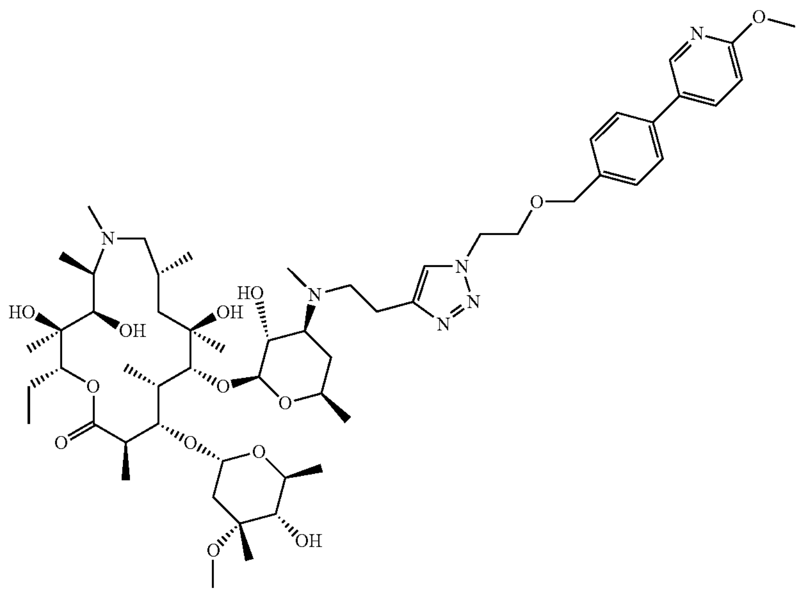 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOCc4ccc(-c5ccc(OC)nc5)cc4)nn3)[C@H]2O)[C@](C)(O)C[C@@H](C)CN(C)[C@H](C)[C@@H](O)[C@]1(C)O] |
| 158 | 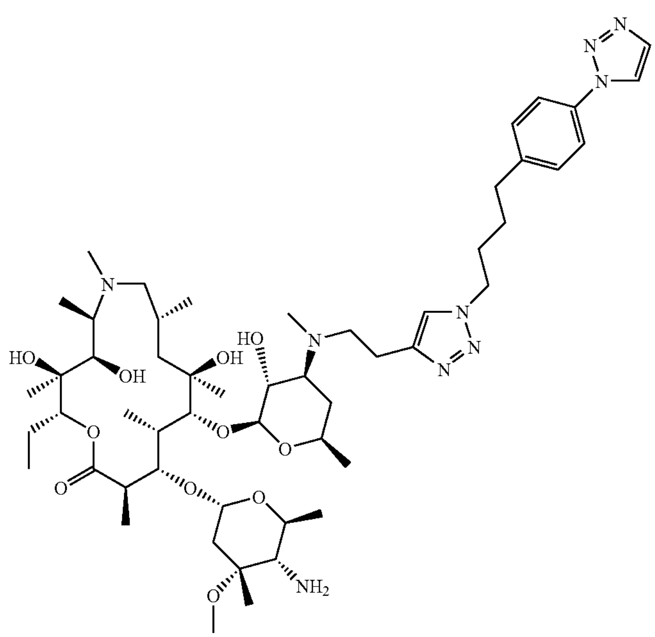 [SMILES: CC[C@H]1OC(=O)[C@H](C)[C@@H](O[C@H]2C[C@@](C)(OC)[C@@H](N)[C@H](C)O2)[C@H](C)[C@@H](O[C@@H]2O[C@H](C)C[C@H](N(C)CCc3cn(CCCCc4ccc(-n5ccnn5)cc4)nn3)[C@H]2O)[C@](C)(O)C[C@@H](C)CN(C)[C@H](C)[C@@H](O)[C@]1(C)O] |

TABLE 1-continued

| Compound | Structure |
|---|---|
| 159 | (structure) |
| 160 | (structure) |

TABLE 1-continued

| Compound | Structure |
|---|---|
| 161 | 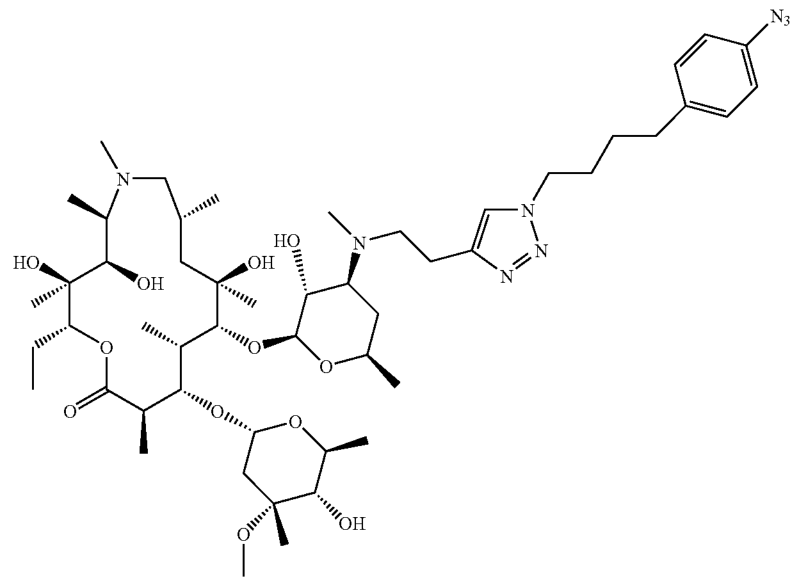 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(N=[N+]=[N-])cc4)nn3)[C@H]2O)[C@](C)(O)C[C@@H](C)CN(C)[C@H](C)[C@@H](O)[C@]1(C)O] |
| 162 | 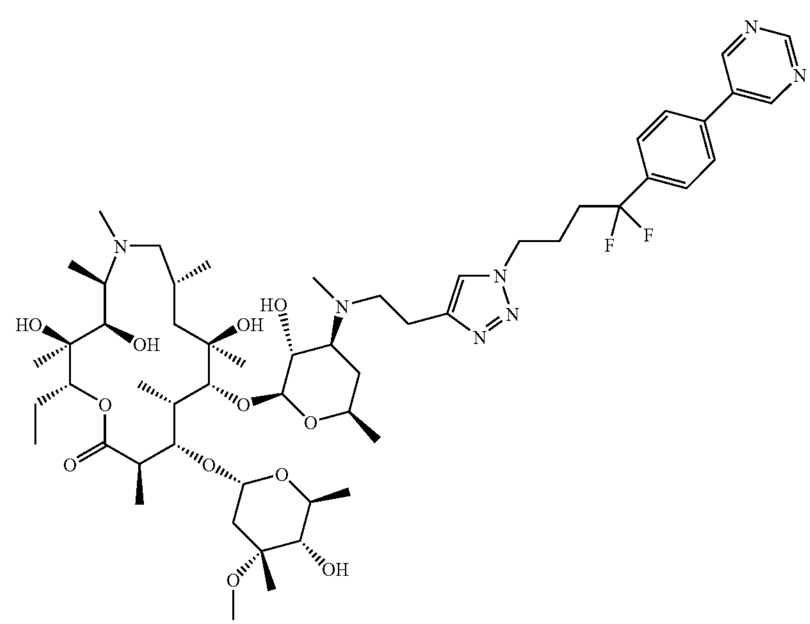 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCC(F)(F)c4ccc(-c5cncnc5)cc4)nn3)[C@H]2O)[C@](C)(O)C[C@@H](C)CN(C)[C@H](C)[C@@H](O)[C@]1(C)O] |

| Compound | Structure |
|---|---|
| 163 | 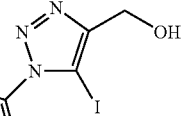 |
| 164 | 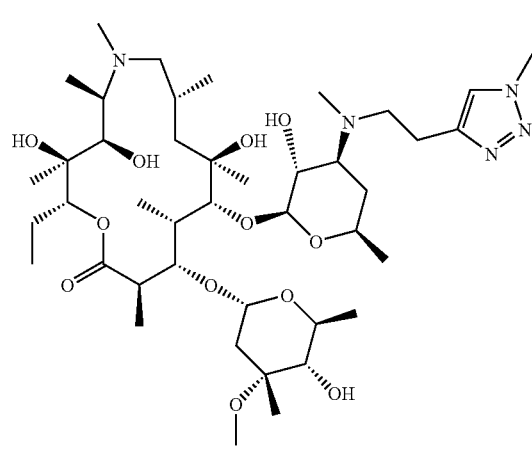 |

TABLE 1-continued
| Compound | Structure |
|---|---|
| 165 | 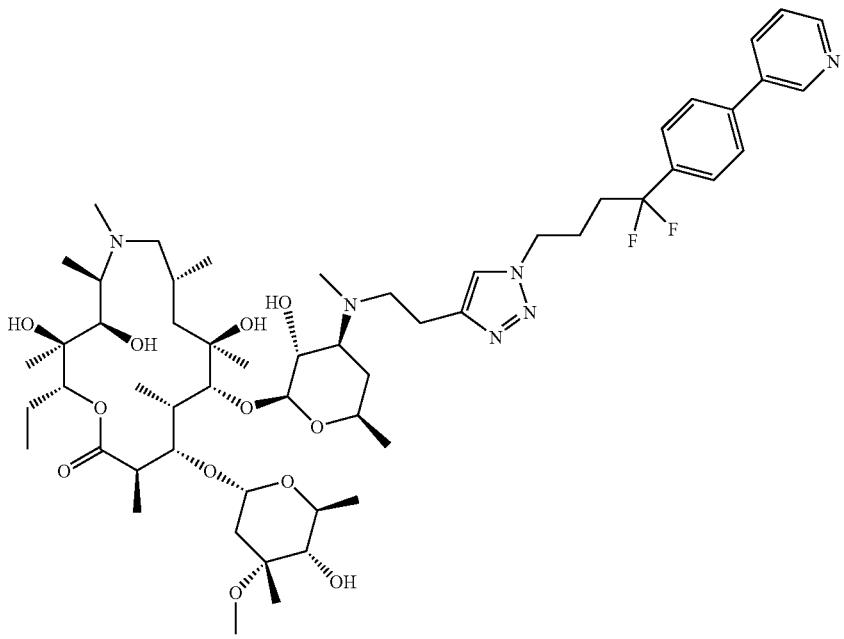 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCC(F)(F)c4ccc(-c5cccnc5)cc4)nn3)[C@H]2O)[C@](C)(O)C[C@@H](C)CN(C)[C@H](C)[C@@H](O)[C@]1(C)O] |
| 166 | 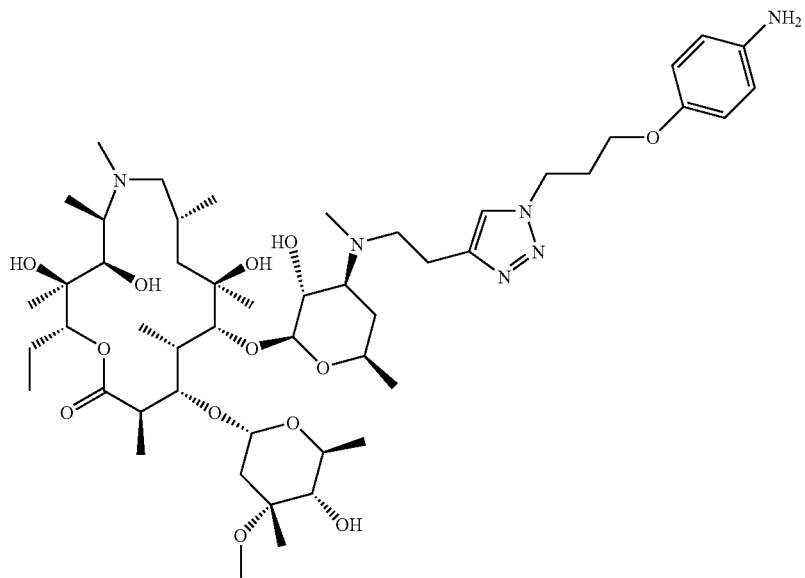 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(N)cc4)nn3)[C@H]2O)[C@](C)(O)C[C@@H](C)CN(C)[C@H](C)[C@@H](O)[C@]1(C)O] |

US 8,470,985 B2
133 134
TABLE 1-continued
| Compound | Structure |
|---|---|
| 167 | 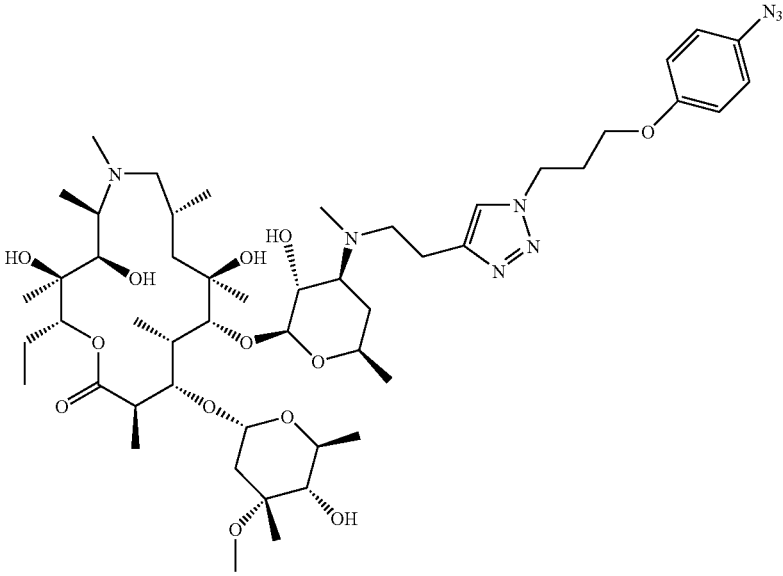 |
| 168 | 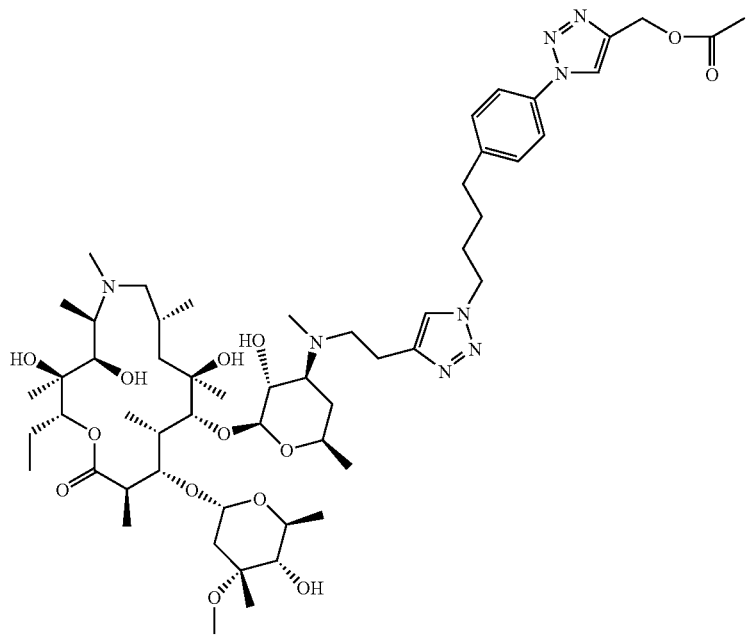 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(COC(C)=O)nn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 169 | 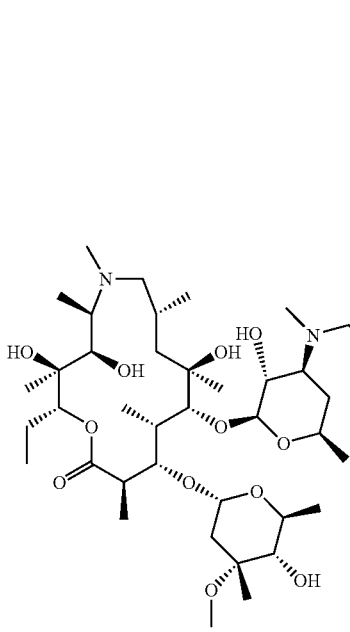 |
| 170 | 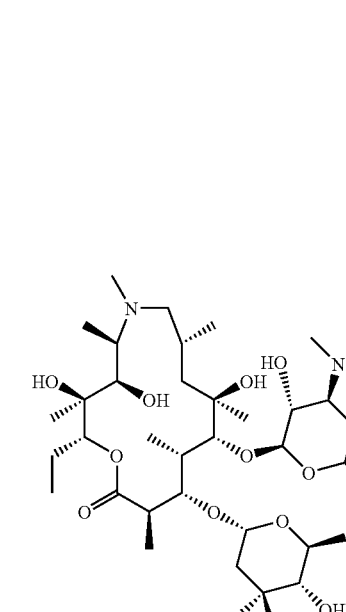 |

TABLE 1-continued
| Compound | Structure |
|---|---|
| 171 | 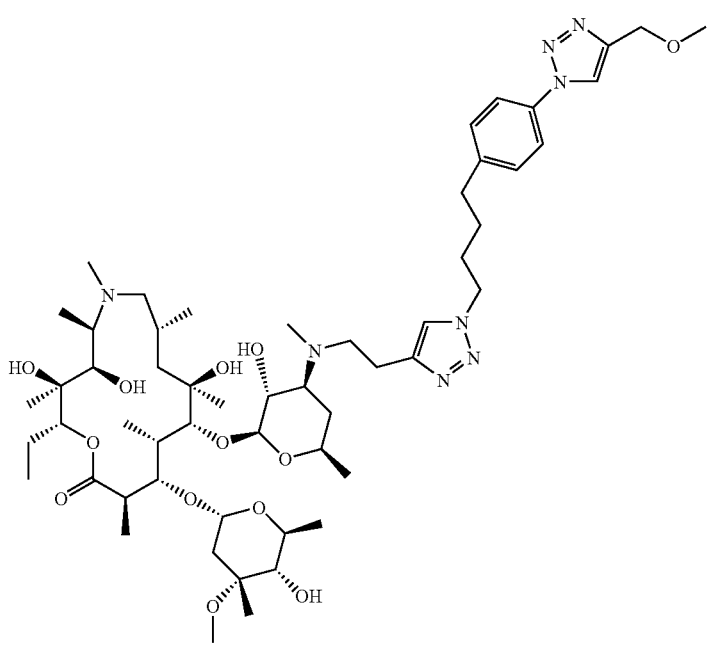 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(COC)nn5)cc4)nn3)[C@H]2O)[C@](C)(O)C[C@@H](C)CN(C)[C@H](C)[C@@H](O)[C@]1(C)O] |
| 172 | 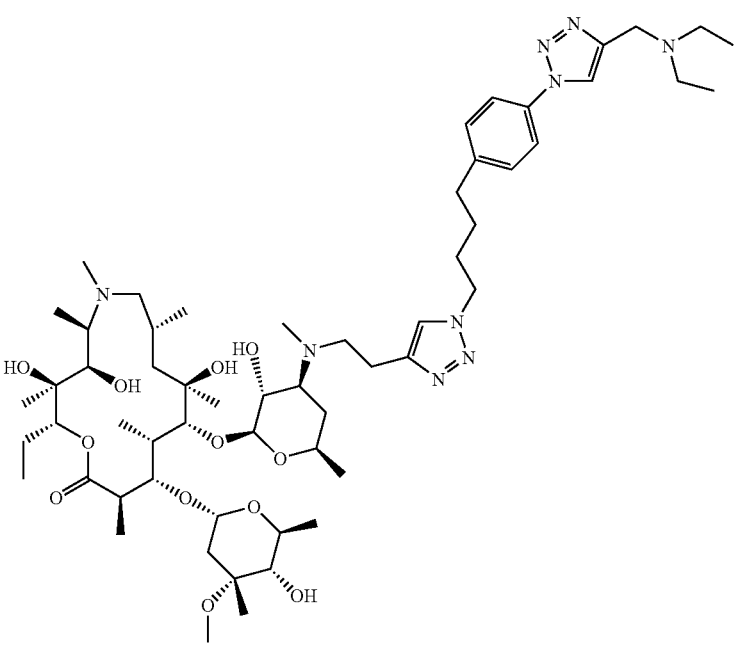 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CN(CC)CC)nn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 173 | 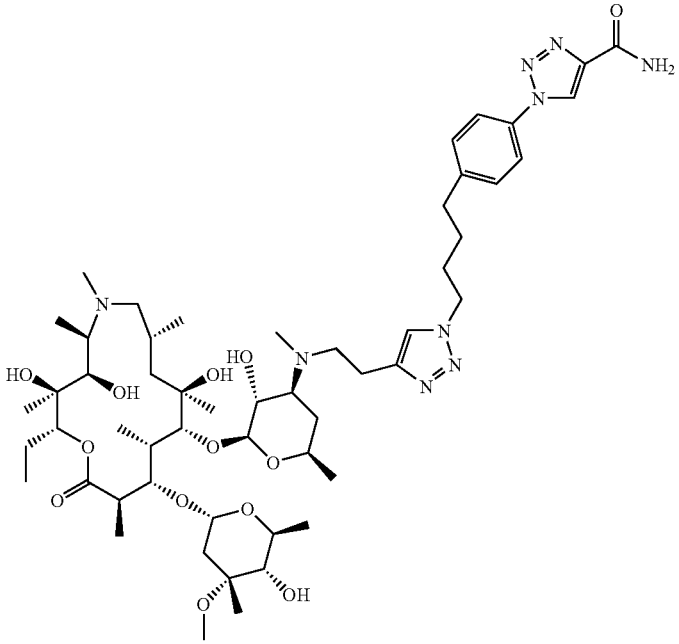 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C(N)=O)nn5)cc4)nn3)[C@H]2O)[C@](C)(O)C[C@@H](C)CN(C)[C@H](C)[C@@H](O)[C@]1(C)O] |
| 174 | 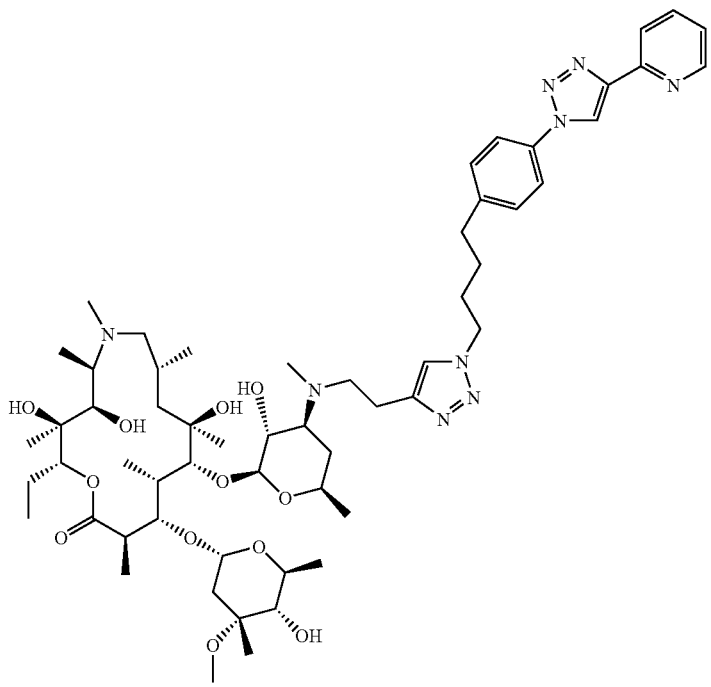 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(-c6ccccn6)nn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 175 | 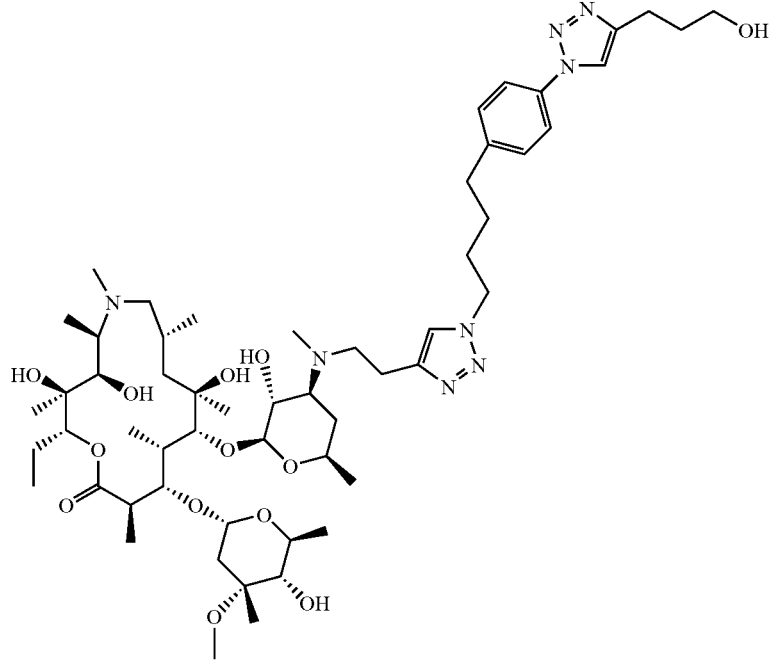 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CCCO)nn5)cc4)nn3)[C@H]2O)[C@](C)(O)C[C@@H](C)CN(C)[C@H](C)[C@@H](O)[C@]1(C)O] |
| 176 | 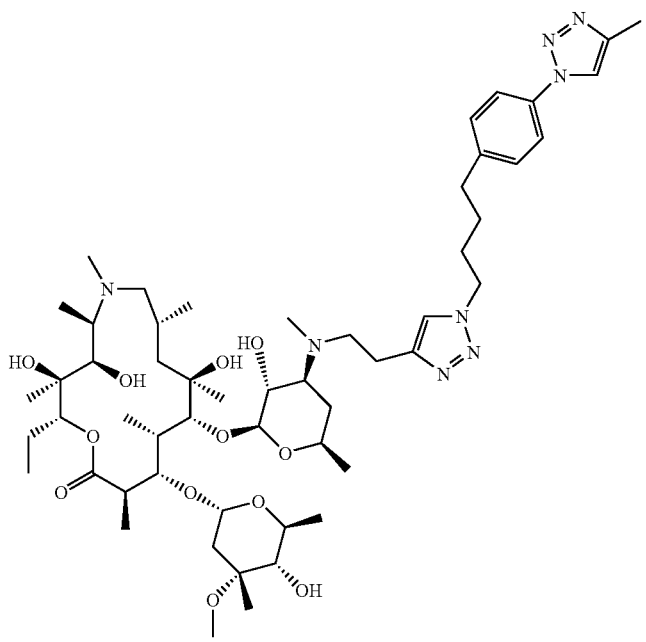 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C)nn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 177 | 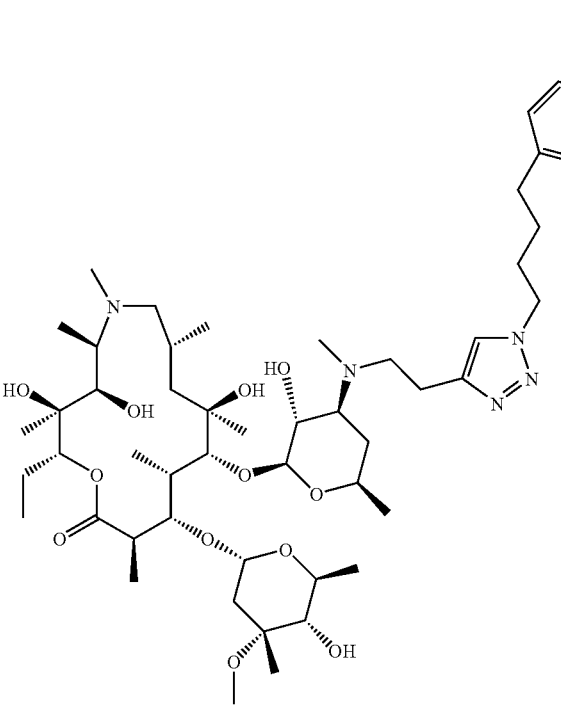 |
| 178 | 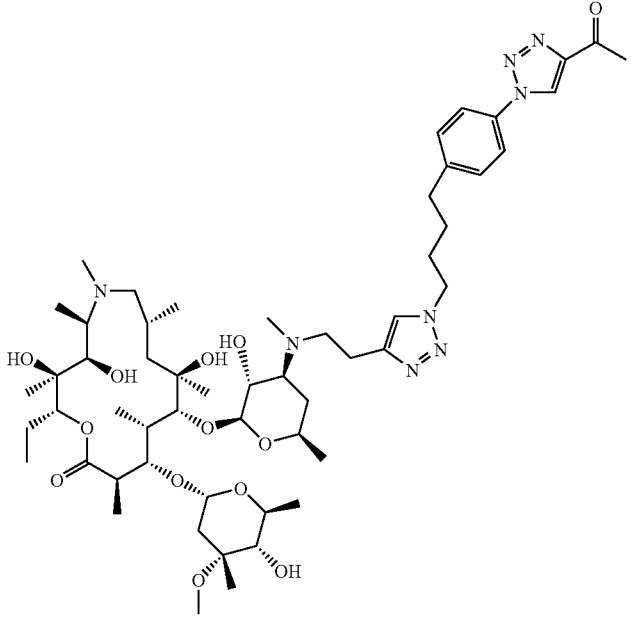 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C(C)=O)nn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 179 | 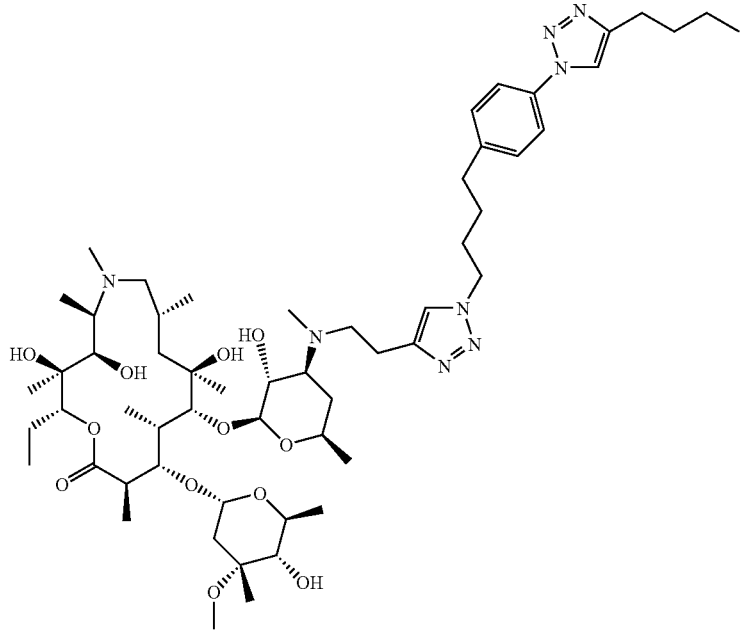 [SMILES: CCCCc1cn(-c2ccc(CCCCn3cc(CCN(C)[C@H]4C[C@@H](C)O[C@@H](O[C@@H]5[C@@H](C)[C@H](O[C@H]6C[C@@](C)(OC)[C@@H](O)[C@H](C)O6)[C@@H](C)C(=O)O[C@H](CC)[C@@](C)(O)[C@H](O)[C@@H](C)N(C)C[C@H](C)C[C@@]5(C)O)[C@@H]4O)nn3)cc2)nn1] |
| 180 | 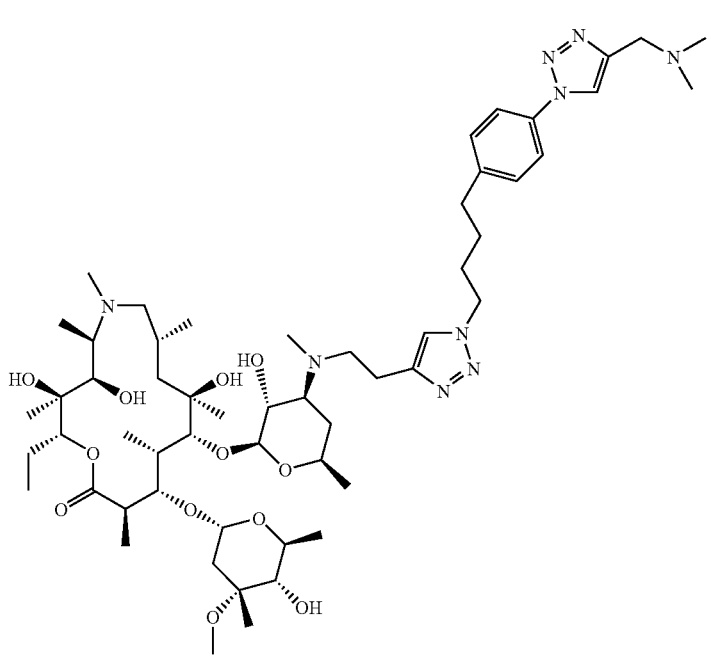 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CN(C)C)nn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 181 | 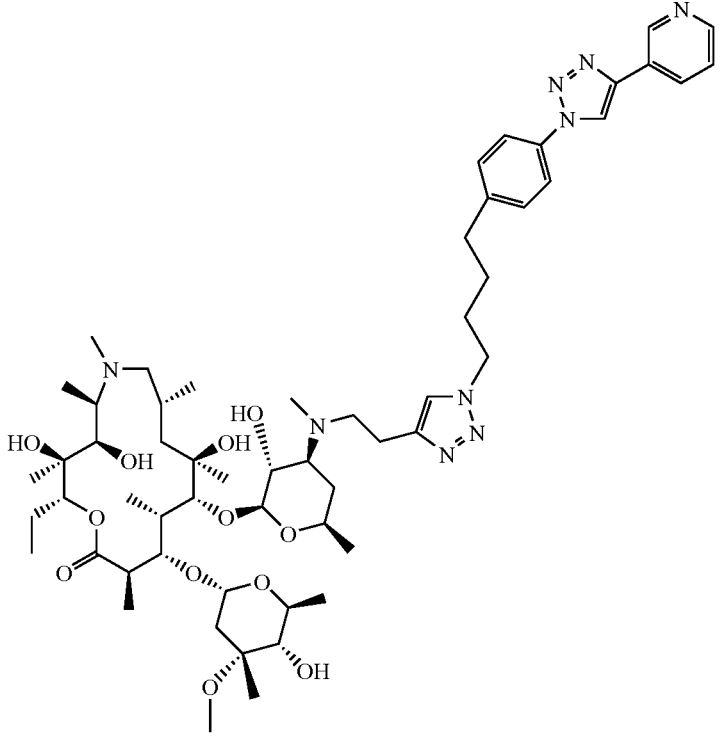 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(-c6cccnc6)nn5)cc4)nn3)[C@H]2O)[C@](C)(O)C[C@@H](C)CN(C)[C@H](C)[C@@H](O)[C@]1(C)O] |
| 182 | 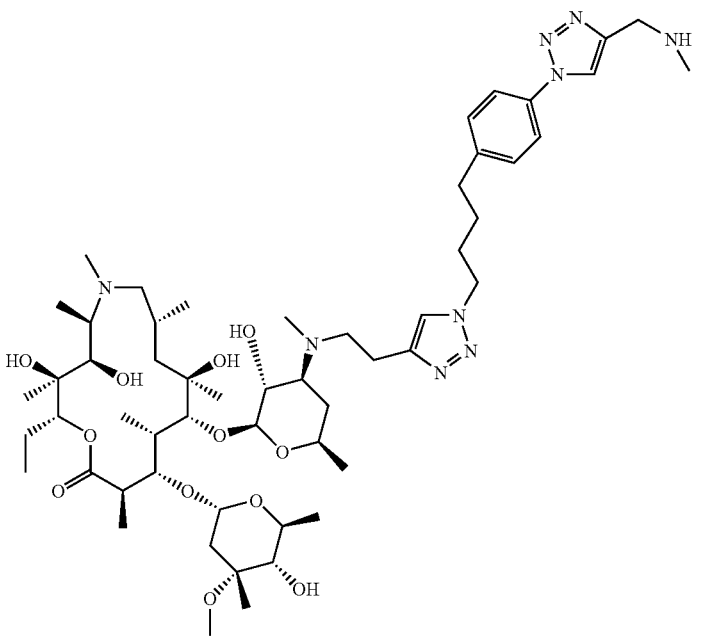 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CNC)nn5)cc4)nn3)[C@H]2O)[C@](C)(O)C[C@@H](C)CN(C)[C@H](C)[C@@H](O)[C@]1(C)O] |

| Compound | Structure |
|---|---|
| 183 | 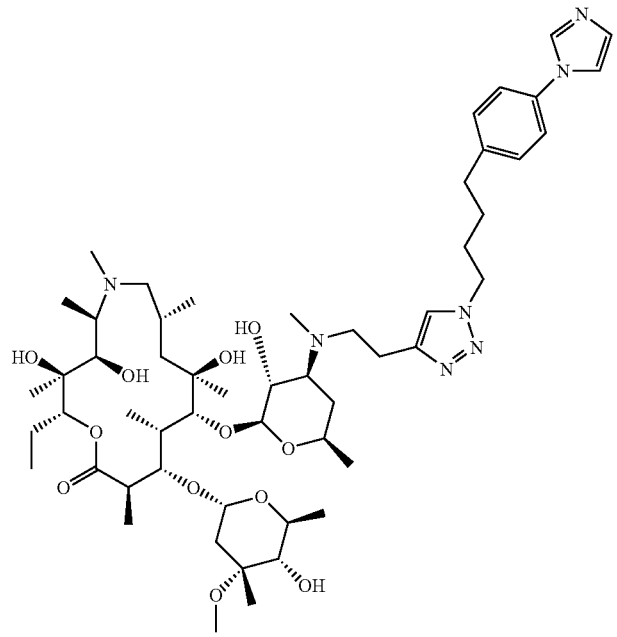 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5ccnc5)cc4)nn3)[C@H]2O)[C@](C)(O)C[C@@H](C)CN(C)[C@H](C)[C@@H](O)[C@]1(C)O] |
| 184 | 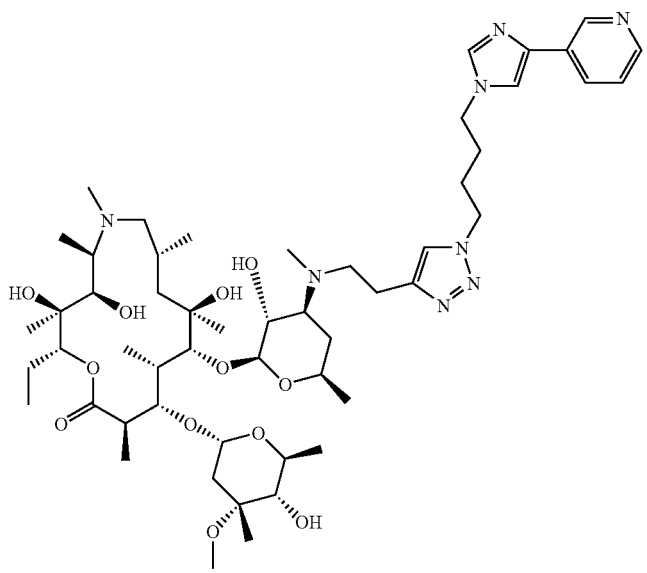 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCn4cnc(-c5cccnc5)c4)nn3)[C@H]2O)[C@](C)(O)C[C@@H](C)CN(C)[C@H](C)[C@@H](O)[C@]1(C)O] |

TABLE 1-continued

| Compound | Structure |
|---|---|
| 185 | 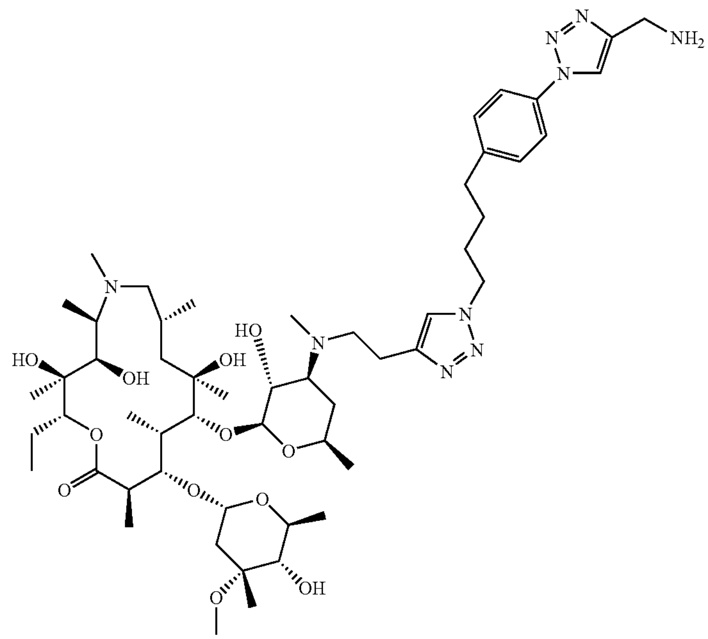 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CN)nn5)cc4)nn3)[C@H]2O)[C@](C)(O)C[C@@H](C)CN(C)[C@H](C)[C@@H](O)[C@]1(C)O] |
| 186 | 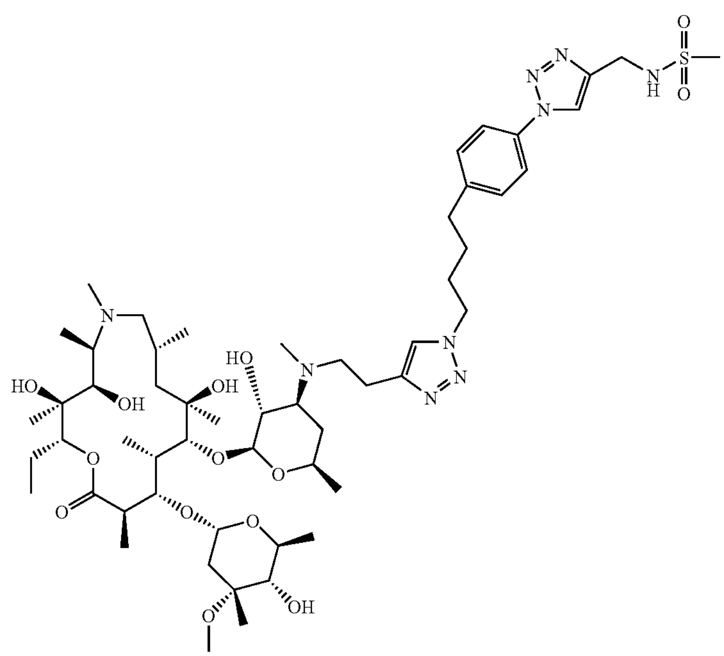 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CNS(C)(=O)=O)nn5)cc4)nn3)[C@H]2O)[C@](C)(O)C[C@@H](C)CN(C)[C@H](C)[C@@H](O)[C@]1(C)O] |

TABLE 1-continued

| Compound | Structure |
|---|---|
| 187 | 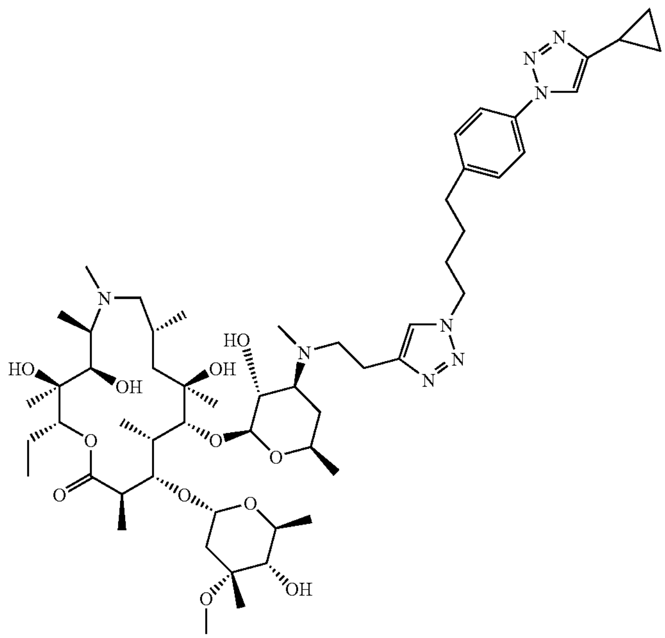 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C6CC6)nn5)cc4)nn3)[C@H]2O)[C@](C)(O)C[C@@H](C)CN(C)[C@H](C)[C@@H](O)[C@]1(C)O] |
| 188 | 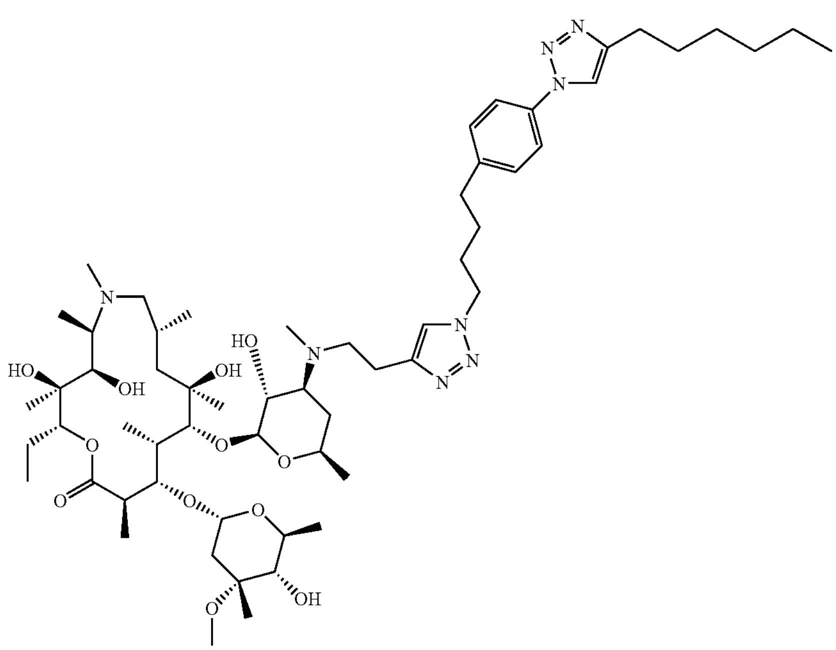 [SMILES: CCCCCCc1cn(-c2ccc(CCCCn3cc(CCN(C)[C@H]4C[C@@H](C)O[C@@H](O[C@@H]5[C@@H](C)[C@H](O[C@H]6C[C@@](C)(OC)[C@@H](O)[C@H](C)O6)[C@@H](C)C(=O)O[C@H](CC)[C@@](C)(O)[C@H](O)[C@@H](C)N(C)C[C@H](C)C[C@@]5(C)O)[C@@H]4O)nn3)cc2)nn1] |

TABLE 1-continued

| Compound | Structure |
|---|---|
| 189 | 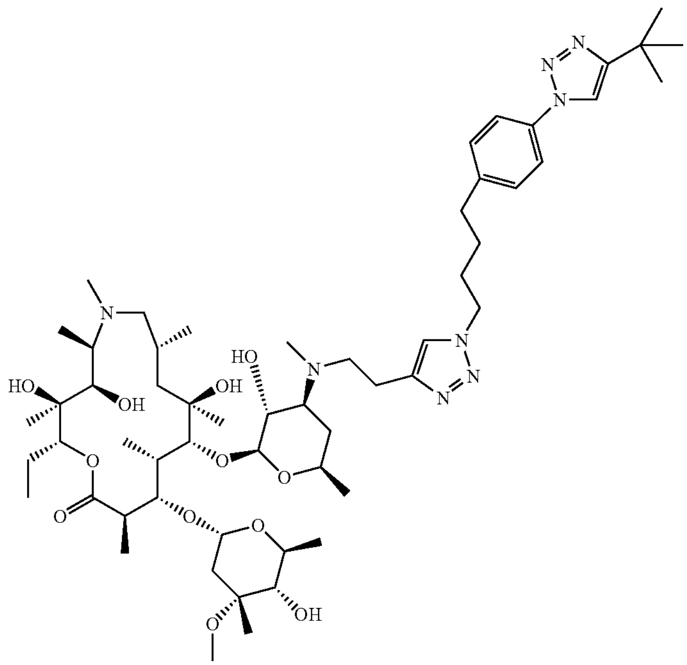 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C(C)(C)C)nn5)cc4)nn3)[C@H]2O)[C@](C)(O)C[C@@H](C)CN(C)[C@H](C)[C@@H](O)[C@]1(C)O] |
| 190 | 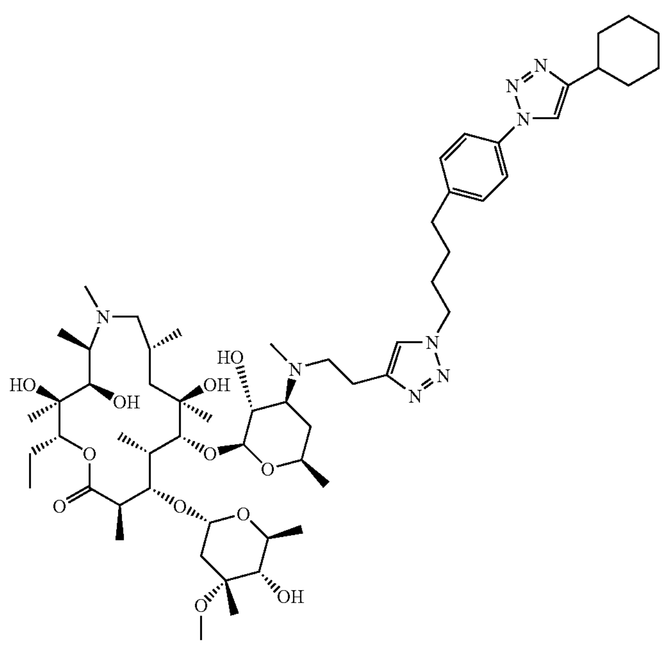 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C6CCCCC6)nn5)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 191 | 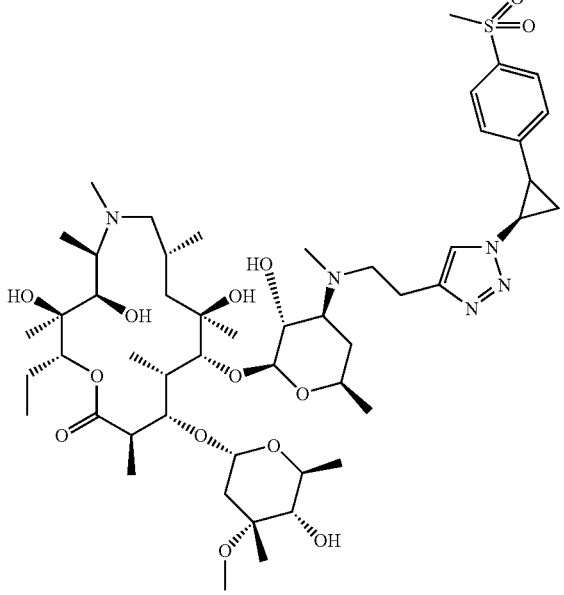 |
| 192 | 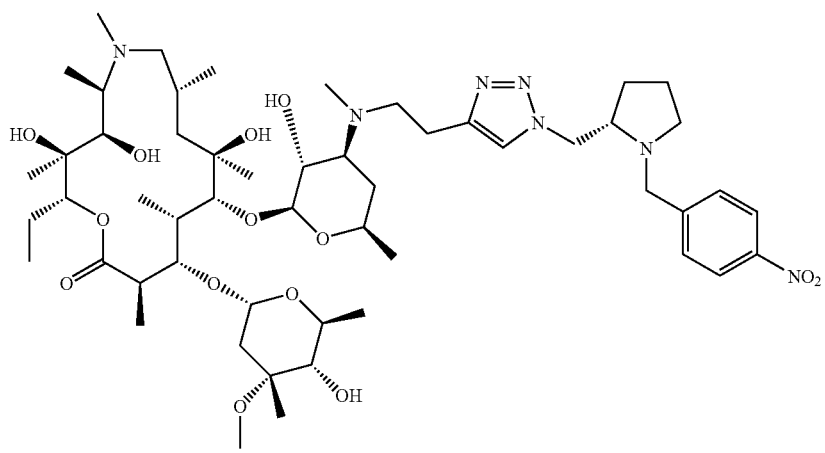 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H]4CCCN4Cc4ccc([N+](=O)[O-])cc4)nn3)[C@H]2O)[C@](C)(O)C[C@@H](C)CN(C)[C@H](C)[C@@H](O)[C@]1(C)O] |
| 193 | 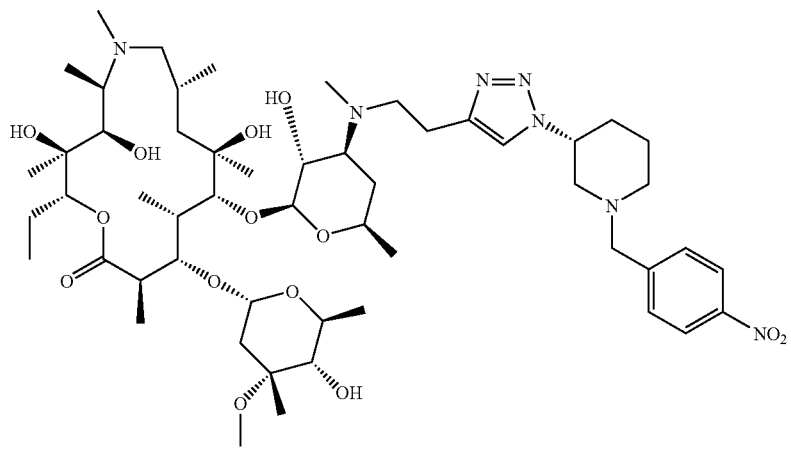 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H]4CCCN(Cc5ccc([N+](=O)[O-])cc5)C4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 194 | 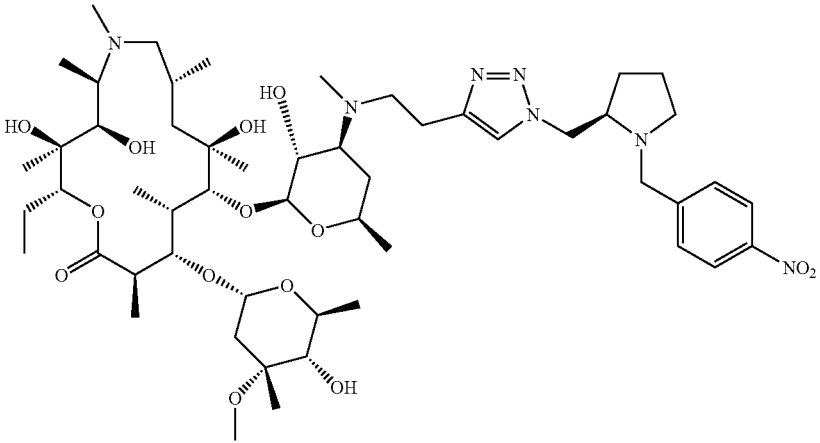 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@H]4CCCN4Cc4ccc([N+](=O)[O-])cc4)nn3)[C@H]2O)[C@](C)(O)C[C@@H](C)CN(C)[C@H](C)[C@@H](O)[C@]1(C)O] |
| 195 | 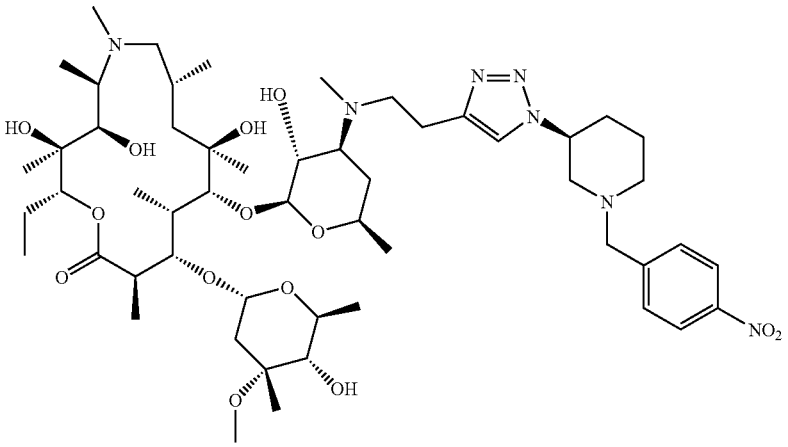 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H]4CCCN(Cc5ccc([N+](=O)[O-])cc5)C4)nn3)[C@H]2O)[C@](C)(O)C[C@@H](C)CN(C)[C@H](C)[C@@H](O)[C@]1(C)O] |
| 196 | 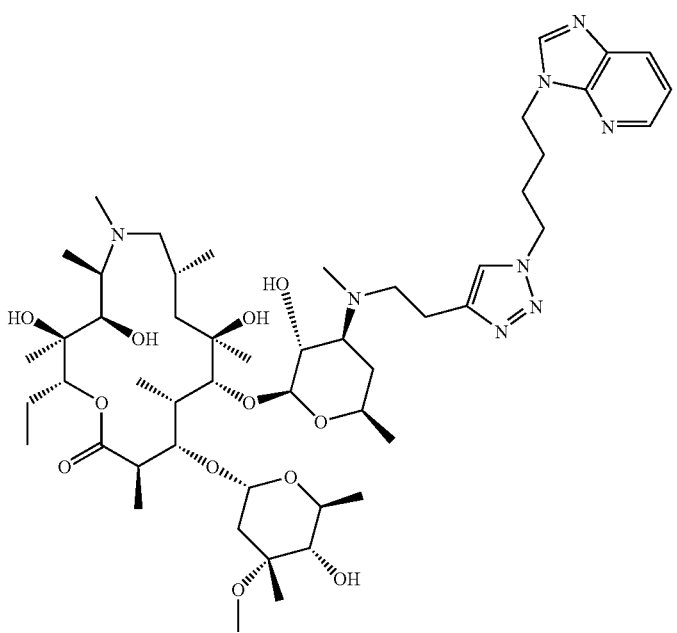 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCn4cnc5cccnc54)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 197 | 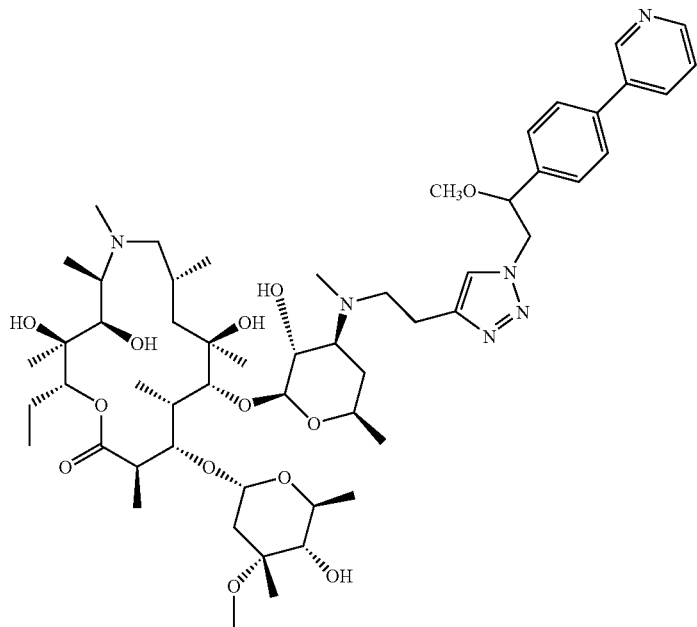 |
| 198 | 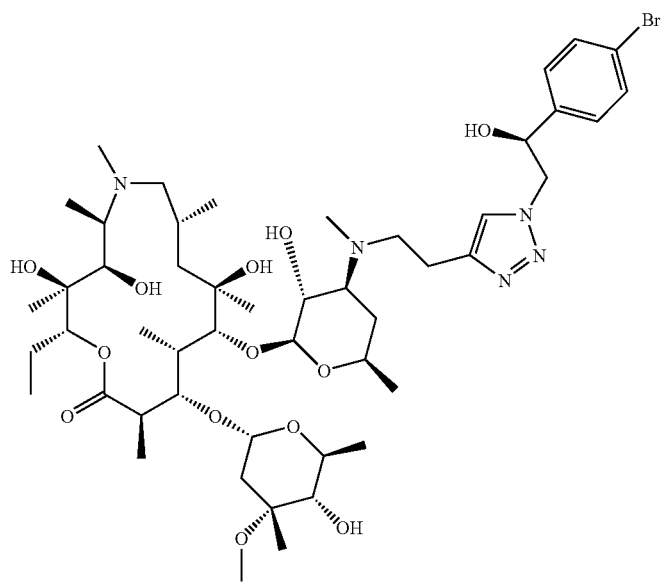 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H](O)c4ccc(Br)cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 201 | 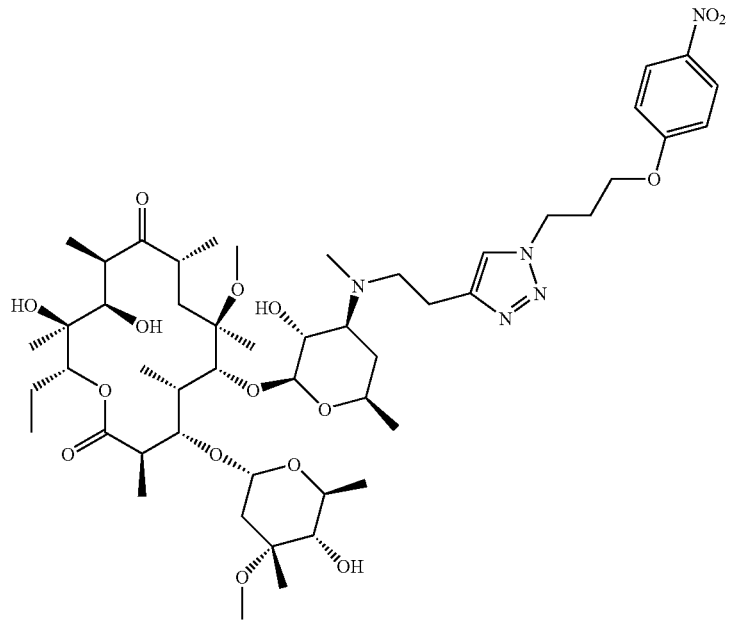 |
| 202 | 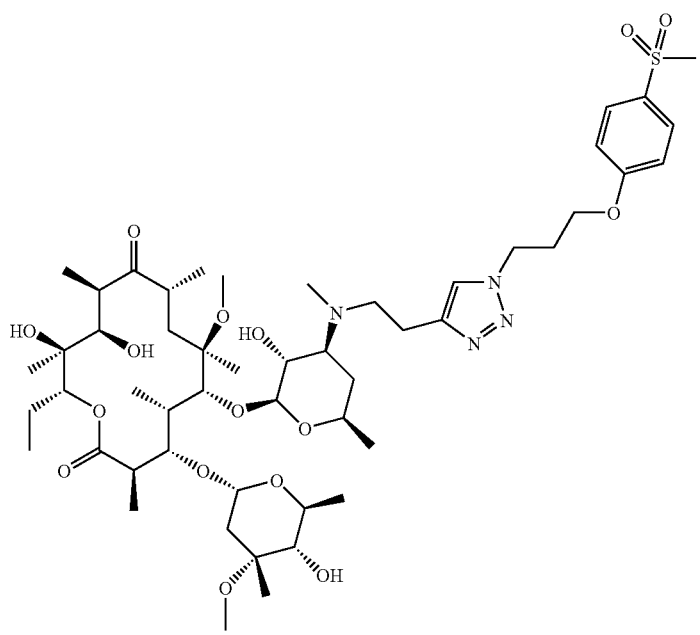 |

TABLE 1-continued
| Compound | Structure |
|---|---|
| 203 | 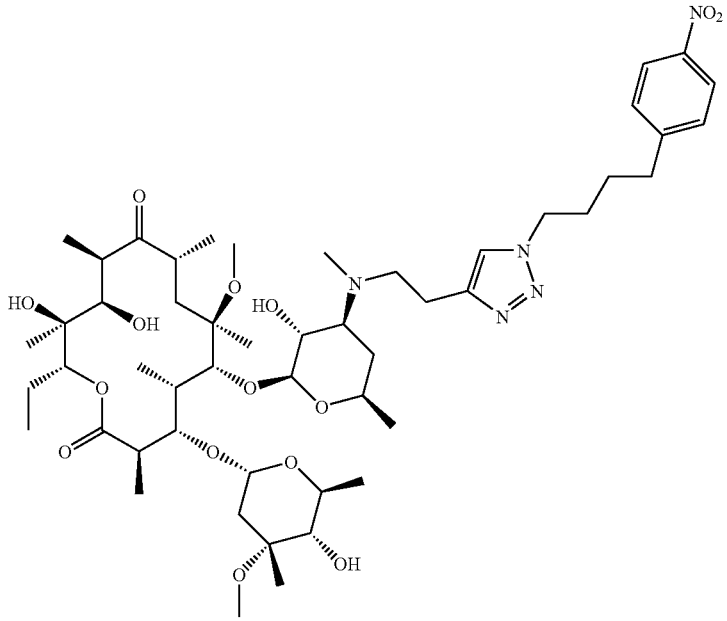 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc([N+](=O)[O-])cc4)nn3)[C@H]2O)[C@](C)(OC)C[C@@H](C)C(=O)[C@H](C)[C@@H](O)[C@]1(C)O] |
| 204 | 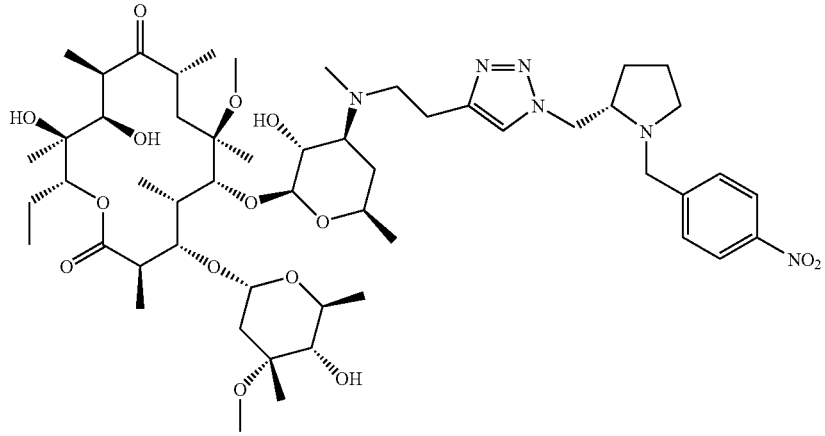 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H]4CCCN4Cc4ccc([N+](=O)[O-])cc4)nn3)[C@H]2O)[C@](C)(OC)C[C@@H](C)C(=O)[C@H](C)[C@@H](O)[C@]1(C)O] |
| 205 | 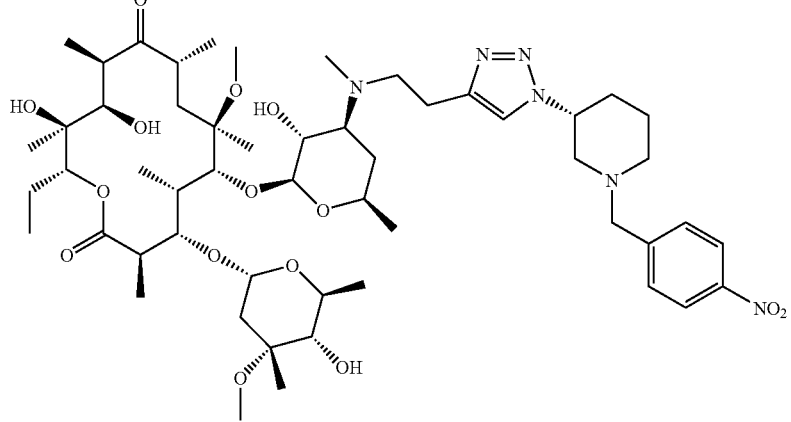 |

TABLE 1-continued
| Compound | Structure |
|---|---|
| 206 | 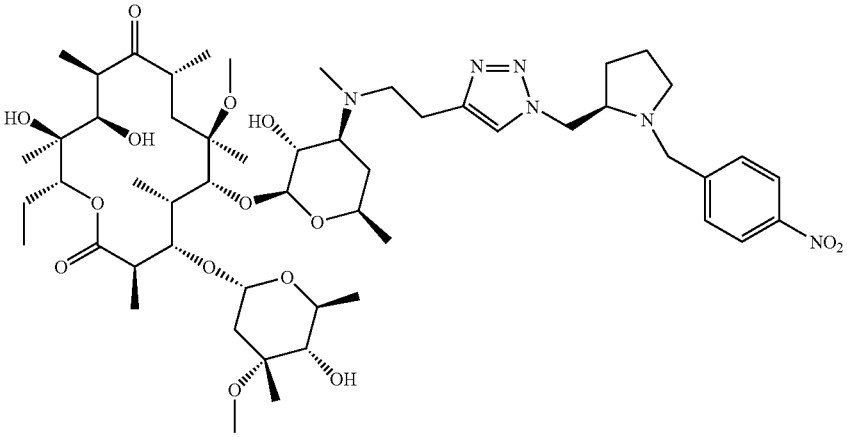 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@H]4CCCN4Cc4ccc([N+](=O)[O-])cc4)nn3)[C@H]2O)[C@](C)(OC)C[C@@H](C)C(=O)[C@H](C)[C@@H](O)[C@]1(C)O] |
| 207 | 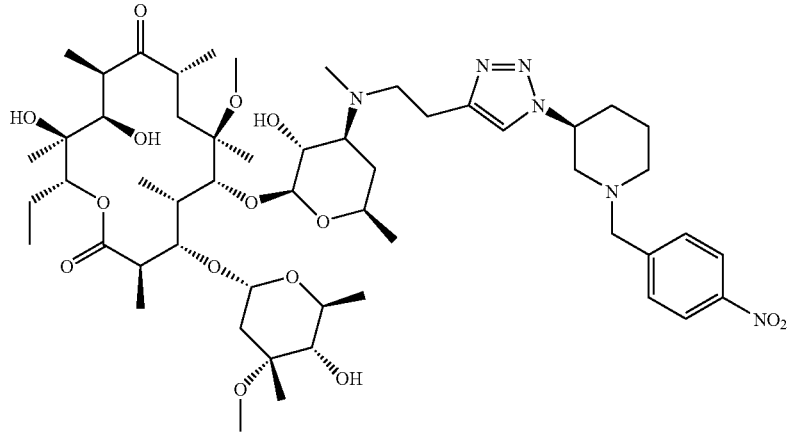 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H]4CCCN(Cc5ccc([N+](=O)[O-])cc5)C4)nn3)[C@H]2O)[C@](C)(OC)C[C@@H](C)C(=O)[C@H](C)[C@@H](O)[C@]1(C)O] |
| 210 | 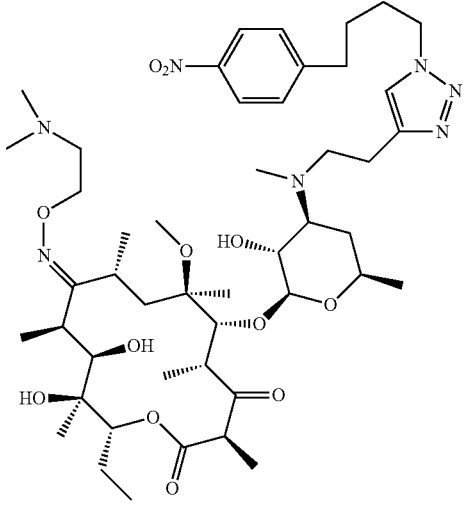 [SMILES: CC[C@H]1OC(=O)[C@H](C)C(=O)[C@H](C)[C@@H](O[C@@H]2O[C@H](C)C[C@H](N(C)CCc3cn(CCCCc4ccc([N+](=O)[O-])cc4)nn3)[C@H]2O)[C@](C)(OC)C[C@@H](C)/C(=N\OCCN(C)C)[C@H](C)[C@@H](O)[C@]1(C)O] |

| Compound | Structure |
|---|---|
| 211 | 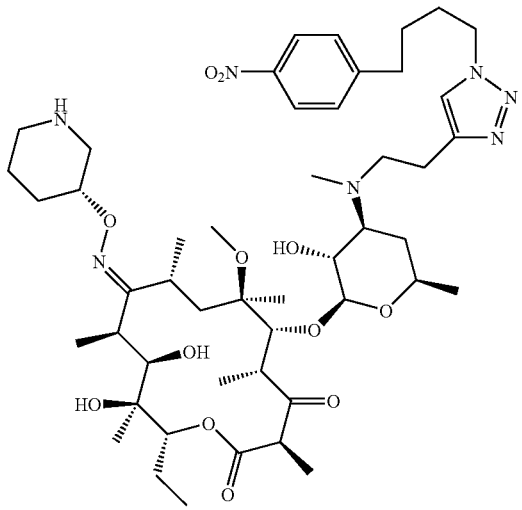 [SMILES: CC[C@H]1OC(=O)[C@H](C)C(=O)[C@H](C)[C@@H](O[C@@H]2O[C@H](C)C[C@H](N(C)CCc3cn(CCCCc4ccc([N+](=O)[O-])cc4)nn3)[C@H]2O)[C@](C)(OC)C[C@@H](C)/C(=N\O[C@@H]2CCCNC2)[C@H](C)[C@@H](O)[C@]1(C)O] |
| 212 | 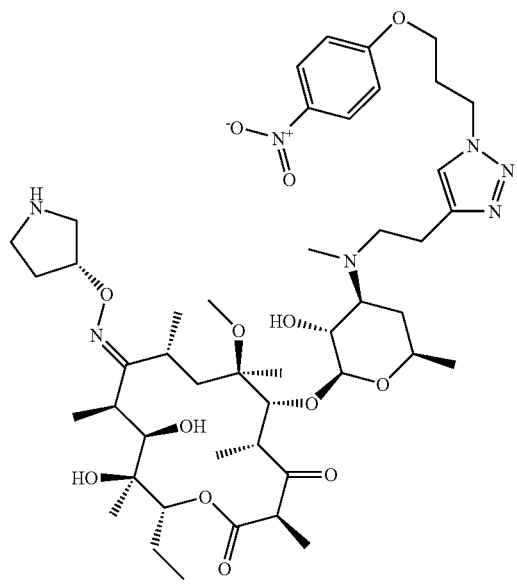 |

US 8,470,985 B2
171 172
TABLE 1-continued
| Compound | Structure |
|---|---|
| 213 | 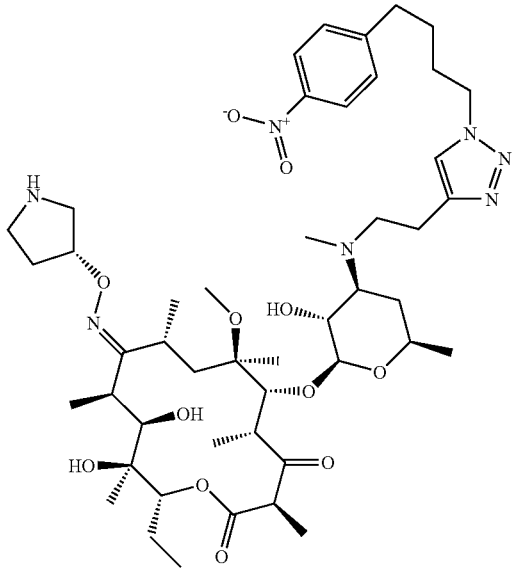 |
| 221 | 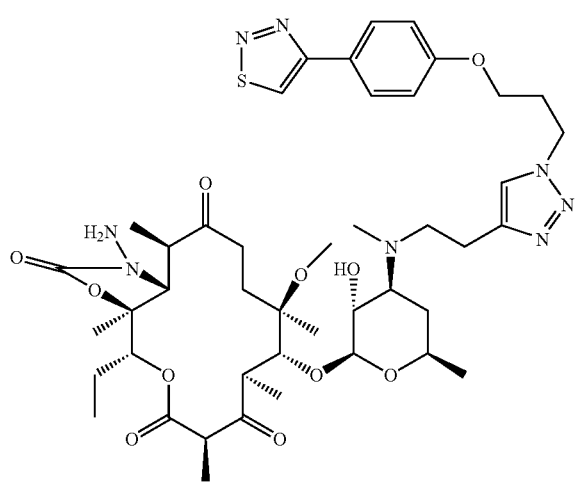 [SMILES: CC[C@H]1OC(=O)[C@H](C)C(=O)[C@H](C)[C@@H](O[C@@H]2O[C@H](C)C[C@H](N(C)CCc3cn(CCCOc4ccc(-c5csnn5)cc4)nn3)[C@H]2O)[C@](C)(OC)CCC(=O)[C@H](C)[C@H]2N(N)C(=O)O[C@]12C] |
| 222 | 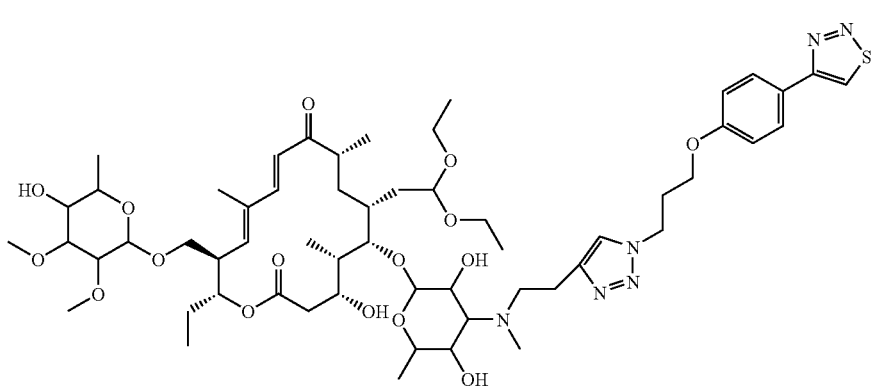 [SMILES: CCOC(C[C@H]1C[C@@H](C)C(=O)/C=C/C(C)=C/[C@H](COC2OC(C)C(O)C(OC)C2OC)[C@@H](CC)OC(=O)C[C@@H](O)[C@H](C)[C@H]1OC1OC(C)C(O)C(N(C)CCc2cn(CCCOc3ccc(-c4csnn4)cc3)nn2)C1O)OCC] |

TABLE 1-continued
| Compound | Structure |
|---|---|
| 223 | 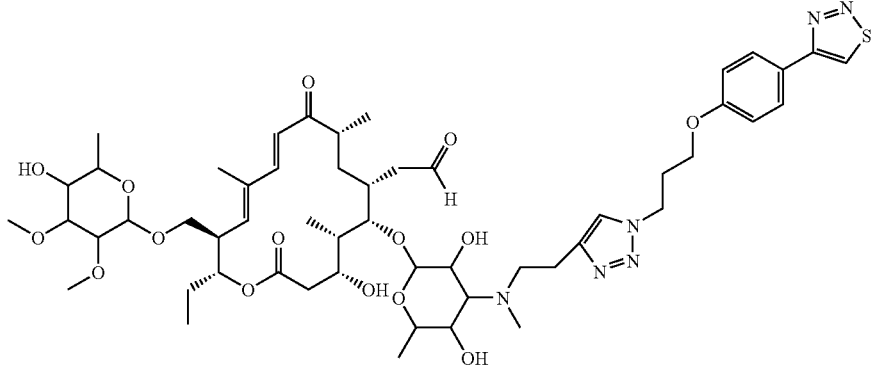 [SMILES: CC[C@H]1OC(=O)C[C@@H](O)[C@H](C)[C@@H](OC2OC(C)C(O)C(N(C)CCc3cn(CCCOc4ccc(-c5csnn5)cc4)nn3)C2O)[C@@H](CC=O)C[C@@H](C)C(=O)/C=C/C(C)=C/[C@@H]1COC1OC(C)C(O)C(OC)C1OC] |
| 224 | 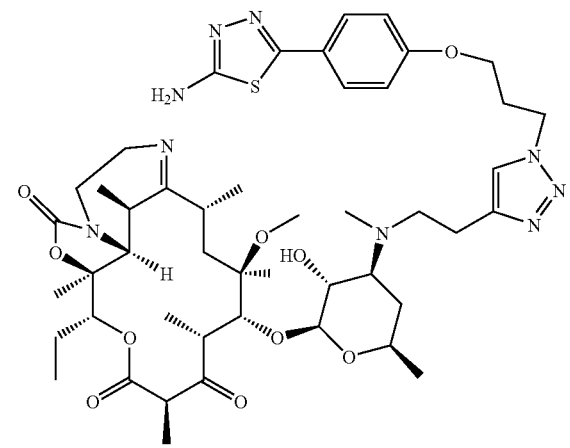 |
| 225 | 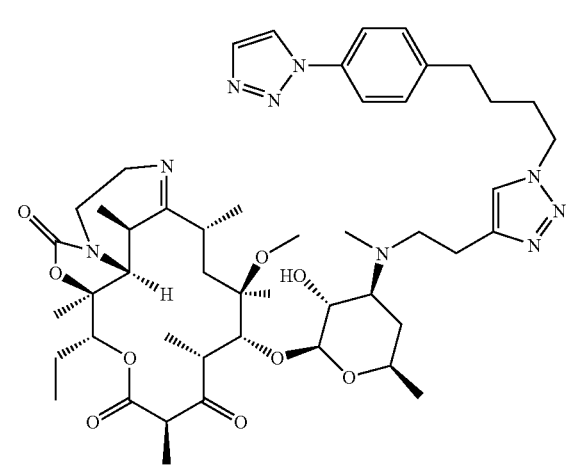 |

TABLE 1-continued
| Compound | Structure |
|---|---|
| 226 | 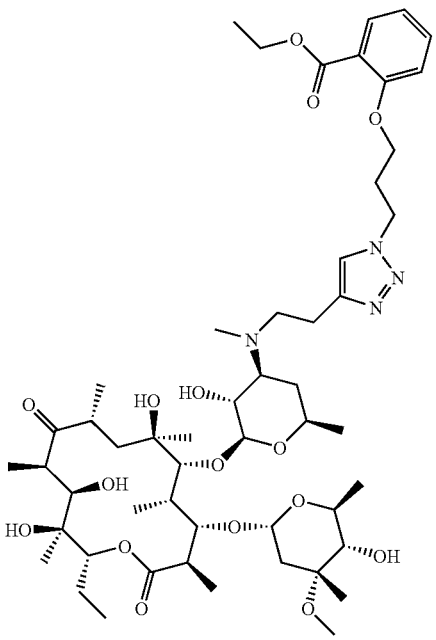 [SMILES: CCOC(=O)c1ccccc1OCCCn1cc(CCN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)C(=O)[C@H](C)C[C@@]3(C)O)[C@@H]2O)nn1] |
| 230 | 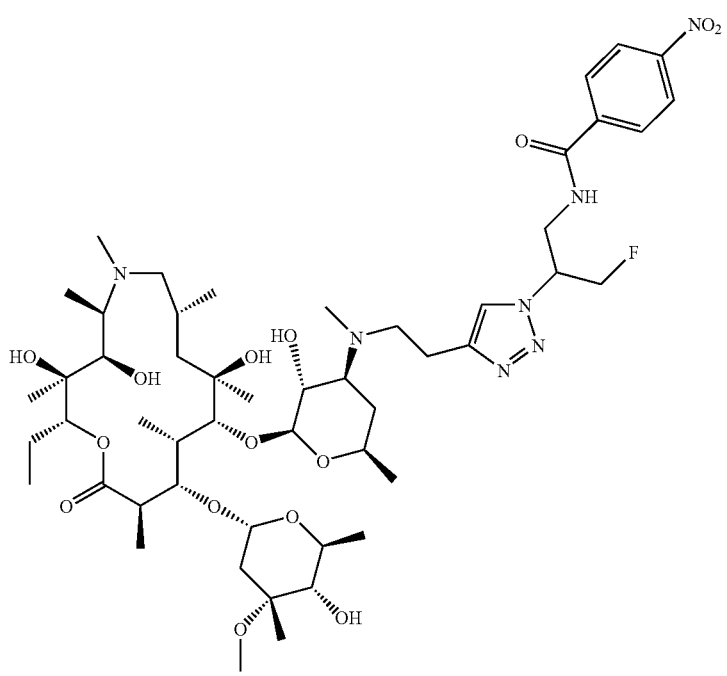 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CF)CNC(=O)c4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound | Structure |
|---|---|
| 231 | 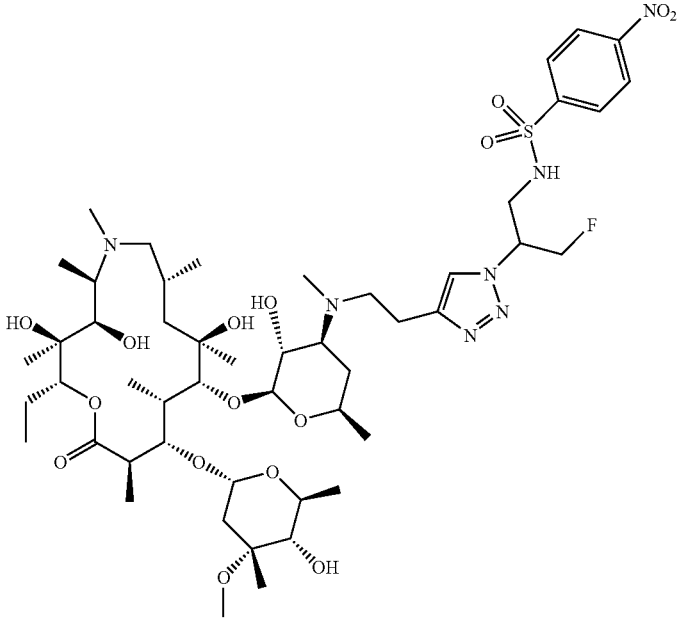 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CF)CNS(=O)(=O)c4ccc([N+](=O)[O-])cc4)nn3)[C@H]2O)[C@](C)(O)C[C@@H](C)CN(C)[C@H](C)[C@@H](O)[C@]1(C)O] |
| 232 | 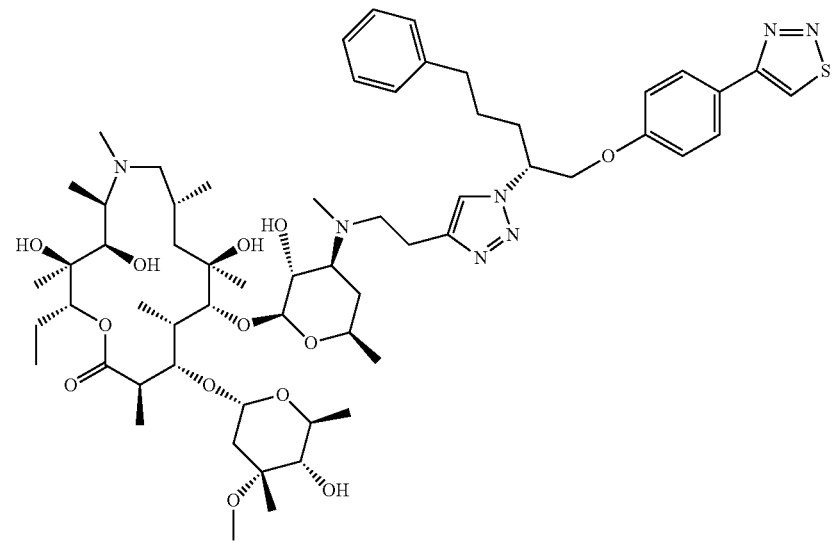 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CCCc4ccccc4)COc4ccc(-c5csnn5)cc4)nn3)[C@H]2O)[C@](C)(O)C[C@@H](C)CN(C)[C@H](C)[C@@H](O)[C@]1(C)O] |

TABLE 1-continued

| Compound | Structure |
|---|---|
| 233 | |
| 234 | |
| 235 | |

TABLE 1-continued

| Compound | Structure |
|---|---|
| 236 | |
| 237 | |
| 238 | |

| Compound | Structure |
|---|---|
| 239 | |
| 240 | |
| 241 | |

TABLE 1-continued

| Compound | Structure |
|---|---|
| 242 | 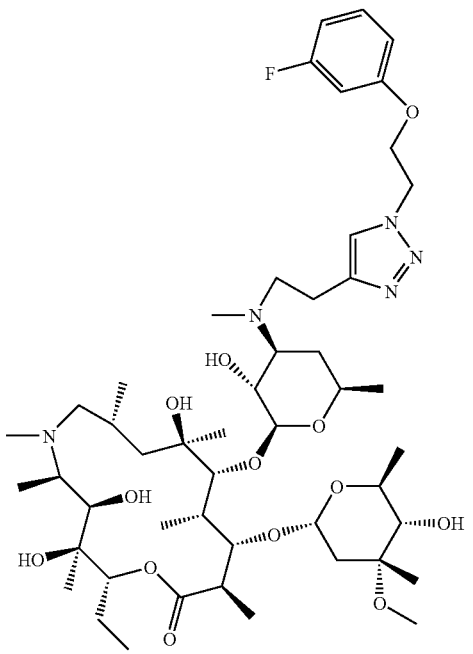 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc(F)c4)nn3)[C@H]2O)[C@](C)(O)C[C@@H](C)CN(C)[C@H](C)[C@@H](O)[C@]1(C)O] |
| 243 | 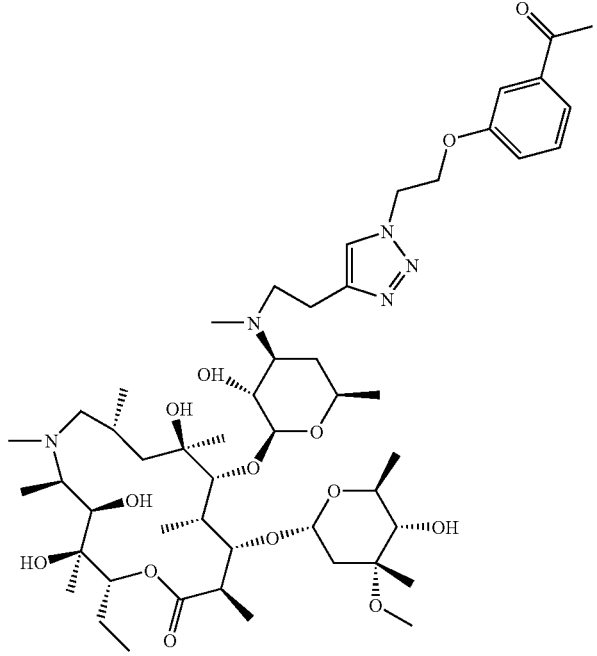 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc(C(C)=O)c4)nn3)[C@H]2O)[C@](C)(O)C[C@@H](C)CN(C)[C@H](C)[C@@H](O)[C@]1(C)O] |

Tables 2-5, below, contain the following information and are organized as follows:

the first column (labeled "Compound") lists the compound numbers corresponding to those of Table 1, above;

the second column (labeled "B") provides a structural representation for each of the compounds for the fragment designated as "-A-G" that is attached to the triazole ring, which is attached to a desosamine sugar or other sugar via a connecting group, where the desosamine sugar or other sugar is attached to T, the 14- to 15-membered macrolide ring. "B" corresponds to that portion of the compound indicated to the right of the dotted line as shown in the generic structure, immediately below. It should be recognized from the synthetic procedures described herein, that the "B" moiety is usually functionalized as an azide, such that the azide after cycloaddition with the appropriate alkyne is incorporated into the triazole ring of the final compounds. The remainder of the molecule, is designated as Mac;

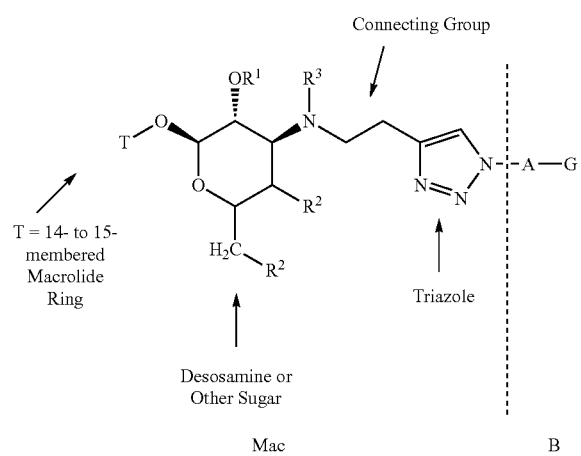

the third column (labeled "Mac") provides a structural representation for each of the compounds for the macrolide fragment (this includes the "T" 14- to 15-membered macrolide ring, the desosamine or other sugar, the connecting group, and the triazole) that is attached to the "B" fragment, and corresponds to that portion of the compound indicated to the left of the dotted line as shown in the generic structure, immediately above. The "Mac" fragments are denoted with an abbreviation and these fragments are shown below in Scheme 7;

the fourth column (labeled "Yield") provides the yield, where available, for the compounds when prepared from cycloaddition of the corresponding azide and alkynyl substituted macrolide compound;

the fifth column (labeled "LCMS") provides the liquid chromatography mass spectral data, where available, for the compound.

Scheme 7: Macrolide fragments "Mac" for Tables 2-5, where "B" is as defined in Tables 2-5 below.

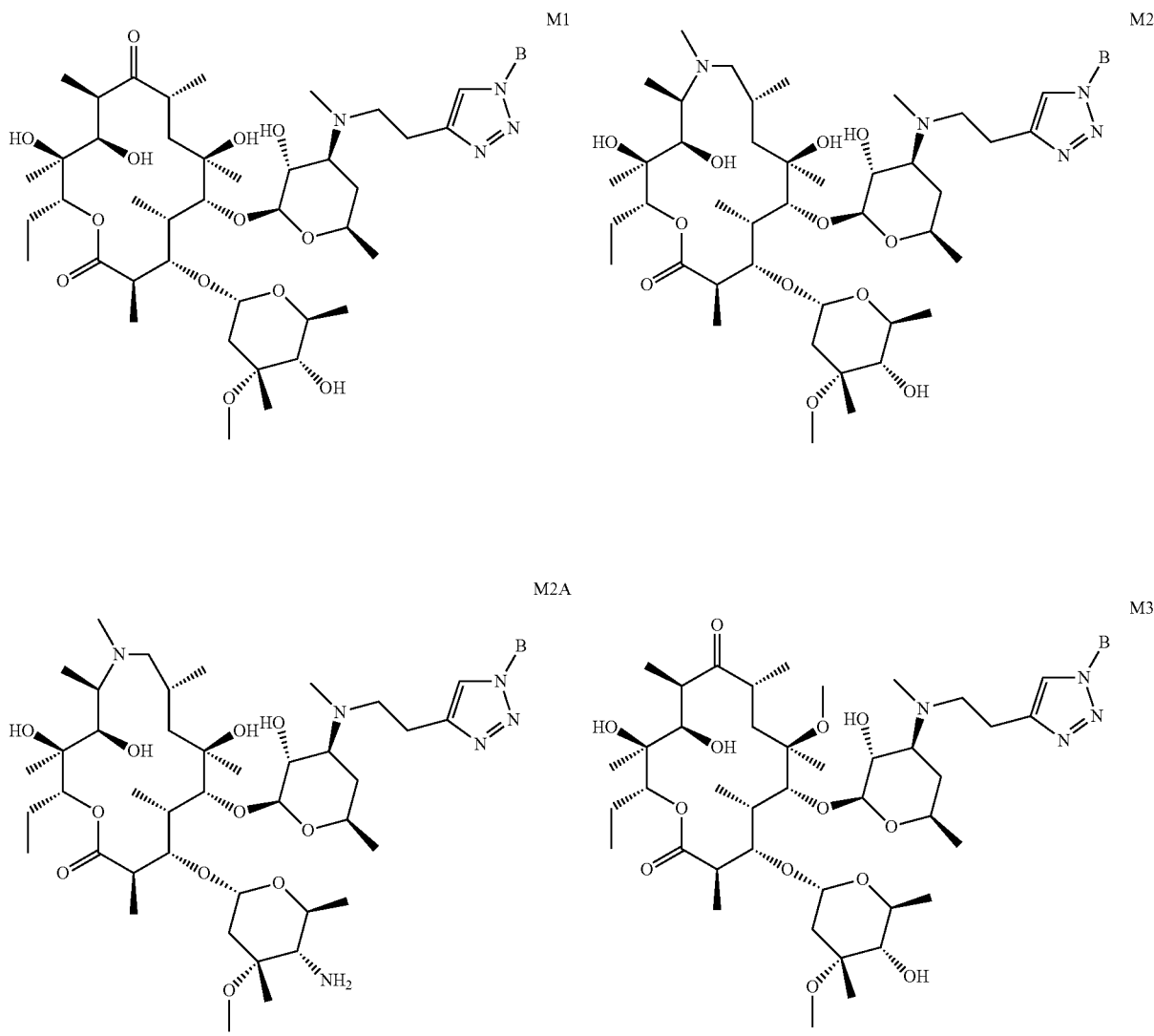

-continued
M3A
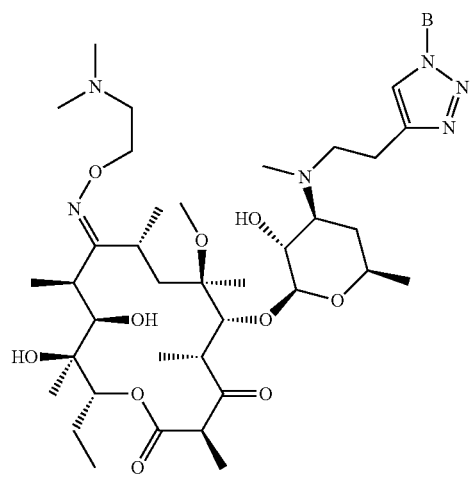
M3B
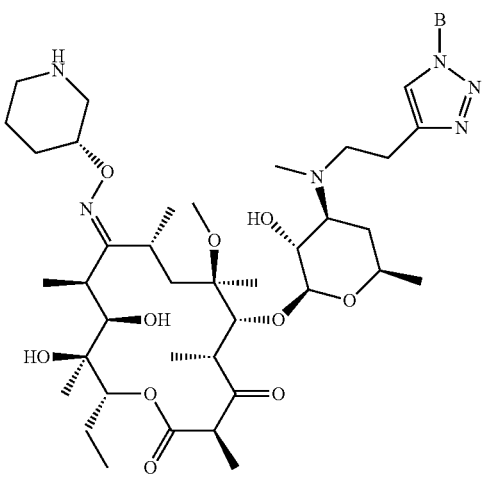
M3C
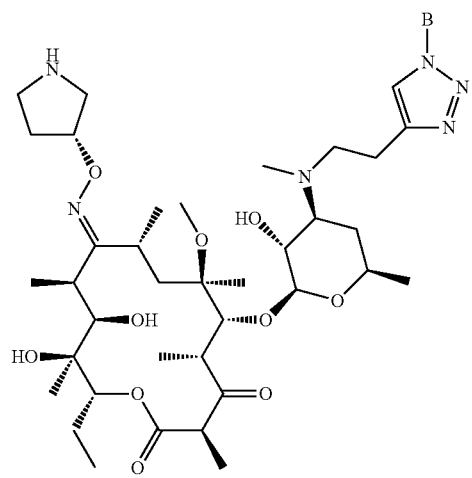
M4A
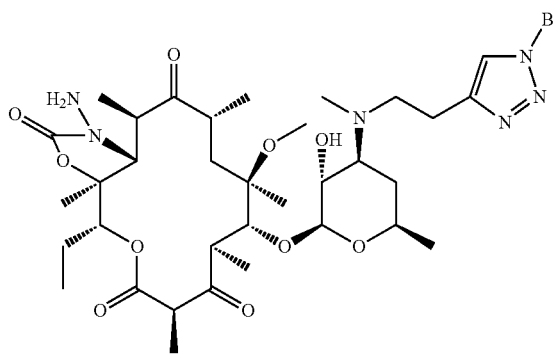
M5A
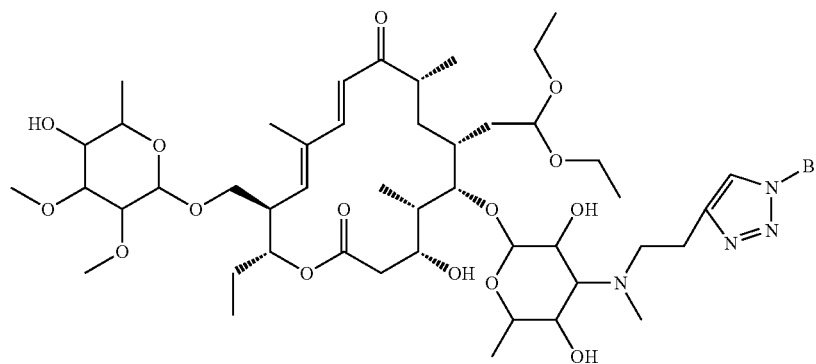
M6
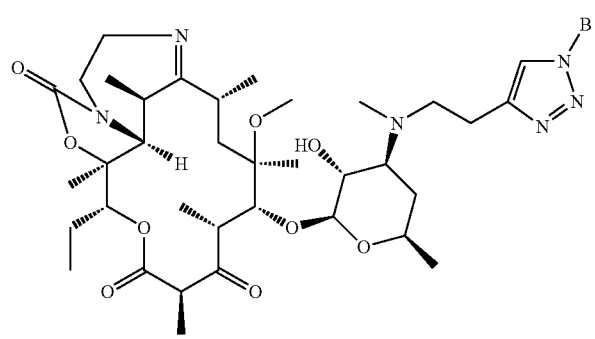

-continued

M5B

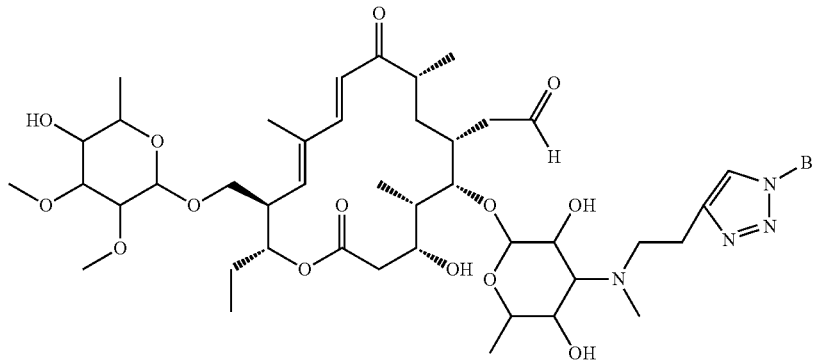

Example 1

Synthesis of Compounds 101-198

Schemes 100-101 and Table 2 below relate to the synthesis of compounds 101-198. Compounds 101-148, 151-160, 162, 164, 165, 183, 184, and 191-198 were made via the alkynyl intermediate, 3.

Alkynyl intermediate 3 was made by selective demethylation of azithromycin 1 to produce 3'-N-desmethylazithromycin 2. This compound 2 was selectively alkylated with alkynyl tosylate 11 to produce alkyne 3, respectively. As shown in Scheme 101 alkyne 3 is reacted with corresponding azides 14 in the presence of copper (I) iodide to selectively afford the triazoles 101-149, 151-160, 162, 164, 165, 183, 184, and 191-198.

The compounds 163, 168, 171-182, and 185-190 were made from azide compound 161. Azide compound 161 was made from amino compound 150, which in turn was made from nitro compound 147.

The compounds 169 and, 170 were made from azide compound 167. Azide compound 167 was made from amino compound 166, which in turn was made from nitro compound 108.

Scheme 100: Synthesis of alkyne 3.

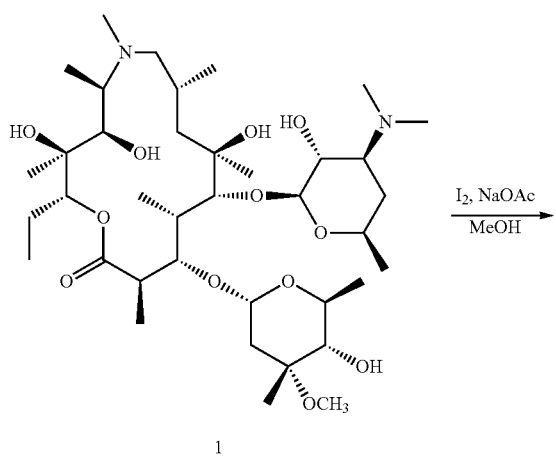

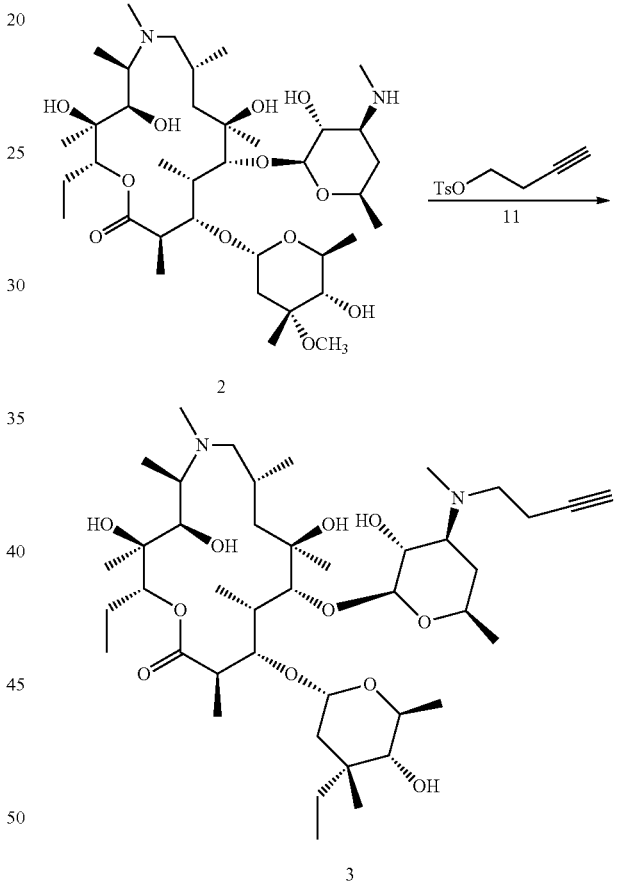

Synthesis of 3'-N-desmethylazithromycin 2

Azithromycin 1 (0.80 g, 1.02 mmol) and sodium acetate (NaOAc) (0.712 g, 8.06 mmol) were dissolved in 80% aqueous MeOH (25 mL). The solution was heated to 50° C. followed by addition of iodine (12) (0.272 g, 1.07 mmol) in three batches within 3 minutes. The reaction was maintained at a pH between 8-9 by adding 1N sodium hydroxide (NaOH) (1 mL) at 10 min and 45 minute intervals. The solution turned colorless within 45 minutes, however, stirring was continued for 2 hours. TLC($CH_2Cl_2$/MeOH/$NH_4OH$ 10:1:0.05) after 2 hours showed a single major product (Rf=0.66). The reaction was cooled to room temperature, poured into $H_2O$ (75 mL)

containing NH$_4$OH (1.5 mL) and extracted with CHCl$_3$ (3×30 mL). The combined organic layers were washed with H$_2$O (30 mL) containing NH$_4$OH (1.5 mL), dried over Na$_2$SO$_4$ and the solvent evaporated to give a white residue. The crude was purified on a silica gel column eluting with CH$_2$Cl$_2$/MeOH/NH$_4$OH 18:1:0.05 to 10:1:0.05 to provide amine 2 (0.41 g, 55%).

Synthesis of Alkyne 3

A mixture of 3'-N-desmethylazithromycin 2 and tosylate 11 in Hunig's base was stirred. The reaction mixture was diluted to EtOAc and washed with NaHCO$_3$(aq) and with brine. The organic layer was dried over K$_2$CO$_3$ and the solvent was evaporated to give product. The crude product was purified on silica gel column to give 3 as a white solid.

TABLE 2

| Compound | B | Mac | Yield | LCMS |
|---|---|---|---|---|
| 101 | *structure: propyl-NH-C(O)-C$_6$H$_4$-NO$_2$* | M2 | 83% | 512.0 (M + 2H)$^{2+}$ |
| 102 | *structure: propyl-NH-CH$_2$-C$_6$H$_4$-NO$_2$* | M2 | 24% | 505.0 (M + 2H)$^{2+}$ |
| 103 | *structure: propyl-NH-CH$_2$-C$_6$H$_4$-SO$_2$CH$_3$* | M2 | 45% | 521.5 (M + 2H)$^{2+}$ |
| 104 | *structure: propyl-N(CH$_3$)-CH$_2$-C$_6$H$_4$-NO$_2$* | M2 | 87% | 511.9 (M + 2H)$^{2+}$ |
| 105 | *structure: propyl-NH-SO$_2$-C$_6$H$_4$-NO$_2$* | M2 | 80% | 530.1 (M + 2H)$^{2+}$ |
| 106 | *structure: propyl-NH-SO$_2$-C$_6$H$_4$-SO$_2$CH$_3$* | M2 | 66% | 546.6 (M + 2H)$^{2+}$ |
| 107 | *structure: butyl-C(O)-C$_6$H$_4$-pyridyl* | M2 | 76% | 527.7 (M + 2H)$^{2+}$ |
| 108 | *structure: propyl-O-C$_6$H$_4$-NO$_2$* | M2 | 74% | 505.6 (M + 2H)$^{2+}$ |

TABLE 2-continued

| Compound | B | Mac | Yield | LCMS |
|---|---|---|---|---|
| 109 | | M2 | 62% | 525.1 (M + 2H)²⁺ |
| 110 | | M2 | 95% | 522.1 (M + 2H)²⁺ |
| 111 | | M2 | 27% | 533.1 (M + 2H)²⁺ |
| 112 | | M2 | 46% | 532.4 (M + 2H)²⁺ |
| 113 | | M2 | 72% | 529.1 (M + 2H)²⁺ |
| 114 | | M2 | 78% | 536.1 (M + 2H)²⁺ |
| 115 | | M2 | 71% | 536.1 (M + 2H)²⁺ |
| 116 | | M2 | 84% | 520.1 (M + 2H)²⁺ |

TABLE 2-continued
| Compound | B | Mac | Yield | LCMS |
|---|---|---|---|---|
| 117 | 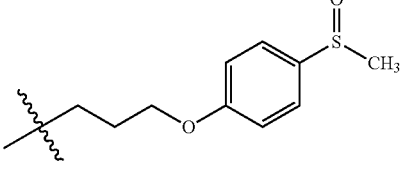 | M2 | 77% | 514.1 (M + 2H)²⁺ |
| 118 | 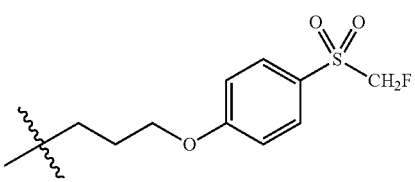 | M2 | 96% | 531.1 (M + 2H)²⁺ |
| 119 | 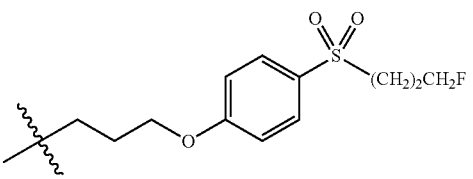 | M2 | 87% | 545.1 (M + 2H)²⁺ |
| 120 | 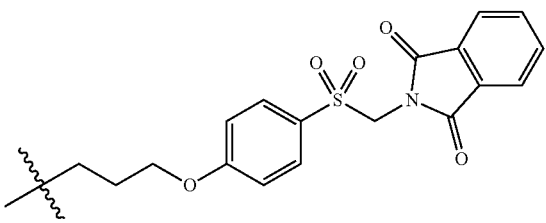 [SMILES: *CCCOc1ccc(S(=O)(=O)CN2C(=O)c3ccccc3C2=O)cc1] | M2 | 86% | 594.6 (M + 2H)²⁺ |
| 121 | 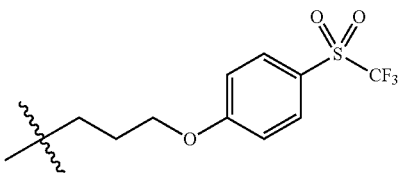 [SMILES: *CCCOc1ccc(S(=O)(=O)C(F)(F)F)cc1] | M2 | 86% | 549.1 (M + 2H)²⁺ |
| 122 | 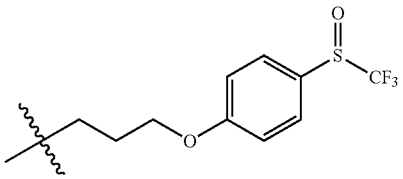 [SMILES: *CCCOc1ccc(S(=O)C(F)(F)F)cc1] | M2 | 88% | 541.1 (M + 2H)²⁺ |
| 123 | 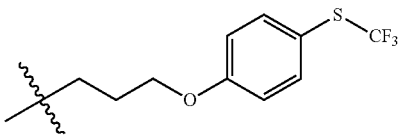 [SMILES: *CCCOc1ccc(SC(F)(F)F)cc1] | M2 | 81% | 533.1 (M + 2H)²⁺ |
| 124 | 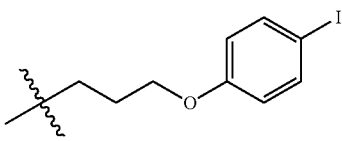 [SMILES: *CCCOc1ccc(I)cc1] | M2 | 36% | 546.1 (M + 2H)²⁺ |

TABLE 2-continued
| Compound | B | Mac | Yield | LCMS |
|---|---|---|---|---|
| 125 | 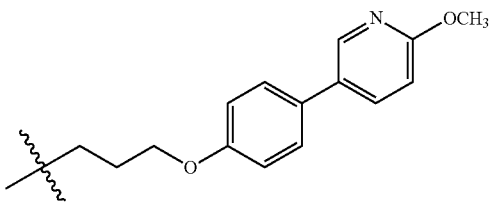 [SMILES: *CCCOc1ccc(-c2ccc(OC)nc2)cc1] | M2 | 74% | 536.6 (M + 2H)$^{2+}$ |
| 126 | 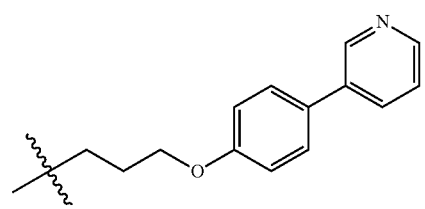 [SMILES: *CCCOc1ccc(-c2cccnc2)cc1] | M2 | 77% | 1042.7 (M + H)$^+$ |
| 127 | 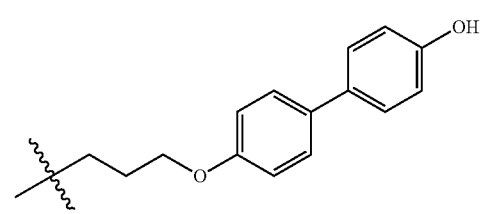 [SMILES: *CCCOc1ccc(-c2ccc(C#N)cc2)cc1] | M2 | 60% | 536.1 (M + 2H)$^{2+}$ |
| 128 | 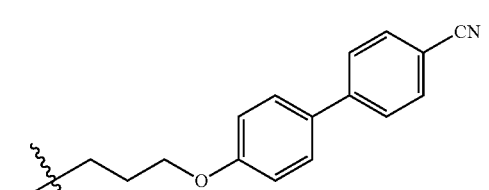 | M2 | 50% | 533.7 (M + 2H)$^{2+}$ |
| 129 | 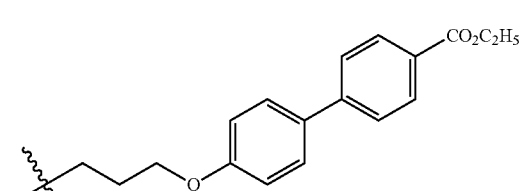 | M2 | 64% | 557.2 (M + 2H)$^{2+}$ |
| 130 | 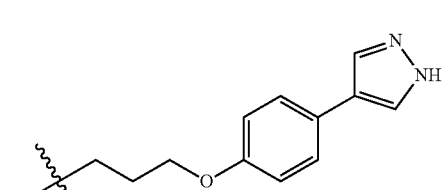 | M2 | 25% | 516.2 (M + 2H)$^{2+}$ |
| 131 | 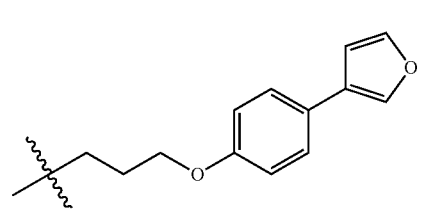 [SMILES: *CCCOc1ccc(-c2ccoc2)cc1] | M2 | 37% | 515.9 (M + 2H)$^{2+}$ |

TABLE 2-continued

| Compound | B | Mac | Yield | LCMS |
|---|---|---|---|---|
| 132 | (4-(pyrimidin-5-yl)phenoxy)butyl | M2 | 60% | 522.1 $(M + 2H)^{2+}$ |
| 133 | (4-(6-methylpyridin-3-yl)phenoxy)butyl | M2 | 80% | 528.2 $(M + 2H)^{2+}$ |
| 134 | 4'-(CH$_2$NH(CH$_2$)$_2$CH$_2$F)-2-fluoro-[1,1':4',1''-terphenyl]-4-yloxy)butyl | M2 | — | — |
| 135 | (4-(1H-1,2,3-triazol-1-yl)phenoxy)butyl | M2 | 82% | 486.1 $(M + 2H)^{2+}$ |
| 136 | 1-(4-(1,2,3-thiadiazol-4-yl)phenoxy)-2-hydroxypropyl | M2 | 88% | 533.1 $(M + 2H)^{2+}$ 1064.8 $(M + H)^+$ |
| 137 | 2-fluoro-3-(4-nitrophenoxy)propyl | M2 | 61% | 514.6 $(M + 2H)^{2+}$ 1064.8 $(M + H)^+$ |
| 138 | 2-methyl-3-(4-nitrophenoxy)propyl | M2 | 85% | 512.6 $(M + 2H)^{2+}$ 1024 $(M + H)^+$ |
| 139 | 2-hydroxy-3-(4-nitrophenoxy)propyl | M2 | 79% | 513.6 $(M + 2H)^{2+}$ |

TABLE 2-continued

| Compound | B | Mac | Yield | LCMS |
|---|---|---|---|---|
| 140 | (structure) | M2 | 75% | 530 $(M+2H)^{2+}$ |
| 141 | (structure) | M2 | 78% | 531 $(M+2H)^{2+}$<br>1060.7 $(M+H)^+$ |
| 142 | (structure) | M2 | 56% | 514.6 $(M+2H)^{2+}$<br>1064.8 $(M+H)^+$ |
| 143 | (structure) | M2 | 88% | 512.6 $(M+2H)^{2+}$<br>1024 $(M+H)^+$ |
| 144 | (structure) | M2 | 94% | 513.6 $(M+2H)^{2+}$ |
| 145 | (structure) | M2 | 92% | 533.1 $(M+2H)^{2+}$ |
| 146 | (structure) | M2 | 90% | 529.5 $(M+2H)^{2+}$ |
| 147 | (structure) | M2 | 81% | 504.5 $(M+2H)^{2+}$ |
| 148 | (structure) | M2 | 64% | 515.6 $(M+2H)^{2+}$<br>1030.0 $(M+H)^+$ |

TABLE 2-continued
| Compound | B | Mac | Yield | LCMS |
|---|---|---|---|---|
| 149 | 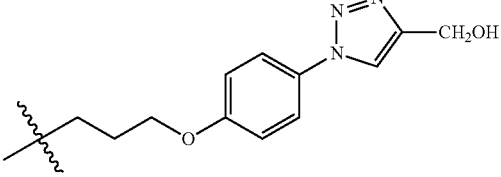 | M2 | 77% | 530.6 (M + 2H)$^{2+}$ |
| 150 | 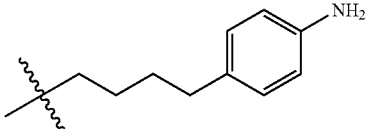 [SMILES: *CCCCc1ccc([N+](=O)[O-])cc1] | M2 | — | 489.4 (M + 2H)$^{2+}$ |
| 151 | 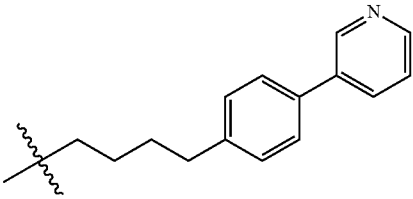 [SMILES: *CCCCc1ccc(-c2cccnc2)cc1] | M2 | 94% | 520.5 (M + 2H)$^{2+}$ |
| 152 | 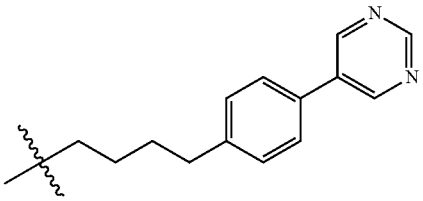 [SMILES: *CCCCc1ccc(-c2cncnc2)cc1] | M2 | 65% | 521.0 (M + 2H)$^{2+}$ |
| 153 | 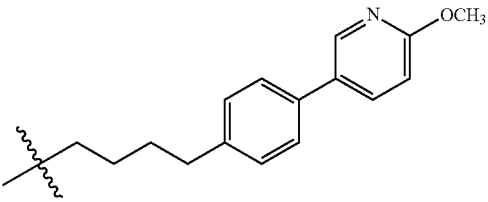 [SMILES: *CCCCc1ccc(-c2ccc(OC)nc2)cc1] | M2 | 98% | 535.6 (M + 2H)$^{2+}$ |
| 154 | 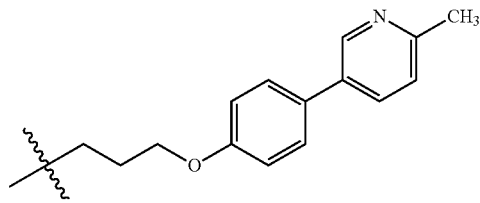 [SMILES: *CCCOc1ccc(-c2ccc(C)nc2)cc1] | M2 | 70% | 528.8 (M + 2H)$^{2+}$ |
| 155 | 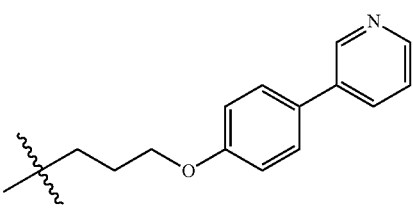 [SMILES: *CCCOc1ccc(-c2cccnc2)cc1] | M2 | 66% | 521.6 (M + 2H)$^{2+}$ |
| 156 | 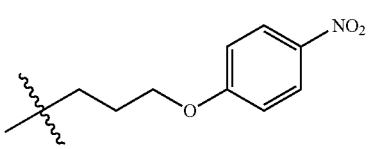 [SMILES: *CCCOc1ccc([N+](=O)[O-])cc1] | M2 | 40% | 505.6 (M + 2H)$^{2+}$ |

TABLE 2-continued
| Compound | B | Mac | Yield | LCMS |
|---|---|---|---|---|
| 157 | 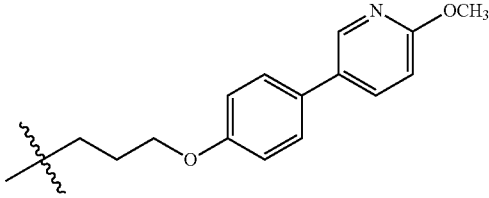 [SMILES: *CCCOc1ccc(-c2ccc(OC)nc2)cc1] | M2 | 82% | 536.8 $(M + 2H)^{2+}$ |
| 158 | 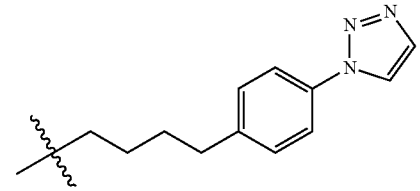 [SMILES: *CCCCc1ccc(-n2ccnn2)cc1] | M2 A | 20% | 515.0 $(M + 2H)^{2+}$ |
| 159 | 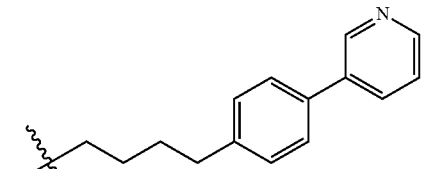 | M2 A | 60% | 520.3 $(M + 2H)^{2+}$ |
| 160 | 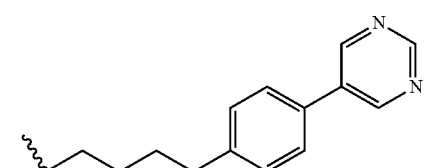 | M2 | 61% | 528.1 $(M + 2H)^{2+}$ |
| 161 | 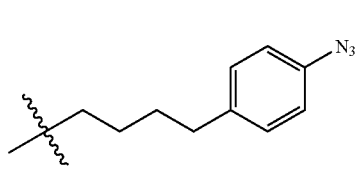 [SMILES: *CCCCc1ccc(N=[N+]=[N-])cc1] | M2 | — | 502.7 $(M + 2H)^{2+}$ |
| 162 | 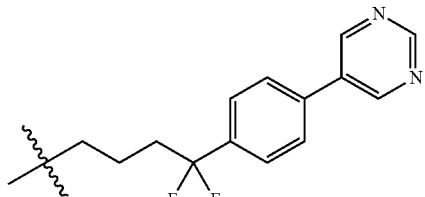 | M2 | 40% | 539.0 $(M + 2H)^{2+}$ |
| 163 | 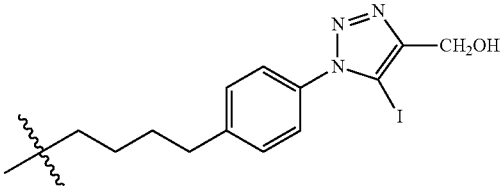 [SMILES: *CCCCc1ccc(-n2nnc(CO)c2I)cc1] | M2 | — | 593.8 $(M + 2H)^{2+}$ |

TABLE 2-continued
| Compound | B | Mac | Yield | LCMS |
|---|---|---|---|---|
| 164 | 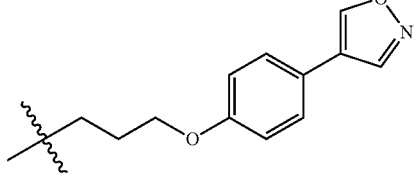 | M2 | 60% | 516.6 $(M + 2H)^{2+}$ |
| 165 | 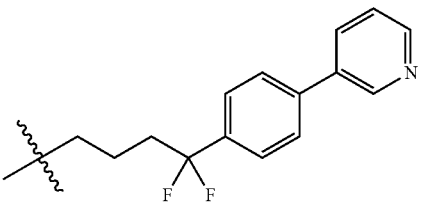 [SMILES: *CCCC(F)(F)c1ccc(-c2cccnc2)cc1] | M2 | 77% | 538.6 $(M + 2H)^{2+}$ |
| 166 | 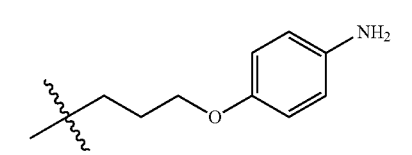 [SMILES: *CCCOc1ccc(N)cc1] | M2 | — | — |
| 167 | 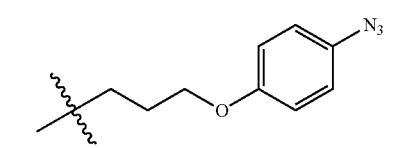 [SMILES: *CCCOc1ccc(N=[N+]=[N-])cc1] | M2 | — | 503.6 $(M + 2H)^{2+}$ |
| 168 | 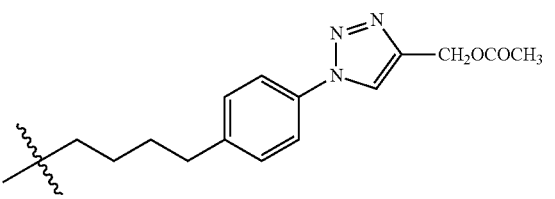 | M2 | — | 551.6 $(M + 2H)^{2+}$ |
| 169 | 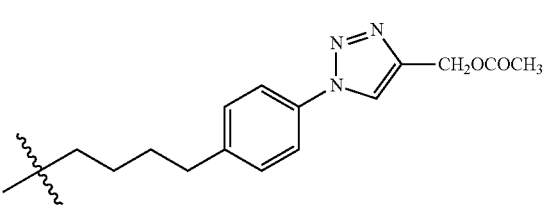 | M2 | — | 552.8 $(M + 2H)^{2+}$ |
| 170 | 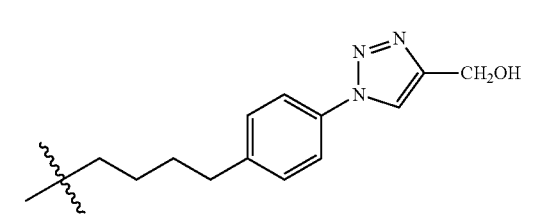 [SMILES: *CCCCc1ccc(-n2cc(CO)nn2)cc1] | M2 | — | 531.6 $(M + 2H)^{2+}$ |
| 171 | 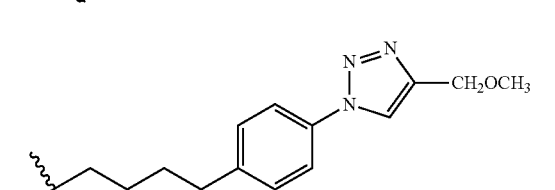 | M2 | — | 537.7 $(M + 2H)^{2+}$ |

TABLE 2-continued

| Compound | B | Mac | Yield | LCMS |
|---|---|---|---|---|
| 172 | (triazole-phenyl-pentyl with -CH₂N(C₂H₅)₂ substituent) | M2 | — | 558.2 (M + 2H)$^{2+}$ |
| 173 | (triazole-phenyl-pentyl with -CONH₂ substituent) | M2 | — | 537.1 (M + 2H)$^{2+}$ |
| 174 | (triazole-phenyl-pentyl with 2-pyridyl substituent) | M2 | — | 554.2 (M + 2H)$^{2+}$ |
| 175 | (triazole-phenyl-pentyl with -CH₂CH₂CH₂OH substituent) | M2 | — | 544.6 (M + 2H)$^{2+}$ |
| 176 | (triazole-phenyl-pentyl with -CH₃ substituent) | M2 | — | 522.8 (M + 2H)$^{2+}$ |
| 177 | (triazole-phenyl-pentyl with -CH₂CH₂OH substituent) | M2 | — | 537.8 (M + 2H)$^{2+}$ |
| 178 | (triazole-phenyl-pentyl with -COCH₃ substituent) | M2 | — | 536.7 (M + 2H)$^{2+}$ |

TABLE 2-continued

| Compound | B | Mac | Yield | LCMS |
|---|---|---|---|---|
| 179 | phenyl-triazole-(CH₂)₃CH₃ | M2 | — | 542.8 (M + 2H)²⁺ |
| 180 | phenyl-triazole-CH₂-N(CH₃)₂ | M2 | — | 544.1 (M + 2H)²⁺ |
| 181 | phenyl-triazole-pyridyl | M2 | — | 554.4 (M + 2H)²⁺ |
| 182 | phenyl-triazole-CH₂-NH-CH₃ | M2 | — | 537.2 (M + 2H)²⁺ |
| 183 | phenoxy-imidazole | M2 | 85% | 515.1 (M + 2H)²⁺ |
| 184 | imidazole-pyridyl | M2 | 47% | 515.4 (M + 2H)²⁺ |
| 185 | phenyl-triazole-CH₂-NH₂ | M2 | — | 530.0 (M + 2H)²⁺ |
| 186 | phenyl-triazole-CH₂-NHSO₂CH₃ | M2 | — | 569.3 (M + 2H)²⁺ |

TABLE 2-continued

| Compound | B | Mac | Yield | LCMS |
|---|---|---|---|---|
| 187 | 4-(4-cyclopropyl-1H-1,2,3-triazol-1-yl)phenyl-pentyl | M2 | — | 535.8 (M + 2H)²⁺ |
| 188 | 4-(4-n-C₆H₁₃-1H-1,2,3-triazol-1-yl)phenyl-pentyl | M2 | — | 557.8 (M + 2H)²⁺ |
| 189 | 4-(4-C(CH₃)₃-1H-1,2,3-triazol-1-yl)phenyl-pentyl | M2 | — | 543.8 (M + 2H)²⁺ |
| 190 | 4-(4-cyclohexyl-1H-1,2,3-triazol-1-yl)phenyl-pentyl | M2 | — | 556.8 (M + 2H)²⁺ |
| 191 | 2-(4-(methylsulfonyl)phenyl)cyclopropyl | M2 | 90% | 1024.9 (M + H)⁺ 513.0 (M + 2H)²⁺ |
| 192 | (2S)-1-(4-nitrobenzyl)pyrrolidin-2-yl-methyl | M2 | 50% | 525.1 (M + 2H)²⁺ |
| 193 | 1-(4-nitrobenzyl)piperidin-3-yl | M2 | 34% | 525.1 (M + 2H)²⁺ |

TABLE 2-continued
| Compound | B | Mac | Yield | LCMS |
|---|---|---|---|---|
| 194 | 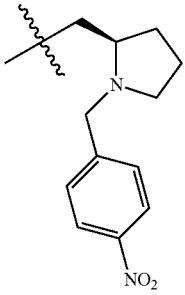 [SMILES: *C[C@H]1CCCN1Cc1ccc([N+](=O)[O-])cc1] | M2 | 33% | 525.1 (M + 2H)$^{2+}$ |
| 195 | 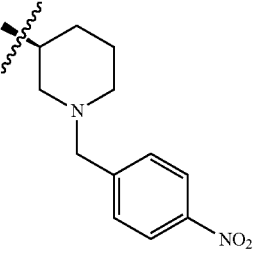 | M2 | 56% | 525.1 (M + 2H)$^{2+}$ |
| 196 | 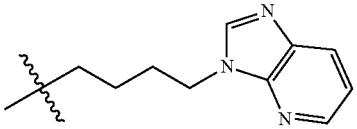 [SMILES: *CCCCn1cnc2cccnc21] | M2 | 93% | 1004.1 (M + H)$^{+}$ 502.5 (M + 2H)$^{2+}$ |
| 197 | 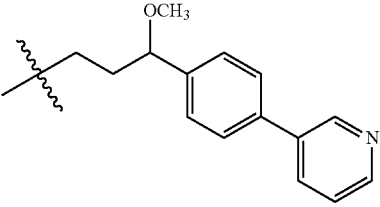 [SMILES: *CCC(OC)c1ccc(-c2cccnc2)cc1] | M2 | 81% | 521.6 (M + 2H)$^{2+}$ |
| 198 | 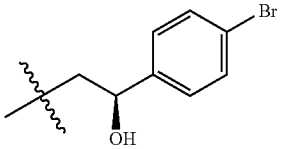 [SMILES: *C[C@H](O)c1ccc(Br)cc1] | M2 | 75% | 516.0 (M + 2H)$^{2+}$ |

Scheme 101: Synthesis of compounds
101-148, 150-160, 162, 164, 165, 183, 184, and 191-198

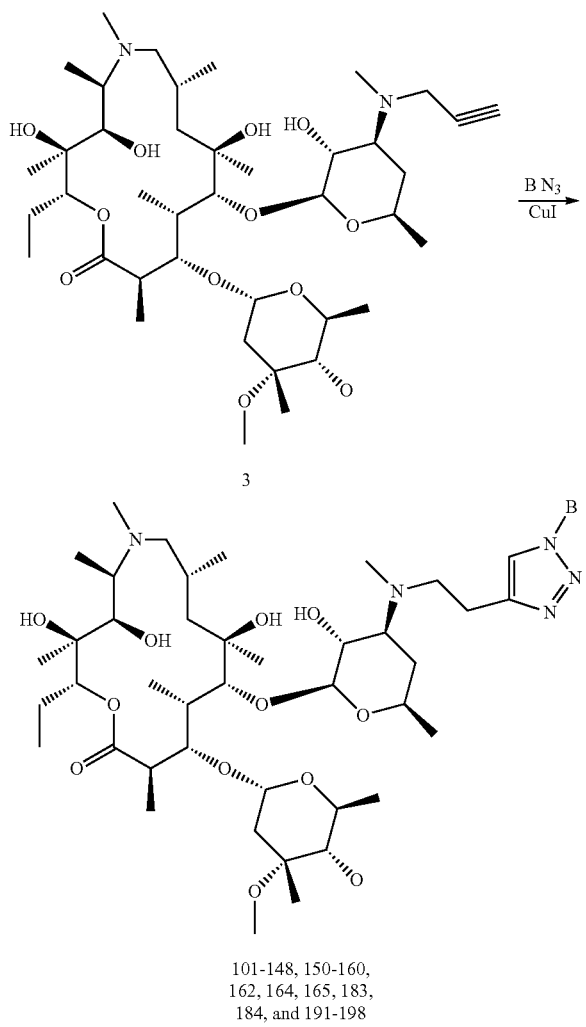

101-148, 150-160,
162, 164, 165, 183,
184, and 191-198

Where B is as defined in Table 2.

The compounds 101-148, 151-160, 162, 164, 165, 183, 184, and 191-198 were produced from alkyne 3 using the corresponding azides 14 (B—N$_3$) using conditions closely analogous to those described below. The time required for each reaction to proceed to completion was variable and was dependent upon several factors including: the specific substrates; the amount of Cu(I) salt used; the presence or absence of Hunig's base; and the concentration of the reactants. Reactions were monitored for the disappearance of the starting materials by TLC and/or LCMS and were typically allowed to run for between about 2 h to about 72 h. Reactions were stopped when analysis demonstrated that the starting alkyne substrate had been substantially consumed. The workup and purification protocols are typical of those used previously. Slight modifications to the described workup procedures may have been used (such modifications include the use of different aqueous wash solutions, different organic solvents for extraction, the use of other anhydrous salts for the drying of organic extracts, and the employment of different solvent mixtures for the chromatographic purification of the compounds). In all cases, the methods used for the workup of the reaction mixtures, the extraction of products, the drying of organic extracts, and for the isolation and purification of the title compounds were typical of procedures familiar to those trained in the art of organic synthesis. There were no specific or unusual protocols employed in the isolation and purification of the reaction products that were found to be critical in these processes. The isolated chemical yields for the synthesis of compounds 101-148, 151-160, 162, 164, 165, 183, 184, and 191-198 were variable and are indicated in the penultimate column of Table 2.

Compounds 149, 171-182 and 185-190 were prepared from a cycloaddition reaction of azide compound 161 with the corresponding alkyne. Azide compound 161 was prepared from amine 150, which in turn was prepared from the nitro compound 147. Compounds 169 and 170 were prepared from a cycloaddition reaction of azide compound 167. Azide compound 167 was prepared from amino compound 166, which in turn was prepared from the nitro compound 108.

The following Schemes demonstrate the general synthesis of compounds such as 149, 168, 171-182, and 185-190.

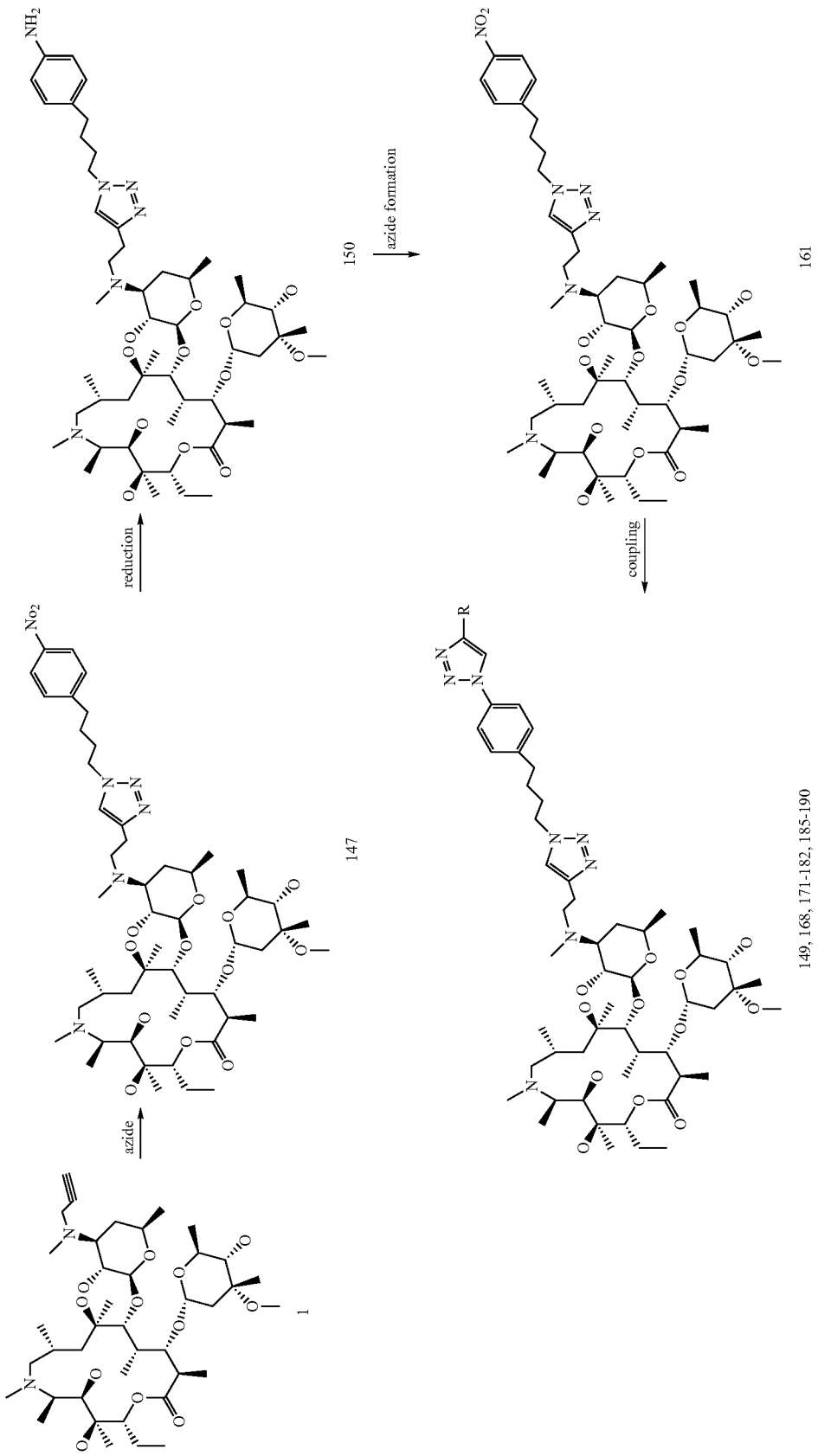

Synthesis of Compound 147

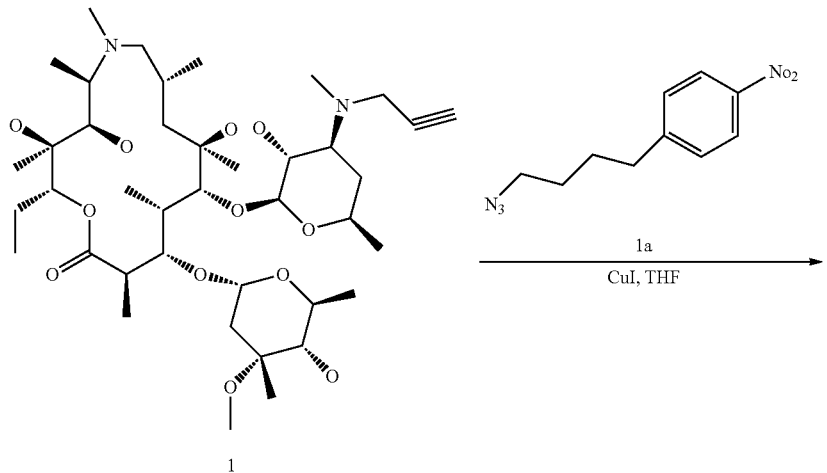

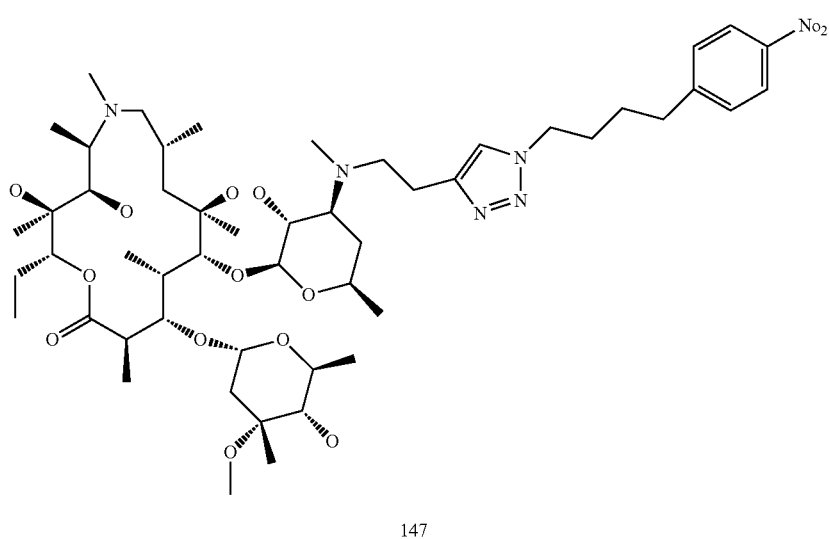

A solution of 1.550 g (1.97 mmol) of compound 1, 0.650 g (2.95 mmol) of azide 1a, and 0.375 g (1.97 mmol) of CuI in 40 ml of THF (a few drops of Hunig's base in it) was stirred under argon for 6 h. To this reaction mixture was added 50 ml of 10% aqueous ammonia solution, and the solution was allowed to stir for 10 min, then extracted with $CH_2Cl_2$ (40×3), the combined $CH_2Cl_2$ layers were washed with brine, dried, concentrated, and purified through silica gel column chromatography to give 1.520 g of pure product 147.

Synthesis of Azide 1a

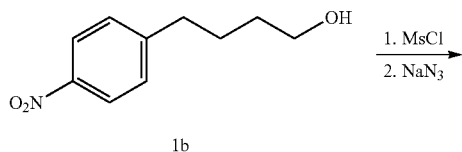

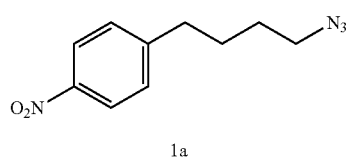

To a solution of 3.000 g (15.37 mmol) of compound 1b, 5.36 ml (30.73 mmol) of Hunig's base in 30 ml of DMF at 0° C. was added 1.79 ml (23.05 mmol) of MsCl. The reaction mixture was warmed tip to 25° C. for 2 h. To the mixture was then added 1.998 g (30.73 mmol) of $NaN_3$, heated up to 70° C. for 16 h. The reaction mixture was diluted with $H_2O$ (50 ml), extracted with ether), the combined ether layers were washed with brine, dried, filtered, and concentrated to give 2.670 g of the desired product 1a.

Synthesis of Compound 150
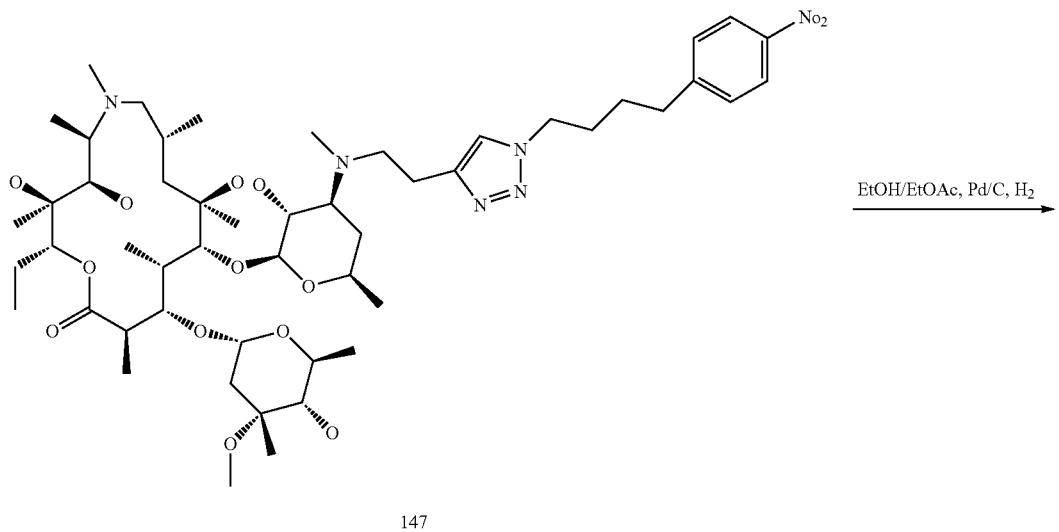
147
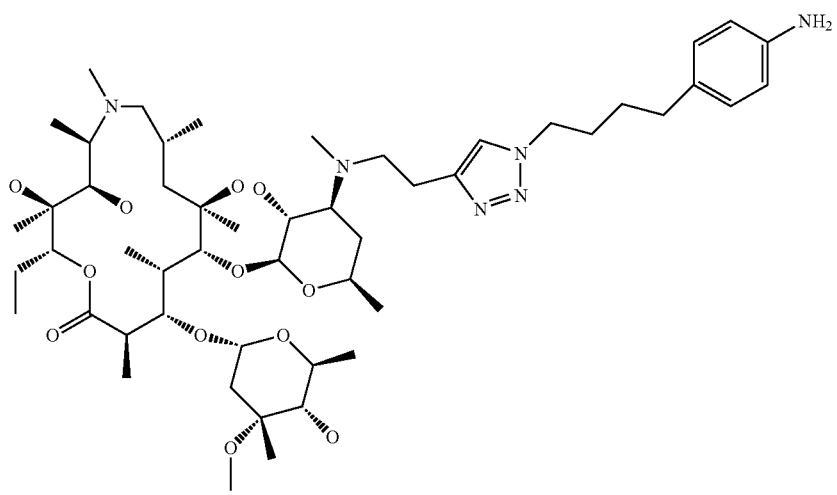
150
A solution of 0.570 g (0.57 mmol) of compound 147, 0.057 g of Pd/C (10%) in 10 ml of EtOH/EtOAc (1:1) was stirred under $H_2$ atmosphere (balloon) for 24 h. The reaction mixture was filtered through celite, washed with $CH_2Cl_2$, the filtrate was concentrated and dried to give the desired product in quantitative yield MS: (M+2)/2 489.4.

Synthesis of Compound 161

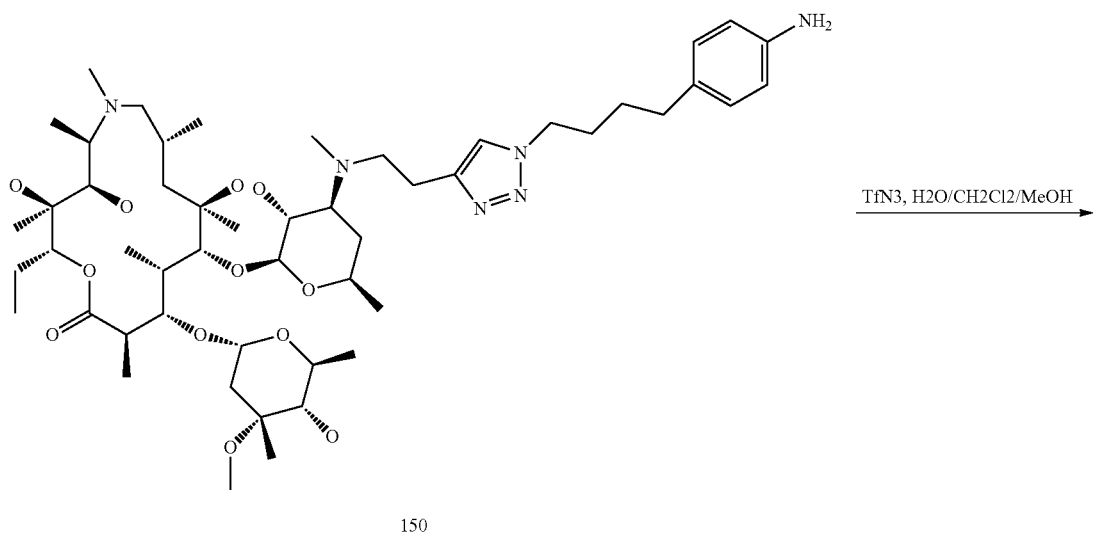

150

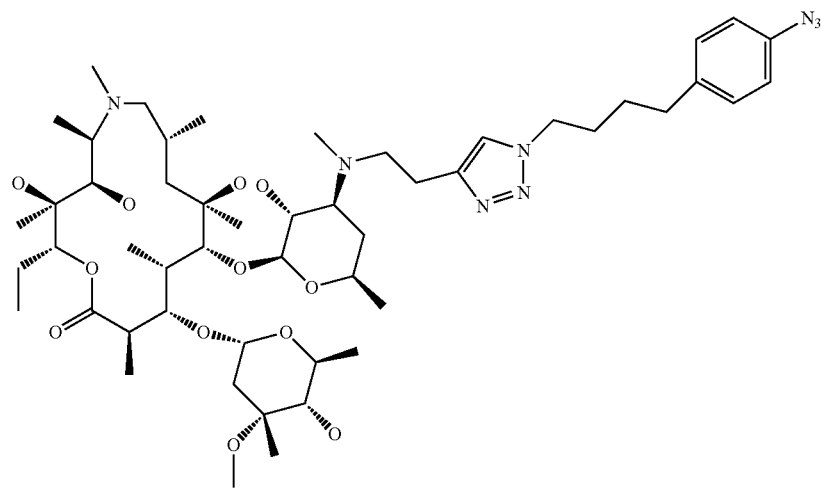

161

To a solution of 0.101 g (1.55 mmol) of NaN$_3$ in 2 ml of H$_2$O and 2 ml of CH$_2$Cl$_2$ at 0° C. was added 0.13 ml (0.78 mmol) of Tf$_2$O. The reaction mixture was stirred at 0° C. for 2 h, followed by extraction with CH$_2$Cl$_2$ (3 ml×2). The combined CH$_2$Cl$_2$ layers were added to a solution of 0.190 g (0.19 mmol) of compound 150, 0.11 ml of Et$_3$N in 2 ml of MeOH, 2 ml of H$_2$O at 0° C. The new reaction mixture was warmed to 25° C. and stirred for 20 h. The reaction was diluted with saturated aqueous NaHCO$_3$ (30 ml), extracted with CH$_2$Cl$_2$ (30 ml×3). The combined CH$_2$Cl$_2$ layers were washed with brine, dried, filtered, concentrated, and purified to give 0.130 g of the product 161. MS: (M+2)/2 502.7.

Synthesis of the Following Compounds

Compounds 149, 168, 171-182, and 185 were made from azide 161 and the corresponding alkyne shown in the Table 2A below.

TABLE 2A

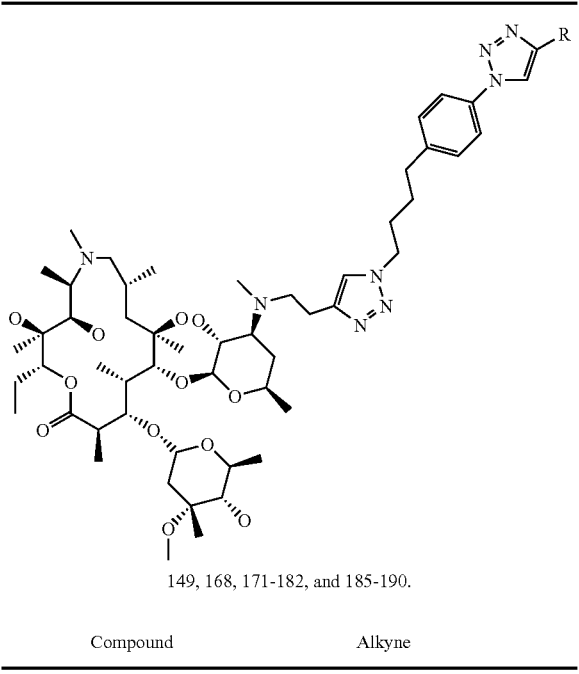

149, 168, 171-182, and 185-190.

| Compound | Alkyne |
|---|---|
| 149 | HC≡C—CH$_2$OH |
| 168 | HC≡C—CH$_2$OC(O)CH$_3$ |
| 171 | HC≡C—CH$_2$OCH$_3$ |
| 172 | HC≡C—CH$_2$N(C$_2$H$_5$)$_2$ |
| 173 | HC≡C—CONH$_2$ |
| 174 | HC≡C—(2-pyridyl) |
| 175 | HC≡C—(CH$_2$)$_3$CH$_2$OH |
| 176 | HC≡C—CH$_3$ |
| 177 | HC≡C—CH$_2$CH$_2$OH |
| 178 | HC≡C—COCH$_3$ |
| 179 | HC≡C—(CH$_2$)$_3$CH$_3$ |
| 180 | HC≡C—CH$_2$N(CH$_3$)$_2$ |

TABLE 2A-continued

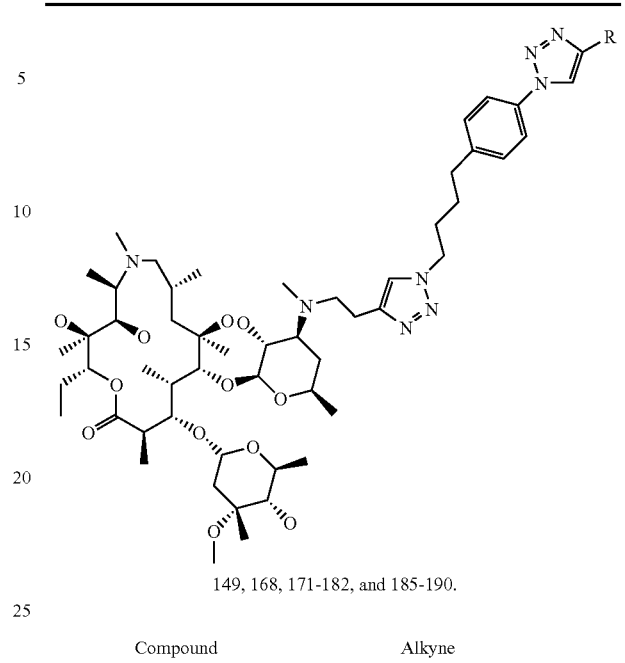

149, 168, 171-182, and 185-190.

| Compound | Alkyne |
|---|---|
| 181 | HC≡C—(3-pyridyl) |
| 182 | HC≡C—CH$_2$NHCH$_3$ |
| 185 | HC≡C—CH$_2$NH$_2$ |
| 186 | HC≡C—CH$_2$NHSO$_2$CH$_3$ |
| 187 | HC≡C—cyclopropyl |
| 188 | HC≡C—(CH$_2$)$_5$CH$_3$ |
| 189 | HC≡C—C(CH$_3$)$_3$ |
| 190 | HC≡C—cyclohexyl |

The above compounds were made through the reaction Scheme shown below. The synthesis of compound 168 is given to demonstrate how the reaction was generally performed.

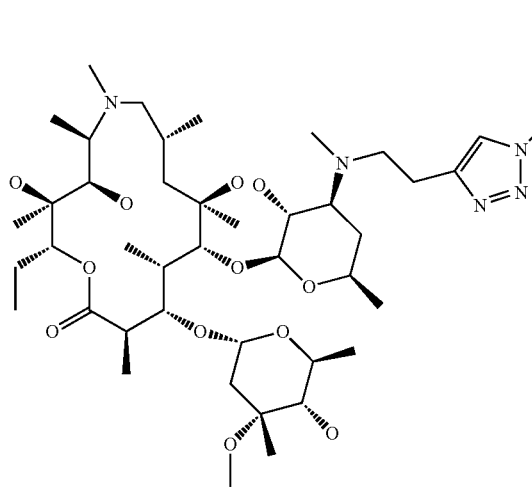

161

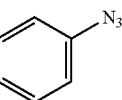

alkyne, CuI, THF, Hunig's base →

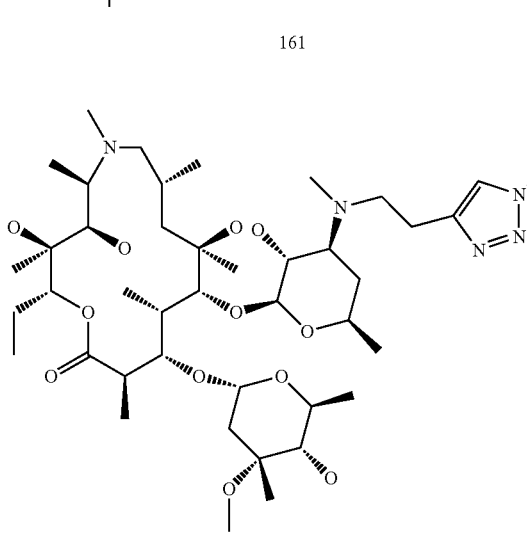

168

A solution of 1.700 g (1.69 mmol) of compound 1, 0.333 g (3.39 mmol) of propargyl acetate, and 0.323 g (1.69 mmol) of CuI in 6.0 ml of THF (with a few drops of Hunig's base) was stirred under argon for 6 h. To the above reaction mixture was added 50 ml of 10% aqueous ammonia solution, the solution was allowed to stir for 10 min, then, extracted with $CH_2Cl_2$ (50 ml×3), the combined $CH_2Cl_2$ layers were washed with brine, dried, concentrated, and purified through silica gel column chromatography to give 1.900 g of pure product (168).

Synthesis of Compound 171
From 0.100 g of Compound 161: 0.060 g of 171.
Synthesis of Compound 172
From 0.100 g of Compound 161: 0.081 g of 172.
Synthesis of Compound 173
From 0.100 g of Compound 161: 0.066 g of 173.
Synthesis of Compound 174
From 0.100 g of Compound 161: 0.072 g of 174.
Synthesis of Compound 175
From 0.100 g of Compound 161: 0.072 g of 175.
Synthesis of Compound 176
From 0.100 g of Compound 161: 0.088 g of 176.
Synthesis of Compound 177
From 0.100 g of Compound 161: 0.073 g of 177.
Synthesis of Compound 178
From 0.100 g of Compound 161: 0.065 g of 178.
Synthesis of Compound 179
From 0.100 g of Compound 161: 0.072 g of 179.
Synthesis of Compound 180
From 0.100 g of Compound 161: 0.072 g of 180.
Synthesis of Compound 181
From 0.100 g of Compound 161: 0.038 g of 181.
Synthesis of Compound 182
From 0.100 g of Compound 161: 0.038 g of 182.
Synthesis of Compound 185
From 0.100 g of Compound 161: 0.042 g of 185.
Synthesis of Compound 186
From 0.100 g of Compound 161: 0.082 g of 186.
Synthesis of Compound 187
From 0.100 g of Compound 161: 0.085 g of 187.
Synthesis of Compound 188
From 0.100 g of Compound 161: 0.082 g of 188.
Synthesis of Compound 189
From 0.100 g of Compound 161: 0.040 g of 189.
Synthesis of Compound 190
From 0.100 g of Compound 161: 0.040 g of 190.

Synthesis of Compounds 166, 167, 169 and 170

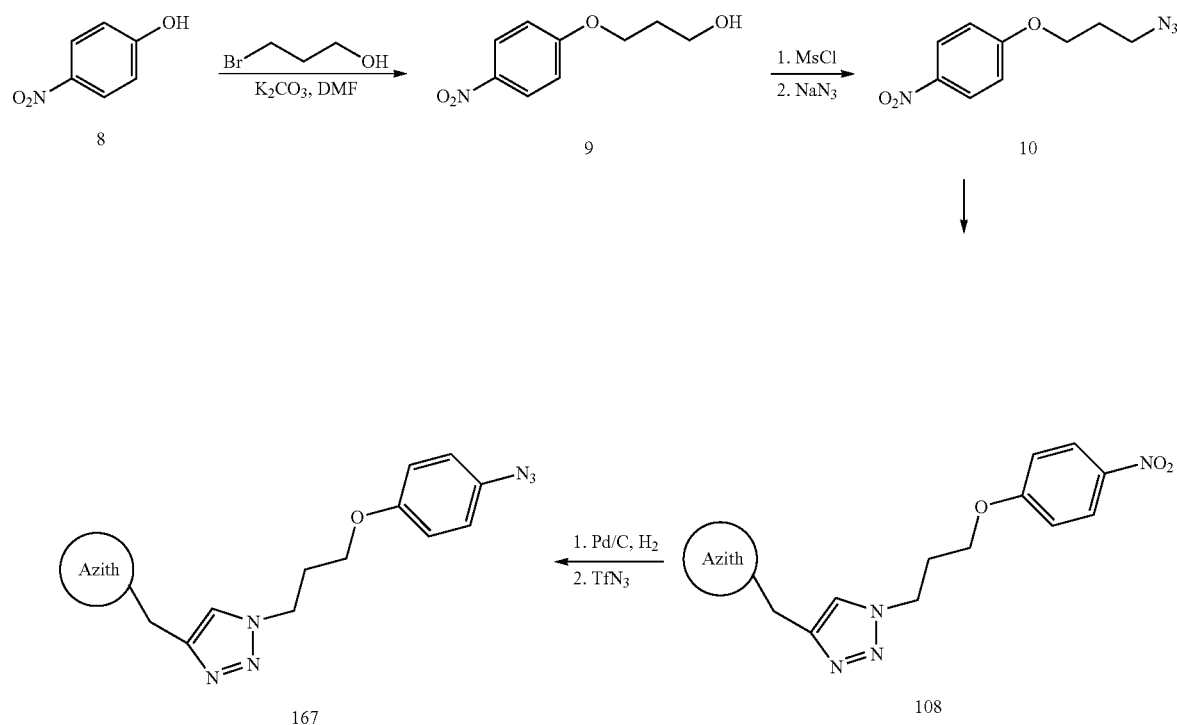

Synthesis of Compound 9

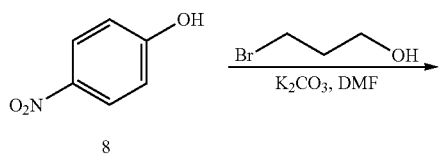

A solution of 0.500 g (3.59 mmol) of compound 8, 0.600 g (4.31 mmol) of the bromide, and 1.490 g (10.78 mmol) of $K_2CO_3$ in 10 ml of DMF was heated at 70° C. for 16 h. The reaction mixture was diluted with $H_2O$ (30 ml), extracted with ether (50 ml×3), the combined ether layers were washed with brine, dried, filtered and concentrated to give 0.720 g of the crude product. No further purification was done, directly used in next reaction.

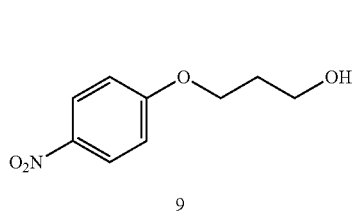

Synthesis of Compound 10

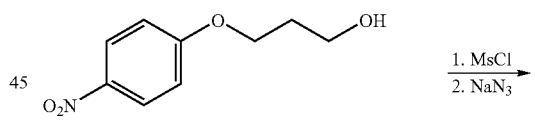

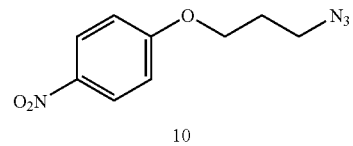

To a solution of 0.720 g (3.65 mmol) of compound 9, 1.27 ml (7.31 mmol) of Hunig's base in 10 ml of DMF at 0° C. was added 0.43 ml (5.48 mmol) of MsCl. The reaction mixture was warmed up to 25° C. for 2 h. To the mixture was added 0.475 g (7.31 mmol) of $NaN_3$. Subsequently, it was heated up to 70° C. for 16 h. The reaction mixture was diluted with $H_2O$ (30 ml), extracted with ether, the combined ether layers were washed with brine, dried, filtered, concentrated to give 0.680 g of the desired product. It was pretty pure. No further purification was necessary.

Synthesis of Compound 108

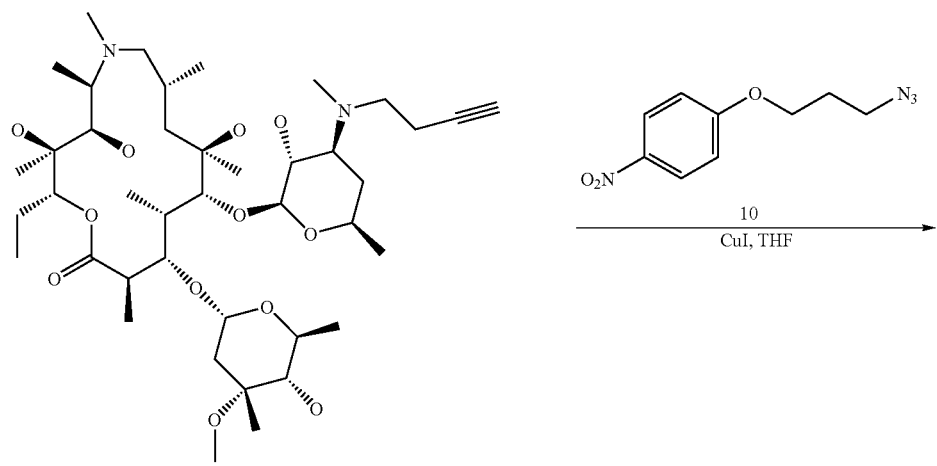

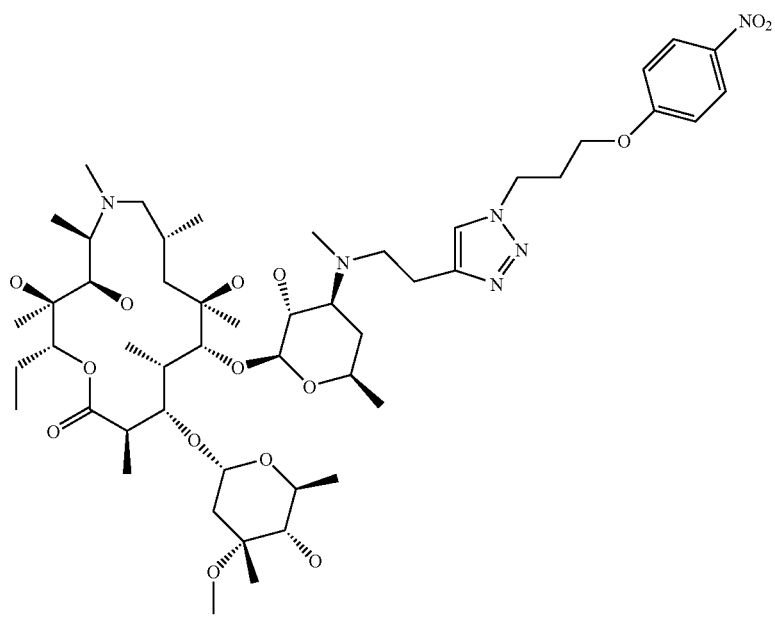

A solution of 0.165 g (0.21 mmol) of compound 1, 0.070 g (0.32 mmol) of azide 10, and 0.060 g (0.32 mmol) of CuI in 5 ml of THF (a few drops of Hunig's base in it) was stirred under argon for 4 h. To the above reaction mixture was added 20 ml of 10% aqueous ammonia solution, and the solution was allowed to stir for 10 min, extracted with $CH_2Cl_2$ (20 ml×3), combined $CH_2Cl_2$ layers were washed with brine, dried, concentrated, and purified through preparative TLC to give 0.120 g of the product 108.

Synthesis of Compound 166
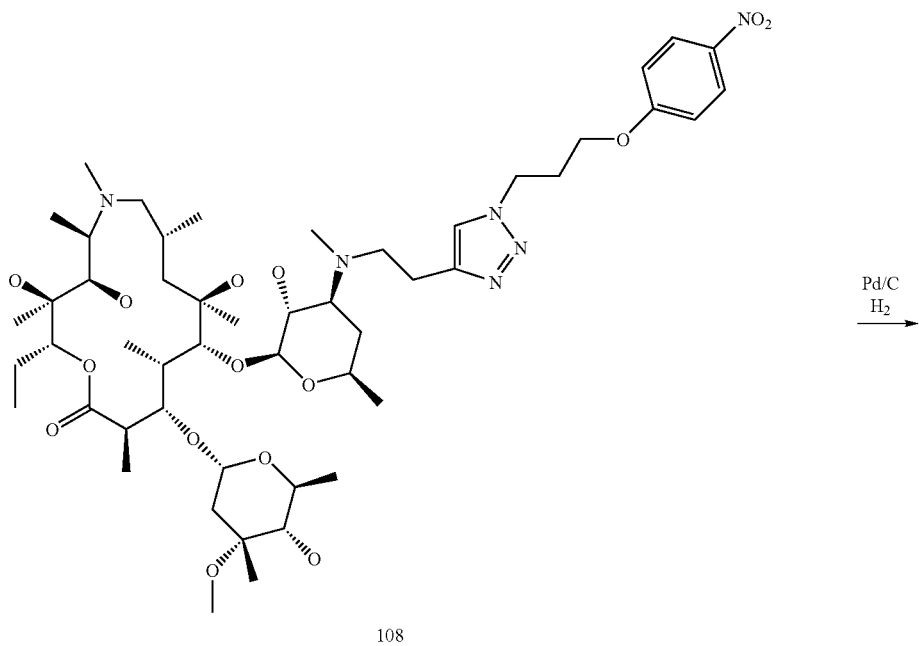
108
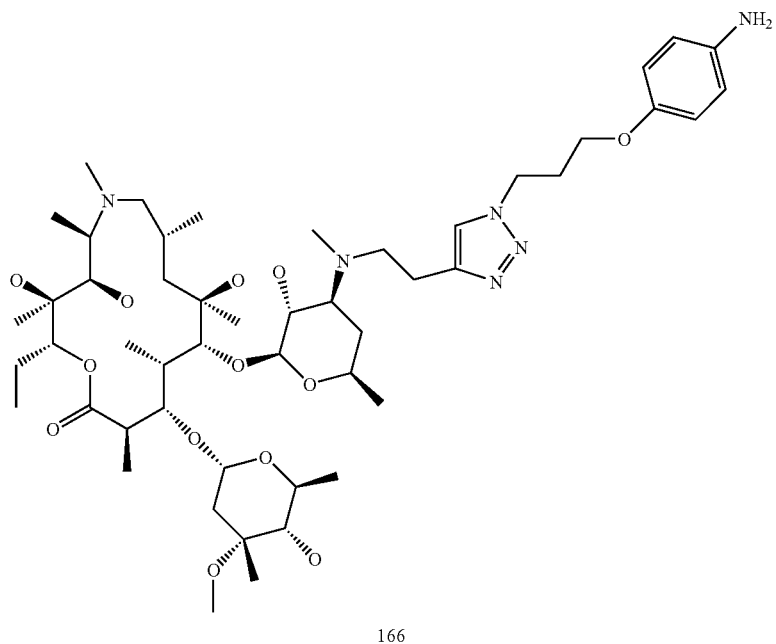
166
A solution of 0.120 g (0.57 mmol) of compound 108, 0.020 g of Pd/C (10%) in 8 ml of EtOH/EtOAc (1:1) was stirred minder $H_2$ atmosphere (balloon) for 24 h. The reaction mixture was the filtered through celite, washed with $CH_2Cl_2$, the filtrate was concentrated and dried to give 0.108 g of 166.

Synthesis of Compound 167

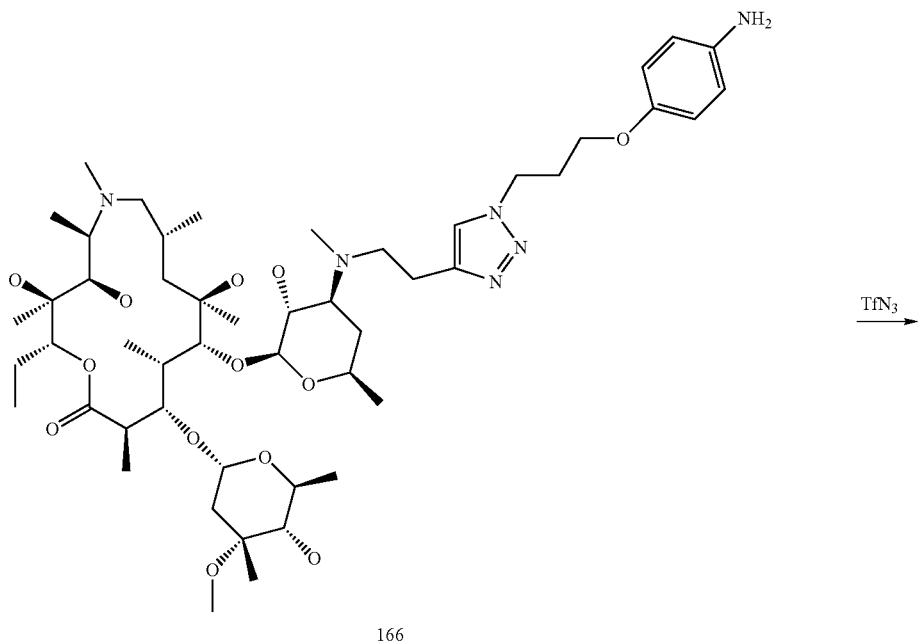

166

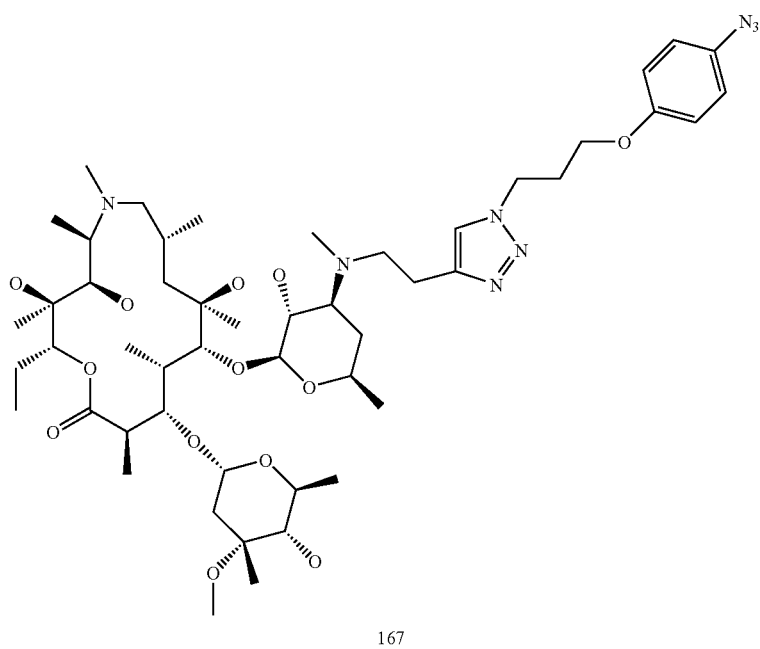

167

To a solution of 0.053 g (0.82 mmol) of NaN₃ in 2 ml of H₂O, 2 ml of CH₂Cl₂ at 0° C. was added 0.07 ml (0.41 mmol) of Tf₂O. The reaction mixture was stirred at 0° C. for 2 h, extracted with CH₂Cl₂ (3 ml×2). The combined CH₂Cl₂ layers were added to a solution of 0.10 g (0.19 mmol) of compound 166, 0.06 ml of Et₃N in 2 ml of MeOH and 2 ml of H₂O at 0° C. The new reaction mixture was warmed to 25° C. and stirred for 20 h. then diluted with saturated aqueous NaHCO₃ (30 ml), extracted with CH₂Cl₂ (30 ml×3). The combined CH₂Cl₂ layers were washed with brine, dried, filtered, concentrated, and purified to give 0.060 g of 167.

Synthesis of Compound 169

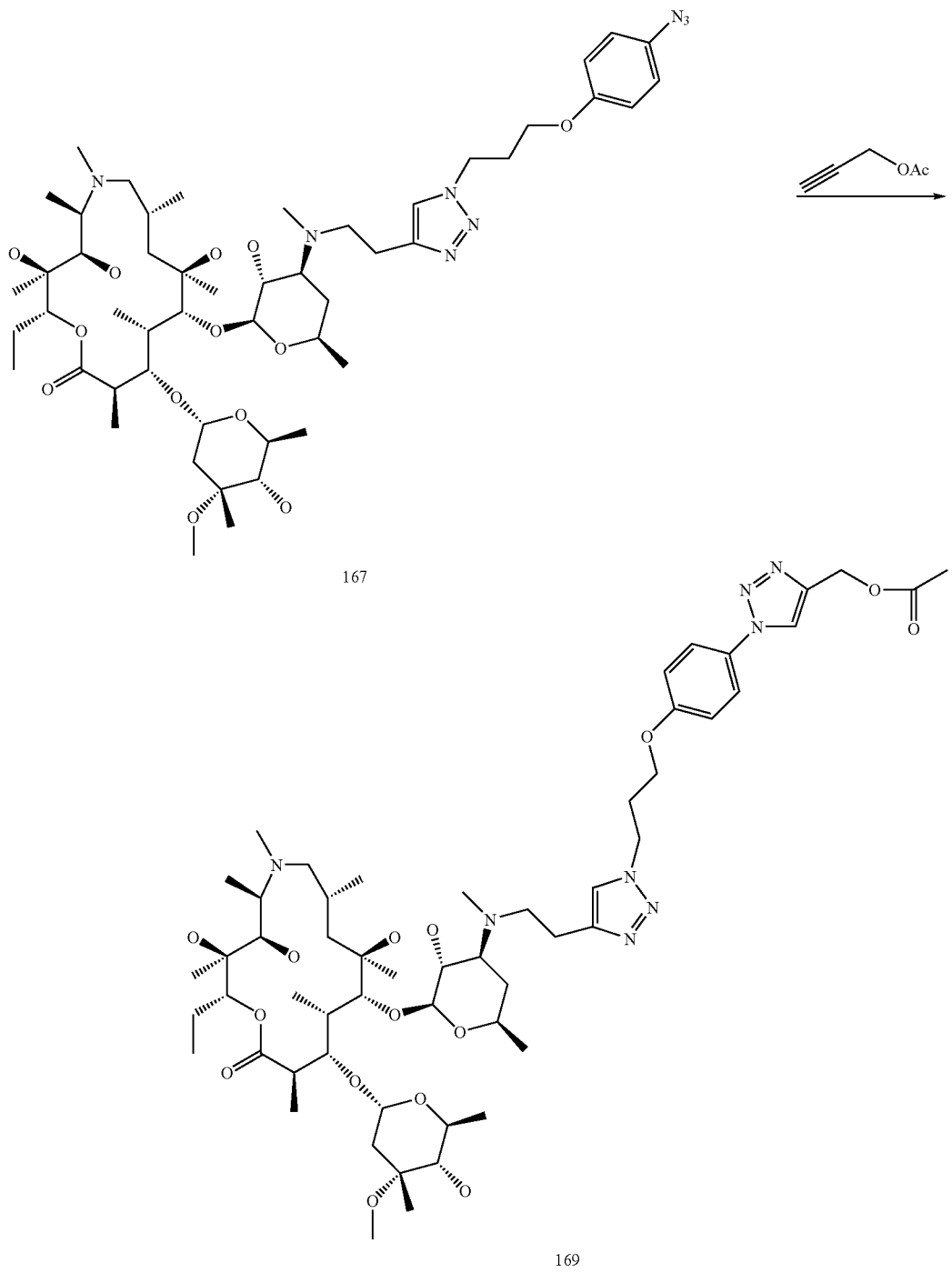

A solution of 0.055 g (0.055 mmol) of compound 167, 0.011 g (0.11 mmol) of propargyl acetate, and 0.010 g (0.055 mmol) of CuI in 1 ml of THF (a few drops of Hunig's base in it) was stirred under argon for 4 h. To the above reaction mixture was added 20 ml of 10% aqueous ammonia solution, and the solution was allowed to stir for 10 min, extracted with $CH_2Cl_2$ (20×3), combined $CH_2Cl_2$ layers were washed with brine, dried, concentrated, and purified through preparative TLC to give 0.038 g of 169. MS: (M+2)/2 552.8.

Synthesis of Compound 170
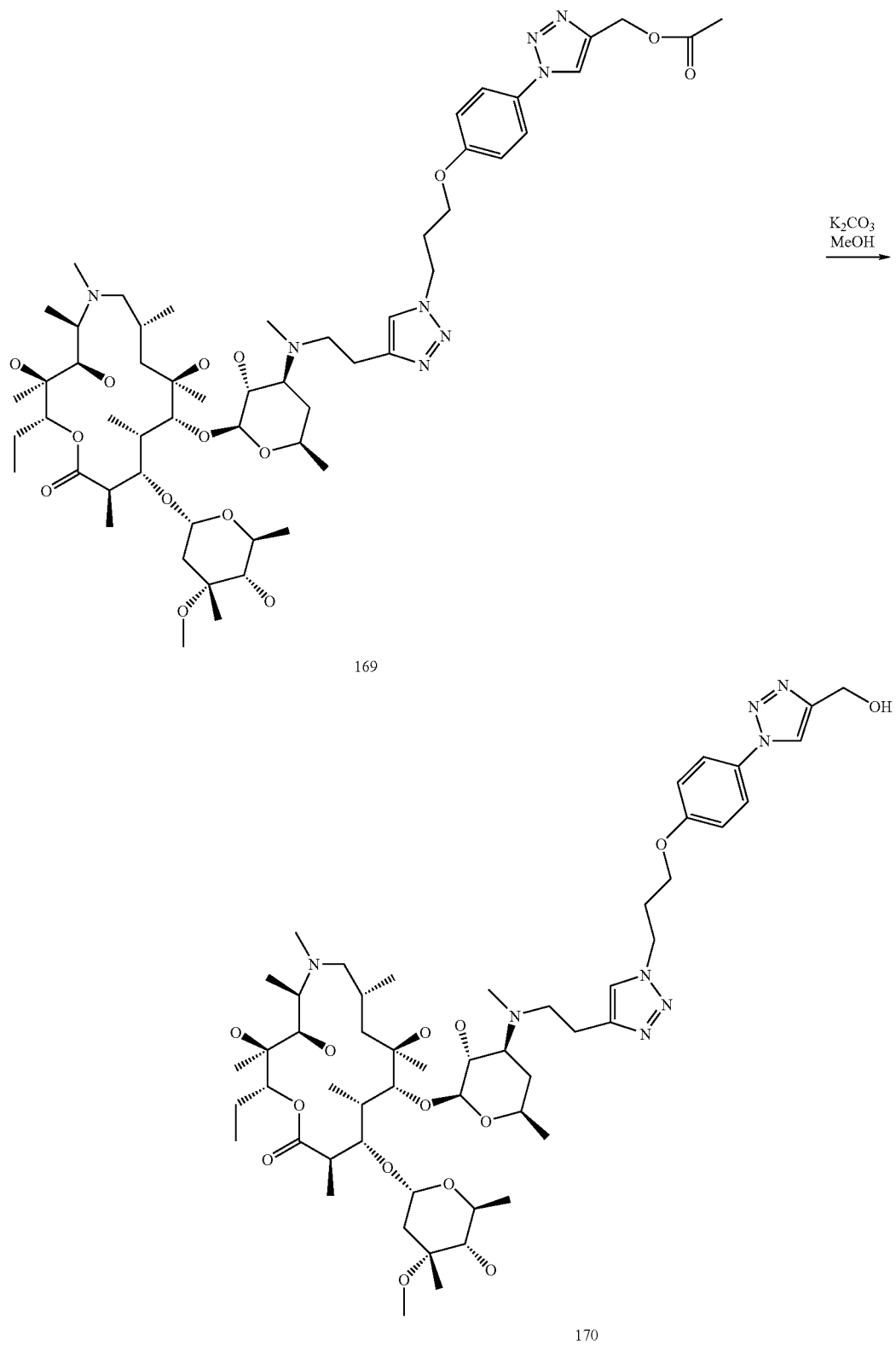
A solution of 0.020 g (0.018 mmol) of compound 169, and 0.006 g (0.036 mmol) of $K_2CO_3$ in 2 ml of MeOH was stirred at 25° C. for 4 h. Solvent was removed and the residue was dissolved in 2 ml of $CH_2Cl_2$. The suspension was filtered through pipette column, and filtrate concentrated to give 0.016 g of 170. MS: (M+2)/2 531.6.

Example 2

Synthesis of Compounds 201-207 and 226

Schemes 103 and 104 below depict the synthesis of compounds 201-207 and 226. See Table 3. Demethylation of clarithromycin yielded 3'-N-desmethyl-clarithromycin 21. Amine 21 was selectively N-alkylated with tosylates 11 to produce alkyne 27. As shown in Scheme 104 alkyne 27 is reacted with corresponding azides 14 in the presence of copper (I) iodide to selectively afford the triazoles 201-207 and 226.

Scheme 103: Synthesis of alkyne 27.

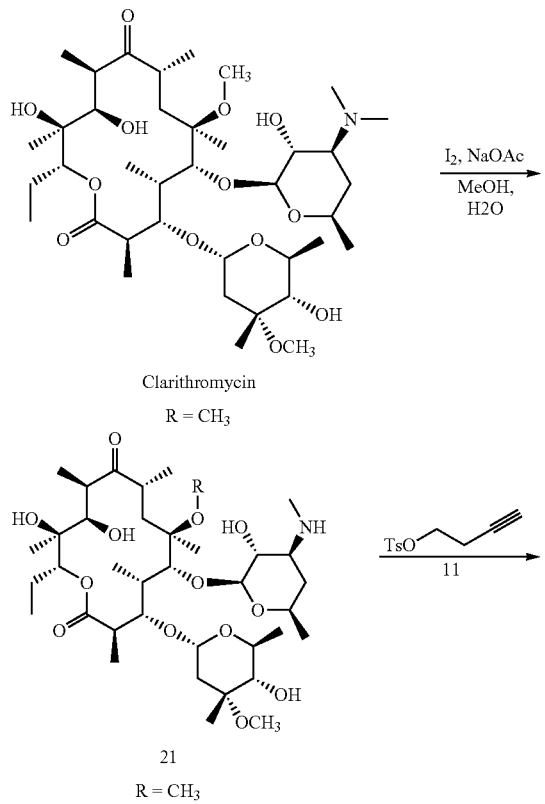

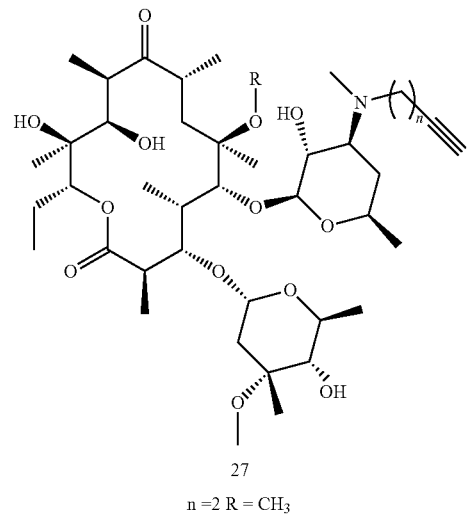

27
n =2 R = CH$_3$

Synthesis of 3'-N-desmethyl-clarithromycin 21

To a mixture of clarithromycin (1.00 g, 1.3 mmol) and NaOAc-3H$_2$O (0.885 g, 6.5 mmol) was added MeOH—H$_2$O (20 mL, 4:1), and the mixture heated to 55-60° C. Iodine (0.330 g, 1.3 mmol) was added portion-wise and the reaction stirred at 55-60° C. for 3 h. The reaction mixture was poured into 50 mL CHCl$_3$ containing 1 mL ammonium hydroxide. It was extracted with CHCl$_3$ (4×50 mL), washed with water (70 mL) containing 5 mL ammonium hydroxide, dried (anhydrous Na$_2$SO$_4$), concentrated, and purified by flash chromatography (silica gel, CHCl$_3$:MeOH:NH$_4$OH 100:10:0.1) to afford 21. Yield: 0.9 g (92%).

Synthesis of Alkyne 27

A mixture of 3'-N-desmethyl-clarithromycin 21 and tosylate 11 in anhydrous THF and Hunig's base was stirred. The reaction was poured into CH$_2$Cl$_2$, extracted with 2% aqueous NH$_4$OH and saturated brine. The organic layer was dried over Na$_2$SO$_4$ and the solvent was evaporated away. The crude was purified on a silica gel column to give 27.

TABLE 3

| Compound | B | Mac | Yield | LCMS |
|---|---|---|---|---|
| 201 | ![4-nitrophenoxybutyl] | M3 | 89% | 1008.9 (M + H)$^+$ |
| 202 | ![4-(methylsulfonyl)phenoxybutyl] | M3 | 95% | 1041.8 (M + H)$^+$ 1063.7 (M + Na)$^+$ |

TABLE 3-continued

| Compound | B | Mac | Yield | LCMS |
|---|---|---|---|---|
| 203 | 4-nitrophenyl-(CH2)4- | M3 | 89% | 1006.9 (M + H)+ 1028.9 (M + Na)+ |
| 204 | (S)-1-(4-nitrobenzyl)pyrrolidin-2-yl-CH2- | M3 | 53% | 1047.9 (M + H)+ |
| 205 | (R)-1-(4-nitrobenzyl)piperidin-3-yl- | M3 | 39% | 1047.9 (M + H)+ |
| 206 | (R)-1-(4-nitrobenzyl)pyrrolidin-2-yl-CH2- | M3 | 28% | 1047.9 (M + H)+ |
| 207 | (S)-1-(4-nitrobenzyl)piperidin-3-yl- | M3 | 43% | 1047.9 (M + H)+ |
| 226 | 2-(ethoxycarbonyl)phenoxy-(CH2)4- | M1 | 50% | — |

Example 3

Synthesis of Compounds 210-213

The macrolide oximes 210-213, see Table 4, were synthesized from alkynes 400a to 400c by copper (I)-promoted cycloaddition with corresponding azides 14 in a manner analogous to the procedures presented previously. Alkyne precursors with substituted oxime functionality at the 9-position of the macrocyclic ring were prepared from alkyne 27 and as shown below.

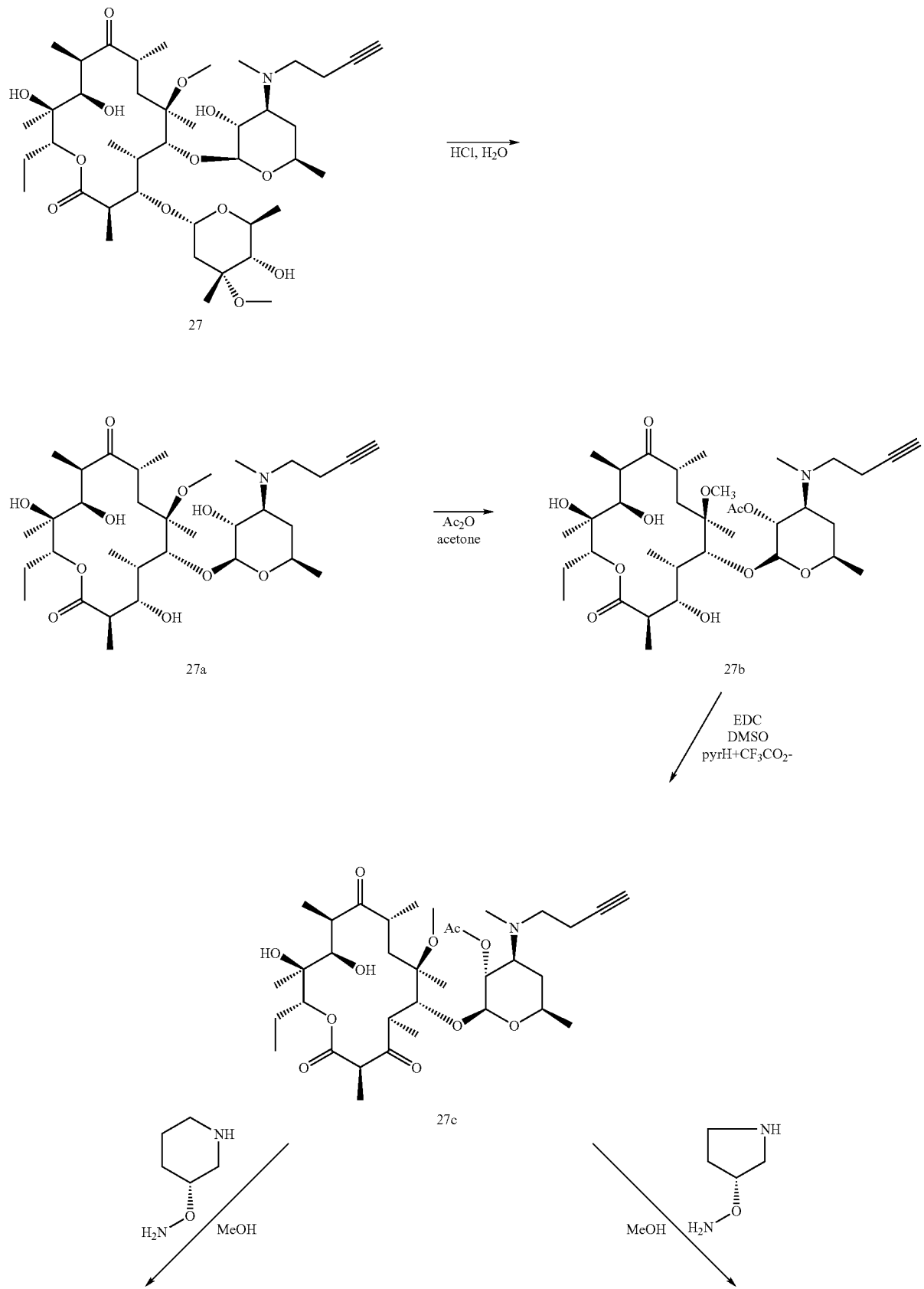

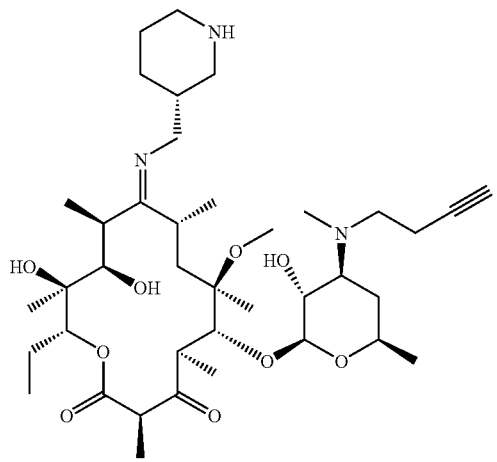

400a

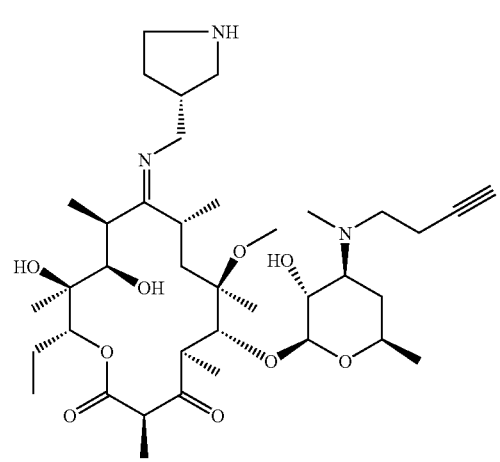

400b

Synthesis of Alcohol 27a

To the alkyne 27 (0.700 g) was added 10 mL 0.9N HCl and the mixture was stirred for 4 h at room temperature. The reaction mixture was saturated with sodium chloride and was adjusted to pH 8 using aqueous $NH_4OH$ solution. The solution was extracted with ethyl acetate (3×30 mL), dried (with $Na_2SO_4$), and concentrated under reduced pressure. Purification of the crude reaction mixture by flash chromatography (silica gel, 60% ethyl acetate in hexane) afforded 0.200 g (35% yield) of the descladinose derivative 27. Data for 27: $^1$HNMR (300 MHz, $CDCl_3$, partial): δ 0.82 (t, 3H), 2.25 (s, 3H), 3.00 (s, 3H), 3.25 (dd, 1H), 3.55 (m, 2H), 3.70 (s, 1H), 3.85 (s, 1H), 3.95 (s, 1H), 4.40 (d, 1H), 5.15 (dd, 1H).

Synthesis of Acetate 27b

To a solution of 27a (0.200 g, 0.32 mmol) in acetone (2 mL) was added acetic anhydride (0.050 mL, 0.5 mmol) and the mixture was stirred overnight at room temperature. The reaction was quenched with water and extracted with ethyl acetate (3×50 mL). The combined organic fractions were washed with saturated sodium bicarbonate (3×50 mL), dried (anhydrous $Na_2SO_4$), and concentrated under reduced pressure. The crude reaction mixture was purified by flash chromatography (silica gel, 50% ethyl acetate in hexane) to yield 0.100 g (50% yield) of acetate 27b. Data for 27b: $^1$HNMR (300 MHz, $CDCl_3$, partial): δ0.84 (t, 3H), 2.00 (s, 3H), 2.20 (s, 3H), 2.90 (s, 3H), 3.00 (q, 1H), 3.25 (s, 1H, 3.47 (m, 2H), 3.70 (bs, 1H), 3.82 (bs, 1H), 3.97 (s, 1H), 4.60 (d, 1H), 4.77 (dd, 1H), 5.15 (dd, 1H).

Synthesis of Ketolide 27c

To a solution of acetate 27b (0.090 g, 0.134 mmol), EDC.HCl (0.172 g, 0.90 mmol), and DMSO (0.171 mL, 2.41 mmol) in $CH_2Cl_2$ (1.5 mL) was added dropwise a solution of pyridinium trifluoroacetate (0.174 g, 0.90 mmol) in $CH_2Cl_2$ (1 mL) at 15° C. The reaction mixture was slowly warmed up to room temperature and stirred for 3 h. The reaction was quenched with water (2 mL), and allowed to stir for 30 min. The mixture was then poured into $CHCl_3$ (50 mL), and the organic layer was washed with water (2×50 mL), dried (over anhydrous $Na_2SO_4$), and concentrated under reduced pressure. The crude material was purified by flash chromatography (silica gel, 30% ethyl acetate in hexane) to yield 0.070 g (78%) of the ketolide 27c. Data for 27c: MS (ESI) m/e 668 $(M+H)^+$; $^1$HNMR (300 MHz, $CDCl_3$, partial): δ 0.86 (t, 3H), 2.00 (s, 3H), 2.24 (s, 3H), 2.70 (s, 3H), 2.95-3.10 (m, 1H), 3.15-3.05 (m, 1H), 3.45-3.65 (m, 1H), 3.80 (q, 1H), 3.90 (s, 1H), 4.28 (d, 1H), 4.40 (d, 1H), 4.76 (dd, 1H), 5.10 (dd, 1H).

Synthesis of oxime 400a

To a solution of 27c (2.0 g, 2.9 mmol) in MeOH (10 mL) was added (R)—N-Piperidin-3-yl-hydroxylamine hydrobromide (1.26 g, 4.4 mmol). The reaction mixture was stirred at rt for 14 h. The mixture was then poured into (50 mL) and water (50 mL) the pH was adjusted to 11 by addition of $NH_4OH$ and the organic layer was separated and washed with brine (50 mL), dried (over anhydrous $Na_2SO_4$), and concentrated under reduced pressure. The crude material was purified by flash chromatography (silica gel, 12:1 $CH_2Cl_2$ and 2M methanolic ammonia) to yield 2 g (78%) of the oxime 400a as a 1:1 mixture of E/Z isomers. Data for 400a: MS (ESI) m/e 724.7 $(M+H)^+$.

Synthesis of Oxime 400b

Oxime 400b was synthesized from alkyne 27c and (R)—N-Pyrollidin-3-yl-hydroxylamine hydrobromide using the conditions described above for the synthesis of oxime 400a. Data for 400b: MS (ESI) m/e 710.6 $(M+H)^+$.

Scheme 108

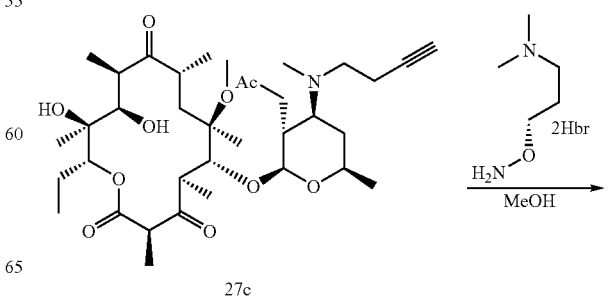

27c

-continued

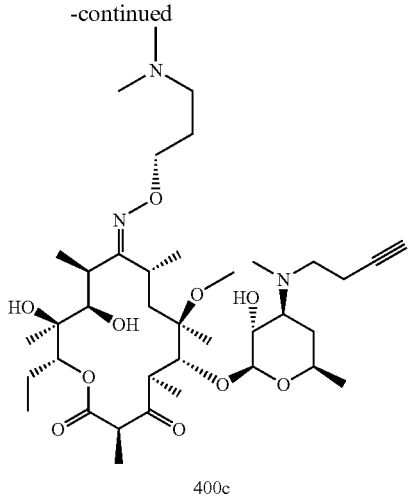

400c

Synthesis of Oxime 400c

Oxime 400e was synthesized from alkyne 27e and N-[2-dimethylaminoethyl]-hydroxylamine hydrobromide using the conditions described above for the synthesis of oxime 400a. Data for 400bc: MS (ESI) m/e 726.5 (M+H)$^+$.

Synthesis of Oxime Triazole 439

This triazole was synthesized from the alkyne 400a and the corresponding azide using the standard copper-promoted cycloaddition conditions as previously described.

Synthesis of Oxime Triazoles 444 and 445

These triazoles were synthesized from the alkyne 400b and the corresponding azides 14 using the standard copper-promoted cycloaddition conditions as previously described.

Synthesis of Oxime Triazole 437

This triazole was synthesized from the alkyne 400c and the corresponding azide using the standard copper-promoted cycloaddition conditions as previously described.

TABLE 4

| Compound | B | Mac | Yield | LCMS |
|---|---|---|---|---|
| 210 | (chain-(CH$_2$)$_4$-C$_6$H$_4$-NO$_2$) | M3A | 76% | 467 (M + 2H)$^{2+}$ 933 (M + H)$^+$ |
| 211 | (chain-(CH$_2$)$_4$-C$_6$H$_4$-NO$_2$) | M3B | 62% | 473 (M + 2H)$^{2+}$ 945 (M + H)$^+$ |
| 212 | (chain-(CH$_2$)$_3$-O-C$_6$H$_4$-NO$_2$) | M3C | 27% | 467 (M + 2H)$^{2+}$ |
| 213 | (chain-(CH$_2$)$_4$-C$_6$H$_4$-NO$_2$) | M3C | 37% | 466 (M + 2H)$^{2+}$ 930.8 (M + H)$^+$ |

Example 4

Synthesis of Compounds 221-225

Compounds 221-225, see Table 5, were derived from a number of macrolide alkynes. A number of representative examples are shown below.

Synthesis of Compounds 222 and 223
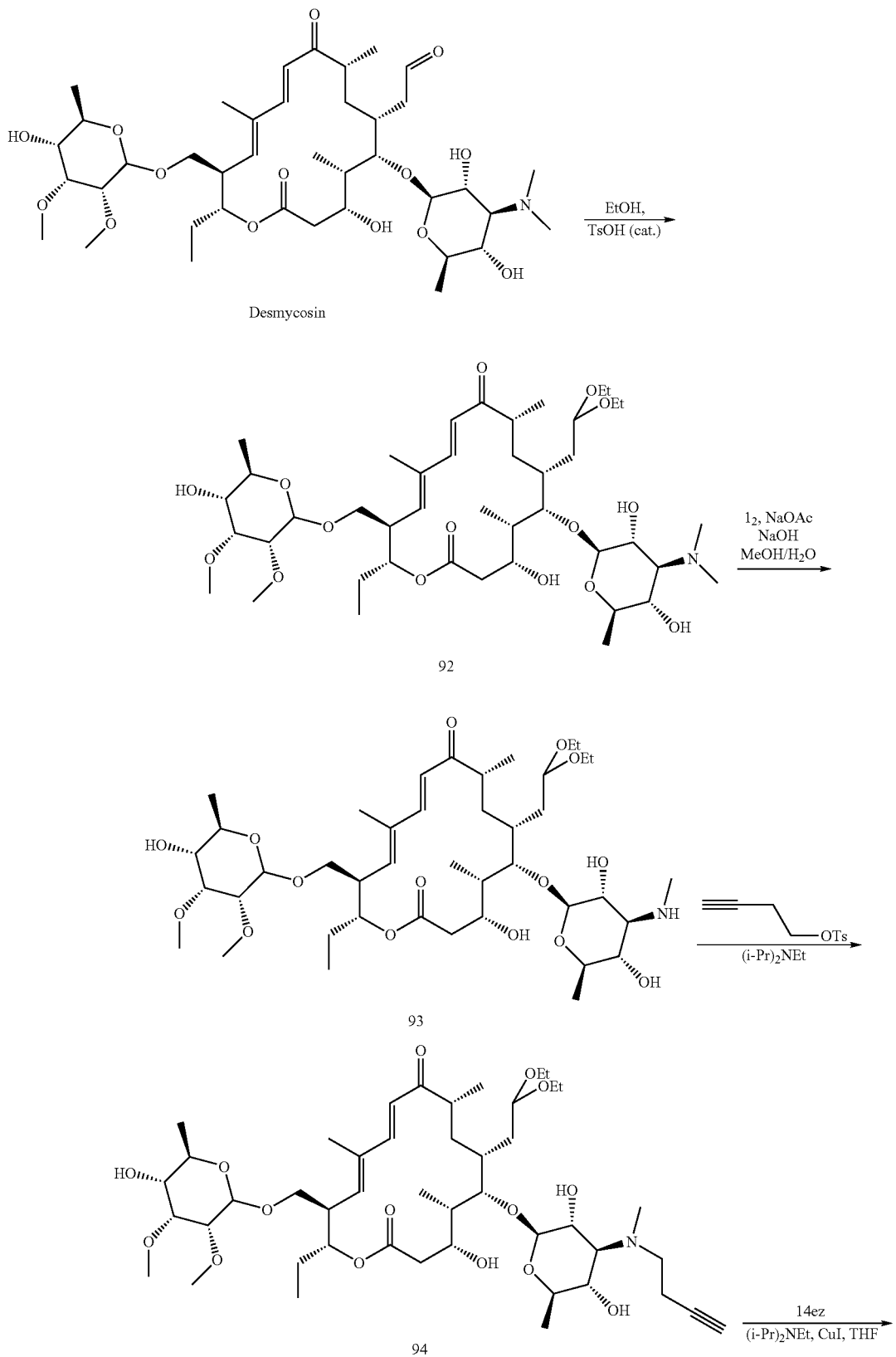
Scheme 163

-continued

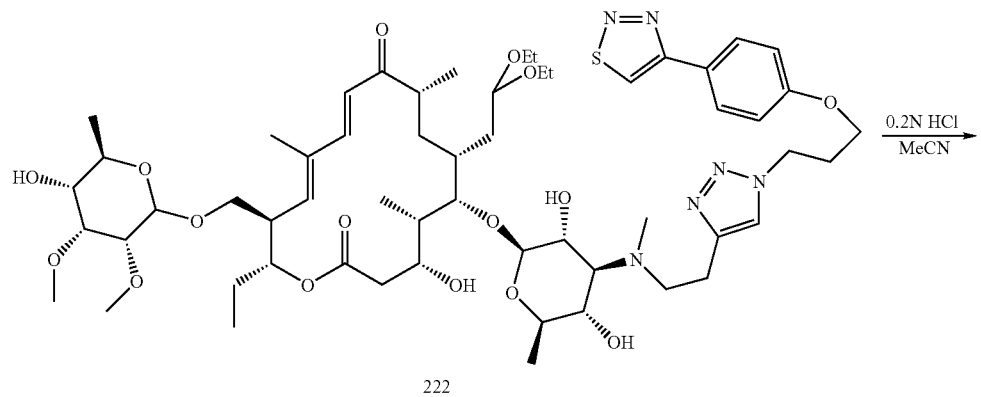

222

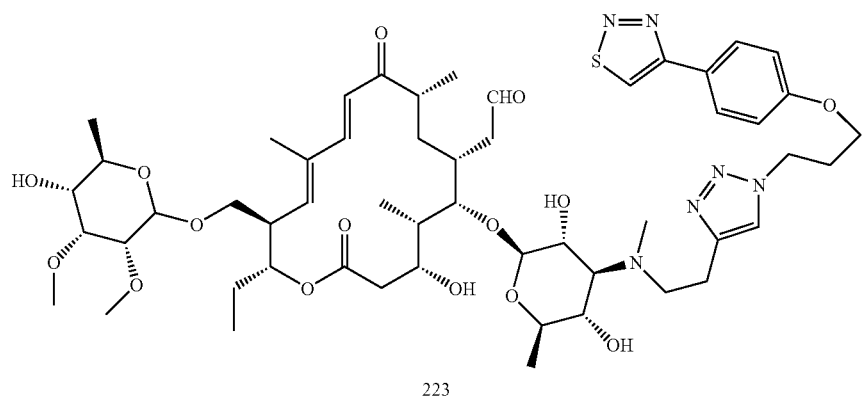

223

Synthesis of Compound 92

To a solution of 1.00 g (1.30 mmol) of desmycocin in 10 ml of ethyl alcohol was added 0.260 g (1.36 mmol) of p-toluene-sulfonic acid at ambient temperature. The reaction mixture was allowed to stir for 3 h, then diluted with 30 ml of saturated aqueous $NaHCO_3$, and extracted with EtOAc. The combined ethyl acetate extracts were washed with brine, dried over $MgSO_4$, and concentrated to give 1.220 g of 92 which was used without further purification.

Synthesis of Compound 93

To a mixture of 0.250 g (0.29 mmol) of 92 and 0.486 g (5.92 mmol) of NaOAc in 10 ml of MeOH/$H_2O$ (80% MeOH) at 55° C. was added 0.075 g (0.29 mmol) of solid iodine. The pH value of the reaction mixture was maintained at 9 by addition of 1N NaOH at time intervals of 10, 30, and 60 minutes after the addition of iodine. The reaction mixture was stirred at 55° C. for 1 h following the last addition of NaOH solution, then diluted with 25 ml of saturated $NaHCO_3$ and extracted with EtOAc (50 ml×2). The combined EtOAc extracts were washed sequentially with 15 ml of 5% $NaS_2O_4$ and brine, dried over $MgSO_4$, filtered and concentrated to give 0.221 g of 93.

Synthesis of Alkyne 94

A mixture of 0.200 g (0.24 mmol) of 93, 0.270 g (1.20 mmol) of tosylate 11, 0.311 g (2.41 mmol) of di-isopropyl-ethylamine and 10 mg of dimethylaminopyridine in 5 ml of THF was allowed to stir at 55° C. for 48 h. The mixture was diluted with 20 ml of saturated $NaHCO_3$, extracted with EtOAc (30 ml×3). The combined organic layers were washed with brine (20 ml), dried over $MgSO_4$, filtered and concentrated to give 0.065 g of desired product 94 and 0.063 g of recovered starting material 93 after purification through flash column chromatography on silica gel.

Synthesis of Compound 222

A solution of 0.300 g (0.03 mmol) of alkyne 94, 0.018 g (0.06 mmol) of azide 14ez and 0.006 g (0.03 mmol) of CuI in 3.0 ml of THF was degassed, then put under argon. To the mixture was added 4 drops of Hunig's base. The reaction was stirred at 25° C. for 6 h. To it was added 20 ml of 10% $NH_4OH$, stirred for 10 min, extracted with $CH_2Cl_2$ (30 ml×3), combined organic layers were washed with brine, dried, concentrated, purified through preparative TLC to give 0.020 g of the final product.

Synthesis of Compound 223

A solution of 0.015 g (0.013 mmol) of compound 222 in 1.0 ml of 0.2 NHCl and 1.0 ml of acetonitrile was stirred at 25° C. for 4 h. To it was added 15 ml of saturated aqueous $NaHCO_3$ solution, the aqueous layer was then extracted with $CH_2Cl_2$ (40 ml×3), combined organic layers were washed with brine, dried, and concentrated to give 0.003 g of pure 223.

TABLE 5

| Compound | B | Mac | Yield | LCMS |
|---|---|---|---|---|
| 221 | [structure: phenyl-thiadiazole with butoxy linker] | M4A | 91% | 927 (M + H)+ |
| 222 | [structure: phenyl-thiadiazole with butoxy linker] | M5A | 52% | 1145.8 (M + H)+ |
| 223 | [structure: phenyl-thiadiazole with butoxy linker] | M5B | 10% | 1071.8 (M + H)+ |
| 224 | [structure: 2-amino-thiadiazole-phenyl with butoxy linker] | M6 | 70% | 477.0 (M + 2H)2+ |
| 225 | [structure: triazolyl-phenyl with pentyl linker] | M6 | 72% | 460.0 (M + 2H)2+ |

Example 5

Synthesis of Azides 14

The azides 14 shown in Table 6 represent a sampling of the azides that were used to synthesize numerous compounds of the invention. The azides were readily synthesized by methods known in the literature from appropriate commercial starting materials.

TABLE 6

| Azide Compound | Structure |
|---|---|
| 14gd | [structure: N3-CH2-CH(OH)-CH2-O-C6H4-NO2] |
| 14ge | [structure: N3-CH2-CH(OH)-CH2-O-C6H4-NO2] |
| 14gf | [structure: N3-CH2-CH(OH)-CH2-O-C6H4-S(O)2-CH3] |

TABLE 6-continued

| Azide Compound | Structure |
|---|---|
| 14gg | 4-(methylsulfonyl)phenyl (S)-2-fluoro-3-azidopropyl ether |
| 14gh | 4-(1,2,3-thiadiazol-4-yl)phenyl 3-azido-2-hydroxypropyl ether |
| 14fc | 4-nitrophenyl (S)-2-methyl-3-azidopropyl ether |
| 14gk | 4-nitrophenyl (S)-2-fluoro-3-azidopropyl ether |
| 14gl | 4-nitrophenyl (R)-2-fluoro-3-azidopropyl ether |
| 14fz | 3-azidopropyl 4-nitrophenyl sulfide |
| 14ga | 3-azidopropyl 4-nitrophenyl sulfone |
| 14gb | N-methyl-N-(2-azidoethyl)-4-nitrobenzylamine |
| 14fd | N-(2-azidoethyl)-4-nitrobenzamide |
| 14fl | N-(2-azidoethyl)-4-nitrobenzenesulfonamide |
| 14bs | 1-(4-azidobutyl)-4-nitrobenzene |
| 14ec | 1-(4-azidobutyl)-imidazo[4,5-b]pyridine |
| 14ew | 1-[4-(4-azidobutyl)phenyl]-1H-1,2,3-triazole |
| 14ey | 1-[4-(4-azidobutyl)phenyl]-4-(hydroxymethyl)-1H-1,2,3-triazole |
| 14fm | N-(2-azidoethyl)-4-(methylsulfonyl)benzenesulfonamide |
| 14fn | N-(2-azidoethyl)-4-nitrobenzylamine |
| 14dv | ethyl 2-(3-azidopropoxy)benzoate |
| 14ep | 4-nitrophenyl (R)-2-methyl-3-azidopropyl ether |
| 14et | 3-azidopropyl 4-nitrophenyl ether |

TABLE 6-continued

| Azide Compound | Structure |
|---|---|
| 14fq | 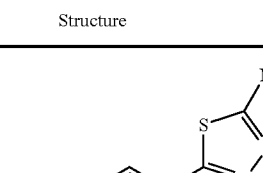 |
| 14ft | 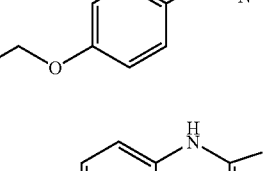 |

Most of the azides compounds in Table 6 can be synthesized according to known procedures with the specific route determined by the available commercial starting materials. When possible azides are produced from the corresponding substituted alkyl bromides by direct displacement with azide ion. When the required alkyl bromides are not readily available, the compounds are derived from substituted alkanols: to accomplish this, the alcohols are first activated as their sulfonyl ester derivatives and then substituted with azide ion. If neither the required bromides nor alkanols are commercially available, the azides are synthesized from the corresponding carboxylic acids by reduction with borohydride to the corresponding alcohols. The resulting alkanols are then treated as above to yield the azides. Finally, some azides of Table 6 are synthesized from the corresponding substituted alkyl amines by reaction with triflic azide. In a few cases, azides are synthesized by modification of other azides that are synthesized according to the methodologies above. An exemplary synthesis of iodo azide 14zz is shown below in Scheme 175, which can further be functionalized with boronic acid derivatives to a further variety of azide compounds.

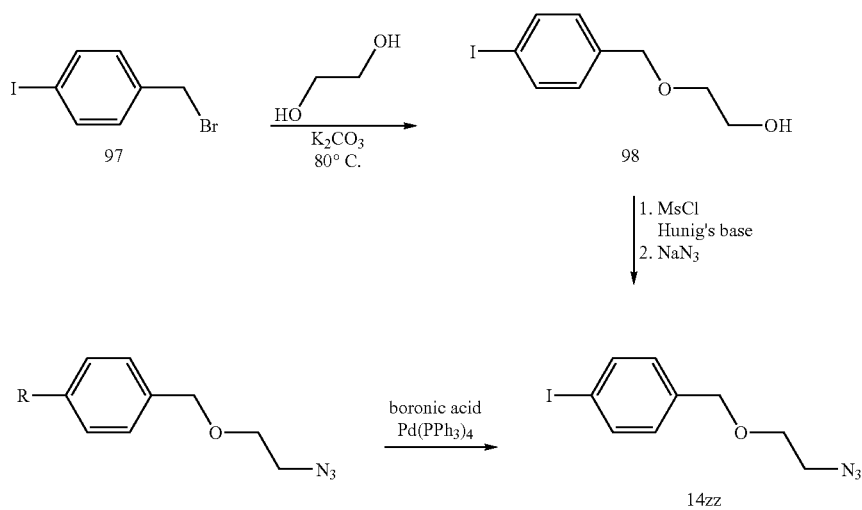

Scheme 175

TABLE 6-continued

| Azide Compound | Structure |
|---|---|
| 14ez | 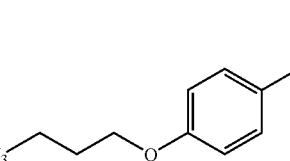 |
| 14fp | 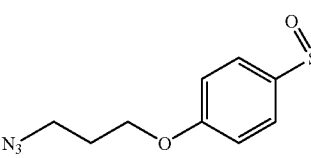 |

Synthesis of Compound 98

A solution of 1.000 g (3.37 mmol) of benzyl bromide 97 and 0.930 g (6.74 mmol) of K$_2$CO$_3$ in 20 ml of ethylene glycol was heated at 80° C. for 3 h. The reaction mixture was diluted with water (30 ml), then, extracted with ethyl acetate (50 ml×3), combined ethyl acetate layers were washed with brine (40 ml), dried (MgSO$_4$), filtered, concentrated, and purified to give 0.650 g of the desired product.

Synthesis of Compound 14zz

To a solution of 0.650 g (2.34 mmol) of compound 98, 0.81 ml (4.68 mmol) of Hunig's base in 10 ml of DMF at 0° C. was added 0.27 ml (3.51 mmol) of MsCl. The reaction mixture was subsequently warmed to ambient temperature and stirred for 2 h. To the above reaction mixture was then added 0.304 g (4.68 mmol) of NaN$_3$. The new mixture was heated up to 70° C. for 24 h. The reaction mixture was diluted with water (50 ml), extracted with diethyl ether (40 ml×3), combined ether layers were washed with water (15 ml×3), brine (30 ml), dried (MgSO$_4$), filtered and concentrated to give 0.510 g of the desired product. This iodo compound can then be used for coupling with various boronic acids to obtain the desired azide compound.

Example 6

Synthesis of Compounds 230-243

Compounds 230-243 were made using general procedures as described above.

Incorporation by Reference

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound having the structure selected from:

| Compound | Structure |
|---|---|
| 101 | *[chemical structure]* |
| 102 | *[chemical structure]* |
| 103 | *[chemical structure]* |
| 104 | *[chemical structure]* |
| 105 | *[chemical structure]* |

267
-continued
| Compound | Structure |
|---|---|
| 106 | 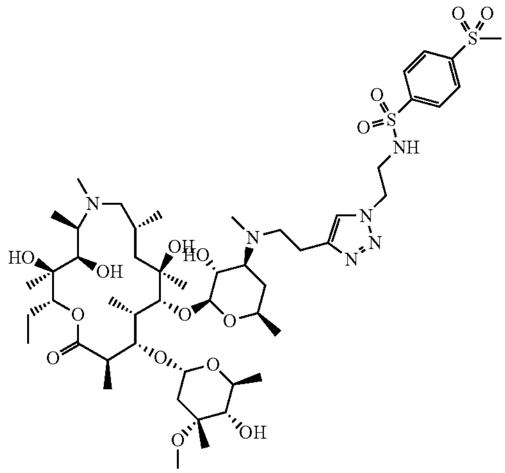 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNS(=O)(=O)c4ccc(S(C)(=O)=O)cc4)nn3)[C@H]2O)[C@](C)(O)C[C@@H](C)CN(C)[C@H](C)[C@@H](O)[C@]1(C)O] |
| 107 | 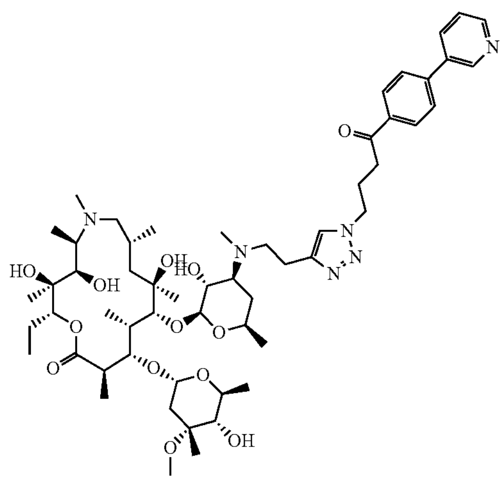 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCC(=O)c4ccc(-c5cccnc5)cc4)nn3)[C@H]2O)[C@](C)(O)C[C@@H](C)CN(C)[C@H](C)[C@@H](O)[C@]1(C)O] |
| 108 | 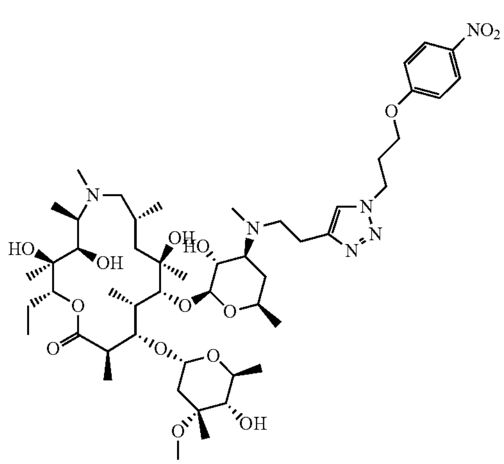 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc([N+](=O)[O-])cc4)nn3)[C@H]2O)[C@](C)(O)C[C@@H](C)CN(C)[C@H](C)[C@@H](O)[C@]1(C)O] |
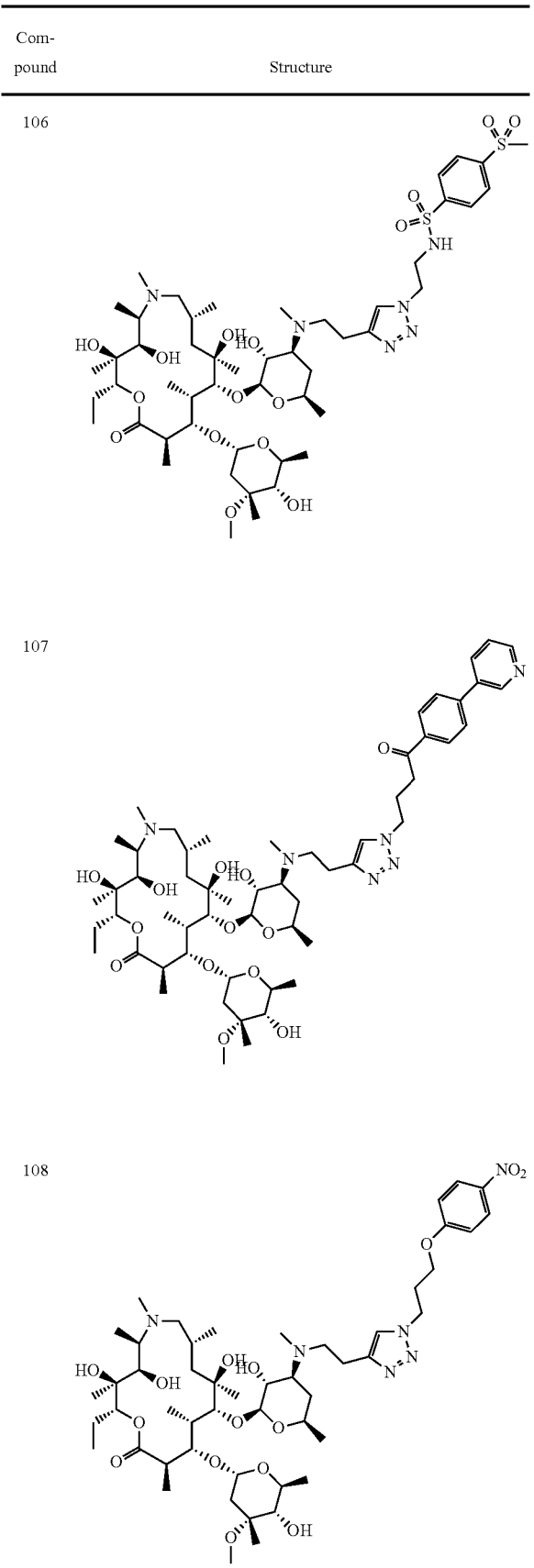
268
-continued
| Compound | Structure |
|---|---|
| 109 | 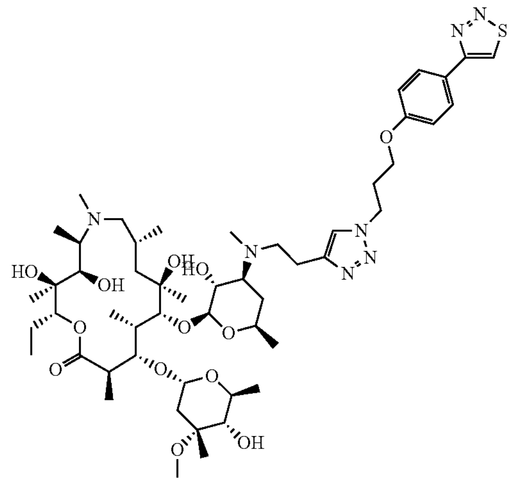 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5csnn5)cc4)nn3)[C@H]2O)[C@](C)(O)C[C@@H](C)CN(C)[C@H](C)[C@@H](O)[C@]1(C)O] |
| 110 | 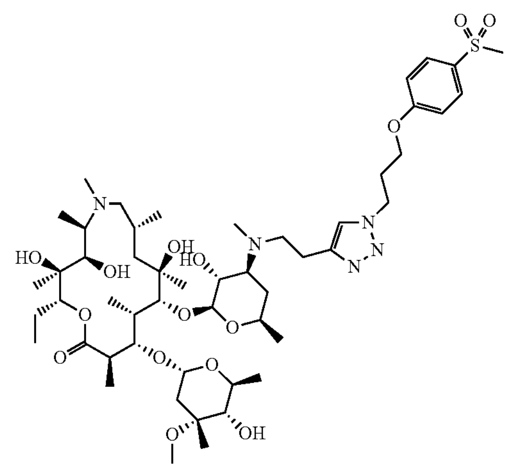 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCC3=CN(CCCOc4ccc(S(C)(=O)=O)cc4)NN3)[C@H]2O)[C@](C)(O)C[C@@H](C)CN(C)[C@H](C)[C@@H](O)[C@]1(C)O] |
| 111 | 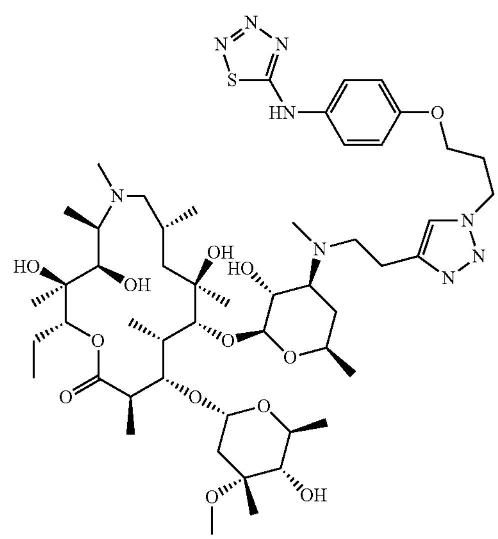 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCC3=CN(CCCOc4ccc(Nc5nnns5)cc4)NN3)[C@H]2O)[C@](C)(O)C[C@@H](C)CN(C)[C@H](C)[C@@H](O)[C@]1(C)O] |
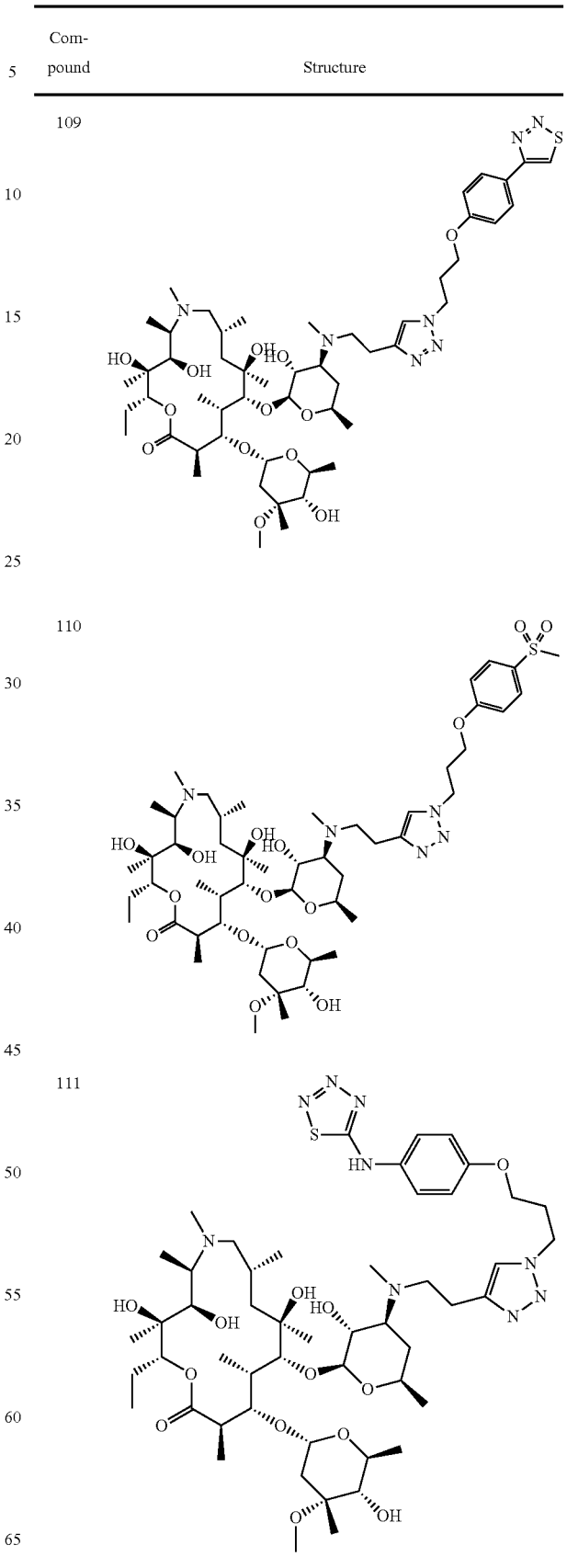

| Compound | Structure |
|---|---|
| 112 | 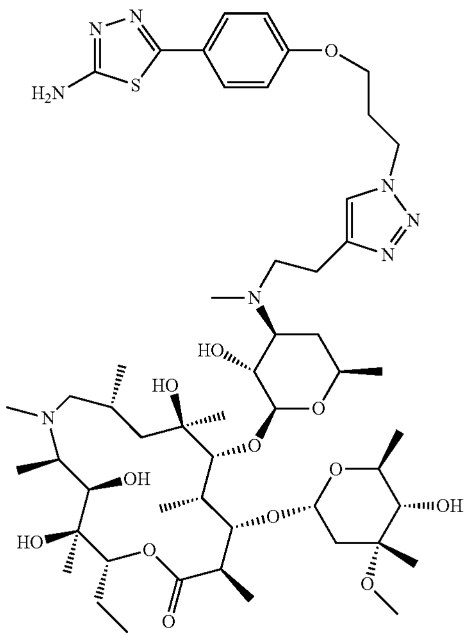 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5nnc(N)s5)cc4)nn3)[C@H]2O)[C@](C)(O)C[C@@H](C)CN(C)[C@H](C)[C@@H](O)[C@]1(C)O] |
| 113 | 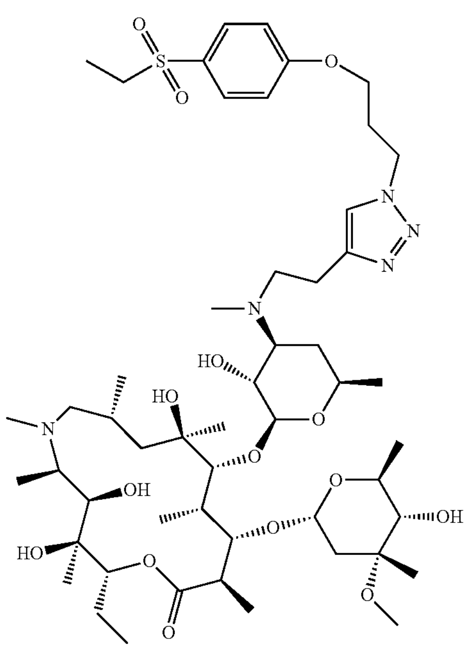 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)CC)cc4)nn3)[C@H]2O)[C@](C)(O)C[C@@H](C)CN(C)[C@H](C)[C@@H](O)[C@]1(C)O] |

| Compound | Structure |
|---|---|
| 114 | 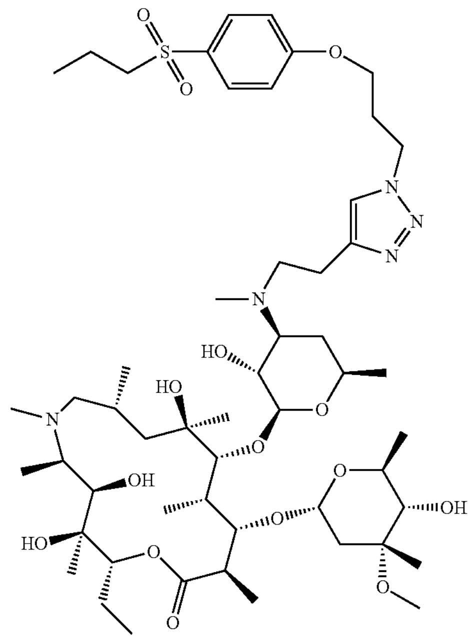 [SMILES: CCCS(=O)(=O)c1ccc(OCCCn2cc(CCN(C)[C@H]3C[C@@H](C)O[C@@H](O[C@@H]4[C@@H](C)[C@H](O[C@H]5C[C@@](C)(OC)[C@@H](O)[C@H](C)O5)[C@@H](C)C(=O)O[C@H](CC)[C@@](C)(O)[C@H](O)[C@@H](C)N(C)C[C@H](C)C[C@@]4(C)O)[C@@H]3O)nn2)cc1] |
| 115 | 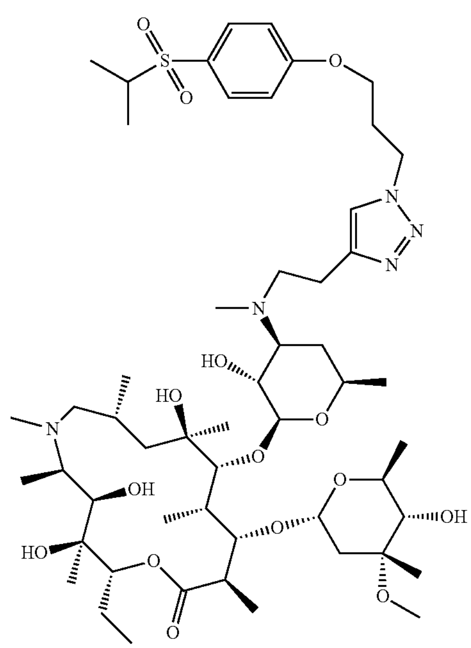 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)C(C)C)cc4)nn3)[C@H]2O)[C@](C)(O)C[C@@H](C)CN(C)[C@H](C)[C@@H](O)[C@]1(C)O] |

| Compound | Structure |
|---|---|
| 116 | 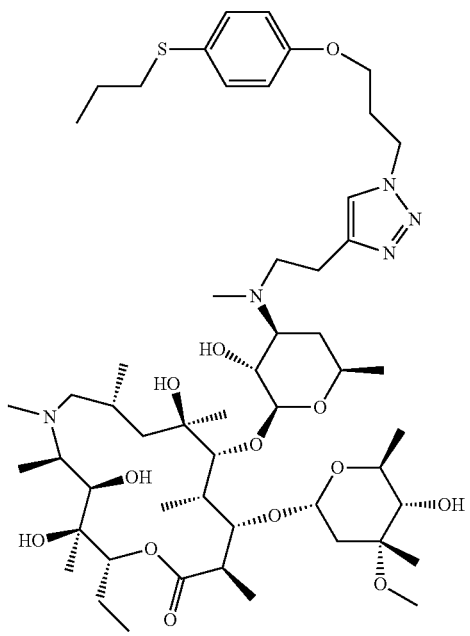 [SMILES: CCCSc1ccc(OCCCn2cc(CCN(C)[C@H]3C[C@@H](C)O[C@@H](O[C@@H]4[C@@H](C)[C@H](O[C@H]5C[C@@](C)(OC)[C@@H](O)[C@H](C)O5)[C@@H](C)C(=O)O[C@H](CC)[C@@](C)(O)[C@H](O)[C@@H](C)N(C)C[C@H](C)C[C@@]4(C)O)[C@@H]3O)nn2)cc1] |
| 117 | 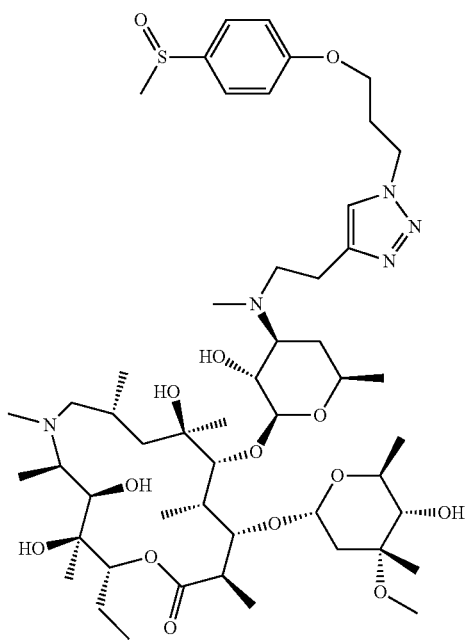 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(C)=O)cc4)nn3)[C@H]2O)[C@](C)(O)C[C@@H](C)CN(C)[C@H](C)[C@@H](O)[C@]1(C)O] |
| Compound | Structure |
|---|---|
| 118 | 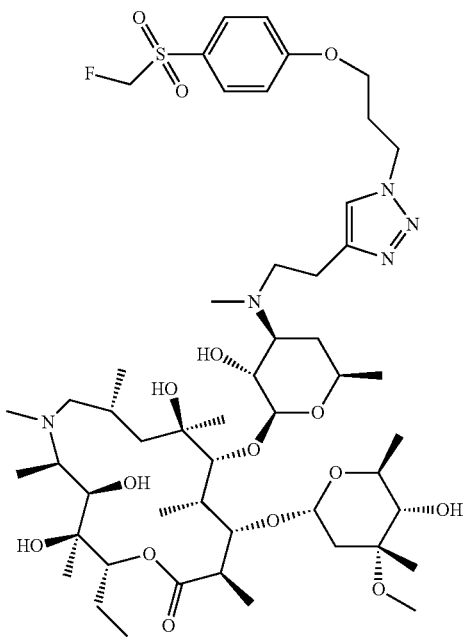 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)CF)cc4)nn3)[C@H]2O)[C@](C)(O)C[C@@H](C)CN(C)[C@H](C)[C@@H](O)[C@]1(C)O] |
| 119 | 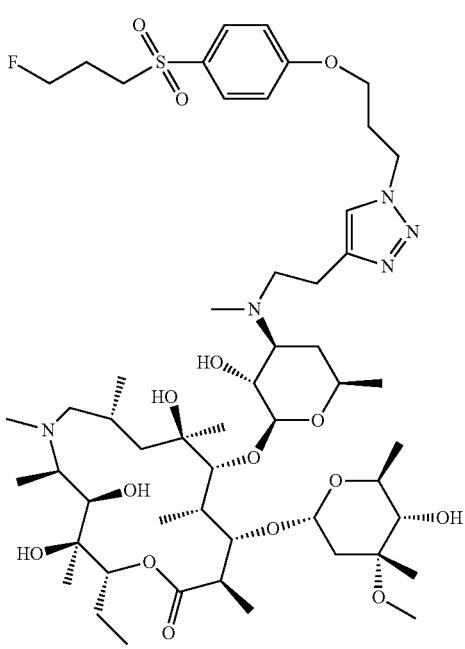 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)CCCF)cc4)nn3)[C@H]2O)[C@](C)(O)C[C@@H](C)CN(C)[C@H](C)[C@@H](O)[C@]1(C)O] |

| Compound | Structure |
|---|---|
| 120 | 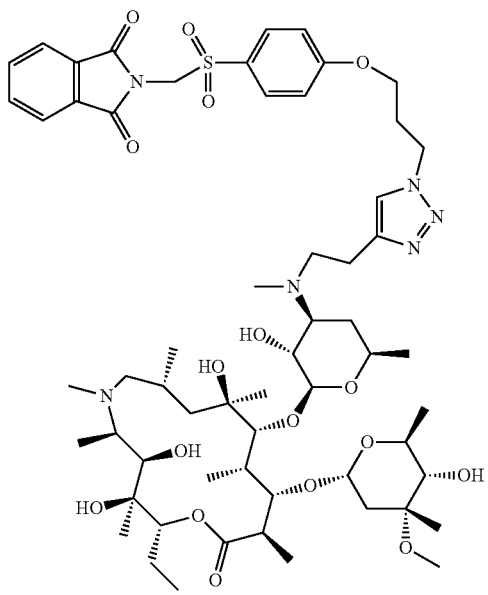 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)CN5C(=O)c6ccccc6C5=O)cc4)nn3)[C@H]2O)[C@](C)(O)C[C@@H](C)CN(C)[C@H](C)[C@@H](O)[C@]1(C)O] |
| 121 | 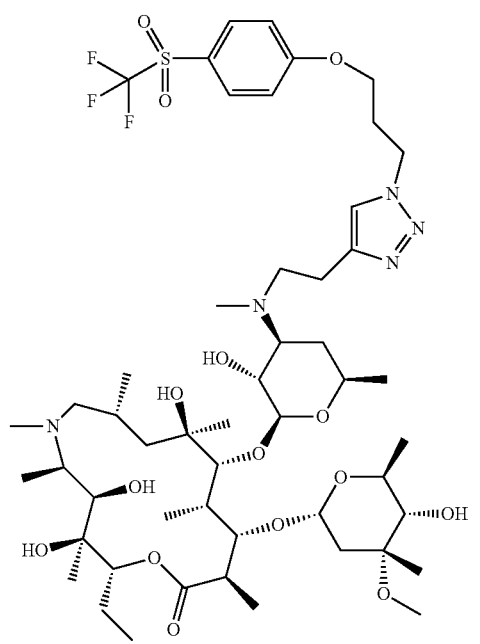 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)(=O)C(F)(F)F)cc4)nn3)[C@H]2O)[C@](C)(O)C[C@@H](C)CN(C)[C@H](C)[C@@H](O)[C@]1(C)O] |
| Compound | Structure |
|---|---|
| 122 | 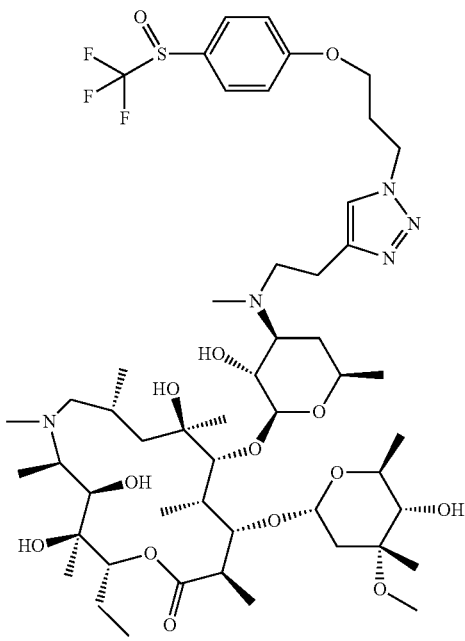 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(=O)C(F)(F)F)cc4)nn3)[C@H]2O)[C@](C)(O)C[C@@H](C)CN(C)[C@H](C)[C@@H](O)[C@]1(C)O] |
| 123 | 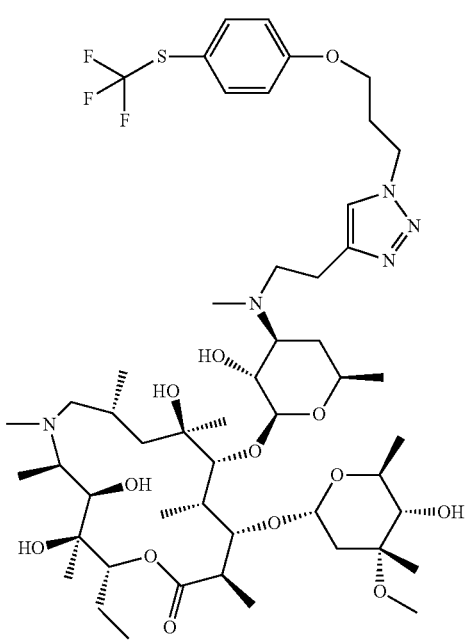 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(SC(F)(F)F)cc4)nn3)[C@H]2O)[C@](C)(O)C[C@@H](C)CN(C)[C@H](C)[C@@H](O)[C@]1(C)O] |

| Compound | Structure |
|---|---|
| 124 | 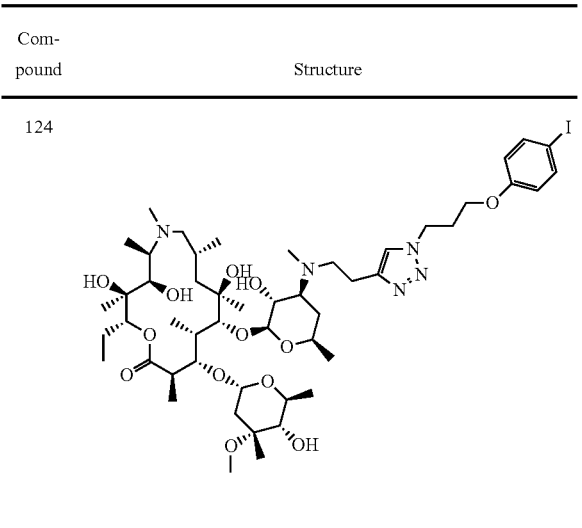 |
| 125 | 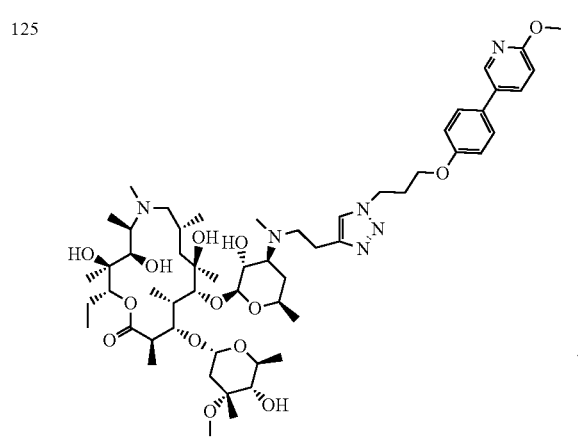 |
| 126 | 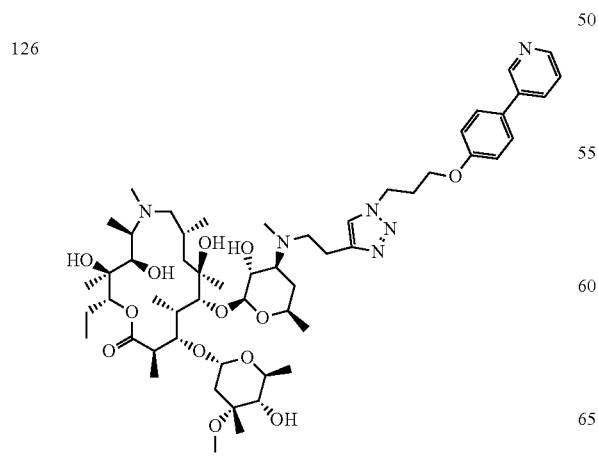 |
| Compound | Structure |
|---|---|
| 127 | 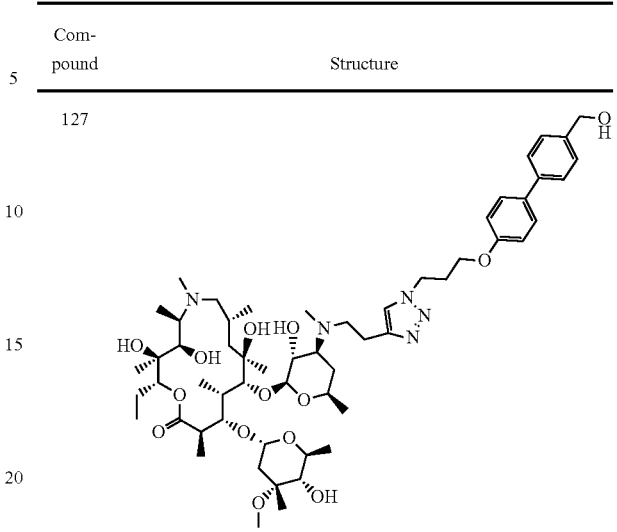 |
| 128 | 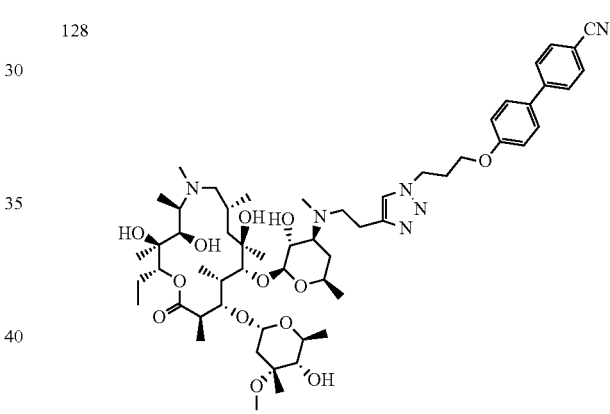 |
| 129 | 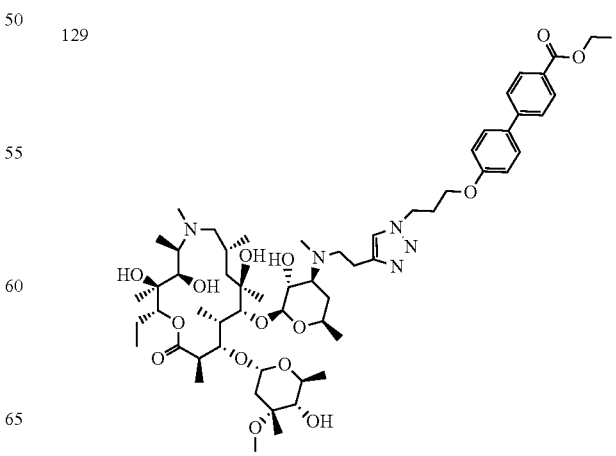 |

277
-continued
| Compound | Structure |
|---|---|
| 130 | 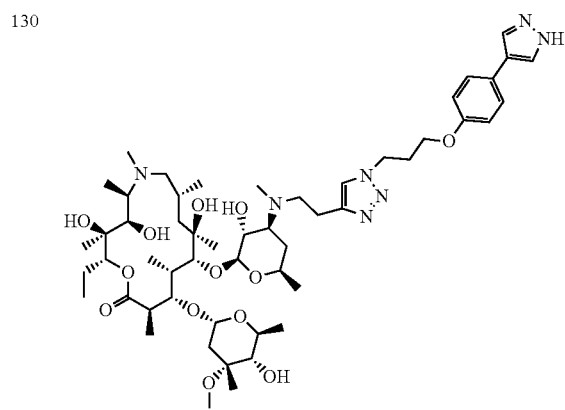 |
| 131 | 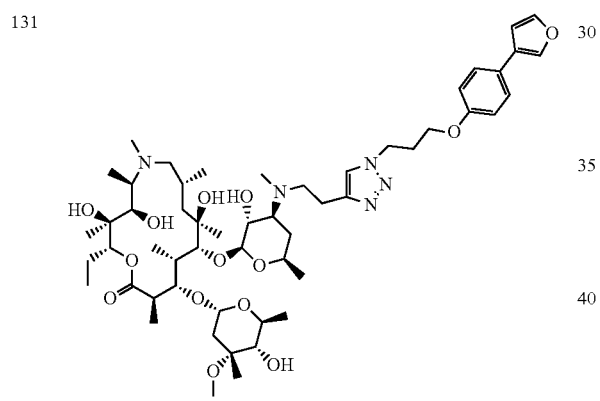 |
| 132 | 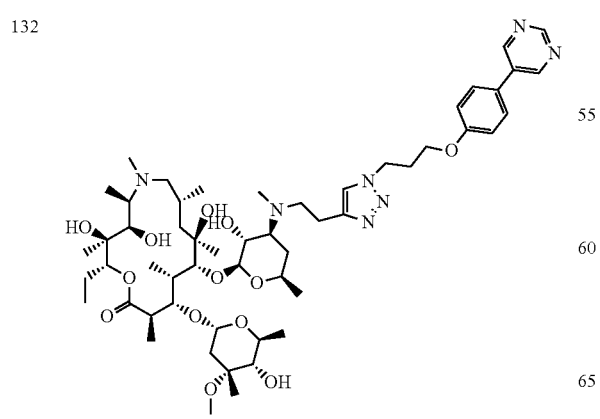 |
278
-continued
| Compound | Structure |
|---|---|
| 133 | 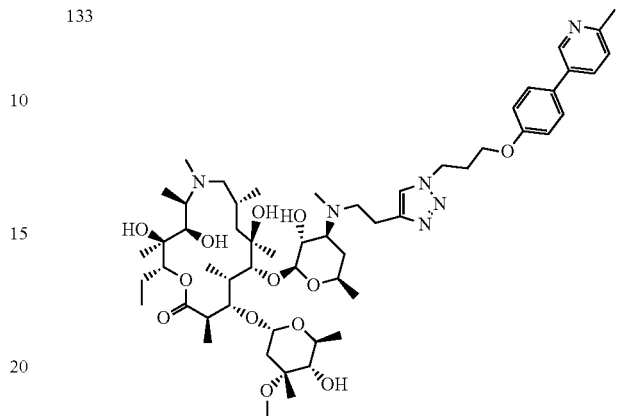 |
| 134 | 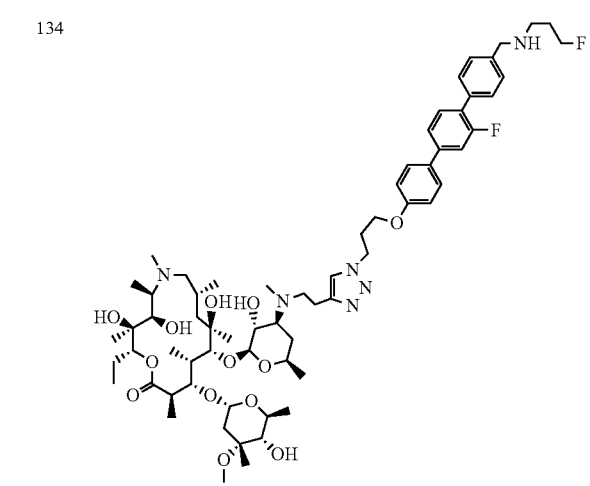 |
| 135 | 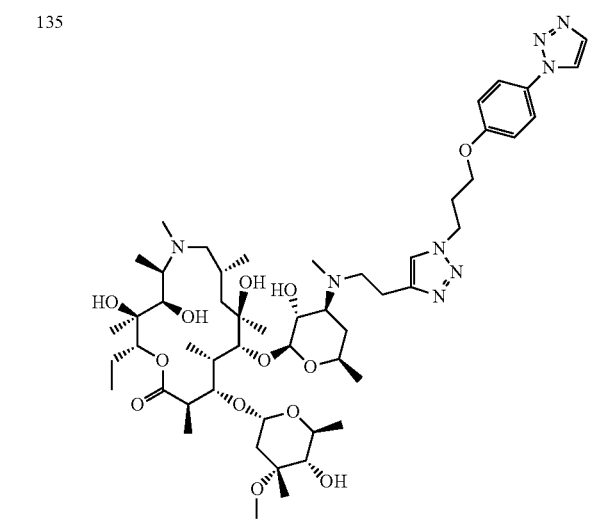 |

| Compound | Structure |
|---|---|
| 136 | 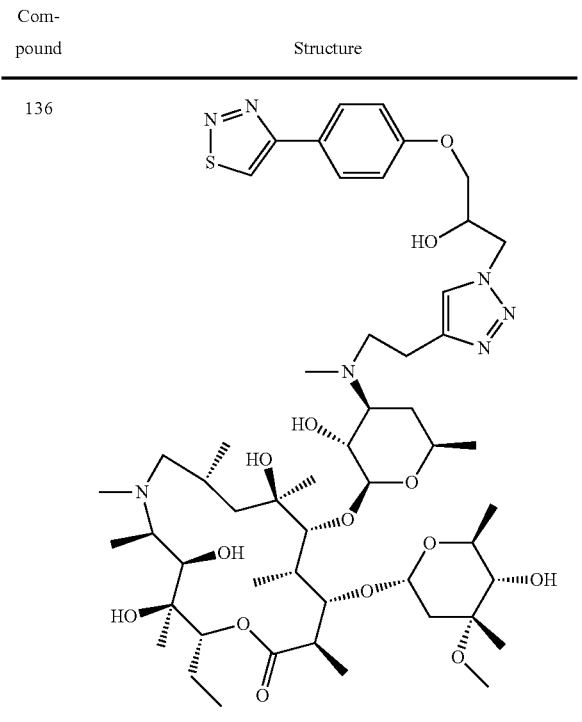 |
| 137 | |
| Compound | Structure |
|---|---|
| 138 | 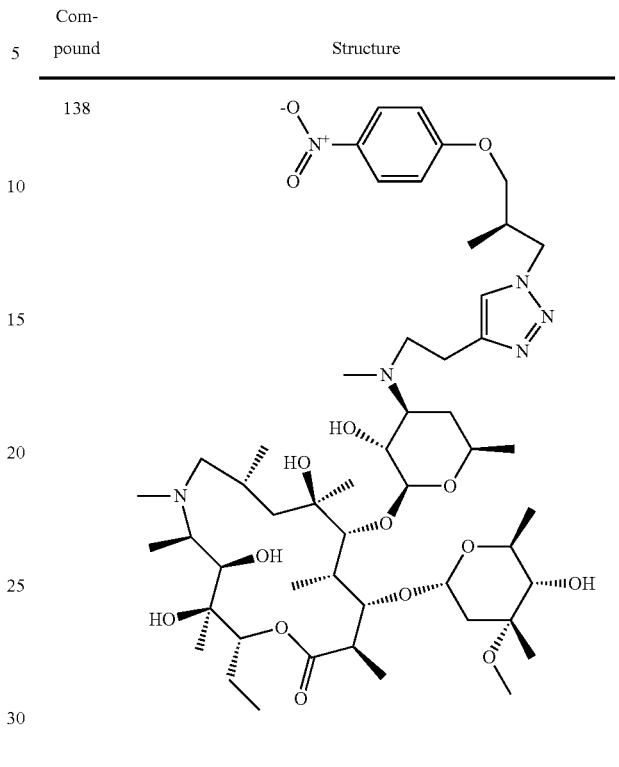 |
| 139 | |
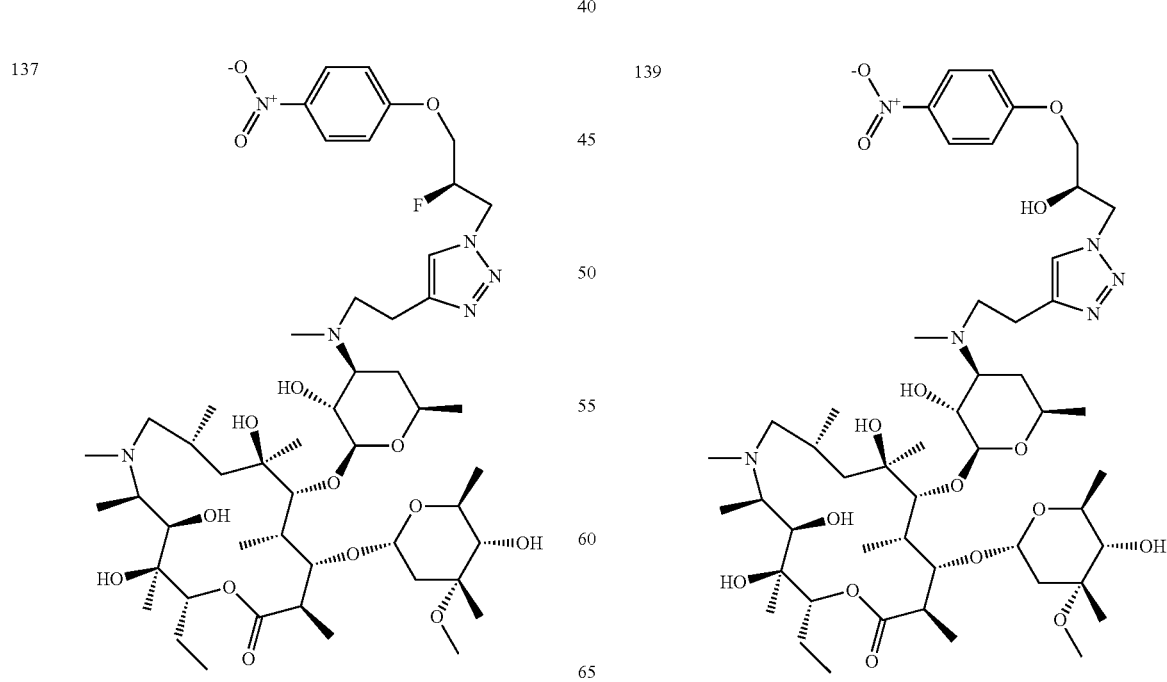

| Compound | Structure |
|---|---|
| 140 | 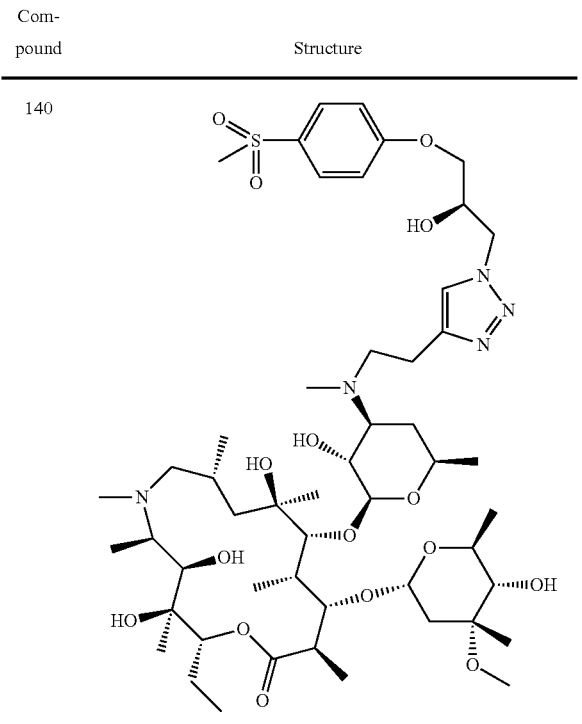 |
| 141 | 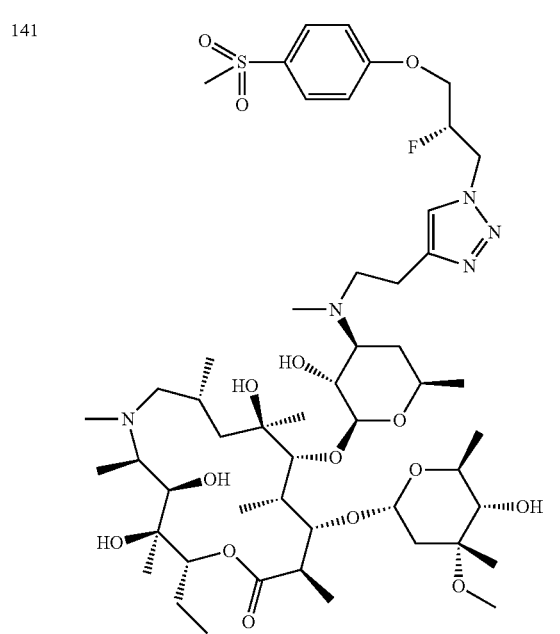 |
| Compound | Structure |
|---|---|
| 142 | 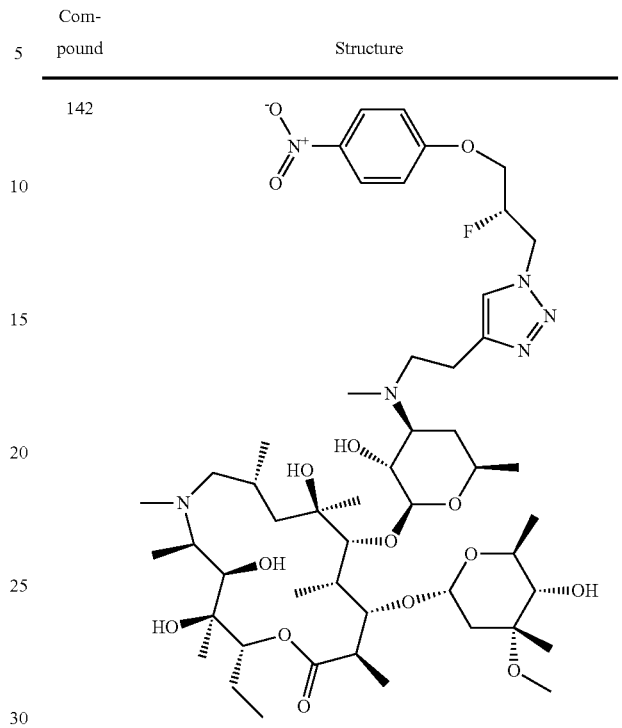 |
| 143 | 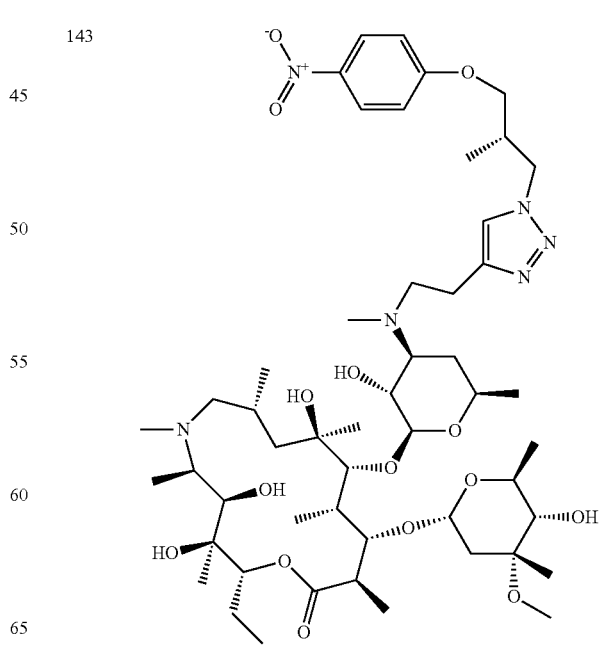 |

283
-continued
| Compound | Structure |
|---|---|
| 144 | 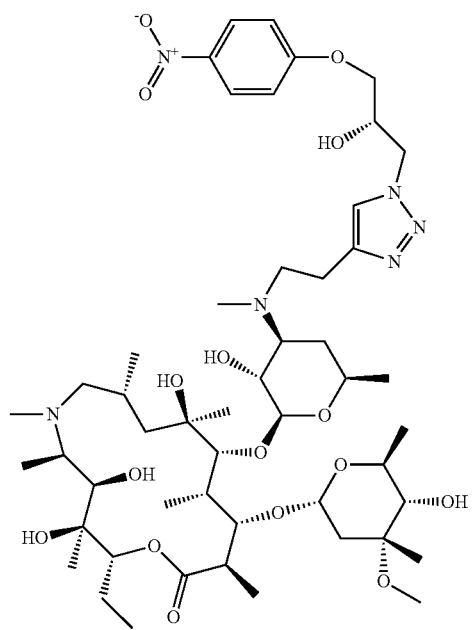 |
| 145 | 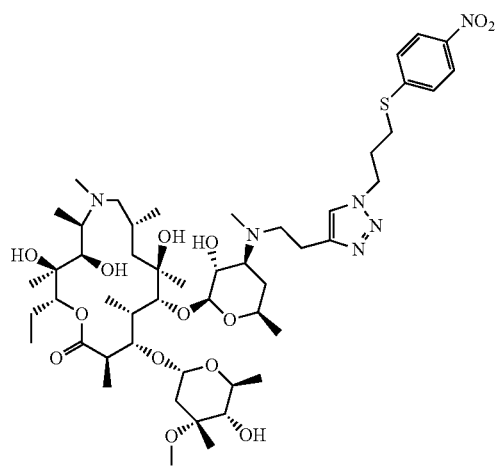 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCSc4ccc([N+](=O)[O-])cc4)nn3)[C@H]2O)[C@](C)(O)C[C@@H](C)CN(C)[C@H](C)[C@@H](O)[C@]1(C)O] |
| 146 | 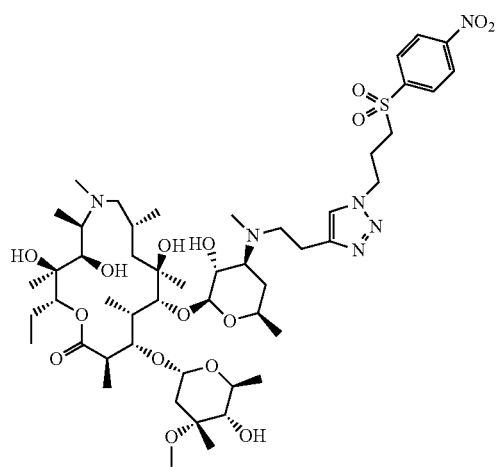 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCS(=O)(=O)c4ccc([N+](=O)[O-])cc4)nn3)[C@H]2O)[C@](C)(O)C[C@@H](C)CN(C)[C@H](C)[C@@H](O)[C@]1(C)O] |
284
-continued
| Compound | Structure |
|---|---|
| 147 | 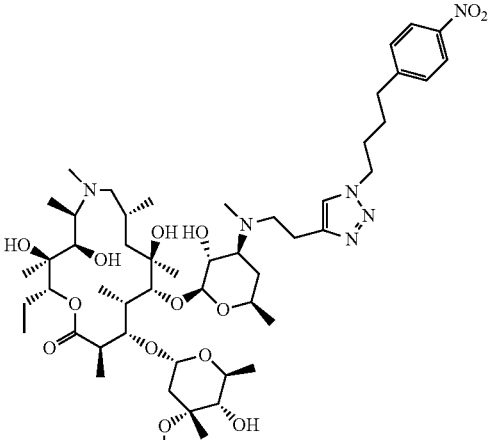 |
| 148 | 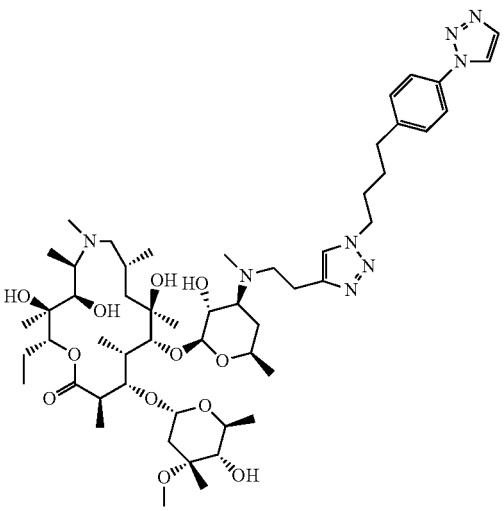 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5ccnn5)cc4)nn3)[C@H]2O)[C@](C)(O)C[C@@H](C)CN(C)[C@H](C)[C@@H](O)[C@]1(C)O] |
| 149 | 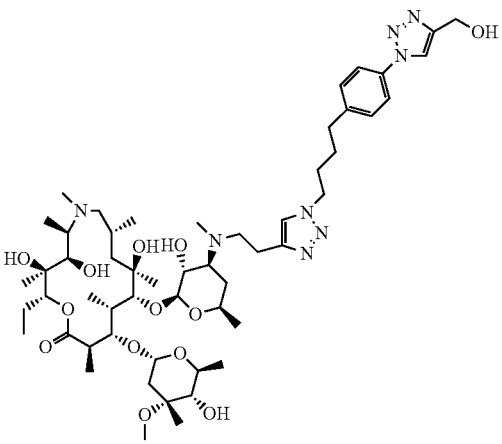 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CO)nn5)cc4)nn3)[C@H]2O)[C@](C)(O)C[C@@H](C)CN(C)[C@H](C)[C@@H](O)[C@]1(C)O] |

285
-continued
| Compound | Structure |
|---|---|
| 150 | 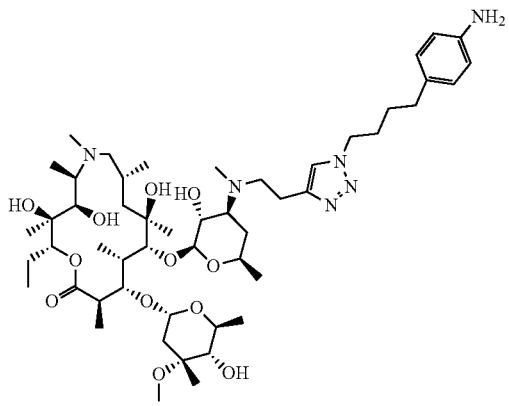 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(N)cc4)nn3)[C@H]2O)[C@](C)(O)C[C@@H](C)CN(C)[C@H](C)[C@@H](O)[C@]1(C)O] |
| 151 | 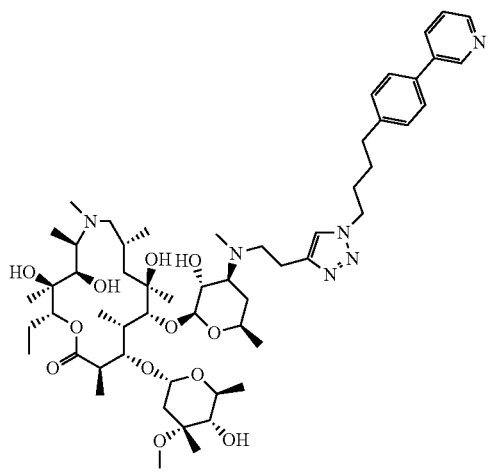 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-c5cccnc5)cc4)nn3)[C@H]2O)[C@](C)(O)C[C@@H](C)CN(C)[C@H](C)[C@@H](O)[C@]1(C)O] |
| 152 | 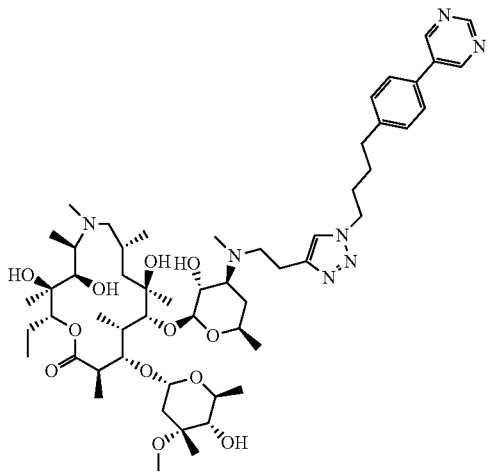 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-c5cncnc5)cc4)nn3)[C@H]2O)[C@](C)(O)C[C@@H](C)CN(C)[C@H](C)[C@@H](O)[C@]1(C)O] |
286
-continued
| Compound | Structure |
|---|---|
| 153 | 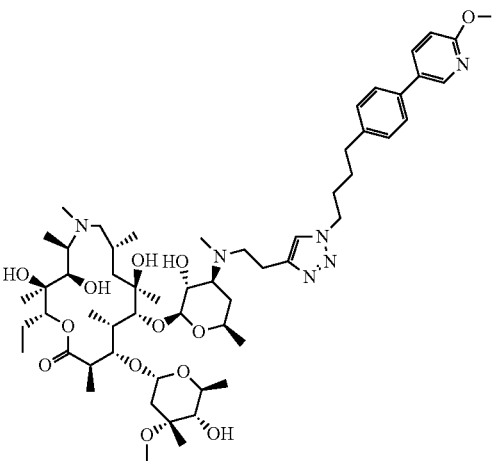 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-c5ccc(OC)nc5)cc4)nn3)[C@H]2O)[C@](C)(O)C[C@@H](C)CN(C)[C@H](C)[C@@H](O)[C@]1(C)O] |
| 154 | 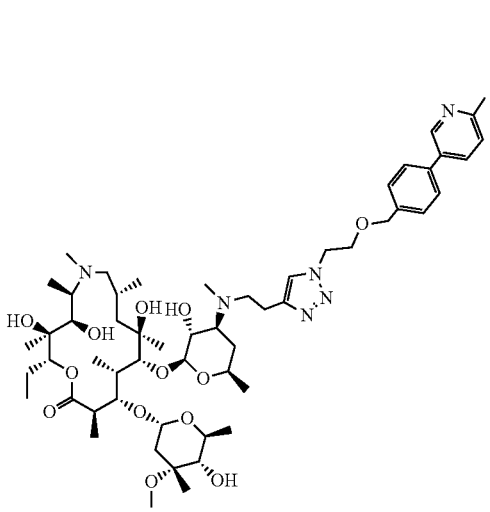 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOCc4ccc(-c5ccc(C)nc5)cc4)nn3)[C@H]2O)[C@](C)(O)C[C@@H](C)CN(C)[C@H](C)[C@@H](O)[C@]1(C)O] |
| 155 | 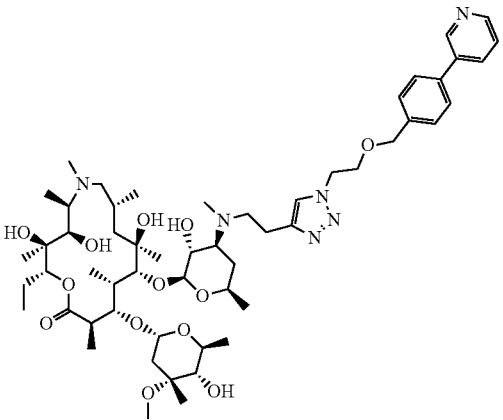 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOCc4ccc(-c5cccnc5)cc4)nn3)[C@H]2O)[C@](C)(O)C[C@@H](C)CN(C)[C@H](C)[C@@H](O)[C@]1(C)O] |

287
-continued

| Compound | Structure |
|---|---|
| 156 | 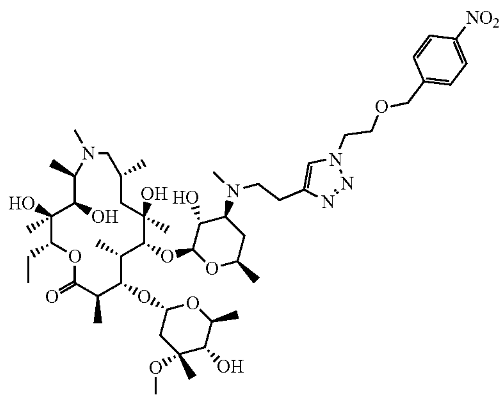 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOCc4ccc([N+](=O)[O-])cc4)nn3)[C@H]2O)[C@](C)(O)C[C@@H](C)CN(C)[C@H](C)[C@@H](O)[C@]1(C)O] |
| 157 | 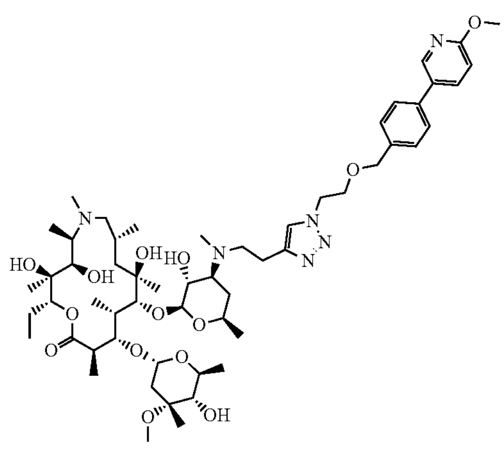 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOCc4ccc(-c5ccc(OC)nc5)cc4)nn3)[C@H]2O)[C@](C)(O)C[C@@H](C)CN(C)[C@H](C)[C@@H](O)[C@]1(C)O] |
| 158 | 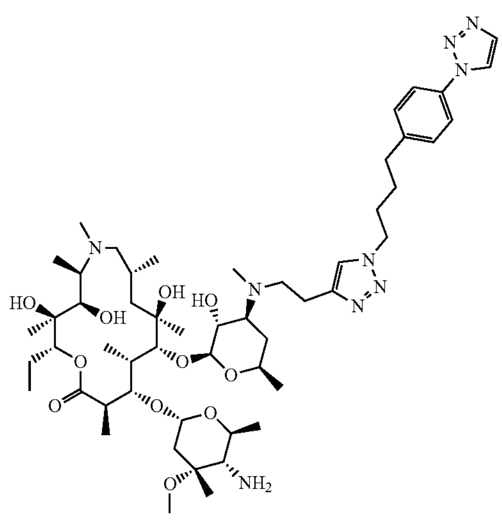 [SMILES: CC[C@H]1OC(=O)[C@H](C)[C@@H](O[C@H]2C[C@@](C)(OC)[C@@H](N)[C@H](C)O2)[C@H](C)[C@@H](O[C@@H]2O[C@H](C)C[C@H](N(C)CCc3cn(CCCCc4ccc(-n5ccnn5)cc4)nn3)[C@H]2O)[C@](C)(O)C[C@@H](C)CN(C)[C@H](C)[C@@H](O)[C@]1(C)O] |

288
-continued

| Compound | Structure |
|---|---|
| 159 | 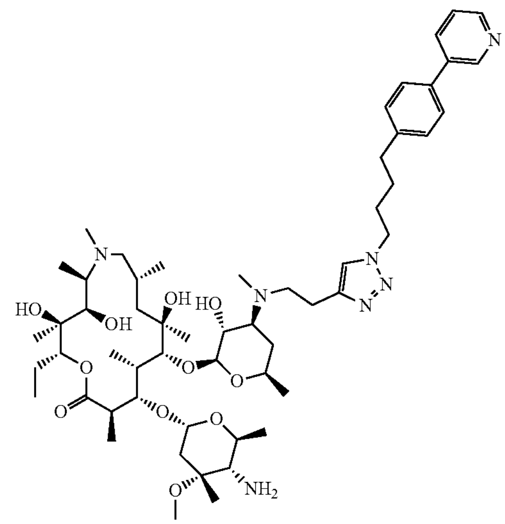 [SMILES: CC[C@H]1OC(=O)[C@H](C)[C@@H](O[C@H]2C[C@@](C)(OC)[C@@H](N)[C@H](C)O2)[C@H](C)[C@@H](O[C@@H]2O[C@H](C)C[C@H](N(C)CCc3cn(CCCCc4ccc(-c5cccnc5)cc4)nn3)[C@H]2O)[C@](C)(O)C[C@@H](C)CN(C)[C@H](C)[C@@H](O)[C@]1(C)O] |
| 160 | 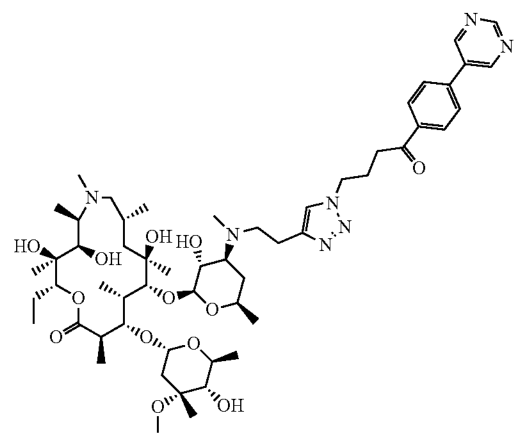 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCC(=O)c4ccc(-c5cncnc5)cc4)nn3)[C@H]2O)[C@](C)(O)C[C@@H](C)CN(C)[C@H](C)[C@@H](O)[C@]1(C)O] |
| 161 | 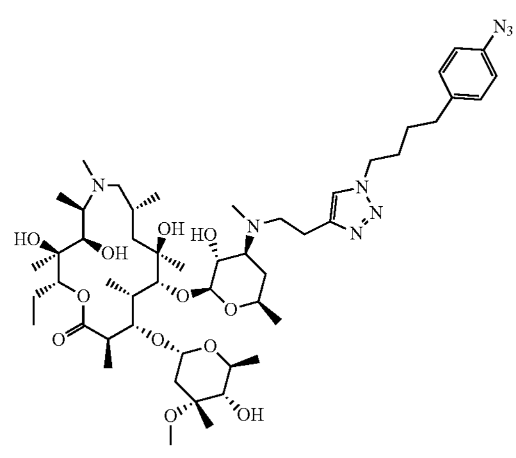 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(N=[N+]=[N-])cc4)nn3)[C@H]2O)[C@](C)(O)C[C@@H](C)CN(C)[C@H](C)[C@@H](O)[C@]1(C)O] |

-continued
| Compound | Structure |
|---|---|
| 162 | 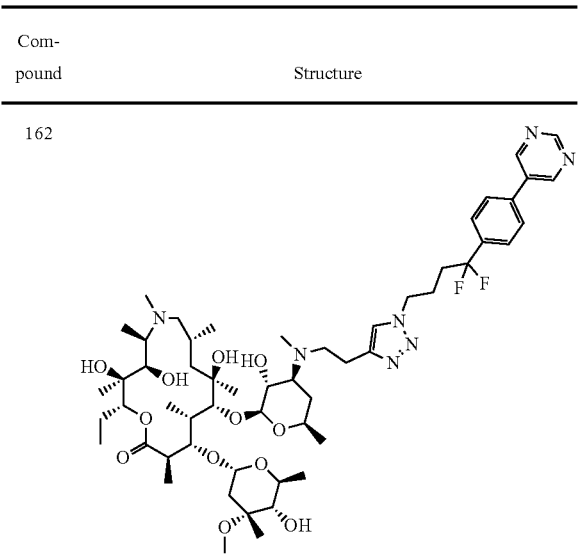 |
| 163 | 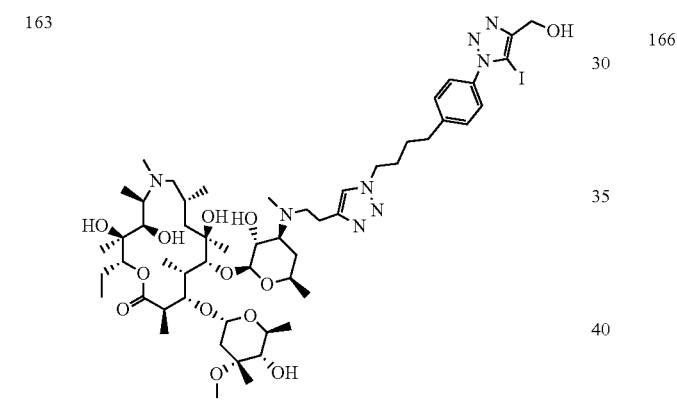 |
| 164 | 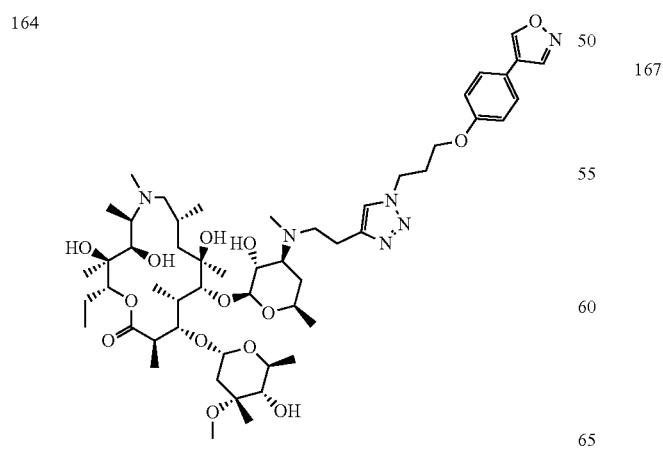 |
-continued
| Compound | Structure |
|---|---|
| 165 | 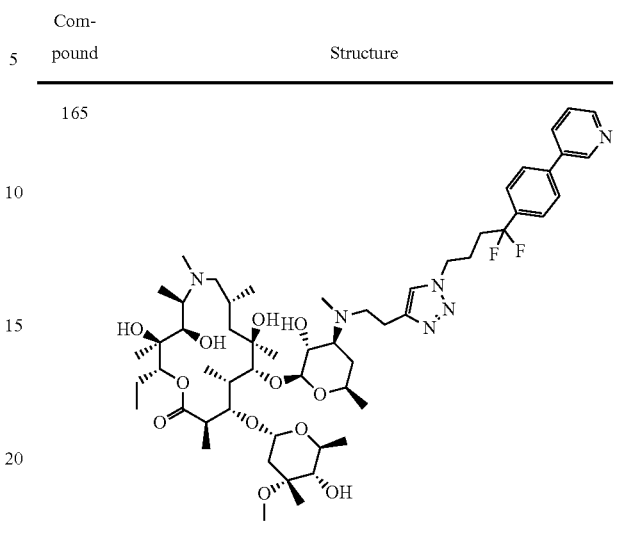 |
| 166 | 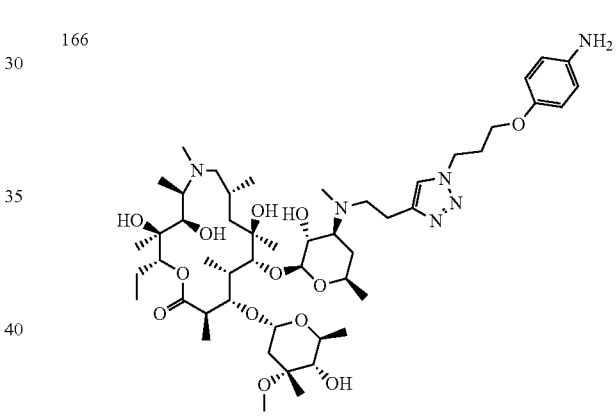 |
| 167 | 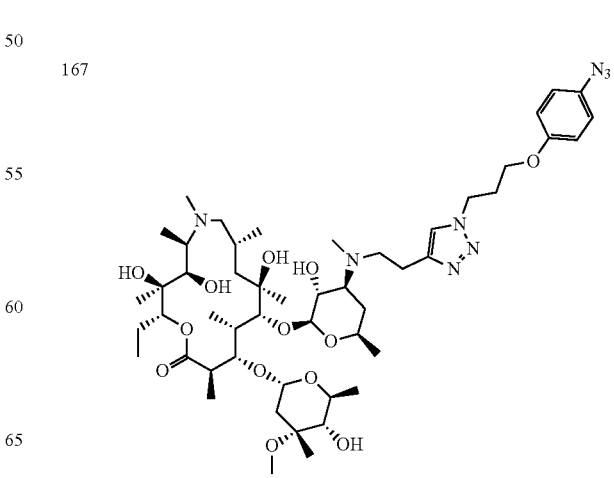 |

291 -continued
| Compound | Structure |
|---|---|
| 168 | 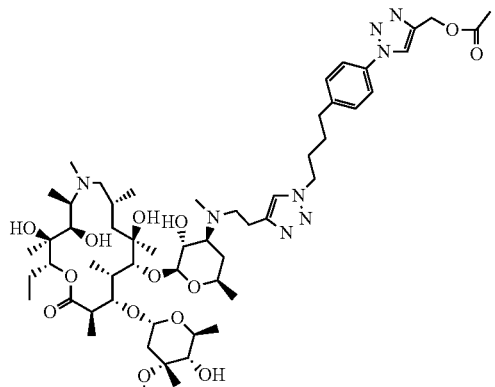 |
| 169 | 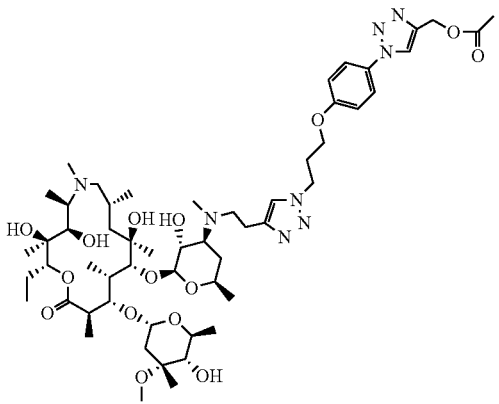 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-n5cc(COC(C)=O)nn5)cc4)nn3)[C@H]2O)[C@](C)(O)C[C@@H](C)CN(C)[C@H](C)[C@@H](O)[C@]1(C)O] |
| 170 | 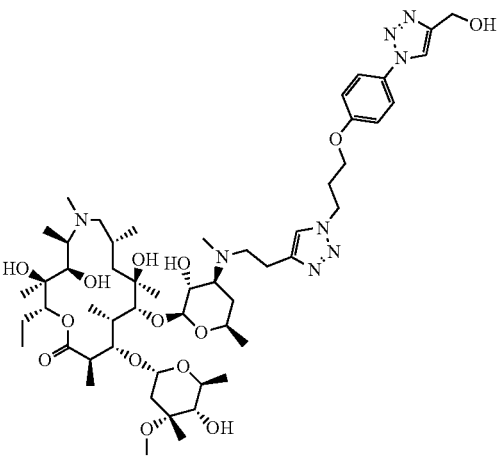 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-n5cc(CO)nn5)cc4)nn3)[C@H]2O)[C@](C)(O)C[C@@H](C)CN(C)[C@H](C)[C@@H](O)[C@]1(C)O] |
292 -continued
| Compound | Structure |
|---|---|
| 171 | 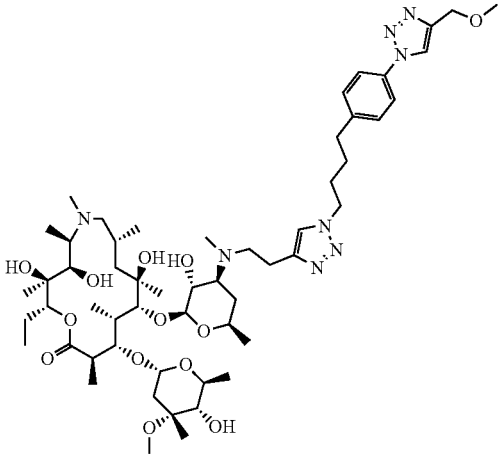 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(COC)nn5)cc4)nn3)[C@H]2O)[C@](C)(O)C[C@@H](C)CN(C)[C@H](C)[C@@H](O)[C@]1(C)O] |
| 172 | 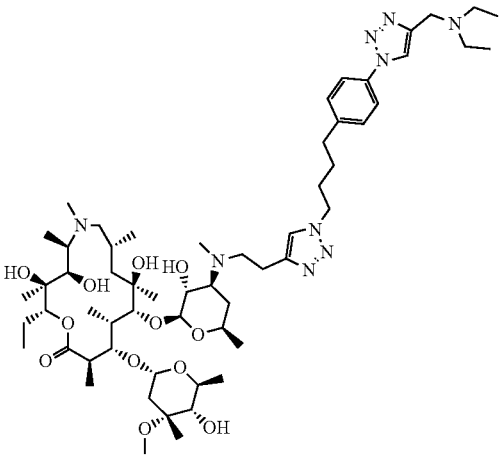 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CN(CC)CC)nn5)cc4)nn3)[C@H]2O)[C@](C)(O)C[C@@H](C)CN(C)[C@H](C)[C@@H](O)[C@]1(C)O] |
| 173 | 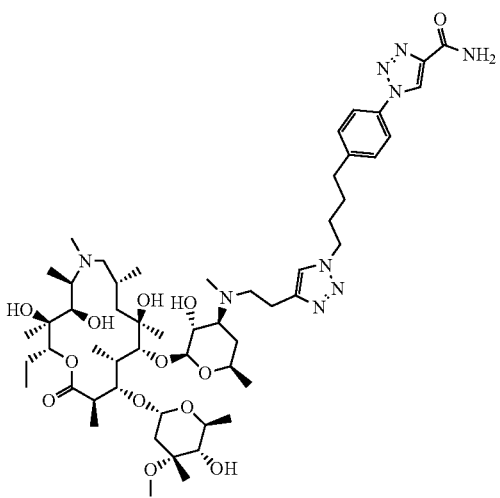 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C(N)=O)nn5)cc4)nn3)[C@H]2O)[C@](C)(O)C[C@@H](C)CN(C)[C@H](C)[C@@H](O)[C@]1(C)O] |

| Compound | Structure |
|---|---|
| 174 | 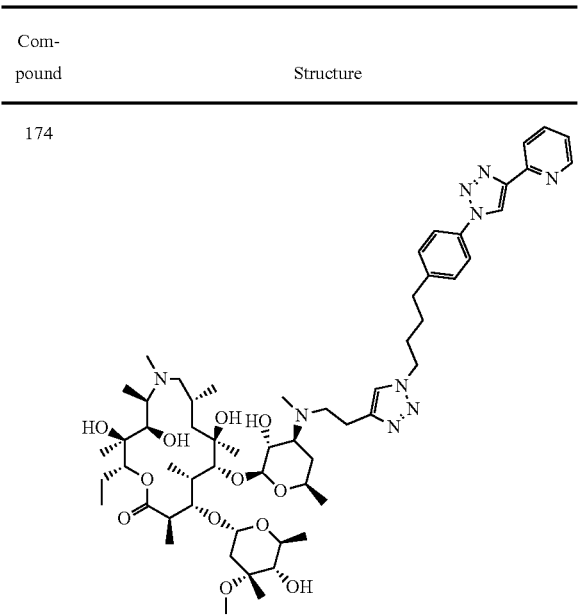 |
| 175 | 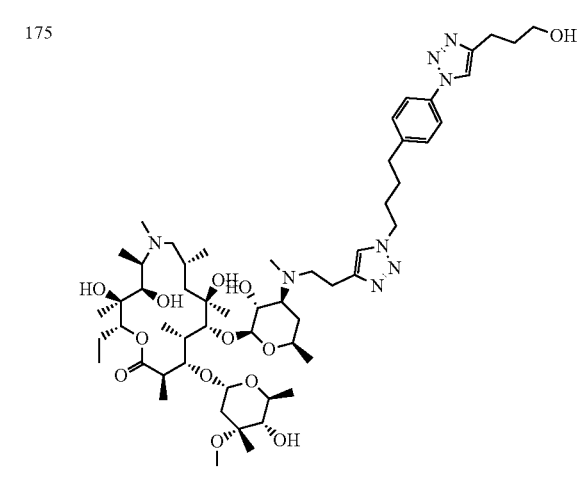 |
| 176 | 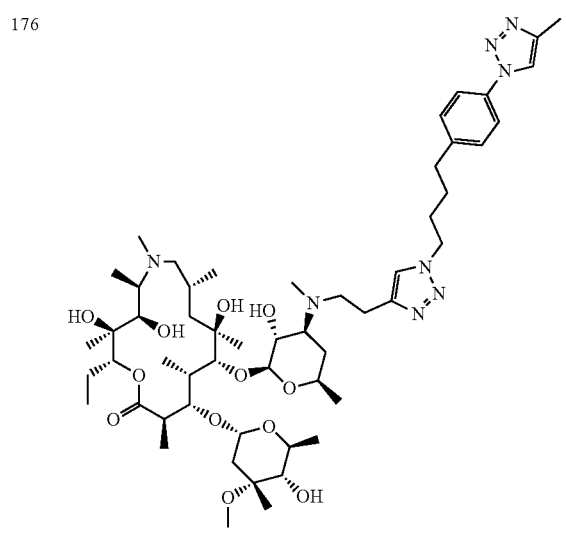 |
| Compound | Structure |
|---|---|
| 177 | 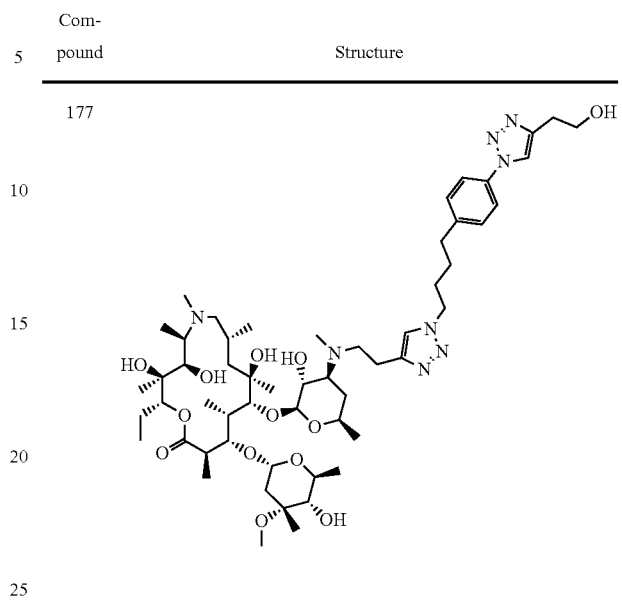 |
| 178 | 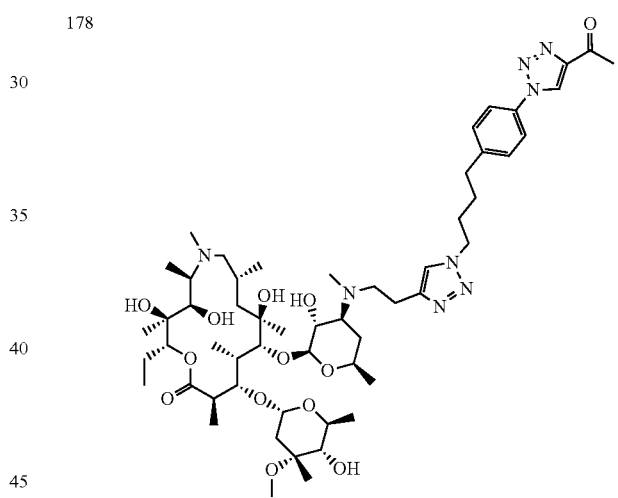 |
| 179 | 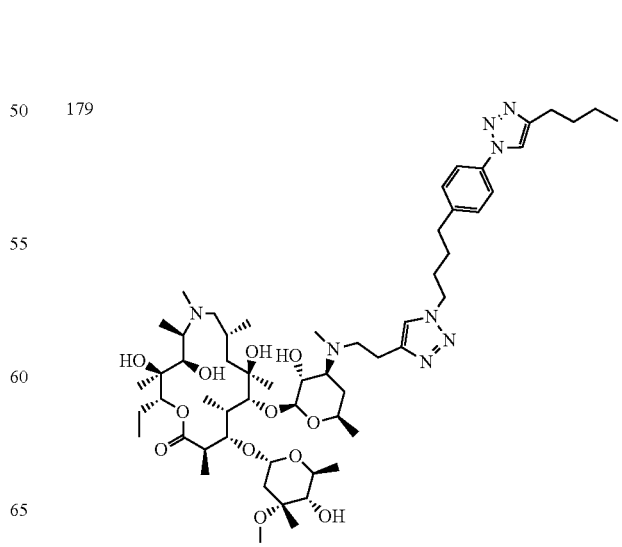 |

| Compound | Structure |
|---|---|
| 180 | 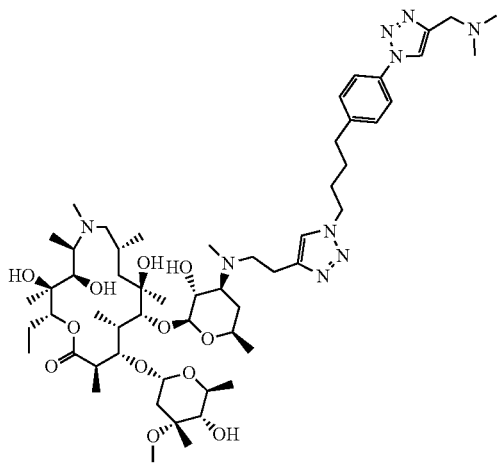 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CN(C)C)nn5)cc4)nn3)[C@H]2O)[C@](C)(O)C[C@@H](C)CN(C)[C@H](C)[C@@H](O)[C@]1(C)O] |
| 181 | 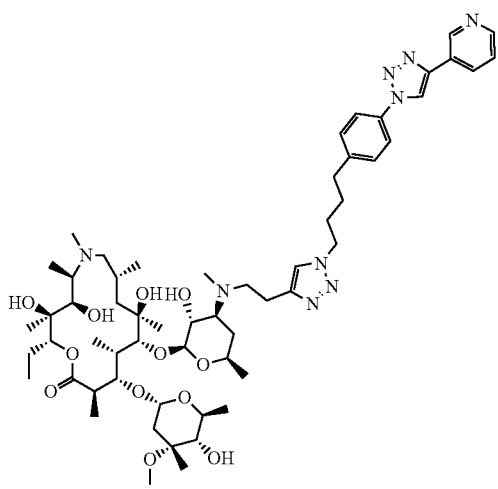 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(-c6cccnc6)nn5)cc4)nn3)[C@H]2O)[C@](C)(O)C[C@@H](C)CN(C)[C@H](C)[C@@H](O)[C@]1(C)O] |
| 182 | 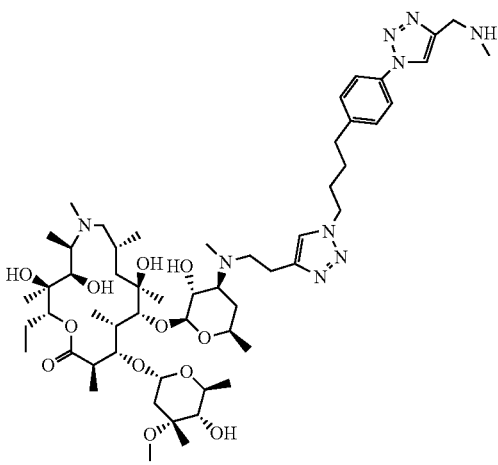 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CNC)nn5)cc4)nn3)[C@H]2O)[C@](C)(O)C[C@@H](C)CN(C)[C@H](C)[C@@H](O)[C@]1(C)O] |
| Compound | Structure |
|---|---|
| 183 | 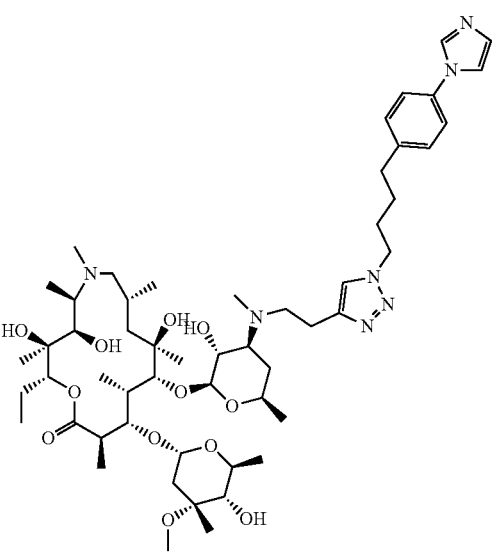 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5ccnc5)cc4)nn3)[C@H]2O)[C@](C)(O)C[C@@H](C)CN(C)[C@H](C)[C@@H](O)[C@]1(C)O] |
| 184 | 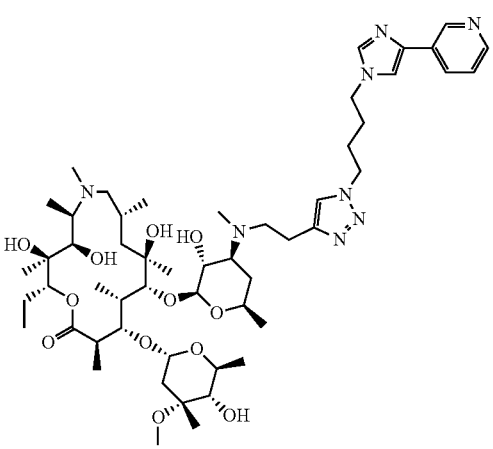 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCn4cnc(-c5cccnc5)c4)nn3)[C@H]2O)[C@](C)(O)C[C@@H](C)CN(C)[C@H](C)[C@@H](O)[C@]1(C)O] |
| 185 | 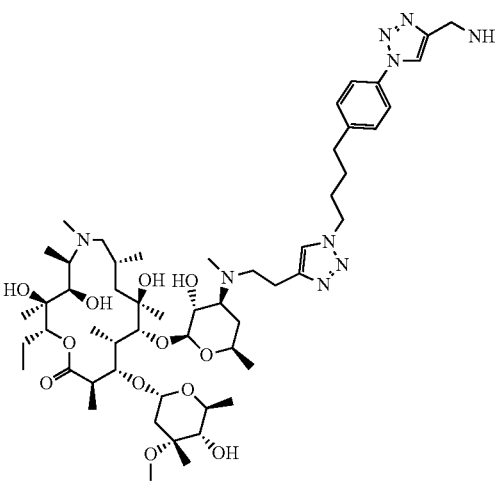 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CN)nn5)cc4)nn3)[C@H]2O)[C@](C)(O)C[C@@H](C)CN(C)[C@H](C)[C@@H](O)[C@]1(C)O] |

| Compound | Structure |
|---|---|
| 186 | 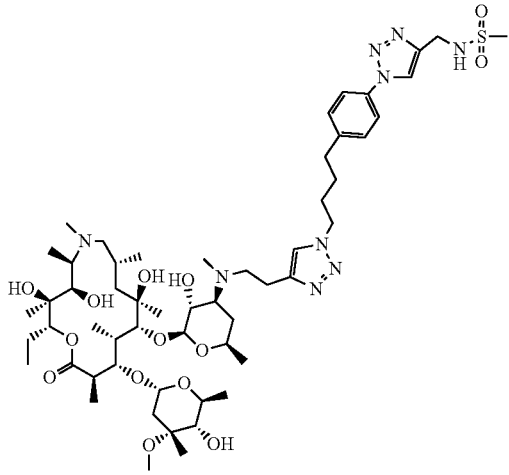 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CNS(C)(=O)=O)nn5)cc4)nn3)[C@H]2O)[C@](C)(O)C[C@@H](C)CN(C)[C@H](C)[C@@H](O)[C@]1(C)O] |
| 187 | 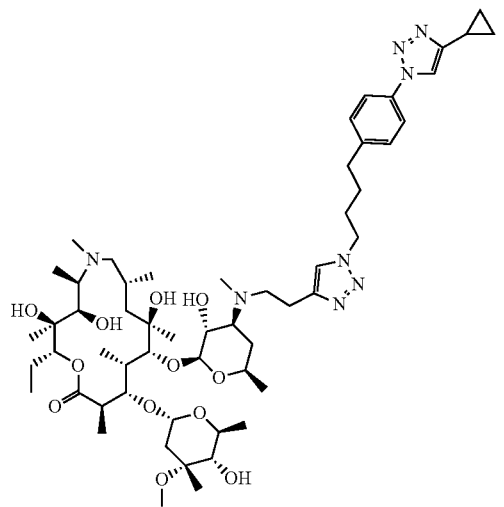 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C6CC6)nn5)cc4)nn3)[C@H]2O)[C@](C)(O)C[C@@H](C)CN(C)[C@H](C)[C@@H](O)[C@]1(C)O] |
| 188 | 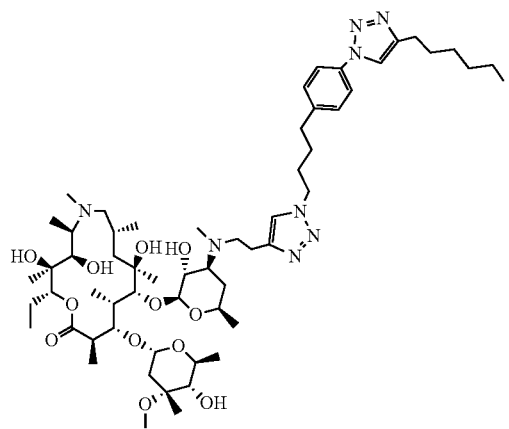 [SMILES: CCCCCCc1cn(-c2ccc(CCCCn3cc(CCN(C)[C@H]4C[C@@H](C)O[C@@H](O[C@@H]5[C@@H](C)[C@H](O[C@H]6C[C@@](C)(OC)[C@@H](O)[C@H](C)O6)[C@@H](C)C(=O)O[C@H](CC)[C@@](C)(O)[C@H](O)[C@@H](C)N(C)C[C@H](C)C[C@@]5(C)O)[C@@H]4O)nn3)cc2)nn1] |
| Compound | Structure |
|---|---|
| 189 | 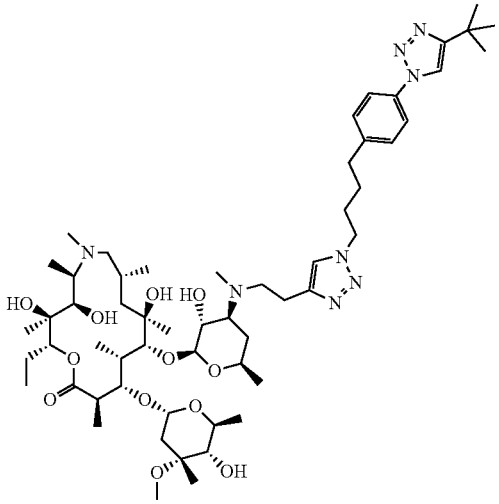 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C(C)(C)C)nn5)cc4)nn3)[C@H]2O)[C@](C)(O)C[C@@H](C)CN(C)[C@H](C)[C@@H](O)[C@]1(C)O] |
| 190 | 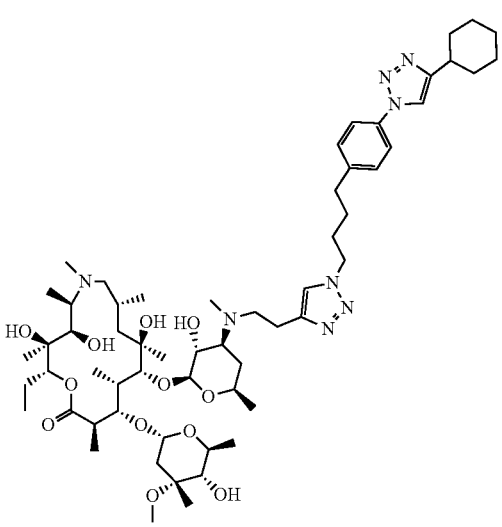 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(C6CCCCC6)nn5)cc4)nn3)[C@H]2O)[C@](C)(O)C[C@@H](C)CN(C)[C@H](C)[C@@H](O)[C@]1(C)O] |
| 191 | 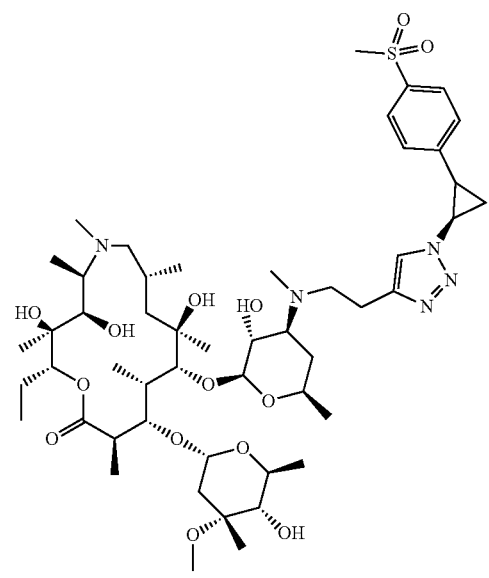 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H]4CC4c4ccc(S(C)(=O)=O)cc4)nn3)[C@H]2O)[C@](C)(O)C[C@@H](C)CN(C)[C@H](C)[C@@H](O)[C@]1(C)O] |

299
-continued
| Compound | Structure |
|---|---|
| 192 | 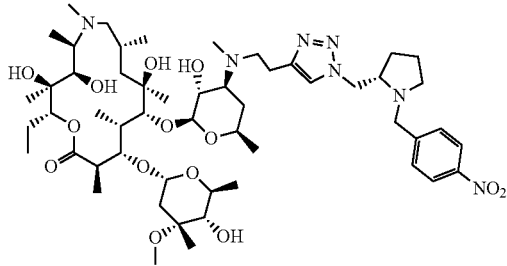 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H]4CCCN4Cc4ccc([N+](=O)[O-])cc4)nn3)[C@H]2O)[C@](C)(O)C[C@@H](C)CN(C)[C@H](C)[C@@H](O)[C@]1(C)O] |
| 193 | 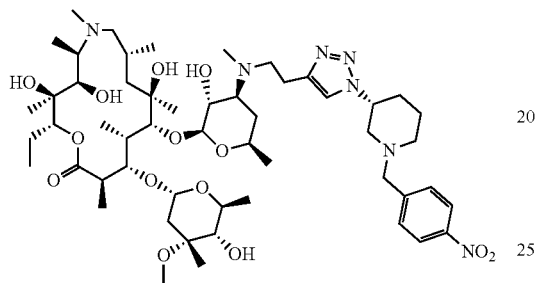 |
| 194 | 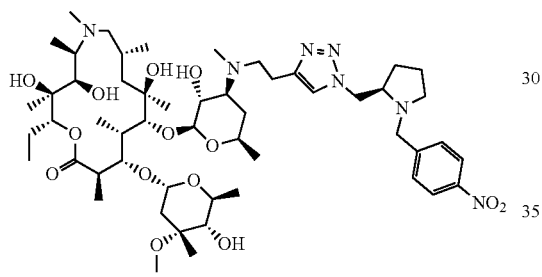 |
| 195 | 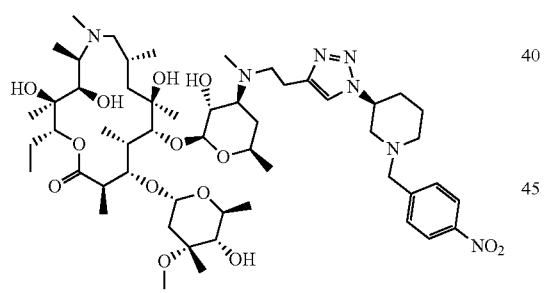 |
| 196 | 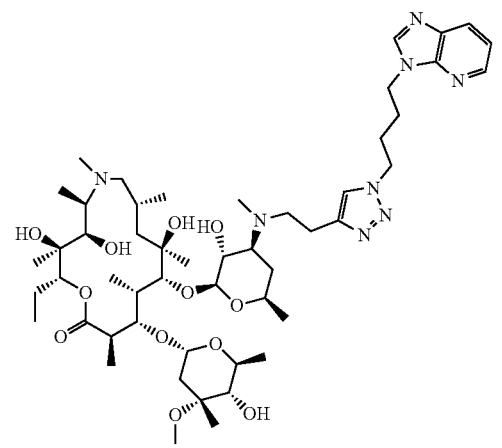 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCn4cnc5cccnc54)nn3)[C@H]2O)[C@](C)(O)C[C@@H](C)CN(C)[C@H](C)[C@@H](O)[C@]1(C)O] |
300
-continued
| Compound | Structure |
|---|---|
| 197 | 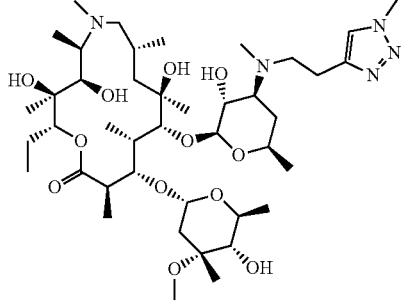 |
| 198 | 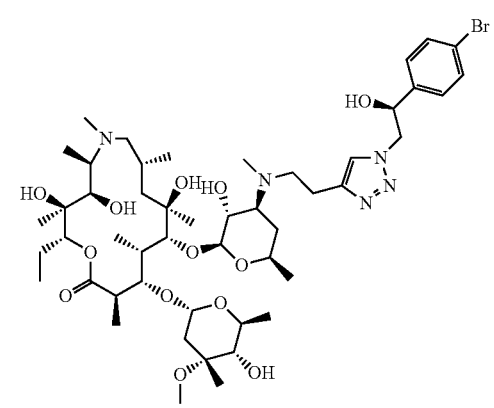 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H](O)c4ccc(Br)cc4)nn3)[C@H]2O)[C@](C)(O)C[C@@H](C)CN(C)[C@H](C)[C@@H](O)[C@]1(C)O] |
| 201 | 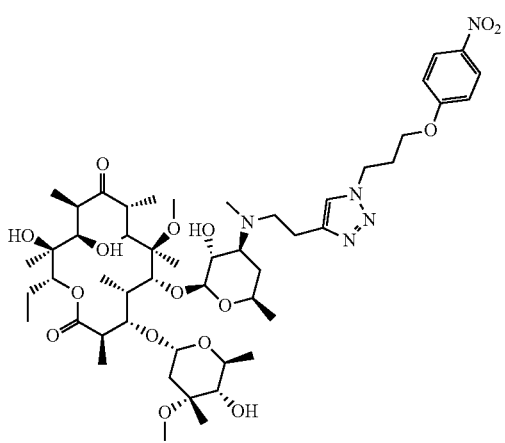 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc([N+](=O)[O-])cc4)nn3)[C@H]2O)[C@](C)(OC)C2O[C@H]([C@@H](C)C(=O)[C@@H]2C)[C@]1(C)O] |

301
-continued
| Compound | Structure |
|---|---|
| 202 | 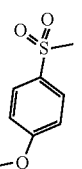 |
| 203 | 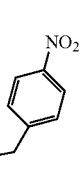 |
| 204 | 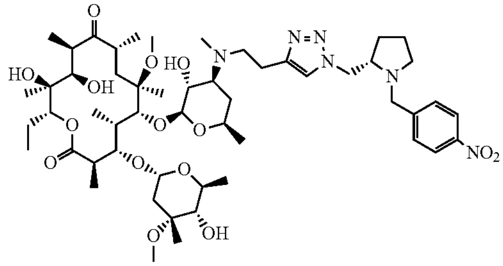 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H]4CCCN4Cc4ccc([N+](=O)[O-])cc4)nn3)[C@H]2O)[C@](C)(OC)C[C@@H](C)C(=O)[C@H](C)[C@@H](O)[C@]1(C)O] |
| 205 | 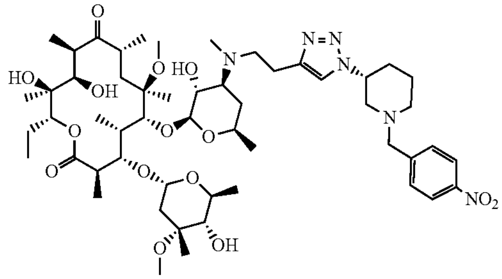 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H]4CCCN(Cc5ccc([N+](=O)[O-])cc5)C4)nn3)[C@H]2O)[C@](C)(OC)C[C@@H](C)C(=O)[C@H](C)[C@@H](O)[C@]1(C)O] |
302
-continued
| Compound | Structure |
|---|---|
| 206 | 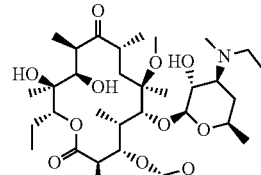 |
| 207 | 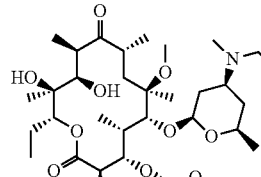 |
| 210 | 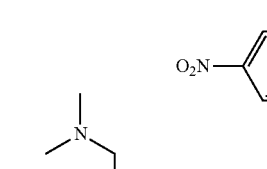 |
| 211 | 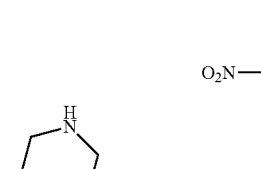 |

| Compound | Structure |
|---|---|
| 212 | 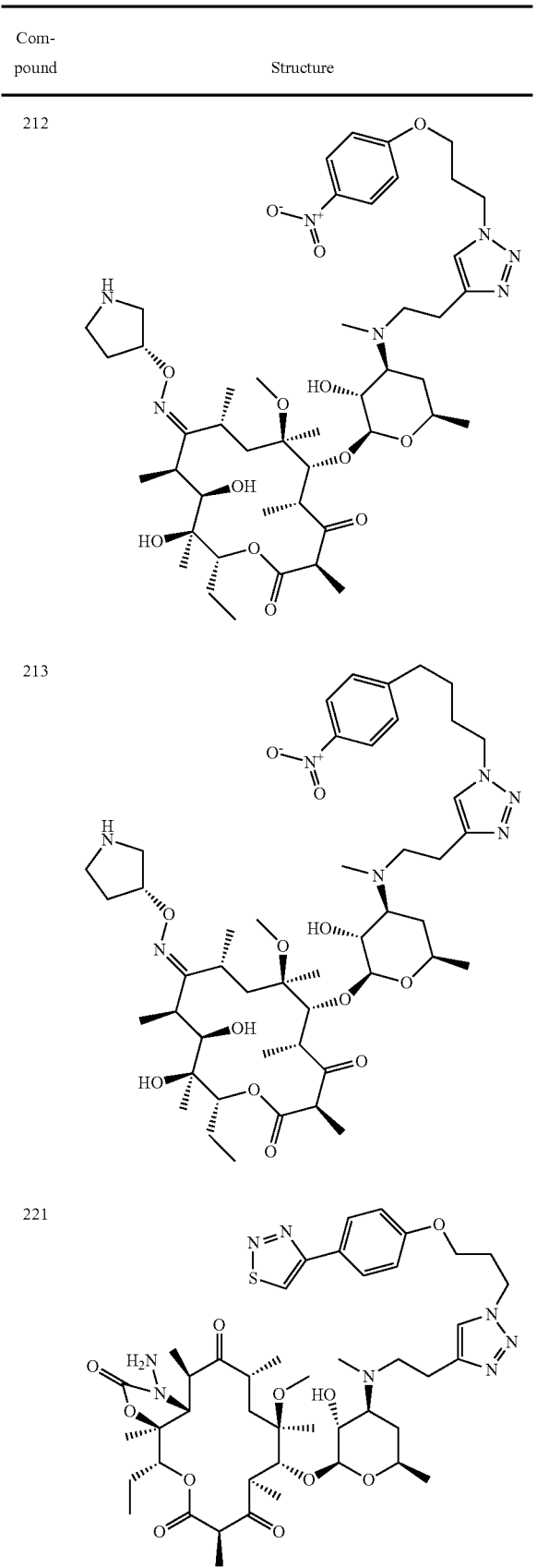 |
| 213 | |
| 221 | |
| Compound | Structure |
|---|---|
| 222 | 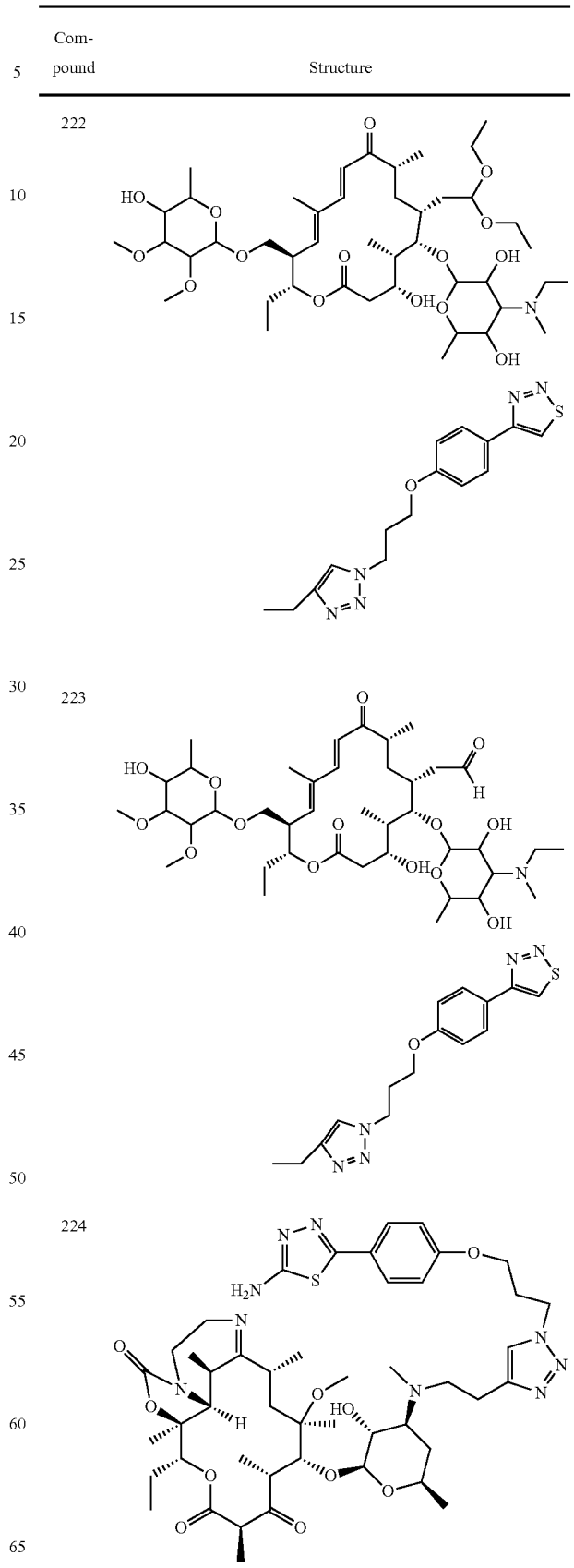 |
| 223 | |
| 224 | |

305
-continued
| Compound | Structure |
|---|---|
| 225 | 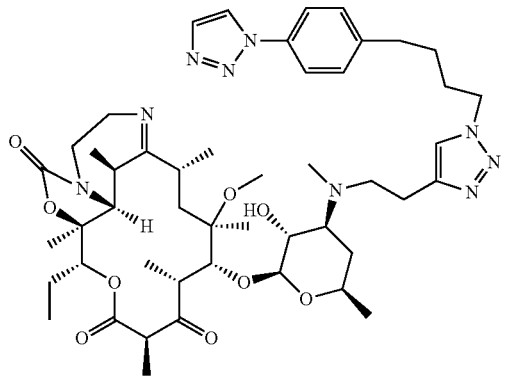 |
| 226 | 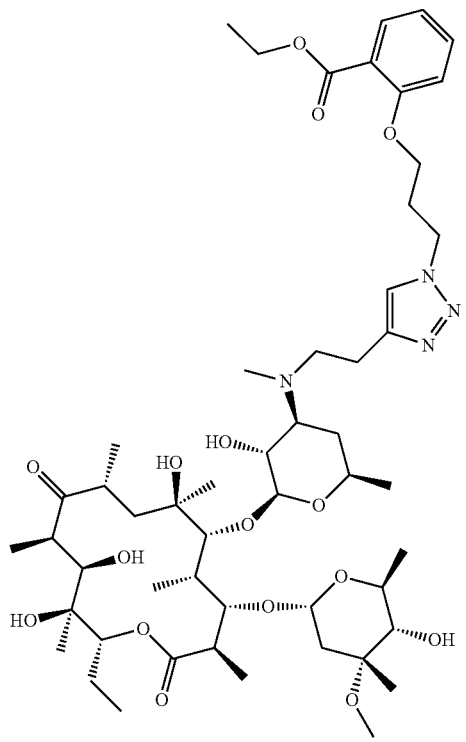 [SMILES: CCOC(=O)c1ccccc1OCCCn1cc(CCN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)C(=O)[C@H](C)C[C@@]3(C)O)[C@@H]2O)nn1] |
306
-continued
| Compound | Structure |
|---|---|
| 230 | 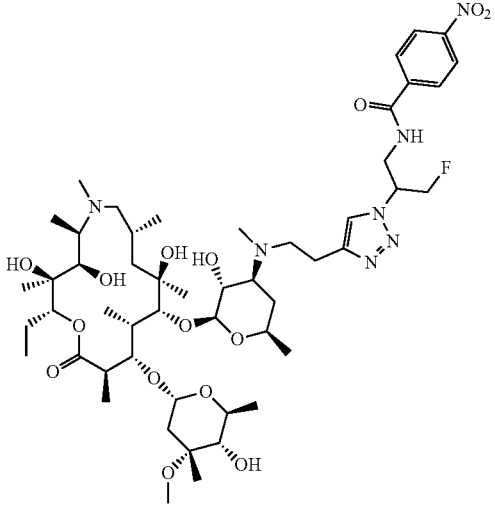 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CF)CNC(=O)c4ccc([N+](=O)[O-])cc4)nn3)[C@H]2O)[C@](C)(O)C[C@@H](C)CN(C)[C@H](C)[C@@H](O)[C@]1(C)O] |
| 231 | 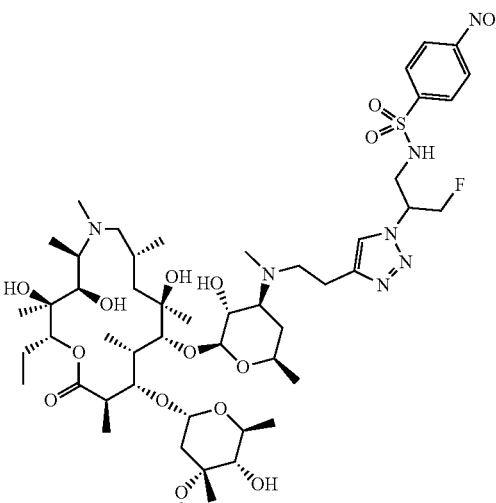 |
| 232 | 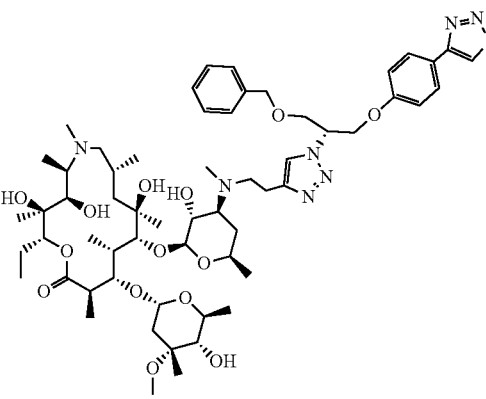 |

307
-continued
| Compound | Structure |
|---|---|
| 233 | 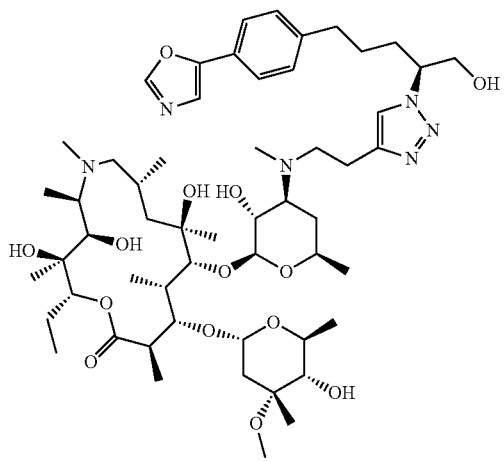 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CO)CCCc4ccc(-c5cnco5)cc4)nn3)[C@H]2O)[C@](C)(O)C[C@@H](C)CN(C)[C@H](C)[C@@H](O)[C@]1(C)O] |
| 234 | 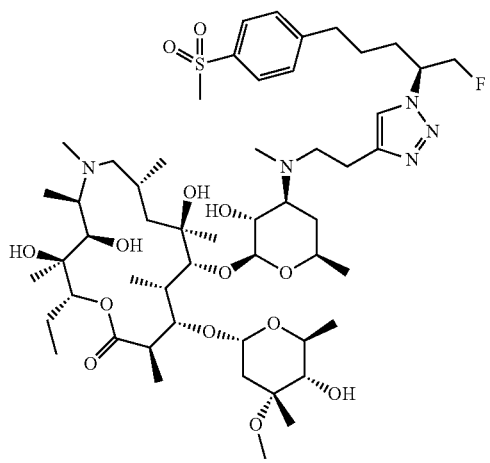 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)CCCc4ccc(S(C)(=O)=O)cc4)nn3)[C@H]2O)[C@](C)(O)C[C@@H](C)CN(C)[C@H](C)[C@@H](O)[C@]1(C)O] |
| 235 | 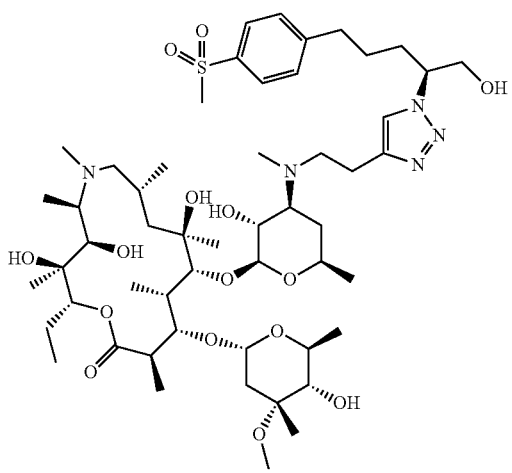 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CO)CCCc4ccc(S(C)(=O)=O)cc4)nn3)[C@H]2O)[C@](C)(O)C[C@@H](C)CN(C)[C@H](C)[C@@H](O)[C@]1(C)O] |
308
-continued
| Compound | Structure |
|---|---|
| 236 | 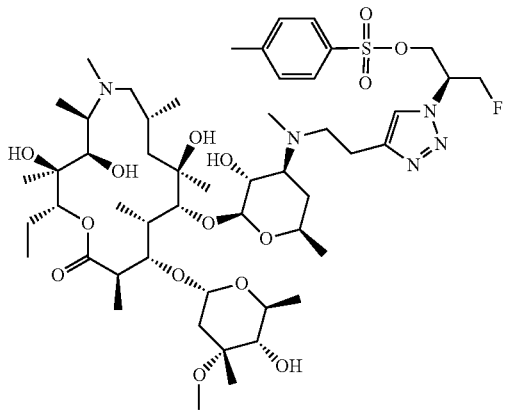 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)COS(=O)(=O)c4ccc(C)cc4)nn3)[C@H]2O)[C@](C)(O)C[C@@H](C)CN(C)[C@H](C)[C@@H](O)[C@]1(C)O] |
| 237 | 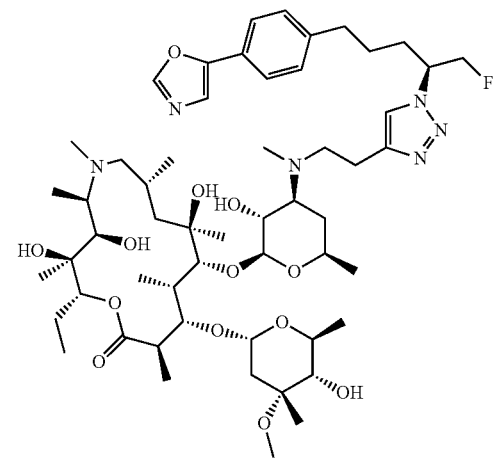 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)CCCc4ccc(-c5cnco5)cc4)nn3)[C@H]2O)[C@](C)(O)C[C@@H](C)CN(C)[C@H](C)[C@@H](O)[C@]1(C)O] |
| 238 | 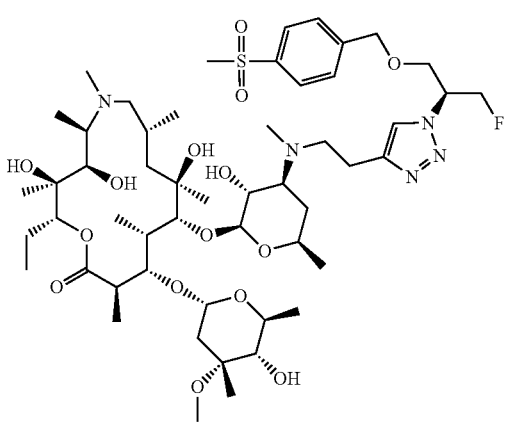 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)COCc4ccc(S(C)(=O)=O)cc4)nn3)[C@H]2O)[C@](C)(O)C[C@@H](C)CN(C)[C@H](C)[C@@H](O)[C@]1(C)O] |

| Compound | Structure |
|---|---|
| 239 | 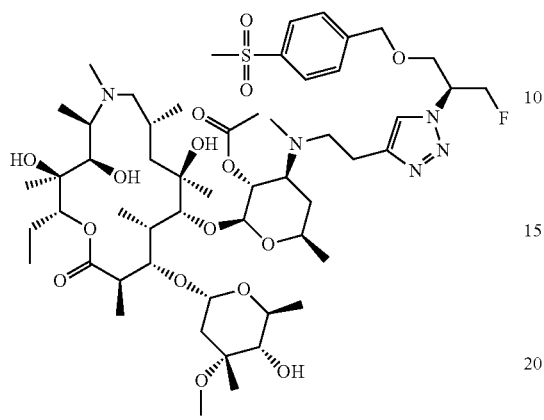 |
| 240 | 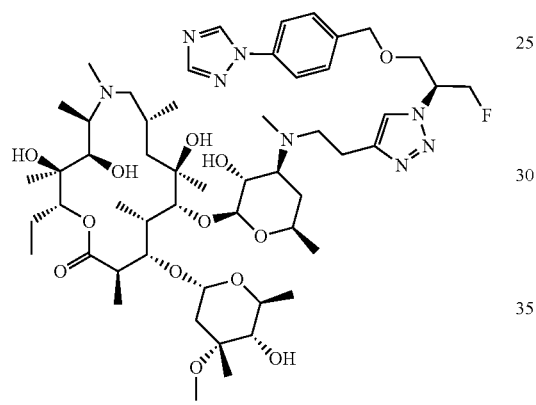 |
| 241 | 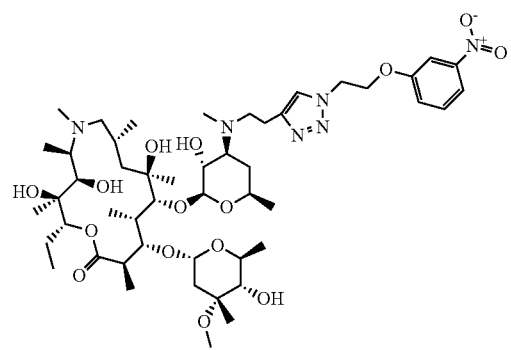 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc([N+](=O)[O-])c4)nn3)[C@H]2O)[C@](C)(O)C[C@@H](C)CN(C)[C@H](C)[C@@H](O)[C@]1(C)O] |
| Compound | Structure |
|---|---|
| 242 | 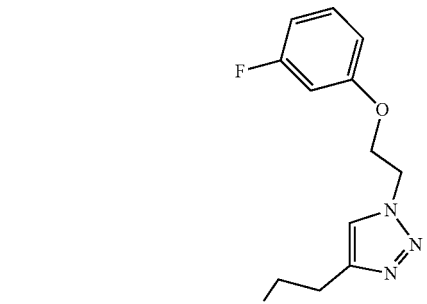 |
| 243 | 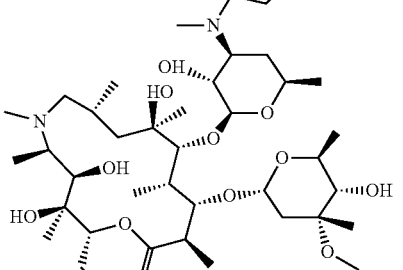 |
and a pharmaceutically acceptable salt, ester, or N-oxide thereof.
* * * * *

UNITED STATES PATENT AND TRADEMARK OFFICE
CERTIFICATE OF CORRECTION

PATENT NO.       : 8,470,985 B2
APPLICATION NO.  : 11/990833
DATED            : June 25, 2013
INVENTOR(S)      : Bhattacharjee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1344 days.

Signed and Sealed this
Third Day of December, 2013

Margaret A. Focarino
*Commissioner for Patents of the United States Patent and Trademark Office*